US012059487B2

(12) United States Patent
Singleton

(10) Patent No.: US 12,059,487 B2
(45) Date of Patent: Aug. 13, 2024

(54) STRUCTURALLY DIVERSE, STABLE, AND RADIATION-PROTECTIVE PARTICLE MATRIX SUNSCREEN AND COSMETIC COMPOSITIONS AND RELATED METHODS

(71) Applicant: LCS Advanced Solutions, LLC, Inglewood, CA (US)

(72) Inventor: Laura C. Singleton, Inglewood, CA (US)

(73) Assignee: LCS Advanced Solutions, LLC, Inglewood, CA (US)

( * ) Notice: Subject to any disclaimer, the term of this patent is extended or adjusted under 35 U.S.C. 154(b) by 0 days.

(21) Appl. No.: 18/488,030

(22) Filed: Oct. 16, 2023

(65) Prior Publication Data

US 2024/0122826 A1   Apr. 18, 2024

Related U.S. Application Data

(60) Provisional application No. 63/475,135, filed on Oct. 15, 2022.

(51) Int. Cl.
*A61K 8/25* (2006.01)
*A61K 8/06* (2006.01)
*A61K 8/27* (2006.01)
*A61K 8/29* (2006.01)
*A61Q 17/04* (2006.01)

(52) U.S. Cl.
CPC .............. *A61K 8/25* (2013.01); *A61K 8/064* (2013.01); *A61K 8/27* (2013.01); *A61K 8/29* (2013.01); *A61Q 17/04* (2013.01); *A61K 2800/31* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 2,435,005 | A | 1/1948 | Huppke |
| 3,175,950 | A | 3/1965 | Abraham |
| 3,479,428 | A | 11/1969 | Maxwell |
| 4,144,325 | A | 3/1979 | Voyt |
| 4,663,157 | A | 5/1987 | Brock |
| 4,671,955 | A | 6/1987 | Palinczar |
| 4,707,354 | A | 11/1987 | Garlen |
| 4,710,371 | A | 12/1987 | Palinczar |
| 4,847,071 | A | 7/1989 | Bissett |
| 5,000,937 | A | 3/1991 | Grollier |
| 5,093,107 | A | 3/1992 | Matravers |
| 5,116,604 | A | 5/1992 | Fogel |
| 5,223,250 | A | 6/1993 | Mitchell |
| 5,229,104 | A | 7/1993 | Sottery |
| 5,256,403 | A | 10/1993 | Gaskin |
| 5,340,567 | A | 8/1994 | Cole |
| 5,468,471 | A | 11/1995 | Zecchino |
| 5,516,457 | A | 5/1996 | Dahms |
| 5,543,136 | A | 8/1996 | Aldous |
| 5,560,917 | A | 10/1996 | Cohen |
| 5,599,533 | A | 2/1997 | Stepniewski |
| 5,618,521 | A | 4/1997 | de Rigal |
| 5,665,368 | A | 9/1997 | Lentini |
| 5,670,139 | A | 9/1997 | Allard |
| 5,744,126 | A | 4/1998 | Horino |
| 5,783,173 | A | 7/1998 | Bonda |
| 5,788,954 | A | 8/1998 | Bonda |
| 5,817,298 | A | 10/1998 | Galley |
| 5,849,273 | A | 12/1998 | Bonda |
| 5,876,699 | A | 3/1999 | DiSomma |
| 5,883,085 | A | 3/1999 | Blank |
| 5,928,660 | A | 7/1999 | Kobayashi |
| 5,935,556 | A | 8/1999 | Tanner |
| 5,939,054 | A | 8/1999 | Msika |
| 5,945,090 | A | 8/1999 | Randall |
| 6,139,823 | A | 10/2000 | Drechsler |
| 6,200,964 | B1 | 3/2001 | Singleton |
| 6,248,340 | B1 | 6/2001 | Maor |

(Continued)

FOREIGN PATENT DOCUMENTS

| | | |
|---|---|---|
| AU | 576863 B2 | 9/1988 |
| AU | 2003233396 A1 | 9/2003 |

(Continued)

OTHER PUBLICATIONS

U.S. Appl. No. 16/220,353, filed Jun. 20, 2019, Singleton, Laura C.
Access Ingredients. UV Absorbers. Mar. 8, 2015. <http://accessingredients.com/products/uv-absorbers/>. (Year: 2015).
FDA Sunscreen Monograph. "Labeling and Effectivness Testing; Sunscreen Drug Products for Over-the-Counter Human Use." vol. 76 Federal Reigster pp. 35620 (Jun. 17, 2011).
Afonso, S. et al. "Photodegradation of avobenzone: stabilization effect of antioxidants." J Photochem Photobiol B. vol. 140, pp. 36-40 (2014).
Akgul, G. "Structural properties of zinc oxide and titanium dioxide nanoparticles prepared by chemical vapor synthesis." Journal of Alloys and Compounds 554 (2013) 177-181. Published Dec. 6, 2012.

(Continued)

*Primary Examiner* — Nannette Holloman
(74) *Attorney, Agent, or Firm* — Len S. Smith; Denise M. Brown; Transformative Legal LLC

(57) ABSTRACT

Matrix compositions comprising structurally diverse matrix particles (1) formed from at least five different types of primary particles distinguishable from one another due to different characteristics, shape characteristics, or both, (2) that constitute 15-50% of the matrix composition by weight, (3) that comprise or more types of particle agglomerates, (4) where at least 33% of the weight concentration of the matrix particle mixture being composed of UV-protectant metal oxide particles having a minimum particle size of over 100 nm, (5) where scanning electron microscope analysis of the composition fails to identify any significant number of discrete matrix particles of having a size of 100 nm or less, and (6) the composition exhibits one or more of sun protection factor (SPF) of at least 30, a critical wavelength of at least 370 nm, UVA/UVB ratio of at least 0.333, and a UVA1 to UV ratio of at least 0.7.

15 Claims, 27 Drawing Sheets

(56) References Cited

U.S. PATENT DOCUMENTS

| | | |
|---|---|---|
| 6,252,100 B1 | 6/2001 | Herzig |
| 6,309,627 B1 | 10/2001 | Golz-Berner |
| 6,322,776 B1 | 11/2001 | Ortega, II |
| 6,326,013 B1 | 12/2001 | Lemann |
| 6,350,894 B1 | 2/2002 | Bonda |
| 6,361,816 B1 | 3/2002 | Amari |
| 6,384,023 B2 | 5/2002 | Singleton |
| 6,699,464 B1 | 3/2004 | Popp |
| 6,830,746 B2 | 12/2004 | SaNogueira |
| 6,906,106 B2 | 6/2005 | Chevalier |
| 6,942,878 B2 | 9/2005 | Ishii |
| 7,014,842 B2 | 3/2006 | Dueva-Koganov |
| 7,029,660 B2 | 4/2006 | Goppel |
| 7,175,834 B2 | 2/2007 | Aust |
| 7,182,938 B2 | 2/2007 | Andre |
| 7,276,230 B2 | 10/2007 | Gonzalez |
| 7,407,666 B2 | 8/2008 | Tarletsky |
| 7,427,690 B2 | 9/2008 | Gupta |
| 7,481,845 B2 | 1/2009 | De La Mettrie |
| 7,892,570 B2 | 2/2011 | Elliott |
| 8,236,287 B2 | 8/2012 | Singleton |
| 8,241,613 B2 | 8/2012 | Candau |
| 8,637,057 B2 | 1/2014 | Dhaval |
| 8,642,018 B2 | 2/2014 | Kurosawa |
| 8,647,609 B2 | 2/2014 | Kim |
| 8,697,035 B2 | 4/2014 | Singleton |
| 8,795,696 B2 | 8/2014 | Milora |
| 9,034,302 B2 | 5/2015 | Gray |
| 9,060,942 B2 | 6/2015 | Harada |
| 9,139,737 B1 | 9/2015 | Shah |
| 9,192,547 B2 | 11/2015 | Fukuhara |
| 9,333,159 B2 | 5/2016 | Hayes |
| 9,487,409 B2 | 11/2016 | Sueda |
| 9,517,190 B2 | 12/2016 | Johncock |
| 9,642,785 B2 | 5/2017 | Itagaki |
| 9,649,263 B2 | 5/2017 | Youssef |
| 9,744,111 B2 | 8/2017 | Norman |
| 10,029,127 B2 | 7/2018 | Gaudry |
| 10,045,918 B2 | 8/2018 | Gershon |
| 10,092,494 B2 | 10/2018 | SaNogueira |
| 10,124,030 B2 | 11/2018 | Goldsberry |
| 10,183,868 B2 | 1/2019 | McCormick |
| 10,238,585 B2 | 3/2019 | Ishida |
| 10,357,569 B2 | 7/2019 | Busch |
| 10,383,811 B1 | 8/2019 | Patel |
| 10,434,048 B2 | 10/2019 | Dudley |
| 10,813,870 B2 | 10/2020 | Shah |
| 10,959,924 B2 | 3/2021 | Gershon |
| 11,213,463 B2 | 1/2022 | Kubota |
| 11,426,336 B2 | 8/2022 | Zickerman |
| 11,458,090 B2 | 10/2022 | Josephson |
| 11,707,422 B2 | 7/2023 | Rigg |
| 2001/0018432 A1 | 8/2001 | Singleton |
| 2002/0034524 A1 | 3/2002 | Poret |
| 2002/0114773 A1 | 8/2002 | Kanji |
| 2002/0155073 A1 | 10/2002 | Fankhauser |
| 2003/0059383 A1 | 3/2003 | SaNogueira |
| 2003/0072723 A1 | 4/2003 | Gers-Barlag |
| 2003/0161795 A1 | 8/2003 | Tsuzuki |
| 2003/0170280 A1 | 9/2003 | Canham |
| 2003/0219391 A1 | 11/2003 | Liew |
| 2004/0028709 A1 | 2/2004 | Dueva |
| 2004/0091433 A1 | 5/2004 | Buchholz |
| 2004/0126337 A1 | 7/2004 | Singleton |
| 2004/0146539 A1 | 7/2004 | Gupta |
| 2004/0219124 A1 | 11/2004 | Gupta |
| 2005/0136012 A1 | 6/2005 | Gonzalez |
| 2005/0175562 A1 | 8/2005 | Hadasch |
| 2005/0209131 A1 | 9/2005 | Singleton |
| 2006/0045890 A1 | 3/2006 | Gonzalez |
| 2006/0067904 A1 | 3/2006 | Russ |
| 2006/0110415 A1 | 5/2006 | Gupta |
| 2006/0115439 A1 | 6/2006 | Lu |
| 2006/0216258 A1 | 9/2006 | Singleton |
| 2007/0009453 A1 | 1/2007 | Willemin |
| 2007/0010408 A1 | 1/2007 | Uehara |
| 2007/0085063 A1 | 4/2007 | Capelli |
| 2007/0149395 A1 | 6/2007 | Kroell |
| 2007/0160549 A1 | 7/2007 | Hunt |
| 2007/0196309 A1 | 8/2007 | Tarletsky |
| 2007/0218021 A1 | 9/2007 | Wells |
| 2007/0243143 A1 | 10/2007 | Patil |
| 2007/0280895 A1 | 12/2007 | Weimer |
| 2008/0081024 A1 | 4/2008 | Beasley |
| 2008/0213200 A1 | 9/2008 | Vromen |
| 2008/0226727 A1 | 9/2008 | Kessell |
| 2009/0010971 A1 | 1/2009 | Shio |
| 2009/0041691 A1 | 2/2009 | Candau |
| 2009/0041712 A1 | 2/2009 | Singleton |
| 2009/0162443 A1 | 6/2009 | Anthony |
| 2009/0202459 A1 | 8/2009 | Spaulding |
| 2009/0258068 A1 | 10/2009 | Shio |
| 2009/0297461 A1 | 12/2009 | Perle |
| 2010/0061947 A1 | 3/2010 | Schlossman |
| 2010/0129299 A1 | 5/2010 | Singleton |
| 2010/0202985 A1 | 8/2010 | SenGupta |
| 2010/0310871 A1 | 12/2010 | McCormick |
| 2010/0316582 A1 | 12/2010 | Tsuzuki |
| 2011/0110990 A1 | 5/2011 | Yu |
| 2011/0293543 A1 | 12/2011 | Yu |
| 2012/0014882 A1 | 1/2012 | Singleton |
| 2012/0015013 A1 | 1/2012 | Schlossman |
| 2012/0058192 A1 | 3/2012 | Singleton |
| 2012/0219515 A1 | 8/2012 | Barrett |
| 2012/0258055 A1 | 10/2012 | Gray |
| 2012/0263661 A1 | 10/2012 | Grune |
| 2012/0288449 A1 | 11/2012 | Singleton |
| 2013/0011348 A1 | 1/2013 | Takakura |
| 2013/0022655 A1 | 1/2013 | Sachweh |
| 2013/0028851 A1 | 1/2013 | Fontaine |
| 2013/0052148 A1 | 2/2013 | Chavan |
| 2013/0089507 A1 | 4/2013 | Milora |
| 2013/0089588 A1 | 4/2013 | Milora |
| 2013/0095050 A1 | 4/2013 | Daly |
| 2014/0004165 A1 | 1/2014 | Novejarque Conde |
| 2014/0335137 A1 | 11/2014 | Hayes |
| 2015/0064224 A1 | 3/2015 | Tong |
| 2015/0086633 A1 | 3/2015 | Sakanishi |
| 2015/0202145 A1 | 7/2015 | Friedman |
| 2015/0265510 A1 | 9/2015 | Johncock |
| 2015/0283059 A1 | 10/2015 | Nagare |
| 2015/0376025 A1 | 12/2015 | McCormick |
| 2016/0058681 A1 | 3/2016 | Li |
| 2016/0206527 A1 | 7/2016 | Hueber |
| 2016/0220457 A1 | 8/2016 | Yamaguchi |
| 2016/0303020 A1 | 10/2016 | Blachechen |
| 2016/0367448 A1 | 12/2016 | Youssef |
| 2017/0181941 A1 | 6/2017 | Gunawan |
| 2017/0189296 A1 | 7/2017 | SaNogueira |
| 2018/0116925 A1 | 5/2018 | Johnson |
| 2018/0185254 A1 | 7/2018 | Jung |
| 2018/0235855 A1 | 8/2018 | Schlossman |
| 2018/0311117 A1 | 11/2018 | Zeng |
| 2018/0353402 A1 | 12/2018 | Fisher |
| 2019/0183754 A1 | 6/2019 | Singleton |
| 2019/0290560 A1 | 9/2019 | Singleton |
| 2020/0157364 A1 | 5/2020 | Shah |
| 2020/0247684 A1 | 8/2020 | Suvaci |
| 2020/0306162 A1 | 10/2020 | Ahmad |
| 2020/0390665 A1 | 12/2020 | El Achkar |
| 2021/0000704 A1 | 1/2021 | Shao |
| 2021/0038494 A1 | 2/2021 | Qu |
| 2021/0052474 A1 | 2/2021 | Fujinohara |
| 2021/0059911 A1 | 3/2021 | Paulucci |
| 2021/0154106 A1 | 5/2021 | Mecca |
| 2021/0244631 A1 | 8/2021 | Fernandes |
| 2021/0315781 A1 | 10/2021 | Mito |
| 2021/0353514 A1 | 11/2021 | Patel |
| 2022/0000732 A1 | 1/2022 | Li |
| 2022/0008300 A1 | 1/2022 | Lee |
| 2022/0023161 A1 | 1/2022 | Milora |
| 2023/0080141 A1 | 3/2023 | Stahl |

(56) References Cited

U.S. PATENT DOCUMENTS

| | | |
|---|---|---|
| 2023/0121763 A1 | 4/2023 | Zachary |
| 2023/0147073 A1 | 5/2023 | Singleton |
| 2023/0165763 A1 | 6/2023 | Shi |

FOREIGN PATENT DOCUMENTS

| | | |
|---|---|---|
| AU | 2007221239 A1 | 9/2007 |
| BR | PI0707029 A2 | 4/2011 |
| CA | 1128864 A | 8/1982 |
| CA | 2029240 A1 | 5/1992 |
| CA | 2168869 A1 | 3/1995 |
| CA | 2642783 A1 | 9/2007 |
| CA | 2643321 A1 | 9/2007 |
| CA | 2710958 A1 | 7/2009 |
| CA | 2913545 A1 | 5/2016 |
| CN | 104224650 A | 12/2014 |
| CN | 110302071 A | 10/2019 |
| DE | 60000474 T2 | 3/2003 |
| DE | 69820243 | 9/2004 |
| EP | 0383540 A2 | 8/1990 |
| EP | 0427411 A2 | 5/1991 |
| EP | 0463030 A1 | 1/1992 |
| EP | 0583308 B1 | 2/1994 |
| EP | 0590014 A1 | 4/1994 |
| EP | 0678015 | 10/1995 |
| EP | 0765656 A1 | 4/1997 |
| EP | 0628303 B1 | 9/1997 |
| EP | 1097695 A1 | 5/2001 |
| EP | 1172083 A2 | 1/2002 |
| EP | 1181329 A1 | 2/2002 |
| EP | 1421931 A2 | 5/2004 |
| EP | 1435230 A2 | 7/2004 |
| EP | 1709953 A1 | 10/2006 |
| EP | 1796619 B1 | 6/2007 |
| EP | 1855642 A2 | 11/2007 |
| EP | 1949886 A1 | 7/2008 |
| EP | 1998737 A2 | 12/2008 |
| EP | 2207525 A2 | 7/2010 |
| EP | 2407148 A1 | 1/2012 |
| EP | 2425810 A2 | 3/2012 |
| EP | 2774604 A1 | 9/2014 |
| EP | 2853255 A1 | 4/2015 |
| EP | 3062769 A1 | 9/2016 |
| EP | 3238704 A1 | 11/2017 |
| EP | 250956888 | 3/2018 |
| EP | 3624756 B1 | 11/2022 |
| ES | 2183771 | 4/2003 |
| FI | I97685 B | 10/1996 |
| FR | 1185943 | 3/1970 |
| FR | 1375436 | 11/1974 |
| FR | 1473483 A | 5/1977 |
| FR | 1488061 A | 10/1977 |
| FR | 2217987 A | 11/1989 |
| FR | 2757380 A1 | 6/1998 |
| FR | 2758985 A1 | 8/1998 |
| FR | 2768926 A1 | 4/1999 |
| FR | 2800605 A1 | 5/2001 |
| FR | 3072291 A1 | 4/2019 |
| FR | 3072292 A1 | 4/2019 |
| GB | 2437056 A | 10/2007 |
| JP | 2001172503 | 6/2001 |
| JP | 2006265253 A | 10/2006 |
| JP | 2009527571 A | 7/2009 |
| KR | 20130134976 A | 12/2013 |
| KR | 102203667 B1 | 1/2021 |
| NZ | 236318 A | 11/1993 |
| NZ | 264108 A | 5/1997 |
| WO | WO1993011742 A1 | 6/1993 |
| WO | WO1994018940 A1 | 9/1994 |
| WO | WO1997003642 A1 | 2/1997 |
| WO | WO1998052529 A1 | 11/1998 |
| WO | WO2000064472 A1 | 11/2000 |
| WO | WO2000073374 A1 | 12/2000 |
| WO | WO2002011717 A1 | 2/2002 |
| WO | WO2007078062 A1 | 7/2007 |
| WO | WO2007097967 A2 | 8/2007 |
| WO | WO2007100689 A2 | 9/2007 |
| WO | WO2008070368 A2 | 6/2008 |
| WO | WO2008155080 A2 | 12/2008 |
| WO | WO2009126722 A1 | 10/2009 |
| WO | WO2010059620 A1 | 5/2010 |
| WO | WO2011116216 A2 | 9/2011 |
| WO | WO2011150034 A2 | 12/2011 |
| WO | WO2012009405 A2 | 1/2012 |
| WO | WO2012104160 A2 | 8/2012 |
| WO | WO20150030702 A | 3/2015 |
| WO | WO2015144331 | 10/2015 |
| WO | WO2015152865 A1 | 10/2015 |
| WO | WO2016036828 A1 | 3/2016 |
| WO | WO2016082061 A1 | 6/2016 |
| WO | WO2017210406 A1 | 12/2017 |
| WO | WO2021174715 A1 | 9/2021 |

OTHER PUBLICATIONS

Allantoin Cream. "Uses, Side Effects, and More." Generic Name: Allantoin. WebMD. Accessed Jul. 5, 2023.

Avenel-Audran M. Archives of Dermatology. "Octocrylene, an emerging photoallergan." 2010. vol. 146, No. 7, pp. at pp. 753-757.

Beasley, DG et al. "Characterization of the UVA protection provided by avobenzone, zinc oxide, and titanium dioxide in broad-spectrum sunscreen products." Am J Clin Dermatol vol. 11, No. 6, pp. 413-421 (2010). Published Aug. 21, 2012.

HallBrite BHB from The Hallstar Company (Chicago, IL). https://www.hallstarbeauty.com/product/hallbrite-bhb/. Accessed Jul. 4, 2023.

Bennis, Chelsey. "Improving sunscreen compliance and awareness of skin cancer and the effects of the sun in adolescents and young adults: A quality improvement project." (2021).

Bhatia, S. "Mycosporine and mycosporine-like amino acids: A paramount tool against ultra violet irradiation." Pharacognosy Review. Jul.-Dec. 2011; 5(10): 138-146. Received Dec. 23, 2011.

Croda. Solaveil MicNo Personal Care Brochure. Oct. 10, 2022.

MicNo Product Overview and Catalogue. Apr. 21, 2021. Document ID 0321PCEP02526v1EN.

Solespheres from AGC Chemicals America, Inc. "Environmentally Safe SOLESPHERE Microsphere Silica Gels Improve Visual and Tactile Aesthetics in Skincare Formulations." (Exton, Pennsylvania). Aug. 25, 2021.

Dispersun DSP OL 300 from Innospec Performance Chemicals (Salisbury, NC). Accessed on Jul. 4, 2023.

Sunsolv BOV from Innospec Performance Chemicals (Salisbury, NC). Accessed on Jul. 5, 2023.

Chen D., et al. "Synthesis of monodisperse mesoporous titania beads with controllable diameter, high surface areas and variable pore diameters (14-23 nm)." J Am Chem Soc. Mar. 4, 2010;132(12):4438-44. doi: 10.1021/ja100040p.PMID: 20201515.

Non-Final Office Action on Sep. 22, 2023 for U.S. Appl. No. 16/566,781.

Chrapusta, E. "Mycosporine-Like Amino Acids: Potential Health and Beauty Ingredients." Marine Drugs. Published Oct. 21, 2017.

Jungbunzlauer. "CITROFOL Citrate Esters in Sunscreen Formulation." Advertorial. Basel, Switzerland. Sep. 8, 2021. https://www.sofw.com/en/news/latest-news/personal-care/2419-citrofol-citrate-esters-in-sunscreen-formulation.

Section 352.76 of Title 21 of the U.S. Code of Federal Regulations. "Determination if a product is water resistant or very water resistant." Accessed Jul. 4, 2023.

Cole C, et al. "Metal oxide sunscreens protect skin by absorption, not by reflection or scattering." Photodermatol Photoimmunol Photomed. Jan. 2016;32(1):5-10. doi: 10.1111/phpp.12214. Epub Nov. 10, 20150. PMID: 26431814.

ARGAN Co. "Disbributor of Specialty Cosmetic Raw Materials." ARGA-SUN ZnO. Feb. 14, 2016.

Technical Data Sheets (TDS), ARGA-SUN ZnO CLR. Reviewed Feb. 19, 2019.

SunSpheres by the Dow Chemical Company (Midland, MI). Accessed on Jul. 4, 2023.

(56) References Cited

OTHER PUBLICATIONS

Jeechem International Corporation. Technical Bulletin. "Jeechem TDTM-MC Maximum Color for Maximum Wow." Accessed Apr. 18, 2018.
Organic Creations. "Panthenol DL Description." Accessed to Jul. 5, 2023. https://organic-creations.com/product/panthenol-dl/.
Cross, S.E., et al. "Human Skin Penetration of Sunscreen Nanoparticles: In-vitro Assessment of a Novel Micronized Zinc Oxide Formulation." Skin Pharmacol. Physiol., vol. 20, pp. 148-154 (2007). Published online Jan. 17, 2007.
Culliney, K. (Mar. 10, 2020). "SPF+, whitening and perfecting: L'Oreal publishes flurry of sunscreen patents." https://www.cosmeticsdesign-europe.com/Article/2020/03/10/L-Oreal-sun-protection-patents-cover-SPF-skin-whitening-and-appearance.
CosmoSurf LS-1 Siltech. CE Series. Technical Data Sheet. (2009).
Covabead Crystal Technical Data Sheet (Mar. 14, 2014; revised Mar. 8, 2017).
Elix-Ir Technical Datasheet. Supplied by Lucas Meyer Cosmetics (IFF). Special Chem. https://cosmetics.specialchem.com/product/i-lucas-meyer-cosmetics-iff-elix-ir.
SkinSave Technical Data Sheet. Supplied by BIONAP (Bioactive Natural Products). Special Chem. Jun. 8, 2023. https://cosmetics.specialchem.com/product/i-bionap-bioactive-natural-products-skin-save. Must be purchased.
Technical Data Sheet for EverZinc for Zano 10, Zano 20, & Zano (Nov. 25, 2016).
De Groot, A.C., and Roberts, D.W. "Contact and photocontact allergy to octocrylene: a review." Contact Dermatitis, vol. 70, pp. 193-204 (2014). First published Mar. 14, 2014.
Dumbuya et al. "Impact of Iron-Oxide Containing Formulations Against Visible Light-Induced Skin Pigmentation in Skin of Color Individuals." J Drug Dermatol. Jul. 2020; 19(7): 712-717. doi: 10.36849/JDD.2020.5032. Epub Jun. 18, 2020.
Elementis Bentone Gel PTM V (East Windor, NJ). Accessed on Jul. 4, 2023.
Fares, H.M. "Formulating Anhydrous Sunscreen products that Applies Clear on Skin that is Wet." Ashland Specialty Ingredients, 1005 Route 202/206, Bridgewater, NJ 08807. Accessed Apr. 16, 2018.
Fuller, A. "Sun care: beyond protection." Cosmetics; Mississauga vol. 28, Iss. 1, (Jan. 2000): 62.
Geoffrey K, et al. "Sunscreen products: Rationale for use, formulation development and regulatory considerations." Saudi Pharm J. Nov. 2019;27(7):1009-1018. doi: 10.1016/j.jsps.2019.08.003. Epub Aug. 16, 2019. PMID: 31997908; PMCID: PMC6978633.
Giannnakopoulou, T. "Optical and photocatalytic properties of composite TiO2/ZnO thin films." Catalysis Today. Oct. 28, 2013.
Plankton. "Plankton Glass Flower: The glass diamond from ancient volcanic lakes." Powerpoint. Nov. 30, 2017.
Australian Gold. "Botanicals Sunscreen 70 Minerals." (NDC 58443-0265; marketed starting Oct. 29, 2018). Https://www.australiangold.com/shop/product-line/botanical/botanical-spf-70-sunscreen-lotion.
Gulson, B. "A review of critical factors for assessing the dermal absorption. . ." Arch Toxicol (2015) 89: 1909-1930. doi: 10.1007/s00204-015-1564-z. Published Jul. 4, 2015.
SunSpheres. "Rohm and Haas Personal Care: ingredients of creativity." Hollow Sphere Technology. Powerpoint. Feb. 1, 2006.
Symire. "Multiple Benefits for Cosmetics with SymSave H." Jul. 26, 2013. Focus on Surfactants, vol. 13, Is. 10, p. 2. https://doi.org/10.1016/S1351-4210(13)70242-7.
Symrise. "Dragosine 844033: Multi-Functional Anti-Aging Peptide." Brochure (2014).
Symrise, Inc. "Symsave H." Accessed on Jul. 4, 2023.
Symrise, Inc. "Corapan TQ." Teterboro, NJ. Accessed on Jul. 4, 2023.
Synrise, Inc. "SymRelief 100." Bisabolol (and) Zingiber Officinale (Ginger) Root Extract. Prospector. Https://www.ulprospector.com/en/na/PersonalCare/Detail/3030/216994/SymRelief-100. Accessed Jul. 4, 2023.
Alzo International, Inc. "Elefac I-205." (Sayreville, NJ). Accessed Jul. 4, 2023.
Symrise, Inc. "Symdoil 68." Teterboro, NJ. Accessed on Jul. 4, 2023.
Access Ingredients. "AccessSIL FF-16." South Pasadena, CA. Accessed on Jul. 4, 2023.
Ishii, N. et al. "Safety Screens : Using a hypercomposite powder of thin-layer silica-coated zinc oxide in sunscreen. . ." Global Cosmetic Industry Feb. 2001: 32. Business Insights: Global. Web. Apr. 18, 2018.
Janjua N.R. et al. "Systemic absorption of the sunscreens benzophenone-3, octyl-methoxycinnamate, and 3-(4-methyl-benzylidene) camphor after whole-body topical application. . ." J. Invest. Dermatol. Jul. 2004; vol. 123, pp. 57-61.
Janjua, N.R. et al. "Sunscreens in human plasma and urine after repeated whole-body topical application." J Eur Acad. Dermatol. Venereol. vol. 22, No. 4, pp. 456-461 (2008). Epub Jan. 23, 2008.
Jimenez Reinosa, J. "Enhancement of UV absorption behavior in ZnO—TiO2 composites." Boletin de la Sociedad Espanola de Ceramica y Vidrio. 55 (2016): 55-62. Published Feb. 8, 2016.
Korzhinsky, M.A. et al. "Native Al and Si Formation." Institute of Experimental Mineralogy, Russian Academy of Sciences. Nature, vol. 375, p. 544. Jun. 15, 1995.
Kumar, P. et al. "Patent review on photostability enhancement of avobenzone and its formulations." Recent Pat Drug Deliv Formul. vol. 9, No. 2, pp. 121-128 (2015). Published Jul. 31, 2015.
Antaria Limited. "ZinClear XP (Zinc Oxide Powder)." Jun. 1, 2016.
Lionetti, N. "The New Sunscreens among Formulation Strategy, Stability Issues, Changing Norms, Safety and Efficacy Evaluations." Cosmetics 2017, 4, 15; doi: 10.3390/cosmetics4020015. Published May 16, 2017.
Non-Final Office Action on Feb. 20, 2019 for U.S. Appl. No. 15/934,312.
Final Office Action on Mar. 22, 2023 for U.S. Appl. No. 15/934,312.
Lohani, A. "Nanotechnology-Based Cosmeceuticals." Review Article. Hindawi Publishing Corporation. ISRN Dermatology. vol. 2014, Article ID 843687, 14 pages. Published May 22, 2014.
CeraVe. "Sunscreen Body Lotion SPF 50." https://incidecoder.com/products/cerave-sunscreen-body-lotion-spf-50; https://www.heb.com/product-detail/cerave-sunscreen-body-lotion-spf-50/1698233.
Lowe, N. "An overview of ultraviolet radiation, sunscreens, and photo-induced dermatoses." Dermatol Clin. Jan. 2006; 24(1): 9-17. doi: 10.1016/j.det.2005.08.001.
Lu, P.J. "Characterization of titanium dioxide and zinc oxide nanoparticles in sunscreen powder by comparing different measurements methods." Journal of Food and Drug Analysis. Published Feb. 15, 2018. pp. 1192-1200.
Lu P, et al. "Analysis of titanium dioxide and zinc oxide nanoparticles in cosmetics." J Food Drug Anal. Sep. 2015;23(3):587-594. doi: 10.1016/j.jfda.2015.02.009. Epub Apr. 20, 2015. PMID: 28911719; PMCID: PMC9351801.
Mwangi et al. "Sunscreen products: Rationale for use, formulation development and regulatory considerations." Saudi Pharm J. Nov. 2019; 27(7): 1009-1018. doi: 10.1016/j.jsps.2019.08.003. Epub Aug. 16, 2019.
Office of Environmental Health Hazard Assessment, California EPA. "Proposition 65 of Safe Drinking Water and Toxic Enforcement Act of 1986." Jun. 2012.
Dow Personal Care. "SUNSPHERES Hollow Sphere Technology: An SPF Booster for More Aesthetically Pleasing Formulations." Feb. 22, 2007.
Dow Personal Care. "SunSpheres SPF Boosters: Hollow Sphere Technology for More Aesthetically—Pleasing Formulations at Higher SPF." Mar. 2, 2016. p. 4.
Dow Personal Care. "SunSpheres SPF Booster in Daily Wear Applications: Achieve Higher SPF and More Aesthetically-Pleasing Daily Moisturizer and Color Cosmetic Formulations with SunSpheres SPF Boosters." Mar. 2, 2016; Revised Jun. 10, 2019. p. 2.
Poluboyarinov A, et al. "Titanium Oxide Microspheres with Tunable Size and Phase Composition." Materials (Basel). May 7, 2019;12(9):1472. doi: 10.3390/ma12091472. PMID: 31067714; PMCID: PMC6539129.

(56) References Cited

OTHER PUBLICATIONS

Bionap S.r.l. "Olea HT-10." Olea Europea (Olive) Fruit Extract (and) Maltodextrin. Personal Care & Cosmetics. Accessed on Jul. 4, 2023.

Kobo Products. "KSL-199A: Elegant W/O White Sunscreen Lotion with Composite ACT-50." Aug. 2011.

Kobo Products. "Formulary: PCHi 2016." Aug. 2016.

Rajabi, L. et al. "Acetophenones with selective antimycobacterial activity." Letters in Applied Microbiology, vol. 40, Is. 3, pp. 212-217. https://doi.org/10.1111/j.1472-765X.2005.01657.x. First published Jan. 26, 2005.

Official Journal of the European Union. "Commission Recommendation of Sep. 22, 2006 on the fficacy of sunscreen products and the claims made relating thereto." 2006/647/EC. Broad Spectrum Sunscreen.

Rincon-Fontan, M. "Design and characterization of greener sunscreen formulations based on mica powder and biosurfactant extract." Powder Technology 327 (2018): 442-448. Published Jan. 5, 2018.

Rodrigues, N.D.N. "Photophysics of the sunscreen ingredient menthyl anthranilate and its precursor methyl anthranilate." Journal of Photochemistry and Photobiology A: Chemistry 353 (2018) 376-384. Published Dec. 1, 2017.

Access Ingredients. "Hectorite Technologies." Sunjin Beauty Science. May 2020, Version 3.5. Powerpoint, 2019.

Shao, Y. "Formulating mineral sunscreens for people of color." New York Society of Cosmetic Chemists. Jan. 28, 2021. https://nyscc.org/blog/formulating-mineral-sunscreens-for-people-of-color/.

Supelco. "Niacinamide PHR1033 Safety Data Sheet." Millipore Sigma. Analytical Reference Materials for the Pharma Industry. Version 6.8. 9 pages. Print date Jul. 1, 2023.

Sinerga. "Feniol, Phenethyl Alcohol (and) Caprylyl Glycol." Prospector. https://www.ulprospector.com/en/na/PersonalCare/Detail/12615/356929/Feniol. Accessed on Jul. 4, 2023.

Sinerga Skin Evolution. "Ewocream W/O skin shield." Varese, Italy. Accessed Jul. 4, 2023.

Smaoui, S. "Development and stability studies of sunscreen cream formulations containing three photo-protective filters." King Saud University. Arabian Journal of Chemistry (2017) 10, S1216-S1222. Published Mar. 14, 2013.

Science Daily, Science News. American Physical Society. "Photonic Crystal Sunscreen For Sea Scum." Sep. 19, 2006. http://www.sciencedaily.com/releases/2006/09/060918202844.htm.

Vigon. "SymRepair 100: Product Specification and Safety Data Sheet." Effective Date: Feb. 3, 2017.

Mayo Clinic Staff. "Coenzyme Q10 (CoQ10) Overview." Nov. 10, 2020. https://www.mayoclinic.org/drugs-supplements-coenzyme-q10/art-20362602.

Jungbunzlauer. "Citrofol AI and Citrofol BI Technical Datasheet." Universal Selector. Last edited Dec. 19, 2022.

Argan Company. "Sun Care." Sep. 14, 2017. http://www.arganco.com/sun-care.html.

Aveeno. "Positively Mineral Sensitive Skin Sunscreen Broad Spectrum SPF 50." NDC 69968-0395. Accessed on Jul. 4, 2023.

Neutrogena. "Sensitive Skin Sunscreen Lotion Broad Spectrum SPF 60+." Marketed Feb. 2017. Now discontinued. Https://www.neutrogena.com/products/sun/sensitive-skin-sunscreen-lotion-broad-spectrum-spf-60/6847260.html.

SkinCeuticals. "Physical Fusion UV Defense Broad Spectrum SPF 50." NDC 49967-077. Marketed Jan. 1, 2011. https://www.skinceuticals.com/skincare/sunscreens/physical-fusion-uv-defense-spf-50/S54.html#tab=key-ingredients.

Vivero-Escoto J, et al. "Recent progress in mesoporous titania materials: adjusting morphology for innovative applications." Sci Technol Adv Mater. Feb. 2, 2012;13(1):013003. doi: 10.1088/1468-6996/13/1/013003. PMID: 27877467; PMCID: PMC5090292.

Wang, J. "Reducing the Photocatalytic Activity of Zinc Oxide Quantum Dots by Surface Modification." Deakin University. J. Am. Ceram. Soc., 92 [9] 2083-2088 (2009). Published Apr. 5, 2009. doi: 10.1111/j.1551-2916.2009.03142.x.

Wang, S.Q. "Comparison of ultraviolet A light protection standards in the United States and European Union . . ." Journal of the American Academy of Dermatology. vol. 77, Issue 1, Jul. 2017, pp. 42-47. Published Feb. 24, 2017.

FIGURE 1

| ISO 24443 RATIO Results: | | |
|---|---|---|
| SPF/UVA RATIOS: | A-0557 | A-0878 |
| *(Maximum Allowable 3.0)* | | |
| Ratio (UVA/PF / Measured SPF in vivo): | 1.63 | 1.81 |
| Ratio (UVA/PF / Labeled SPF in vivo): | 1.63 | 1.59 |
| | | |
| UVA/SPF RATIOS: | | |
| *(Minimum Required 0.333)* | | |
| Ratio (UVA/PF / Measured SPF in vivo): | 0.613 | 0.552 |
| Ratio (UVA/PF / Labeled SPF in vivo): | 0.613 | 0.629 |
| | | |
| Critical Wavelength: | | |
| *(Minimum Required 370.00 nm)* | 378.00 nm | 376.00 nm |
| | | |
| Proposed FDA UV I / UV RATIO Results: | | |
| *(Proposed Requirement Min. 0.70)* | | |
| UV I / UV Ratio: | 0.89 | 0.81 |

FIGURE 2

| IN-HOUSE IN-VITRO HIGH ENERGY VISIBLE LIGHT (HEV 380-530 nm; "Blue Light") RADIATION PROTECTION POTENTIAL OF SKIN CARE/SUN CARE PRODUCT: | | |
|---|---|---|
| | A-0557 | A-0878 |
| In-House In-Vitro HEV Protection Factor: | 2.13 | 1.99 |
| Percent Solar Spectral Irradiance Blocked (% SSI-HEV): | 53.1% | 48.6% |
| IN-HOUSE IN-VITRO VISIBLE LIGHT (VIS 400-700 nm; "Visible Light") RADIATION PROTECTION POTENTIAL OF SKIN CARE/SUN CARE PRODUCT: | | |
| | A-0557 | A-0878 |
| In-House In-Vitro VIS Protection Factor: | 1.69 | 1.54 |
| Percent Solar Spectral Irradiance Blocked (% SSI-VIS): | 40.7% | 34.9% |

| BLUE LIGHT: A-0557 ||
|---|---|
| Test Conditions: ||
| Substrate: | 1 HD 6u PMMA Plate |
| Application Rate: | 1.3 mg/cm² |
| Dry Time: | 15-30 min |
| Test Results: ||
| IN-HOUSE IN-VITRO HIGH ENERGY VISIBLE LIGHT (HEV 380-530 nm) RADIATION PROTECTION POTENTIAL OF SKIN CARE/SUN CARE PRODUCT ||
| In-House In-Vitro Protection Factor (HEV-PF) | Percent Solar Spectral Irradiance Blocked (%SSI-HEV) |
| 2.13% | 53.1% |

| BLUE LIGHT: A-0878 | |
|---|---|
| Test Conditions: | |
| Substrate: | 1 HD 6u PMMA Plate |
| Application Rate: | 1.3 mg/cm$^2$ |
| Dry Time: | 15-30 min |
| Test Results: | |
| IN-HOUSE IN-VITRO HIGH ENERGY VISIBLE LIGHT (HEV 380-530 nm) RADIATION PROTECTION POTENTIAL OF SKIN CARE/SUN CARE PRODUCT | |
| In-House In-Vitro Protection Factor (HEV-PF) | Percent Solar Spectral Irradiance Blocked (%SSI-HEV) |
| 1.99 | 49.6% |

| VISIBLE LIGHT: A-0557 ||
|---|---|
| Test Conditions: ||
| Substrate: | 1 HD 6u PMMA Plate |
| Application Rate: | 1.3 mg/cm$^2$ |
| Dry Time: | 15-30 min |
| Test Results: ||
| IN-HOUSE IN-VITRO VISIBLE LIGHT (VIS 400-700 nm) RADIATION PROTECTION POTENTIAL OF SKIN CARE/SUN CARE PRODUCT ||
| In-House In-Vitro Protection Factor (VIS-PF) | Percent Solar Spectral Irradiance Blocked (%SSI-VIS) |
| 1.69% | 40.7% |

| VISIBLE LIGHT: A-0878 ||
|---|---|
| Test Conditions: ||
| Substrate: | 1 HD 6u PMMA Plate |
| Application Rate: | 1.3 mg/cm² |
| Dry Time: | 15-30 min |
| Test Results: ||
| IN-HOUSE IN-VITRO VISIBLE LIGHT (VIS 400-700 nm) RADIATION PROTECTION POTENTIAL OF SKIN CARE/SUN CARE PRODUCT ||
| In-House In-Vitro Protection Factor (VIS-PF) | Percent Solar Spectral Irradiance Blocked (%SSI-VIS) |
| 1.54 | 34.9% |

| EVALUATION OF SUN PROTECTION BY SPF DETERMINATION (FDA) – Sample: A-0878 | | | | | | | |
|---|---|---|---|---|---|---|---|
| 40 MINUTE WATER IMMERSION | | | | | | | |
| Subject ID | Sex | MED/Hr* | Skin Type | MED I $J/m^2$ | MED II $J/m^2$ | WR Control | WR |
| 11 3764 | F | 100.0 | I | 239.1 | 239.0 | 12.0 | 57.5 |
| MEAN (x) | | | | | | 12.0 | 57.5 |
| N= | | | | | | 1 | 1 |
| 80 MINUTE WATER IMMERSION | | | | | | | |
| Subject ID | Sex | MED/Hr* | Skin Type | MED I $J/m^2$ | MED II $J/m^2$ | WR Control | WR |
| 70 9820 | M | 80.0 | I | 182.00 | 180.00 | 10.00 | 57.50 |
| 60 5135 | F | 80.0 | I | 152.00 | 152.00 | 12.00 | 50.00 |
| MEAN (x) | | | | | | 11.00 | 53.75 |
| N= | | | | | | 2 | 2 |

*MED = mean erythemal dose; MED/Hr = Solar stimulator output

FIGURE 13C

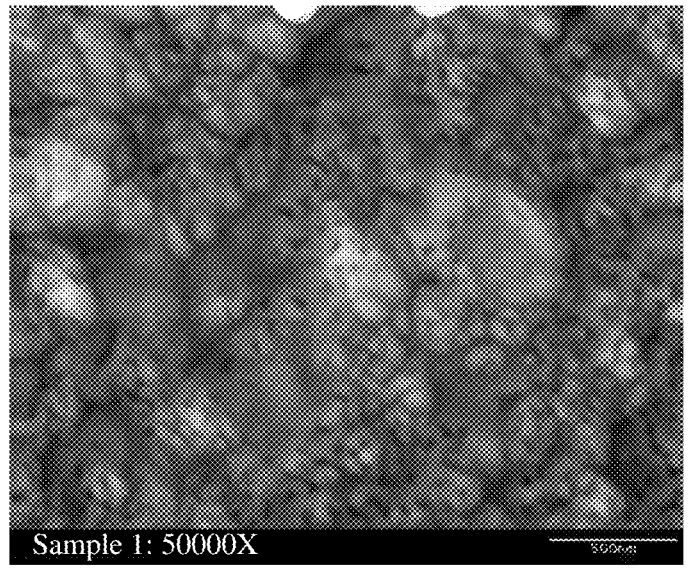

FIGURE 14

| ISO 24443 RATIO Results | | |
|---|---|---|
| LABEL SPF 36 | | |
| Ratios | A-1515 | A-1554 |
| Labeled SPF in vivo / UVA-PF: (Maximum Allowable 3.0) | 2.96 | 2.91 |
| UVA/PF / Labeled SPF in vivo: (Minimum Allowable 0.333) | 0.338 | 0.343 |
| LABEL SPF 30 | | |
| Ratios | A-1515 | A-1554 |
| Labeled SPF in vivo / UVA-PF: (Maximum Allowable 3.0) | 2.46 | 2.43 |
| UVA/PF / Labeled SPF in vivo: (Minimum Allowable 0.333) | 0.405 | 0.412 |
| CRITICAL WAVELENGTH | | |
| Critical Wavelength: (Minimum Required 370.00 nm) (ISO 20443) | 374.00 nm | 374.00 nm |
| Critical Wavelength: (Minimum Required 370.00 nm) (FDA) | 374.00 nm | 372.00 nm |
| FDA PROPOSED RULE RATIO | | |
| UV 1 / UV Ratio: (Proposed Requirement Min. 0.70) | 0.72 | 0.73 |

FIGURE 15:

| | A-1515 | A-1554 |
|---|---|---|
| IN-HOUSE IN-VITRO HIGH ENERGY VISIBLE LIGHT (HEV 380-530 nm; "Blue Light") RADIATION PROTECTION POTENTIAL OF SKIN CARE/SUN CARE PRODUCT: | | |
| In-House In-Vitro HEV Protection Factor: | 1.62 | 1.52 |
| Percent Solar Spectral Irradiance Blocked (% SSI-HEV): | 38.4% | 34.2% |
| IN-HOUSE IN-VITRO VISIBLE LIGHT (VIS 400-700 nm; "Visible Light") RADIATION PROTECTION POTENTIAL OF SKIN CARE/SUN CARE PRODUCT: | | |
| | A-1515 | A-1554 |
| In-House In-Vitro VIS Protection Factor: | 1.36 | 1.30 |
| Percent Solar Spectral Irradiance Blocked (%SSI-VIS): | 26.6% | 23.0% |

FIGURE 16

| SPF/UVA and UVA/SPF RATIOS as per ISO 24443 | | |
|---|---|---|
| RESULT | A-1515 | A1554 |
| Average In-Vitro UVA-PF: | 12.16 | 12.35 |
| Critical Wavelength: Post-Irradiation | 374.00 nm | 374.00 nm |
| Label SPF 50 | | |
| *SPF/UVA Ratios (Maximum Allowable 3.0)* | | |
| Ratio (Labeled SPF in vivo / UVA-PF) | 4.11 | 4.05 |
| *UVA/SPF Ratios (Minimum Required 0.333)* | | |
| Ratio (UVA/PF / Labeled SPF in vivo) | 0.243 | 0.247 |
| Label SPF 36 | | |
| *SPF/UVA Ratios (Maximum Allowable 3.0)* | | |
| Ratio (Labeled SPF in vivo / UVA-PF) | 2.96 | 2.91 |
| *UVA/SPF Ratios (Minimum Required 0.333)* | | |
| Ratio (UVA/PF / Labeled SPF in vivo) | 0.338 | 0.343 |
| Label SPF 30 | | |
| *SPF/UVA Ratios (Maximum Allowable 3.0)* | | |
| Ratio (Labeled SPF in vivo / UVA-PF) | 2.46 | 2.43 |
| *UVA/SPF Ratios (Minimum Required 0.333)* | | |
| Ratio (UVA/PF / Labeled SPF in vivo) | 0.405 | 0.412 |

| BLUE LIGHT: A-1515 ||
|---|---|
| Test Conditions: ||
| Substrate: | 1 HD 6u PMMA Plate |
| Application Rate: | 1.3 mg/cm$^2$ |
| Dry Time: | 15-30 min |
| Test Results: ||
| IN-HOUSE IN-VITRO HIGH ENERGY VISIBLE LIGHT (HEV 380-530 nm) RADIATION PROTECTION POTENTIAL OF SKIN CARE/SUN CARE PRODUCT ||
| In-House In-Vitro Protection Factor (HEV-PF) | Percent Solar Spectral Irradiance Blocked (%SSI-HEV) |
| 1.62 | 38.4 |

| BLUE LIGHT: A-1554 | |
|---|---|
| Test Conditions: | |
| Substrate: | 1 HD 6u PMMA Plate |
| Application Rate: | 1.3 mg/cm$^2$ |
| Dry Time: | 15-30 min |
| Test Results: | |
| IN-HOUSE IN-VITRO HIGH ENERGY VISIBLE LIGHT (HEV 380-530 nm) RADIATION PROTECTION POTENTIAL OF SKIN CARE/SUN CARE PRODUCT | |
| In-House In-Vitro Protection Factor (HEV-PF) | Percent Solar Spectral Irradiance Blocked (%SSI-HEV) |
| 1.52 | 34.2 |

| VISIBLE LIGHT: A-1515 ||
|---|---|
| Test Conditions: ||
| Substrate: | 1 HD 6u PMMA Plate |
| Application Rate: | 1.3 mg/cm$^2$ |
| Dry Time: | 15-30 min |
| Test Results: ||
| IN-HOUSE IN-VITRO VISIBLE LIGHT (VIS 400-700 nm) RADIATION PROTECTION POTENTIAL OF SKIN CARE/SUN CARE PRODUCT ||
| In-House In-Vitro Protection Factor (VIS-PF) | Percent Solar Spectral Irradiance Blocked (%SSI-VIS) |
| 1.36 | 26.6 |

| VISIBLE LIGHT: A-1554 ||
|---|---|
| Test Conditions: ||
| Substrate: | 1 HD 6u PMMA Plate |
| Application Rate: | 1.3 mg/cm$^2$ |
| Dry Time: | 15-30 min |
| Test Results: ||
| IN-HOUSE IN-VITRO VISIBLE LIGHT (VIS 400-700 nm) RADIATION PROTECTION POTENTIAL OF SKIN CARE/SUN CARE PRODUCT ||
| In-House In-Vitro Protection Factor (VIS-PF) | Percent Solar Spectral Irradiance Blocked (%SSI-VIS) |
| 1.30 | 23.0 |

FIGURE 19
| EVALUATION OF SUN PROTECTION BY SPF DETERMINATION (FDA) – Sample: A-1554 | | | | | | | | |
|---|---|---|---|---|---|---|---|---|
| 80 MINUTE WATER IMMERSION: | | | | | | | | |
| Subject ID # | Sex | MED/ Hr | Skin Type | MED I | MED II | STATIC SPF (16.3) Control | WR SPF (12.0) Control | A-1554 SPF WR |
| 94 8643 | M | 64.0 | III | 223.0 | 223.0 | 14.2 | 12.0 | 50.0 |
| | | | | | MEAN (x) | 14.2 | 12.0 | 50.0 |
| | | | | | N | 1 | 1 | 1 |
*MED: Minimal Erythemal Dose*
*MED/h: Solar Simulator Output*
FIGURE 20A
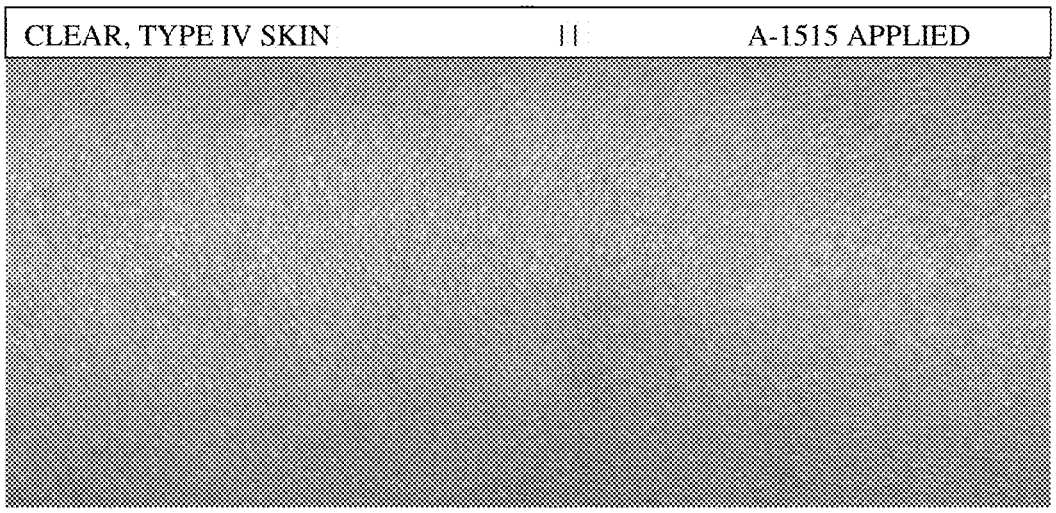
FIGURE 20B
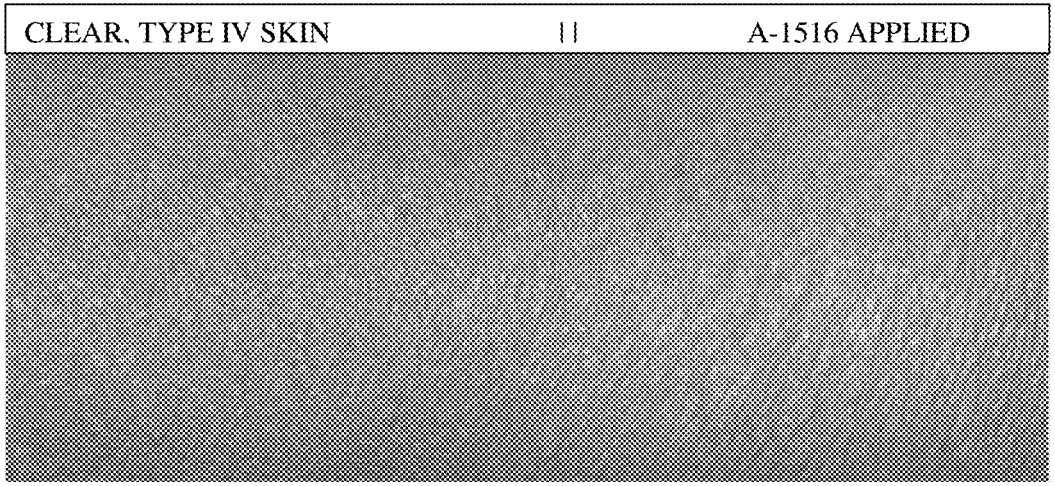

STRUCTURALLY DIVERSE, STABLE, AND RADIATION-PROTECTIVE PARTICLE MATRIX SUNSCREEN AND COSMETIC COMPOSITIONS AND RELATED METHODS

RELATED APPLICATIONS/PRIORITY

This patent Application claims priority to U.S. Provisional Patent Application No. 63/475,135 filed Oct. 15, 2022, entitled, "Structurally diverse, stable, and radiation-protective particle matrix sunscreen and cosmetic compositions and methods comprising UV protective metal oxide particles." This application claims the benefit of priority to, and incorporates by reference the entirety of, this above-referenced priority application.

FIELD OF THE INVENTION

The invention primarily relates to the formulation of cosmetically suitable mineral sunscreen composition(s) comprising a matrix of photoprotective particles, which offer advanced protection from UV radiation and provide(s) anti-aging benefit(s).

BACKGROUND OF THE INVENTION

The skin is the largest organ and the outer-most tissue of the human body. As a result, people are very aware of, and very sensitive to, the appearance of their skin. As such, skin appearance is a target indication for many scientific and technological endeavors. In fact, the global skin care market is estimated to exceed $200 billion dollars by 2026. Esteé Lauder, a leader in the development of skincare related products, spent about 307 million U.S. dollars on research and development of skincare products in 2021 alone.

Excessive sun exposure is widely known as one of the most significant risks to skin health, with solar ultraviolet (UV) radiation being well established as a leading cause of skin cancer and other skin-related disorders. Skin cancer is the most common form of cancer in the United States, with over 5.4 million cases of skin cancer requiring treatment annually. (See, e.g., Bennis, Chelsey, "Improving sunscreen compliance and awareness of skin cancer and the effects of the sun in adolescents and young adults: A quality improvement project." (2021)). Experiencing 5 sunburns between the ages of 15-20 years has been demonstrated to increase one's nonmelanoma skin cancer risk by 68% and melanoma skin cancer risk by 80%.

Unsurprisingly, the sun protection product market reportedly exceeded $15 billion dollars in 2021. As of this submission, a search of Amazon.com alone returns over 8,000 product records in response to the query "sunscreen."

These products include complex formulations, varying significantly in terms of composition and other characteristic(s), such as, e.g., sun protection factor (SPF) level, UV ray (e.g., UVA and UVB) protection, etc.

Examples of such products include: (1) SkinCeuticals® Physical Fusion UV Defense Broad Spectrum SPF 50 (NDC 49967-077), containing 6% zinc oxide (ZnO), 5% titanium dioxide (TiO$_2$), and plankton extract (*Artemia salina*) to reduce "UV- and heat-induced stress," claiming 40 minute-water resistance and comprising inactive ("non-active pharmaceutical ingredient" or "non-API") ingredients including styrene/acrylamide copolymer (notably different from styrene acrylates/copolymer), iron oxide (as ferric oxide red), polyhydroxy stearic acid, butyl octyl salicylate, and silicon dioxide; (2) Stream2Sea® Everyday Shimmer Mineral Sunscreen, SPF 45, claiming to provide broad spectrum UVA/UVB protection, a water resistance of 80 min, and a non-greasy and light weight feel while containing 19% by weight (% w/w) non-nano (larger than 100 nm) zinc oxide as the only active ingredient in the complex formulation comprising numerous inactive ingredients such as water, Aloe barbadensis leaf juice, coco-caprylate/caprate, isoamyl laurate, vegetarian glycerin, polyglyceryl-3-oleate, propanediol, polyhydroxystearic acid, di-isostearoyl polyglyceryl-3 dimer dilinoleate, mica, caprylic/capric triglyceride, sodium chloride, ethyl lauroyl arginate HCl, jojoba esters, olive squalane oil, *Alaria esculenta* (Wakame Seaweed) extract, *Olea europaea* (Olive) leaf extract, *Camellia sinensis* (Green Tea) leaf extract, *Ocimum tenuiflorum* (Tulsi) leaf extract, *Cocos nucifera* (Coconut) Oil, *Curcuma longa* (turmeric) root extract, tetrasodium glutamate diacetate, mixed tocopherols, sodium stearoyl glutamate, silica, xanthan gum, calcium sodium borosilicate, and iron oxides CI 77491; (3) Australian Gold Botanicals® Sunscreen 70 Minerals (NDC 58443-0265), claiming to be water resistant for 80 minutes and "non-whitening," and containing 4.36% TiO$_2$ and 4.95% ZnO in addition to silicon dioxide, *Porphyra umbilicalis* (red algae) extract, and disteardimonium hectorite; (4) Cerave® Sunscreen Body Lotion SPF 50 allegedly providing 80-minute water resistance and containing TiO$_2$ (4.9%), ZnO (4.7%), hydrated silica, styrene/acrylates copolymer, and polyhydroxystearic acid; (5) CVS® Health 60 Plus Sensitive Skin Sun (the National Brand Equivalent of Neutrogena® Sensitive Skin Sunscreen Lotion Broad Spectrum SPF 60), allegedly providing 80-minute water resistance while containing 4.9% TiO$_2$ and 4.7% ZnO in addition to butyl octyl (butyloctyl) salicylate, styrene/acrylates copolymer, silica, and polyhydroxystearic acid; (6) Aveeno® Positively Mineral Sensitive Skin Sunscreen Broad Spectrum SPF 50, a purportedly 80-minute water resistant sunscreen (NDC 69968-0395) containing ZnO (21.6%), silicon dioxide, cetyl dimethicone/bis-vinyl dimethicone crosspolymer, and polyhydroxystearic acid, and (7) the Sunbetter products developed by the inventor of this disclosure (e.g., Sunbetter TONE SMART SPF 75, Sunbetter SHEER SPF 70 sunscreen lotion, and Sunbetter TONE SMART SPF 68 sunscreen compact (skinbetter.com/technology-platforms/sunbetter/).

Mineral-based, effective sunscreen products comprising similarly complex formulations were described in patent applications directed to prior inventions of the present inventor, Laura C. Singleton (see U.S. Patent Publication Nos. 2019/0183754 and 2019/0290560, each assigned to Amavara, Inc., of San Diego, CA, USA, and US20230147073A1 (entitled "Mineral, Anhydrous, Broad-Spectrum Sunscreen" assigned to LCS Advanced Solutions). The inventor also has filed other patent applications, pending at the USPTO, which are directed to other metal oxide particle formulations, but which have not yet published (application Ser. Nos. 15/934,312 and 18/357,695).

There are numerous other patent disclosures relating to mineral based sunscreens and/or particle matrix compositions that can be sunscreens. Examples of such disclosures include U.S. Pat. Nos. 9,034,302, 10,383,811, US 2007/0085063, US 2012/0015013, WO 2009/126722, US 2012/0219515 A1, US 2009/0041691, US 2013/0095050, US 2009/0297461, US 2010/0310871, US 2003/0059383, US 2015/0265510, U.S. Pat. No. 5,935,556, and US 2020/0306162 A1. Additional disclosures relating to such compositions include US20220000732A1, U.S. Ser. No. 11/426, 336B2, US20150202145A1, US20170181941, U.S. Ser. No. 10/238,585B2, US20210353514A1, US20230121763A1, U.S. Pat. No. 9,744,111B2, U.S. Ser. Nos. 11/458,090B2, 10/434,048B2, 11/707,422B2, US20150283059A1, U.S. Pat. No. 9,060,942B2, US20160206527A1, US20210315781A1, U.S. Pat. No. 5,670,139, US20180235855A1, US20210052474, U.S. Ser. No. 10/959,924B2, U.S. Pat. Nos. 5,744,126A, 5,939,054, US20200390665A1, US20210244631A1, U.S. Pat. No. 9,192,547B2, US20100202985A1, US20070280895A1, US20090258068A1, US20210000704A1, US20160220457A1, US20080213200A1, US20100061947A1, US20060115439A1, US20180116925A1, US20180185254A1, US20180311117A1, U.S. Pat. Nos. 7,481,845B2, 8,642,018B2, US20150086633A1, US20230165763A1, US20230080141A1, US20220023161A1, US20130028851A1, U.S. Pat. Nos. 7,182,938B2, 6,942,878B2, 8,647,609B2, 5,817,298A, U.S. Ser. No. 10/045,918B2, US20080226727A1, U.S. Pat. No. 9,642,785B2, US20200157364A1, U.S. Pat. No. 6,309,627B1, US20050175562A1, WO2021174715A1, KR102203667B1, EP1709953A1, EP0628303B1, and EP1855642A2.

As exemplified by these numerous products and disclosures, much of the extensive research relating to the development of such a large and rapidly growing number of sunscreen products relates to the development of formulations that are both effective against risk of skin damage from UV exposure and exhibit properties making adoption and compliant use easy for consumers.

Among the challenges and concerns associated with topical sunscreens formulation(s) is/are stability, broad spectrum efficacy, effective incorporation of a sufficient amount of active ingredients, suitable and (or) pleasing cosmetic and sensory effect(s), safety and tolerability for topical use, resistance to water exposure, spread-ability, demonstration of a high extinction coefficient, avoidance of staining clothing and discoloration of skin, as well as being otherwise cosmetically elegant, the phrase, "cosmetically elegant" being a recognized term in the art used to describe product(s) characterizable as appealing in appearance, texture and scent. See, e.g., Mwangi et al. Saudi Pharm J. 2019 November; 27(7):1009-1018. doi: 10.1016/j.jsps.2019.08.003. Indeed, even leading global cosmetics company L'Oreal has reportedly described the development of stable and pleasant high sun protection factor (SPF) formulations as an ongoing, "challenge for industry," with oil-soluble components of such products leaving the skin feeling greasy or sticky after application. See Culliney (2020) online at Cosmeticsdesign-europe.com (cosmeticsdesign-europe.com/Article/2020/03/10/L-Oreal-sun-protection-patents-cover-SPF-skin-whitening-and-appearance).

For example, high SPF and UVA protection ratings are desirable; however, obtaining such properties requires, e.g., high formulation loading of physical sunscreen filters (e.g., metal oxide particles). High particle loading can result in formula instability and the agglomeration and settling of particles, resulting in a formulation that is difficult to spread, and which can leave a colored residue (e.g., a white residue in the case of zinc oxide particles) on the skin. Thus, such products often leave a white cast or exhibit other undesirable aesthetic characteristics such as, e.g., a perception of being sticky or greasy. As such, unsurprisingly, a tremendous number of approaches have been described in connection with the development of sunscreen products that address these factors. In demonstration of this fact, a search of a leading patent database for the word "sunscreen" present in the title or abstract results in the return of over 250,000 patent documents representing an overwhelming number of different approaches to the development of such products.

Despite such significant research and development effort(s), there remains, as evidenced by the large number of somewhat relevant patent documents, intensive ongoing investment in the field with the aim of developing products that satisfy most, nearly all, or all the target requirements and preferences of a successful sunscreen product, reflecting that the need for new and improved sunscreen and related cosmetic products remains, at present, unmet.

These facts clearly demonstrate that the development of new sunscreen products that can provide suitable functionality will require the application of significant inventive ingenuity.

Construction, Terms, and Acronyms

This section offers guidelines for reading this disclosure.

The intended audience for this disclosure ("readers") are persons having ordinary skill in the practice of technologies discussed or used herein. Readers may also be called "skilled persons," and such technologies and related publicly available prior knowledge are collectively referred to as "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," "respects," or "embodiments"). The invention encompasses all aspects as described individually and as can be arrived at by any combination of such individual aspects. In this respect, the breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here, should be read, at least in one aspect, to have the same meanings as commonly understood by skilled persons, regardless of any narrower examples or descriptions provided here (including any term introduced initially in quotations). However, readers will also recognize that some aspects can characterized by the inclusion of elements, steps, features, characteristics etc., associated with specific descriptions provided here, and that such specific disclosures represent distinct embodiments of the invention apart from the corresponding aspect that is provided by interpreting the invention using any broader commonly used terminology or concept. Uncontradicted, disclosure of any aspect using known terms, which terms are narrowed by example or otherwise, implicitly discloses one or more related aspects in which the applicable terms are alternatively interpreted using the broadest reasonable interpretation of skilled persons.

Uncontradicted, the term "or" means "and/or" here, regardless of any occasional inclusion of the actual phrase "and/or" (e.g., phrases such as "A, B, or C" and "A, B, and/or C" each simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, the term "also" means "also or alternatively." Uncontradicted, the terms "here" & "herein" mean "in this disclosure." The term "i.a." is an acronym standing for "inter alia" or meaning "(possibly) among other things." "Also known as" is abbreviated "aka" or "AKA." The term "elsewhere" means "elsewhere herein."

For conciseness, symbols are used where appropriate. E.g., "&" is used for "and," & "~" for "about." Symbols such as <and > are given their ordinary meaning (e.g., "≤" means "less than or equal to" & "≥" means "greater than or equal to"). A slash "/" between terms here can represent "or" ("A/B" means "A or B") or identify synonyms of an element, as will be clear from context. The inclusion of "(s)" after an element or a step indicates that ≥1 of such an element is present, step performed, and the like. E.g., "element(s)" refers to both 1 element and ≥2 elements, with the understanding that each thereof is an independent aspect of the invention.

The inclusion of "(s)" after an element or a step indicates that ≥1 of such an element is present, step performed, and the like. E.g., "element(s)" means both 1 element or ≥2 elements, with the understanding that each thereof is an independent aspect of the invention. Uncontradicted, where an element is only provided in standard plural form (e.g., "compositions" as opposed to composition(s)), the reader should interpret such disclosure as encompassing a single composition as if presented as "composition(s)". Uncontradicted, any aspect disclosed herein in with an element or step expressed in the singular provides implicit support for a corresponding embodiment in which the element(s)/step(s) are present in the plural (two or more), and vice versa.

Use of the abbreviation "etc." (or "et cetera") in association with a list of elements/steps means any or all suitable combinations of the recited elements/steps or any known equivalents of such recited elements/steps for achieving the function(s) of such elements/steps known in the art. Readers should interpret phrases like "and the like" similarly.

Uncontradicted, terms such as "and combinations," "combinations thereof," or "or combinations," and "combinations of any thereof" regarding listed elements/steps means any or all possible/suitable combinations of the associated elements/steps. Thus, e.g., uncontradicted, a phrase like "combination of any thereof" refers to any or all combinations.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all an intended function, without causing or imparting significant negative/detrimental impact.

Uncontradicted, heading(s) (e.g., "Construction, Terms . . . ") and subheadings here are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593). Uncontradicted, readers will understand that any two values in a range provided as a list herein can be combined as endpoints to form a range defining a more particular aspect of the invention (e.g., if a list of values 1, 2, 3, 4, and 5 of element X is provided, readers will understand that the disclosure implicitly discloses an aspect comprising 2-4×, 3-5×, and 1-3×, etc.

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

This disclosure includes aspects associated with particular characteristics, such as amounts of components (or ranges thereof), In cases, several such characteristics of varying scope may be provided. Readers will understand that each such characteristic can be associated with particular properties that distinguish such aspects from other aspects, and, accordingly, each such range can be viewed as critical to a particular aspect of the invention, even if the associated results, properties, functions, etc., associated with such aspects are not directly communicated in association with such characteristics.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys." "Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value provided here that is not accompanied by a unit of measurement (e.g., a weight of 50 or a length of 20), either any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps). Uncontradicted, "a" means one or more, even when terms such as "one or more" or "at least one" are used in association with the referent "a."

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure. Uncontradicted, any disclosure of an object (e.g., composition, device, or system) "comprising" or "including" element(s) provides implicit support for an alternative corresponding aspect that is characterized by the object consisting of that element or "consisting essentially of" that element (excluding anything that would "materially affect" the "basic and novel characteristic(s)" of the invention. Uncontradicted, any specific uses of phrases such as "consists" and "consisting essentially of" herein does not undermine this principle of construction.

Readers will understand "basic and novel characteristic(s)" of the invention and the scope of what constitutes a "material effect" of such "basic and novel characteristics" will vary with the specific applicable aspect. In aspects, the basic and novel characteristics include one or more intended functions and levels of performance. In one aspect, the basic and novel characteristics include suitability, effectiveness, or both. The basic and novel characteristics also include, of course, the specific recited elements. In an aspect, a material effect is an effect that reduces, diminishes, eliminates, counteracts, cancels, prevents, one or more of such functions in one or more respects (e.g., delaying onset, reducing scope, reducing duration, reduced output, reducing level of applicability, reducing effect, or combinations thereof). In an aspect, a material effect is one that changes such functions by making such functions impractical, difficult to obtain, or materially more expensive or otherwise costly in terms of inputs. From this and the other guidance provided herein, readers can understand the scope of an aspect that is defined by consisting essentially of a collection of elements. E.g., a composition that consists essentially of elements A and B, which are helpful towards human health, would exclude element C, which is known to reduce the efficacy of A, and also exclude element D, which is known to be toxic.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition/article or system can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a type of component of a composition/system/article).

Uncontradicted, the term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). Terms such as "predominately," "most," or "mostly," (and "primarily" when not used to refer to an order of events or "mainly") means detectably >50% (e.g., mostly comprises, predominately includes, etc., mean >50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" uncontradicted means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤25~% of an element and, uncontradicted, terms such as "substantially free" of an element mean comprising ≤~5% of an element.

In certain embodiments describing API(s), excipient(s), or both present in amounts of "at least" or "greater than" a given amount or, e.g., present in amounts of "no more than" or "no greater than" or "less than" a given amount, the reader should interpret such disclosure as disclosing, e.g., encompassing and explicitly including, such undefined low or high amount(s) ranging to the opposite amount (high or low) that is maximally/minimally therapeutically effective, typically suitable, or both. For example, use of the phrase "at least" (and similar descriptors) in connection with an amount of a component of a formulation or of an entire formulation/composition can be interpreted as at least the amount described but that is no more than a maximally suitable or therapeutically effective amount (in the individual or in a population, such as determined in a clinical study). Similarly, phrases such as "less than" (and similar descriptors) an indicated amount can be interpreted referring to an amount that is still suitable (including, where appropriate, no amount, e.g., 0 units of the indicated component) or therapeutically effective (e.g., an amount that results in a DOS result in a significant number of individuals in a well-controlled and adequate study) but is less than the indicated amount.

Constituents herein are typically present in "effective amounts," and uncontradicted, any described class/type of, e.g., excipient (often referred to as a "component" herein—e.g., a "suspension component" may include one or more suspension agent(s)/constituent(s), wherein each suspension agent may be referred to as a constituent of the suspension component, a constituent of the composition(s)/formulation(s) or both) or specific excipient, or, e.g., in certain aspects active pharmaceutical ingredient(s) (API(s)) is understood to be present in the associated composition/formulation in an effective amount, which generally means, in this context, an amount that is effective for the described function(s) associated with the excipient/API (it being understood that some excipient or API compound(s)/ingredient(s) exhibit more than one effect). E.g., a suspension agent will be understood to be present in a composition/formulation in an amount that is effective to impart an indicated suspension effect, a suspension effect that is required for suitability of the composition, or an effect that imparts a detectable or significant suspension-maintaining effect alone or in combination with other suspension component constituent(s) on a composition (with respect to a comparator composition lacking the compound(s)/ingredient(s)).

The phrase "substantially identical" may be used in certain contexts to reflect that tests that would be considered substantially identical by those of skill in the art (not differing meaningfully in terms of outcome) or that component(s) or step(s) can achieve the same result in a similar way as a referenced set of component(s)/step(s) so as to not meaningfully differ in intended result and manner of achieving such a result. It will be appreciated that the phrase "substantially identical" in such contexts comprises the use of identical amounts, identical formulations, and identical conditions, or, e.g., in other respects, composition(s) demonstrate an identical performance as a comparator.

Except where explicitly indicated or clearly indicated by context, "improved" herein means "increased." In aspects, "improved" means "reduced," such as with respect to the toxicity of a composition. Uncontradicted, terms such as "enhanced," "improved," and the like are used synonymously.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X. Uncontradicted, readers should interpret terms such as "essentially all" or "essentially" consistent with the concept of "consisting essentially of."

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments in at least the broadest version of the relevant aspect. Uncontradicted, the use of ordinal numbers such as "first," "second," "third," and so on is to distinguish respective elements rather than to denote a particular order of those elements, importance, or configuration.

Uncontradicted, any elements, steps, components, or features of aspects and all variations thereof, etc., are within the scope of the invention and broadest version of any aspect.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated using the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

Readers will understand that any element, feature, step, or characteristic of any aspect of the invention recited herein as being present in an aspect also implicitly provides support for the element, feature, step, or characteristic as being excluded from a corresponding/similar aspect of the invention implicitly disclosed by the explicit positive disclosure.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

Uncontradicted, terms such as "UV-protective" or "UV protectant" means exhibiting a DOS protective effect or effect(s) against UV radiation. Readers will recognize that not all UV-protective compounds or compositions are "active." Active particles/ingredients (APIs) are limited to suitable forms of zinc oxide and titanium dioxide particles. However, other materials, such as SPF boosters, other pigments, etc., can be UV-protective. Moreover, readers will understand that, uncontradicted, any characterization of an element as, e.g., UV-protective also provides implicit support for aspects where the particle is characterized by or is used in connection with other protective functions disclosed herein or known to be associated with the element (e.g., protection against visible light radiation, blue light radiation, etc.).

All original claims contained in this disclosure when filed are incorporated into this specification as if they were a part of the description.

Uncontradicted, the following summary and detailed description portions of this disclosure are exemplary in nature and is not intended to limit application and uses. Any embodiment described herein as "exemplary" is not necessarily to be construed as possible or advantageous over other embodiments.

SUMMARY OF THE INVENTION

The invention(s) provided herein comprise formulation(s) of cosmetically/dermatologically suitable mineral sunscreen composition(s) comprising a matrix of photoprotective particle populations of various types, size, shape, composition, or other characteristic(s), present in particular amount(s) relative to one another, which in aspects when provided together offer advanced protection from UV radiation. Such inventive compositions can be characterized by different groupings of particles (e.g., by size classes, by shape classes, by compositional class, or through a combination of any or all thereof). Alternatively, such compositions can be characterized by the components of the matrix formulations. Still, in other aspects, compositions of the invention are characterized by combinations or relationships between formulation/matrix elements and particle elements.

In a first exemplary aspect, the invention provides a matrix composition comprising a mixture of structurally diverse matrix particles (1) that are formed from at least three, four, or five different types of primary particles that are distinguishable from one another due to different characteristics, shape characteristics, or both, (2) that constitute 15-50% of the matrix composition by weight, (3) that comprise or more types of matrix particle agglomerates, (4) where at least 33% of the weight concentration of the matrix particle mixture being composed of UV-protectant metal oxide particles having a minimum primary, matrix, or both primary and matrix particle size of over 100 nm, (5) where scanning electron microscope ("SEM") analysis of the composition fails to identify any significant or substantial number of discrete matrix particles of having a size of 100 nm or less (e.g., any analyzed area or population of particles contains less than 1%, less than 0.5%, or less than 0.1% particles, if any, that have a size of under 100 nm (where a population of particles comprises >50, >100, >200, >500, >1000, >2000, or even more detected/visible particles), and (6) where the particle mixture comprises particles that can be classified according to at least three or at least four of the following (a) a first primary particle population having a maximum particle size of 250 nm and making up less than 2% of the composition by weight, (b) a second primary particle population having an average particle size of greater than 250 nm and less than 500 nm and making up 5-15% of the composition by weight, at least 25% of the second particle population being composed of UV-protective particles that are at least mostly composed of styrene acrylate copolymer, (c) a third primary particle population having an average particle size of greater than 500 nm and less than 750 nm and making up 5-15% of the composition by weight, at least 75% of the third particle population being composed of UV protective metal oxide particles, (d) a fourth primary particle population having an average particle size of greater than 750 nm and less than 1000 nm and making up 1.75-7% of the composition by weight, at least 75% of the fourth particle population being composed of UV protective metal oxide particles, (e) a fifth primary particle population having an average particle size of greater than 1000 nm and less than 8500 nm and making up 4-9% of the composition by weight, 20-70% of the fifth particle population comprising a glass composition, and (f) a sixth primary particle population having an average particle size of 8500 nm or more and comprising less than 3.5% of the composition by weight, at least 50% of the sixth particle composition being composed of silica particles, wherein (7) the composition exhibits at least one if not all of a sun protection factor (SPF) of at least 30, a critical wavelength of at least 370 nm, UVA/UVB ratio of at least 0.333, and a UVA1 to UV ratio of at least 0.7.

In an aspect, the invention provides a matrix composition that also or alternatively comprise structurally diverse matrix particles of the matrix composition are (1) distributed among five shape-defined particle populations comprising (a) spherical solid porous particles (SSPPs), (b) spherical solid nonporous particles (SSNPs), (c) irregular porous aggregate particles (IPAPs), (d) spherical hollow particles (SHPs), and (e) platelet particles (PPs) and (2) optionally the weight concentration distribution of the particles among the five shape-defined particle populations comprise at least 3, 4, or all 5 of (a) 0.5-2.5 of the composition being made up of SSPPs; (b) 0.75-10%, of the composition being made up of SSNPs; (c) 12-24% of the composition being made up of IPAPs; (d) about 3-7% SHPs; and (e) 0.5-3.5% of the composition being made up of PPs. In aspects, most of the particles are metal oxide particles. In aspects, most or generally all of the metal oxide particles are zinc oxide particles. In aspects, most or generally all of the zinc oxide (ZnO) particles are irregular, porous particles (e.g., mesoporous particles formed from aggregates of smaller zinc particles as described herein).

In another aspect, the invention provides a matrix composition that also or alternative is characterized by the matrix composition, when spread across a surface using manual distribution comprises multiple layers of the matrix particles, wherein (1) the particles in a first layer cover at least about 65% of the surface and (2) the particles in at least one other layer comprise particles in gaps in the first layer such that the first layer and second layer cover at least about 75% of the surface (e.g., >80%, >85%, or even >90% of the surface). The surface can be an area that can contain, e.g., a distribution of >100, >200, >500, >1000, >2000, >5000 or more visible/detectable particles.

Matrix compositions of the invention also or alternatively can be characterized by unique and surprising/inventive combinations of ingredients that are key elements of new compositions exhibiting remarkable characteristics. Using exemplary formulations provided herein, for example, readers can construct aspects defining classes of matrix defined by the ratios of 2, 3, 4, or more of the functional classes of ingredients in such formulations (e.g., having+/−20%, =/−15%, +/−10%, +/−5%, or +/−2.5% of any one or more of such defining elements). One such aspect is matrix formulations characterized by, i.a., (1) the ratio of film forming component composition to active metal oxide particles of the composition (which can be, e.g., 1:15 to 1:50, e.g., 1:17 to 1:35 or 1:16 to 1:40 or 1:20 to 1:30) (e.g., where the composition comprises 0.5-1.5%, 0.7-1.25%, or about 1% of a film forming component), (2) the ratio of zinc oxide particles to either titanium dioxide particles, iron oxide particles, or both, (3) the ratio of calcium borosilicate particles to metal oxide particles, active metal oxide particles (API metal oxide particles), or zinc oxide particles, (4) the ratio of styrene acrylate copolymer particles to metal oxide particles, API particles, or ZnO particles, (5) the ratio of calcium borosilicate particles to styrene acrylate copolymer particles, (6) the ratio of clay (e.g., hectorite) to calcium borosilicate particles, (6) the ratio of clay to styrene acrylate copolymer particles, (7) the ratio of clay to metal oxide particles, API particles, or ZnO particles, (8) the ratio of clay to film forming component/element, and combinations of any thereof (e.g., one such combination is the ratio of clay to film forming component to calcium borosilicate particles to metal oxide particles or ZnO particles). Similar ratios can also or alternatively characterize formulations of a specific form type. E.g., in aspects an emulsion composition can be characterized by the ratio of co-emulsifier to emulsifier (e.g., polyglyceryl-2 emulsifier, or specific example thereof provided herein) to metal oxide particles, API particles or ZnO particles. A similar characterizing ratio can relate to the amount of one or more types of emollient (e.g., monohydric alkyl ester or silicone or both) to metal oxide particles (or API particles or ZnO particles). Alternatively, the ratio of structurer waxes in an anhydrous formulation to metal oxide particles (or, e.g., only ZnO particles) can be used to characterize those types of compositions.

Matrix compositions of the invention can also or alternatively be characterized by the methods of production, such as those exemplified or described herein or that are substantially or generally the same thereto (in terms of defining parameters—e.g., time, temperature, etc.), e.g., the use of multiple homogenization steps applied to the exemplary phases used herein that have been found to contribute to the construction of a stable matrix having advantageous properties described herein (e.g., exhibiting a critical wavelength characteristic of at least 370, at least 372, at least 374, at least 375, at least 376, at least 378, at least 380 or more; exhibiting a UVA1/UV ratio of at least 0.7; exhibiting no visually detectable whitening effect on Fitzpatrick skin types I-IV, I-V, or even I-VI; or a combination thereof) despite including a high concentration of particulates, particularly as compared to prior art compositions (e.g., comprising 15-50%, 17.5-45%, 19-43%, etc. of particulates, including 90%, 95%, 97.5%, etc., of primary particles having an average particle size of over 250 nm, including at least 2.5%, at least 5%, at least 7.5%, etc., of particles having an average particle size in excess of 850 nm, e.g., in excess of 1 micron). Matrix compositions also or alternatively can be characterized based on other properties such as being judged in a relevant study of typical product users or product evaluation experts, or both, to be less tacky than one, some, most, generally all, or all of the prior art products described herein (e.g., in the Background of this application) or leading mineral sunscreen products on the market as of this disclosure to be less tacky, to have a lighter feel, to spread better, to be less whitening, to have a more attractive appearance or to perform a combination of any or all thereof. Matrix compositions also can be characterized by, e.g., stability characteristics, viscosity characteristics, and coverage characteristics provided herein.

In another exemplary aspect, the invention provides a dermatologically suitable sunscreen composition (e.g., an emulsion such as an O/W emulsion or an anhydrous composition) comprising a particle mixture that makes up 20-50% of the composition by weight, at least 40% of the weight concentration of the overall particle mixture (at least 8-20% of overall the composition) being composed of metal oxide particles, the particle mixture comprising particles from (1) a first primary particle population having a maximum particle size of 250 nm or less and comprising less than 3.5% of the composition by weight, less than 5% of the first particular population being composed of metal oxide particles, (2) a second primary particle population having an average particle size of greater than 250 nm and less than 500 nm and making up 5-15% of the composition by weight, at least 25% of the second particle population being composed of UV protective particles that are at least mostly composed of styrene acrylate copolymer, (3) a third primary particle population having an average particle size of greater than 500 nm and less than 750 nm and making up 5-15% of the composition by weight, at least 75% of the third particle population being composed of UV protective metal oxide particles, (4) a fourth primary particle population having an average particle size of greater than 750 nm and less than 1000 nm and making up 1.75-7% of the composition by weight, at least 75% of the fourth particle population being composed of UV protective metal oxide particles, (5) a fifth primary particle population having an average particle size of greater than 1000 nm and less than 8500 nm and making up 4-9% of the composition by weight, 20-70% of the fifth particle population particles comprising a glass composition, and (6) a sixth primary particle population having an average particle size of 8500 nm or more and comprising less than 3.5% of the composition by weight, at least 50% of the sixth particle composition being composed of silica particles, wherein at least most of the particles in the particle mixture form agglomerates in the water-in-oil emulsion that have an average size of 1 micron or greater and the composition exhibits a sun protection factor (SPF) of at least 20 and a UVA I to UV (UVA1/UV) ratio of at least 0.7.

In another aspect, the invention provides a dermatologically suitable composition comprising a combination of (1) a "microscale" particle component comprising an effective amount of dermatologically suitable microscale particles having particle sizes (i.e., maximal single-direction particle sizes) of about 100-about 1,000 nm, in aspects wherein at least about 50% (or at least about 60% or at least about 65% by weight) of the microscale particle component is composed of ultraviolet (UV) light scattering particles; (2) a "mesoscale" particle component that comprises an effective amount of dermatologically suitable particles having particle sizes of about 1000-about 10,000 nm, in aspects wherein at least about 50% (or at least about 60%, about 70%, about 80%, or about 90%) of the mesoscale particle component is composed of particles made of a material that causes the mesoscale particle component to significantly enhance (i.e., statistically significantly improve) the light scattering capability of the composition; and (3) a macroscale particle component comprising an effective amount of dermatologically suitable particles having particle sizes (i.e., maximal singe-direction particle sizes; maximum particle size in any one direction) of about 10,000-about 15,000 nm, in aspects wherein at least about 50% of the macroscale particle component is composed of particles that are made of a material that (a) causes the macroscale particle component to significantly enhance the light scattering capability of the composition, (b) significantly reflects or absorbs blue light (light with wavelengths in the range of 380-495 nm, such as 380-450 nm, e.g., 400-450 nm, 450-495 nm, or 425-475 nm), or (c) performs both (a) and (b). In further aspects, (I) the ratio of mesoscale particles to microscale particles in the composition is about 1:5 to 1:65 (e.g., about 1:10 to about 1:40), (II) the ratio of macroscale particles to microscale particles in the composition is about 1:5 to 1:65 (e.g., about 1:10 to about 1:40), or (III) the ratio of mesoscale particles to microscale particles in the composition is about 1:5 to 1:65 (e.g., about 1:10 to about 1:40) and the ratio of macroscale particles to microscale particles in the composition is about 1:5 to 1:65 (e.g., about 1:10 to about 1:40).

Readers will understand that throughout this disclosure wherever terms like absorption, reflection/refraction, scattering, etc., with respect to radiation that any or all of such terms/phrases implicitly provides support for the terms or phrase to detectably or significantly block, reflect, refract, or otherwise attenuate the applicable radiation (e.g., UV radiation, IR radiation, visible radiation, or HEV/blue light radiation).

In aspects, the invention provides a dermatologically suitable composition comprising an effective combination of particles comprising a plurality of particle types comprising at least three distinct shape types and comprising microscale, mesoscale, and macroscale particle sizes, the particles comprising an effective amount of UV scattering metal oxide particles, the difference in size between at least some of the microscale particles and macroscale particles being at least about 10× (that is, about ten times larger), the particles being subjected to multiple rounds of prolonged homogenization to form the composition, wherein the composition when applied to skin of a typical subject forms a stable matrix wherein changes in the light scattering properties of the composition across a selected area of skin, changes in the distribution of particles in the matrix in a selected area of skin, or both, are significantly reduced as compared to a composition lacking the mixture of particle sizes and shapes, a composition not subjected to the same homogenization conditions, or both. Stated alternatively, in aspects, composition(s) herein, when applied to the skin of a typical subject form a stable matrix wherein one or more light scattering property(ies), distribution of particles, or both is at least generally, at least substantially, at least essentially, is essentially, or is uniform across two or more selected areas of skin to which composition is applied, In aspects, a selected area of skin is an area of skin of at least about 5 cm$^2$, such as ≥~4 cm$^2$, ≥~3 cm$^2$, ≥~2 cm$^2$, ≥~1 cm$^2$, ≥~10 mm$^2$, ≥~9 mm$^2$, ≥~8 mm$^2$, ≥~7 mm$^2$, ≥~6 mm$^2$, ≥~5 mm$^2$, ≥~4 mm$^2$, ≥~3 mm$^2$, ≥~2 mm$^2$, or, in aspects, an area of skin ≥~1 mm$^2$. In aspects, such uniformity of particulate distribution within or forming the stable matrix of composition(s) provided herein is detectably or significantly more uniform than that provided by composition(s) comprising at least generally the same, at least substantially the same, at least essentially the same, essentially the same or the same populations of particles but which is not manufactured according to the same one or more method of manufacture step(s) provided here, e.g., one or more homogenization step(s) or characteristic(s) thereof such as speed, time, temperature, etc.

BRIEF DESCRIPTION OF FIGURES

FIG. 1 provides a first set of data, illustrating ISO 24443 RATIO results for two exemplary formulations.

FIG. 2 provides results from in-house in-vitro high energy visible light radiation protection potential testing, and in-house in-vitro visible light radiation protection potential for two exemplary formulations.

FIG. 13C provides a high magnification black and white microscopy photograph of zinc oxide particles as they exist in an exemplary formulation.

FIG. 14 provides results for ISO 24443 RATIO testing of two exemplary compositions, including critical wavelength.

FIG. 15 provides the results of in-house in-vitro high energy visible light radiation protection potential of two exemplary compositions.

FIG. 16 provides results of SPF/UVA and UVA/SPF RATIO testing as per ISO 24443 for two exemplary compositions.

FIG. 19 provides results for 80-minute water resistance testing of an exemplary composition.

FIGS. 20A and 20B provide photographic results of a skin whitening test performed using two exemplary compositions on Fitzpatrick Type IV skin.

EXEMPLARY ASPECTS OF THE INVENTION

Figure 3A:
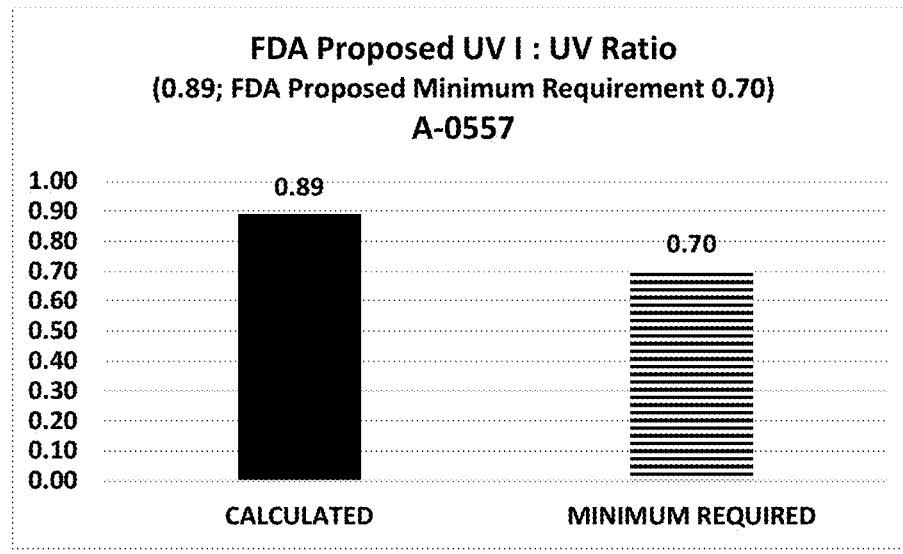
FIGS. 3A and 3B provide UVA I/UV Ratio results for two exemplary formulations.

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may make reference to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2).

Lists of aspects describing specific exemplary embodiments of the invention are sometimes employed to aid the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in combination with one another as unique embodiment(s) of the invention, according to the presentation provided of such aspects unless such an aspect within such a referenced range is either contradictory or non-sensical. If contradicted, reference to the contradictory aspect should be excluded.

In aspects, the invention provides a composition that is suitable for topical application comprising a matrix composition comprising a mixture of structurally diverse matrix particles (1) that are formed from at least 3, 4, or 5 different types of primary particles that are distinguishable from one another due to different characteristics, shape characteristics, or both (wherein a particle can be in 2 or more populations based on its different characteristics), (2) that constitute 15-50% of the matrix composition by weight, (3) that comprise or more types of particle assemblies (e.g., one or more types of particle agglomerates), (4) where at least 20%, at least 25%, at least 33%, or at least 40%, or even at least 50% of the weight concentration of the matrix particle mixture being composed of UV-protectant metal oxide particles having a minimum particle size of over 100 nm (e.g., over 125, over 150, over 175, or over 150 nm), (5) where scanning electron microscope analysis of the composition fails to identify any significant number of discrete matrix particles of having a size of 100 nm or less (e.g., fails to identify more than 5%, more than 3%, more than 1%, more than 0.5%, more than 0.1%, or more than 0.01% in an analyzed part of the matrix comprising ≥50, ≥100, ≥200, ≥500, ≥1000, ≥2000, ≥5000, or ≥10000 seen/determined particles), and (6) where the particle mixture comprises particles that can be classified according to at least four of the following (a) a first primary particle population having a maximum particle size of 250 nm and making up less than 5%, less than 3%, or less than 2% of the composition by weight, (b) a second primary particle population having an average particle size of greater than 250 nm and less than 500 nm and making up 5-15% of the composition by weight (optionally wherein at least 25% of the second particle population being composed of UV-protective particles that are at least mostly composed of styrene acrylate copolymer), (c) a third primary particle population having an average particle size of greater than 500 nm and less than 750 nm and making up 5-15% of the composition by weight (optionally wherein at least 75% of the third particle population being composed of UV protective metal oxide particles), (d) a fourth primary particle population having an average particle size of greater than 750 nm and less than 1000 nm and making up 1.75-7% of the composition by weight (optionally wherein at least 75% of the fourth particle population being composed of UV protective metal oxide particles), (e) a fifth primary particle population having an average particle size of greater than 1000 nm and less than 8500 nm and making up 4-9% of the composition by weight (optionally wherein 20-70% of the fifth particle population comprising a glass composition, such as calcium borosilicate "glass" particles), and (f) a sixth primary particle population having an average particle size of 8500 nm or more and comprising less than 3.5% of the composition by weight (optionally where at least 50% of the sixth particle composition being composed of silica particles), wherein (7) the composition exhibits at least one if not all of (a) a sun protection factor (SPF) of at least 30, (b) a critical wavelength of at least 370 nm, (c) a UVA/UVB ratio of at least 0.333, and (d) a UVA1 to UV ratio of at least 0.7. ASPECT 1.

In aspects, the invention provides a composition comprising, mostly comprising, generally consisting of, substantially consisting of, consisting essentially of, or consisting of, a matrix composition comprising, mostly comprising, generally consisting of/comprising, substantially consisting of, consisting essentially of, or consisting of a mixture of structurally diverse matrix particles (1) that are formed from at least 4 or 5 different types of primary particles that are distinguishable from one another due to different characteristics, shape characteristics, or both, (2) that constitute 15-50% of the matrix composition by weight, (3) that comprise or more types of particle agglomerates, (4) where at least 33% of the weight concentration of the matrix particle mixture being composed of UV-protectant metal oxide particles having a minimum particle size of over 100 nm, (5) where scanning electron microscope analysis of the composition fails to identify any significant number of discrete matrix particles of having a size of 100 nm or less, and (6) where the particle mixture comprises particles that can be classified according to at least four of the following (a) a first primary particle population having a maximum particle size of 250 nm and making up less than 2% of the composition by weight, (b) a second primary particle population having an average particle size of greater than 250 nm and less than 500 nm and making up 5-15% of the composition by weight, at least 25% of the second particle population being composed of UV-protective particles that are at least mostly composed of styrene acrylate copolymer, (c) a third primary particle population having an average particle size of greater than 500 nm and less than 750 nm and making up 5-15% of the composition by weight, at least 75% of the third particle population being composed of UV protective metal oxide particles, (d) a fourth primary particle population having an average particle size of greater than 750 nm and less than 1000 nm and making up 1.75-7% of the composition by weight, at least 75% of the fourth particle population being composed of UV protective metal oxide particles, (e) a fifth primary particle population having an average particle size of greater than 1000 nm and less than 8500 nm and making up 4-9% of the composition by weight, 20-70% of the fifth particle population comprising a glass composition, and (f) a sixth primary particle population having an average particle size of 8500 nm or more and comprising less than 3.5% of the composition by weight, at least 50% of the sixth particle composition being composed of silica particles, wherein (7) the composition exhibits at least one if not all of a sun protection factor (SPF) of at least 30, a critical wavelength of at least 370 nm, UVA/UVB ratio of at least 0.333, and a UVA1 to UV ratio of at least 0.7. ASPECT 2.

In aspects, the invention provides a cosmetically/dermatologically suitable composition comprising a matrix composition comprising a mixture of structurally diverse matrix particles (1) that are formed from at least five different types of primary particles that are distinguishable from one another due to different characteristics, shape characteristics, or both, (2) that constitute 15-50% of the matrix composition by weight, (3) that comprise or more types of particle agglomerates, (4) where at least 33% of the weight concentration of the matrix particle mixture being composed of UV-protectant metal oxide particles having a minimum particle size of over 100 nm, (5) where scanning electron microscope analysis of the composition fails to identify any significant number of discrete matrix particles of having a size of 100 nm or less, and (6) where the particle mixture comprises particles that can be classified as (a) a first primary particle population having a maximum particle size of 250 nm and making up less than 2% of the composition by weight, (b) a second primary particle population having an average particle size of greater than 250 nm and less than 500 nm and making up 5-15% of the composition by weight, at least 25% of the second particle population being composed of UV-protective particles that are at least mostly composed of styrene acrylate copolymer, (c) a third primary particle population having an average particle size of greater than 500 nm and less than 750 nm and making up 5-15% of the composition by weight, at least 75% of the third particle population being composed of UV protective metal oxide particles, (d) a fourth primary particle population having an average particle size of greater than 750 nm and less than 1000 nm and making up 1.75-7% of the composition by weight, at least 75% of the fourth particle population being composed of UV protective metal oxide particles, (e) a fifth primary particle population having an average particle size of greater than 1000 nm and less than 8500 nm and making up 4-9% of the composition by weight, 20-70% of the fifth particle population comprising a glass composition, and (f) a sixth primary particle population having an average particle size of 8500 nm or more and comprising less than 3.5% of the composition by weight, at least 50% of the sixth particle composition being composed of silica particles, wherein (7) the composition exhibits a sun protection factor (SPF) of at least 30, UVA/UVB ratio of at least 0.333, and a UVA1 to UV ratio of at least 0.7. ASPECT 3.

In aspects, the invention provides a sunscreen comprising a matrix composition comprising a mixture of structurally diverse matrix particles (1) that are formed from at least five different types of primary particles that are distinguishable from one another due to different characteristics, shape characteristics, or both, (2) that constitute 15-50% of the matrix composition by weight, (3) that comprise or more types of particle agglomerates, (4) where at least 33% of the weight concentration of the matrix particle mixture being composed of UV-protectant metal oxide particles having a minimum particle size of over 100 nm, (5) where scanning electron microscope analysis of the composition fails to identify any significant number of discrete matrix particles of having a size of 100 nm or less, and (6) where the particle mixture comprises particles that can be classified as (a) a first primary particle population having a maximum particle size of 250 nm and making up less than 2% of the composition by weight, (b) a second primary particle population having an average particle size of greater than 250 nm and less than 500 nm and making up 5-15% of the composition by weight, at least 25% of the second particle population being composed of UV-protective particles that are at least mostly composed of styrene acrylate copolymer, (c) a third primary particle population having an average particle size of greater than 500 nm and less than 750 nm and making up 5-15% of the composition by weight, at least 75% of the third particle population being composed of UV protective metal oxide particles, (d) a fourth primary particle population having an average particle size of greater than 750 nm and less than 1000 nm and making up 1.75-7% of the composition by weight, at least 75% of the fourth particle population being composed of UV protective metal oxide particles, (e) a fifth primary particle population having an average particle size of greater than 1000 nm and less than 8500 nm and making up 4-9% of the composition by weight, 20-70% of the fifth particle population comprising a glass composition, and (f) a sixth primary particle population having an average particle size of 8500 nm or more and comprising less than 3.5% of the composition by weight, at least 50% of the sixth particle composition being composed of silica particles, wherein (7) the composition exhibits a sun protection factor (SPF) of at least 30, UVA/UVB ratio of at least 0.333, and a UVA1 to UV ratio of at least 0.7. ASPECT 4.

In aspects, the invention provides a composition suitable for topical application to the skin (e.g., as a sunscreen) comprising a particle mixture that makes up 20-50% of the composition by weight, at least 40% of the weight concentration of the overall particle mixture being composed of metal oxide particles, the particle mixture comprising particles from (1) a first primary particle population having a maximum particle size of 250 nm or less and comprising less than 3.5% of the composition by weight, less than 5% of the first particular population being composed of metal oxide particles, (2) a second primary particle population having an average particle size of greater than 250 nm and less than 500 nm and making up 5-15% of the composition by weight, at least 25% of the second particle population being composed of UV protective particles that are at least mostly composed of styrene acrylate copolymer, (3) a third primary particle population having an average particle size of greater than 500 nm and less than 750 nm and making up 5-15% of the composition by weight, at least 75% of the third particle population being composed of UV protective metal oxide particles, (4) a fourth primary particle population having an average particle size of greater than 750 nm and less than 1000 nm and making up 1.75-7% of the composition by weight, at least 75% of the fourth particle population being composed of UV protective metal oxide particles, (5) a fifth primary particle population having an average particle size of greater than 1000 nm and less than 8500 nm and making up 4-9% of the composition by weight, 20-70% of the fifth particle population particles comprising a glass composition, and (6) a sixth primary particle population having an average particle size of 8500 nm or more and comprising less than 3.5% of the composition by weight, at least 50% of the sixth particle composition being composed of silica particles, wherein at least most of the particles in the particle mixture form agglomerates in the water-in-oil emulsion that have an average size of 1 micron or greater and the composition exhibits a sun protection factor (SPF) of at least 20 and a UVA I to UV ratio of at least 0.7. ASPECT 5.

In aspects, the invention provides a composition that is suitable for topical application comprising a matrix composition comprising a mixture of structurally diverse matrix particles (1) that are formed from at least 3, 4, or 5 different types of primary particles that are distinguishable from one another due to different characteristics, shape characteristics, or both (wherein, in this or, uncontradicted, any other aspect, a particle can be in 2 or more populations based on its different characteristics), (2) that constitute 15-50% of the matrix composition by weight, and (3) where the particle mixture comprises particles that can be classified according to at least four of the following shape-defined particle populations comprising (a) spherical solid porous particles (SSPPs), (b) spherical solid nonporous particles (SSNPs), (c) irregular porous aggregate particles (IPAPs), (d) spherical hollow particles (SHPs), and (e) platelet particles (PPs). ASPECT 6.

In aspects, the invention provides the composition of aspect 6, wherein the weight concentration distribution of the particles among the five shape-defined particle populations is, as applicable (depending on the types of populations present) (a) 0.5-2.5 of the composition being made up of SSPPs; (b) 0.75-10%, of the composition being made up of SSNPs; (c) 12-24% of the composition being made up of IPAPs; (d) about 3-7% SHPs; and (e) 0.5-3.5% of the composition being made up of PPs. ASPECT 7.

In aspects, the invention provides the composition of aspect 7, wherein the structurally diverse matrix particles of the matrix composition are (1) distributed among five shape-defined particle populations comprising (a) spherical solid porous particles (SSPPs), (b) spherical solid nonporous particles (SSNPs), (c) irregular porous aggregate particles (IPAPs), (d) spherical hollow particles (SHPs), and (e) platelet particles (PPs) and (2) the weight concentration distribution of the particles among the five shape-defined particle populations is (a) 0.5-2.5 of the composition being made up of SSPPs; (b) 0.75-10%, of the composition being made up of SSNPs; (c) 12-24% of the composition being made up of IPAPs; (d) about 3-7% SHPs; and (e) 0.5-3.5% of the composition being made up of PPs. ASPECT 8.

In aspects, the invention provides a composition that is suitable for topical application comprising a matrix composition comprising a mixture of structurally diverse matrix particles (1) that are formed from at least 3, 4, or 5 different types of primary particles that are distinguishable from one another due to different characteristics, shape characteristics, or both, at least 20% of the primary particles being UV-protective particles (and at least most of the UV-protective particles being composed of irregular aggregate zinc oxide particles), and the matrix particles accounting for a least about 20% of the weight of the composition, wherein (2) the matrix composition when spread across a surface using manual distribution comprises multiple layers of the matrix particles, wherein (1) the particles in a first layer cover at least about 65% of the surface and (2) the particles in at least one other layer comprise particles in gaps in the first layer such that the first layer and second layer cover at least about 75% of the surface, and wherein the surface comprises at least 50, at least 100, at least 200, at least 500, at least 1000, at least 2000, at least 5000, or at least 10000 visible/detectable particles, and (3) the composition provides an SPF of at least 30 (e.g., at least 40, at least 45, or at least 50) and a UVA I to UV ratio (UVA1/UV ratio) of at least 0.7. ASPECT 9.

In aspects, the invention provides the composition of any one or more of aspects 1-9, wherein at least 50% of the particles of the first primary particle population comprise hectorite clay particles. ASPECT 10.

In aspects, the invention provides the composition of any one or more of aspects 1-10, wherein (a) at least most of the hectorite particles are flake-shaped or platelet-shaped, (b) at least 90% of the particles of the first primary particle population comprise hectorite clay particles, (c) some, most, or generally all of the hectorite particles have a height:length:width size ratio of about 1:50:250, or (d) any combination of (a)-(c) are true. ASPECT 11.

In aspects, the invention provides the composition of aspect 10 or aspect 11, wherein at least most of the hectorite particles are flake-shaped or platelet-shaped. ASPECT 12.

In aspects, the invention provides the composition of any one or more of aspects 10-12, wherein at least 90% of the particles of the first primary particle population comprise hectorite clay particles. ASPECT 13.

In aspects, the invention provides the composition of any one or more of aspects 10-13, wherein at least some, most, or generally all of the hectorite particles have a height:length:width size ratio of about 1:50:250. ASPECT 14.

In aspects, the invention provides the composition of any one or more of aspects 1-14, wherein the first primary particle population makes up less than 1% of the composition by weight. ASPECT 15.

In aspects, the invention provides the composition of any one or more of aspects 1-14, wherein the second primary particle population comprises zinc oxide particles and styrene acrylate copolymer particles in a concentration ratio of 1:3 to 1:1. ASPECT 16.

In aspects, the invention provides the composition of aspect 16, wherein at least most of the styrene acrylate copolymer particles have a hollow spherical shape. ASPECT 17.

In aspects, the invention provides the composition of any one or more of aspects 1-16, wherein the second primary particle population makes up 6-12% of the composition by weight. ASPECT 18.

In aspects, the invention provides the composition of any one or more of aspects 1-18, wherein the second primary particle population makes up 7-10% of the composition by weight. ASPECT 19.

In aspects, the invention provides the composition of any one or more of aspects 1-19, wherein at least 33% of the particles of the second primary particle population are hollow spherical particles. ASPECT 20.

In aspects, the invention provides the invention further provides a composition of any one or more of aspects 1-20, wherein the third primary particle population makes up 5-15%, such as 6-13.5, e.g., 6.5-12.5% of the composition by weight, and optionally wherein the highest concentration of metal oxide particles in any primary particle population is in the third primary particle population. ASPECT 21.

In aspects, the invention provides the composition of any one or more of aspects 1-21, wherein the fourth primary particle population makes up 2-5% of the composition by weight. ASPECT 22.

In aspects, the invention provides the composition of any one or more of aspects 1-22, wherein the fifth primary particle population makes up 4-7.5% of the composition by weight. ASPECT 23.

In aspects, the invention provides the composition of aspect 23, wherein at least 80% of the particles of the fifth primary particle population are composed at least mostly of a glass material or a metal oxide material. ASPECT 24.

In aspects, the invention provides the composition of aspect 24, wherein at least most of the glass particles of the fifth primary particle population are solid nonporous spherical particles. ASPECT 25.

In aspects, the invention provides the composition of any one or more of aspects 1-26, wherein at least 15% of the particles of the fifth primary particle population are composed of solid, nonporous, spherical particles. ASPECT 26.

In aspects, the invention provides the composition of any one or more of aspects 1-24, wherein at least 75% of the particles of the sixth primary particle composition are composed at least mostly of a silica material. ASPECT 27.

In aspects, the invention provides the composition of any one or more of aspects 1-24, wherein at least 75% of the particles of the sixth primary particle composition are composed of solid porous particles. ASPECT 28.

In aspects, the invention provides the composition of any one or more of aspects 1-28, wherein most of the metal oxide particles of the composition comprise zinc oxide. ASPECT 29.

In aspects, the invention provides the composition of aspect 29, wherein at least 75% of the metal oxide particles in the composition are irregularly shaped zinc oxide aggregate particles and the irregularly shaped zinc oxide aggregate particles make up 12-24% of the composition by weight. ASPECT 30.

In aspects, the invention provides a dermatologically suitable sunscreen composition (any sunscreen composition herein also being implicitly disclosed for any other compositional use) comprising a water-in-oil emulsion comprising one or more types of UV protective microparticles produced by a process comprising homogenizing the UV protective microparticles for a period of at least 20 minutes (e.g., at least 25 minutes), adding hollow styrene acrylate copolymer particles to a final concentration of 4-6% and homogenizing for at least 20 minutes (e.g., at least 25 minutes), forming an emulsion comprising a polyglyceryl-2 emulsifier at a concentration of 8-14% and homogenizing at high temperature (e.g., 35-50° C., such as about 40° C.) for 2-10 minutes at 5,000-10,000 rpm. ASPECT 31.

In aspects, the invention provides a dermatologically suitable composition comprising a matrix composition comprising a mixture of structurally diverse matrix particles (1) that are formed from at least 3, 4, or 5 different types of primary particles that are distinguishable from one another due to different characteristics, shape characteristics, or both, at least 20% of the primary particles being UV-protective particles (and at least most of the UV-protective particles being composed of irregular aggregate zinc oxide particles), and the matrix particles accounting for a least about 20% of the weight of the composition, wherein (2) the matrix composition when spread across a surface using manual distribution and subjected to elemental SEM analysis as exemplified in the figures and examples provided herein, provides an elemental analysis for silica, calcium, and zinc or for silica, calcium, zinc, and titanium, which is determined to be substantially similar to the elemental analysis figures provided herein (e.g., being statistically similar in terms of the placement/distribution of such particles by one or more measurements such as average distance, maximum distance, minimum distance, mean distance, median distance, and the like, or being recognized as substantially similar by computer program image analysis, artificial intelligence image analysis, or as judged by similar standards known in the art). ASPECT 32.

In aspects, the invention provides a dermatologically suitable composition comprising a matrix composition comprising a mixture of structurally diverse matrix particles (1) that are formed from at least 3, 4, or 5 different types of primary particles that are distinguishable from one another due to different characteristics, shape characteristics, or both, at least 20% of the primary particles being UV-protective particles (and at least most of the UV-protective particles being composed of irregular aggregate zinc oxide particles), and the matrix particles accounting for a least about 20% of the weight of the composition, the particles optionally characterized in comprising calcium borosilicate particles, the composition further comprising (2) one or more of (a) film-forming means, (b) particle suspension means, and (c) particle dispersant means. ASPECT 33.

In aspects, the invention provides the composition of aspect 33, wherein the composition comprises a stable emulsion and further comprises (1) emulsifier means and, optionally, (2) emollient means. ASPECT 34.

In certain aspects, the invention provides multi-dimensional, multi-particulate mineral-based composition(s) providing detectable or significant photoprotection, wherein the ratio of clay to metal oxides is between about 1:70 and about 1:2.2, such as, e.g., about 1:70-about 1:5.5, about 1:70-about 1:7, or about 1:70-about 1:22, such as, e.g., about 1:22-about 1:2.2, about 1:17.5-about 1:2.2, about 1:7-about 1:2.2, about 1:5-about 1:2.2, as in, e.g., about 1:22-about 1:5.5 or, e.g., about 1:17.5-about 1:5.5, e.g., about 1:60, about 1:50, about 1:40, about 1:30, or about 1:20. ASPECT 35.

In certain aspects, the invention provides multi-dimensional, multi-particulate mineral-based composition(s) providing detectable or significant photoprotection, wherein the ratio of clay to API metal oxides is between about 1:60 and about 1:2.1, such as about 1:60-about 1:15, or, e.g., about 1:15-about 1:2.1, such as about 1:21, about 1:6, about 1:5.25, or about 1:2.1, such as, e.g., about 1:50, about 1:40, about 1:30, about 1:20, about 1:10, or about 1:1. ASPECT 36.

In certain aspects, the invention provides multi-dimensional, multi-particulate mineral-based composition(s) providing detectable or significant photoprotection, wherein the ratio of clay to zinc oxide is between about 1:60 and about 1:1.5, such as about 1:50-about 1:3, about 1:46, about 1:30, about 1:20, about 1:15, about 1:6, about 1:5, about 1:5, or, e.g., about 1:2, as in, for example about 1:15-about 1:2, about 1:12.5-about 1:1.5, about 1:11.5-about 1:3, e.g., about 1:5, about 1:2, about 1:3.75, or, e.g., about 1:7.5, e.g., about 1:50, about 1:40, about 1:30, about 1:20, about 1:10, or, e.g., about 1:1. ASPECT 37.

In certain aspects, the invention provides multi-dimensional, multi-particulate mineral-based composition(s) providing detectable or significant photoprotection, wherein the ratio of clay to calcium borosilicate is between about 10:1 and about 1:6, such as, e.g., about 10:1-about 1:1, about 1:1-about 1:6, e.g., about 1.6:1, about 4:1, or, e.g., about 1:1.5, e.g., about 8:1, about 6:1, about 4:1, about 2:1, about 1:1, about 1:2, or, e.g., about 1:4. ASPECT 38.

In certain aspects, the invention provides multi-dimensional, multi-particulate mineral-based composition(s) providing detectable or significant photoprotection, wherein the ratio of clay to styrene acrylates copolymer is, e.g., between about 1.6:1 and about 1:12, such as, e.g., about 1:6 or about 1:1.2, e.g., about 1:1, about 1:2, about 1:4, about 1:6, about 1:8, or, e.g., about 1:10. ASPECT 39.

In certain aspects, the invention provides multi-dimensional, multi-particulate mineral-based composition(s) providing detectable or significant photoprotection, wherein the ratio of clay to an emollient component of composition(s) comprising one or more emollient(s) or classes (groups of emollients) is between about 1.1:1 and about 1:96, such as between about 1.1:1 and about 1:9.6, or between about 1:9 and about 1:96, e.g., about 1:1, about 1:10, about 1:20, about 1:30, about 1:40, about 1:50, about 1:60, about 1:70, or, e.g., about 1:80. ASPECT 40.

In certain aspects, the invention provides multi-dimensional, multi-particulate mineral-based composition(s) providing detectable or significant photoprotection, wherein the ratio of clay to a silicon emollient component of composition(s), wherein the silicon emollient component of composition(s) comprises one or more, two or more, or, e.g., three or more silcone-comprising emollient compounds, is between about 3.6:1 and about 1:16, such as, e.g., about 3.6:1-about 1:1.3, or about 1:1.6-about 1:3, e.g., about 1:2, or, e.g., about 1:2.5. ASPECT 41.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to clay is between about 6:1 and about 1:10, such as about 6:1-about 3:1, about 3:1-about 1:1, or, e.g., about 1:1-about 1:10, e.g., about 4:1, about 2:1, about 1:1, or about 1:2. ASPECT 42.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to metal oxide component is between about 1:3 and about 1:70, such as, e.g., about 1:4-about 1:22, about 1:12-about 1:22, about 1:12-about 1:70, or about 1:4-about 1:12, e.g., about 1:5, about 1:10, about 1:20, about 1:30, about 1:40, about 1:50, or, e.g., about 1:60. ASPECT 43.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to API metal oxide component is between about 1:60 and about 1:3.5, such as, e.g., about 1:25-about 1:3.5, about 1:10-about 1:3.5, or, e.g., about 1:10-about 1:25 or, e.g., about 1:3.5-about 1:10, e.g., about 1:50, about 1:40, about 1:30, about 1:20, about 1:10, about 1:5, about 1:1, or, e.g., about 1:2. ASPECT 44.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to zinc oxide is between about 1:60 and about 1:2.5, such as about 1:60-about 1:10, about 1:60-about 1:30, about 1:30-about 1:3, e.g., about 1:15, about 1:46, or about 1:7, e.g., about 1:50, about 1:40, about 1:30, about 1:20, about 1:10, about 1:5, or, e.g., about 1:1. ASPECT 45.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to calcium borosilicate is between about 1:6 and about 6:1, such as, e.g., about 1:6-about 1:1, about 1:1-about 1:6, as in, e.g., about 1:1-about 1:3, about 3:1-about 1:1, or, e.g., about 2:1-about 1:2, or e.g., about 1:1, e.g., about 1:4, about 1:2, about 1:1, about 2:1, or, e.g., about 4:1. ASPECT 46.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to styrene acrylates copolymer to metal oxides is about 1:1-12:3-70, e.g., about 1:2-6:3.6-22, e.g., about 1:6-12:1:11.6-70. ASPECT 47.

In certain aspects, the invention provides multi-dimensional, multi-particulate mineral-based composition(s) providing detectable or significant photoprotection, wherein the ratio of a film forming component, e.g., comprising or consisting of a dimethicone, dimethicone copolymer to styrene acrylates copolymer to metal oxides is about 1:1-12:3-50, e.g., about 1:2-6:8.3-20, e.g., about 1:1-6:1:3.3-20. ASPECT 48.

In certain aspects, the invention provides multi-dimensional, multi-particulate mineral-based composition(s) providing detectable or significant photoprotection, wherein the ratio of styrene acrylates copolymer to clay to metal oxides is about 1:0.5-12:1.5-12, e.g., about 1:6-12:5-12, e.g., about 1:0.5-6:4-12. ASPECT 49.

In certain aspects, the invention provides multi-dimensional, multi-particulate mineral-based composition(s) providing detectable or significant photoprotection, wherein the ratio of styrene acrylates copolymer to clay to API metal oxides is about 0.5-12:1:2-60, e.g., about 1.2-12:1:6-25, e.g., 6:12:1:2-6. ASPECT 50.

In certain aspects, the invention provides multi-dimensional, multi-particulate mineral-based composition(s) providing detectable or significant photoprotection, wherein the ratio of styrene acrylates copolymer to clay to zinc oxide is about 0.5-12:1:2-50, e.g., about 1.5-12:1:5-50, e.g., about 1.5-6:1:2-20. ASPECT 51.

In certain aspects, the invention provides multi-dimensional, multi-particulate mineral-based composition(s) providing detectable or significant photoprotection, wherein the ratio of emollient component, wherein the emollient component comprises one or more silicon-based emollient compound(s) and one or more monohydric alkyl ester(s), and the silicon-based emollient component is between about 1:1.5 and about 32:1, such as, e.g., about 1:1-about 6:1, about 1:1.5-about 3:1, or, e.g., about 3:1-about 6:1, e.g., about 1:1, about 2:1, about 5:1, about 10:1, about 15:1, about 20:1, about 25:1, or, e.g., about 30:1. ASPECT 52.

In certain aspects, the invention provides multi-dimensional, multi-particulate mineral-based composition(s) providing detectable or significant photoprotection, wherein the ratio of emollient component, wherein the emollient component comprises one or more silicon-based emollient compound(s) and one or more monohydric alkyl ester(s), and the monohydric alkyl ester(s) emollient component is between about 1:9 and about 16:1, such as, e.g., about 1:9-about 1.5:1, or about 1:1-about 16:1, e.g., about 1:8, about 1:6, about 1:4, about 1:2, about 1:1, about 2:1, about 4:1, about 6:1, about 8:1, about 10:1, about 12:1, or, e.g., about 14:1. ASPECT 53.

In certain aspects, the invention provides multi-dimensional, multi-particulate mineral-based composition(s) providing detectable or significant photoprotection, wherein the composition comprises an emollient component comprises a silicon-based emollient portion and a monohydric alkyl ester portion, wherein the ratio of the silicon-based emollient portion of the emollient component to the monohydric alkyl ester portion of the emollient component is between about 1:30 and about 3:1, such as, e.g., about 1:25-about 2:1, about 1:30-about 1:2, about 1:25-about 1:5, about 1:5-about 3:1, or, e.g., about 1:2-about 2:1, e.g., about 1:25, about 1:20, about 1:15, about 1:10, about 1:5, about 1:1, about 1:1.5, about 1:2, or, e.g., about 1:2.5. ASPECT 54.

In aspects, the invention provides the invention further provides a dermatologically suitable sunscreen composition comprising a water-in-oil emulsion comprising a mixture of UV protective metal oxide particles and a polyglyceryl-2 emulsifier (e.g., comprising some, mostly, generally only, substantially only, or only polyglyceryl-2 sesquioleate), wherein at least 85% of the UV protective metal oxide particles have a particle size of greater than 200 nm, such as greater than 250 nm, and wherein the ratio of the polyglyceryl-2 emulsifier to the UV protective metal oxide particles is 1:1.3 to 1:3. ASPECT 55.

In aspects, the invention provides a dermatologically suitable sunscreen composition comprising a water-in-oil emulsion comprising a hectorite clay composition that detectably or significantly supports the suspension of other particles in the composition, a polyglyceryl-2 emulsifier, and one or more types of UV protective metal oxide particles, wherein the hectorite clay, polyglyceryl-2 emulsifier, and metal oxide particles are present in a ratio of 1:20-25:30-50. ASPECT 56.

In aspects, the invention provides a dermatologically suitable sunscreen composition comprising a water-in-oil emulsion comprising a mixture of hollow styrene acrylate copolymer particles and UV-protective metal oxide particles, wherein the ratio of hollow styrene acrylate copolymer particles to UV-protective metal oxide particles is 1:2 to 1:6, such as 1:3 to 1:5. ASPECT 57.

In aspects, the invention provides a dermatologically suitable sunscreen composition comprising a water-in-oil emulsion comprising a mixture of solid nonporous glass particles having an average particle size of between 1000 and 8500 nm and one UV-protective metal oxide particles, wherein the ratio of the solid glass particles to the UV-protective metal oxide particles is 1:5 to 1:15. ASPECT 58.

In aspects, the invention provides a dermatologically suitable sunscreen composition comprising a water-in-oil emulsion comprising a mixture of solid nonporous glass particles having an average particle size of between 1000 and 8500 nm, hollow styrene acrylate copolymer particles, and one or more types of UV-protective metal oxide particles, wherein the ratio of the concentrations of the solid glass particles to the hollow styrene acrylate copolymers, to the UV-protective metal oxide particles is 1:1.5-3.5:5-9. ASPECT 59.

In aspects, the invention provides a dermatologically suitable sunscreen composition comprising a water-in-oil emulsion comprising a mixture of solid nonporous glass particles having an average particle size of between 1000 and 8500 nm, a polyglycerl-2 emulsifier, and one or more types of UV protective metal oxide particles, wherein the ratio of the concentrations of the solid glass particles to the 2-polyglyceryl emulsifier to the UV-protective metal oxide particles is 1:4-7:5-15. ASPECT 60.

In aspects, the invention provides a dermatologically suitable sunscreen composition comprising a water-in-oil emulsion comprising a polyglyceryl-2 emulsifier, a monohydric alkyl ester emollient that detectably promotes the solubilization, stability, or both, of at least most of the metal oxide particles in the composition, and one or more types of UV-protective metal oxide particles, wherein the ratio of the concentrations of the emulsifier, monohydric alkyl ester emollient, and metal oxide particles is 1:1.5-2:1.3-2. ASPECT 61.

In aspects, the invention provides a dermatologically suitable sunscreen composition comprising a water-in-oil emulsion comprising a silicone-based emollient component, a polyglyceryl-2 emulsifier, and one or more types of UV-protective metal oxide particles, wherein the ratio of the concentrations of the emulsifier, monohydric alkyl ester emollient, and metal oxide particles is 1:1.75-2.25:2-5. ASPECT 62.

In aspects, the invention provides a dermatologically suitable sunscreen composition comprising a water-in-oil emulsion comprising a film former component, a polyglyceryl-2 emulsifier, and one or more types of UV protective metal oxide particles, wherein the ratio of concentrations of the film former component to emulsifier to metal oxide particles is 1:0.5-1.5:8-15. ASPECT 63.

In aspects, the invention provides a dermatologically suitable sunscreen composition comprising a water-in-oil emulsion comprising a mixture of UV protective metal oxide particles, at least 90% of which have a size of over 200 nm, at least 80% of which are composed of either spherical or quasi-spherical solid titanium dioxide microparticles and irregular zinc dioxide aggregates, wherein the ratio of titanium dioxide particles to zinc oxide microparticles in the composition is 1:4-105. ASPECT 64.

In aspects, the invention provides a dermatologically suitable sunscreen composition comprising a water-in-oil emulsion comprising a hectorite clay, a film former component, a co-emulsifier component, a polyglyceryl-2 emulsifier, and one or more types of UV protective metal oxide particles, wherein the ratio of concentrations of the clay to film former to co-emulsifier to emulsifier to metal oxide particles is 1:2-4:2-4:20-45:40-70. ASPECT 65.

In aspects, the invention provides a composition according to any one or more of aspects 31-65, wherein the composition is further in accordance with the elements of any one or more of aspects 1-29. ASPECT 66.

In aspects, the invention provides the composition of any one or more of aspects 1-66, wherein the matrix composition when spread across a surface using manual distribution comprises multiple layers of the matrix particles, wherein (1) the particles in a first layer cover at least about 65% of the surface and (2) the particles in at least one other layer comprise particles in gaps in the first layer such that the first layer and second layer cover at least about 75% of the surface. ASPECT 67.

In aspects, the invention provides the composition of any one or more of aspects 1-67, wherein at least most of the zinc oxide particles in the composition are irregularly shaped aggregate particles. ASPECT 68.

In aspects, the invention provides the composition of aspect 68, wherein most of the zinc oxide microparticles in the composition are mesoporous zinc aggregate particles. ASPECT 69.

In aspects, the invention provides the composition of aspect 69, wherein at least 95% of the zinc oxide microparticles in the composition are mesoporous zinc aggregate particles. ASPECT 70.

In aspects, the invention provides the composition of any one or more of aspects 1-70, wherein zinc oxide particles make up 12-24% of the composition by weight. ASPECT 71

In aspects, the invention provides the composition of aspect 71, wherein zinc oxide particles make up 13-23% of the composition by weight. ASPECT 72.

In aspects, the invention provides the composition of any one or more of aspects 1-72, wherein the particle mixture comprises particles of at least two different types of UV protective metal oxide particles. ASPECT 73.

In aspects, the invention provides the composition of aspect 73, wherein the composition comprises a UV protective amount of titanium dioxide particles. ASPECT 74.

In aspects, the invention provides the composition of aspect 74, wherein at least most of the titanium dioxide particles are spherical or quasi-spherical in shape. ASPECT 75.

In aspects, the invention provides the composition of any one or more of aspects 1-75, wherein the composition comprises 0.1-4%, e.g., 0.2-3.8% or 0.3-3.9%, 0.1-1%, 0.2-0.8%, 0.1-0.7%, 0.2-0.8%, 0.3-0.6%, or 0.25-0.75% titanium dioxide particles by weight. ASPECT 76.

The composition of any one or more of aspects 1-76, wherein the composition comprises 0.1%-0.5% of a natural or synthetic mica composition. ASPECT 77.

In aspects, the invention provides the composition of any one or more of aspects 1-77, wherein the composition comprises at least three types of UV protective metal oxide particles. ASPECT 78.

In aspects, the invention provides the composition of any one or more of aspects 1-78, wherein the composition comprises a UV protective amount of iron oxide particles, an effective pigmenting amount of iron oxide particles (an amount effective to provide a detectable tint to the composition), or both ASPECT 79.

In aspects, the invention provides the composition of aspect 79, wherein the composition comprises 0.75-3% iron oxide particles, wherein optionally most of the iron oxide particles are contained in the first primary particle population, and optionally the composition comprises at least 0.15% of a natural or synthetic mica (e.g., 0.2-1.2%, 0.2-1%, or 0.25-1%). ASPECT 80.

In aspects, the invention provides the composition of aspect 79 or aspect 80, wherein the first primary particle population (if present in the composition—i.e., a particle population defined by a maximum particle size of 250 nm) comprises at least most of the iron oxide particles by weight. ASPECT 81.

In aspects, the invention provides the composition of aspect 81, wherein the first primary particle population comprises at least 90% of the iron oxide particles of the composition by weight. ASPECT 82.

In aspects, the invention provides the composition of any one or more of aspects 1-82, wherein the composition is an emulsion, such as a water in oil emulsion, and 5-20%, such as 6-18%, or 7-15.5%, or 8-14% of the composition by weight is composed of a polyglyceryl-2 emulsifier. ASPECT 83.

In aspects, the invention provides the composition of aspect 83, wherein 10-12% of the composition by weight is composed of a polyglyceryl-2 emulsifier. ASPECT 84.

In aspects, the invention provides the composition of aspect 83 or aspect 84, wherein at least most of the polyglyceryl-2 emulsifier (e.g., generally all, substantially all, essentially all, or all of the emulsifier) is polyglyceryl-2 sesquioleate. ASPECT 85.

In aspects, the invention provides the composition of aspect 85, wherein at least 95% of the polyglyceryl-2 emulsifier is polyglyceryl-2 sesquioleate. ASPECT 86.

In aspects, the invention provides the composition of any one or more of aspects 83-86, wherein the composition comprises an effective amount of a co-emulsifier. ASPECT 87.

In aspects, the invention provides the composition of aspect 87, wherein 0.5-1.5% of the composition is composed of the co-emulsifier. ASPECT 88.

In aspects, the invention provides the composition of aspect 88, wherein at least most of the co-emulsifier is glyceryl dibehenate. ASPECT 89.

In aspects, the invention provides the composition of aspect 89, wherein at least 90% of the co-emulsifier is glyceryl dibehenate. ASPECT 90.

In aspects, the invention provides the composition of any one or more of aspects 1-90, wherein the composition comprises 14%-24% by weight of one or more monohydric alkyl esters. ASPECT 91.

In aspects, the invention provides the composition of aspect 91, wherein at least most of the monohydric alkyl esters exhibit a detectable solubilizing effect on at least most of the metal oxide particles of the composition, exhibit a detectable stabilizing effect on at least most of the metal oxide particles of the composition, or both. ASPECT 92.

In aspects, the invention provides the composition of aspect 92, wherein at least most of the one or more monohydric alkyl esters is octyldodecyl neopentanoate. ASPECT 93.

In aspects, the invention provides the composition of aspect 93, wherein at least 95% of the one or more monohydric alkyl esters is octyldodecyl neopentanoate. ASPECT 94.

In aspects, the invention provides the composition of any one or more of aspects 1-94, wherein 5-15% of the composition by weight is composed of one or more silicone polymer emollients. ASPECT 95.

In aspects, the invention provides the composition of aspect 95, wherein the composition comprises two or more silicone polymer emollients. ASPECT 96.

In aspects, the invention provides the composition of aspect 96, wherein the composition comprises 6-12% of a silicone polymer emollient component by weight. ASPECT 97.

In aspects, the invention provides the composition of any one or more of aspects 1-97, wherein at least 0.3% and less than 3.5% of the composition is composed of film forming component. ASPECT 98.

In aspects, the invention provides the composition of aspect 98, wherein 0.4-2% of the composition is composed of a film forming component. ASPECT 99.

In aspects, the invention provides the composition of aspect 99, wherein 0.85-1.15% of the composition is composed of a film forming component. ASPECT 100.

In aspects, the invention provides the composition of aspect 100, wherein at least most of the film forming component by weight is composed of dimethicone, dimethicone copolymer. ASPECT 101.

In aspects, the invention provides the composition of aspect 101, wherein at least 90% of film forming component by weight is composed of dimethicone, dimethicone copolymer. ASPECT 102.

In aspects, the invention provides the composition of any one or more of aspects 1-102, wherein the composition comprises about 0.5-2.5% of a dimethicone, dimethicone copolymer film-forming component. ASPECT 103.

In aspects, the invention provides the composition of any one or more of aspects 1-102, wherein the composition comprises an effective amount of a dispersant component. ASPECT 104.

In aspects, the invention provides the composition of aspect 104, wherein the dispersant component makes up 0.75% to 1.25% of the composition by weight. ASPECT 105.

In aspects, the invention provides the composition of aspect 105, wherein at least most of the dispersant is composed of polyhydroxystearic acid. ASPECT 106.

In aspects, the invention provides the composition of aspect 106, wherein at least 90% of the dispersant is composed of polyhydroxystearic acid. ASPECT 107.

In aspects, the invention provides the composition of any one of aspects 1-107, wherein 0.2-2% of the composition by weight is composed of a *Deinococcus* extract. ASPECT 108.

In aspects, the invention provides the composition of any one of aspects 1-108, wherein the composition comprises an amount of L-carnosine this is effective to detectably reduce infrared radiation absorption, high energy visible (HEV) (380-530 nm) light absorption, ultraviolet radiation absorption, or a combination thereof. ASPECT 109.

In aspects, the invention provides the composition of any one of aspects 1-109, wherein the composition comprises an antioxidant effective amount of an *Echinacea Purpurea* extract. ASPECT 110.

In aspects, the invention provides the composition of any one of aspects 1-110, wherein the composition is anhydrous, comprising less than 2%, less than 1%, or less than 0.5% water, such as less than 0.1%, less than 0.01%, or less than 0.001% water (or comprising no detectable amount of water). ASPECT 111.

In aspects, the invention provides the composition of aspect 111, wherein the composition is an anhydrous composition comprising a structural wax component that makes up about 5-20% of the composition by weight and wherein the composition comprises less than 0.5% water. ASPECT 112.

In aspects, the invention provides the composition of any one of aspects 1-110, wherein the composition is a lotion. ASPECT 113.

In aspects, the invention provides the composition of aspect 113, wherein the composition comprises 15-25% water, e.g., 18-22%, or 18.5-21.5% water. ASPECT 114.

In aspects, the invention provides the composition of any one or more of aspects 1-114, wherein the composition exhibits a critical wavelength of at least 370 nm. ASPECT 115.

In aspects, the invention provides the composition of any one or more of aspects 1-115, wherein the ratio of SPF to UVA protective factor (PF) (UVA/PF) is less than 3. ASPECT 116.

In aspects, the invention provides the composition of any one or more of aspects 1-116, wherein the composition exhibits a ratio of UVA/PF to SPF is 0.333 or greater. ASPECT 117.

In aspects, the invention provides the composition of any one or more of aspects 1-117, wherein the percentage of high energy visible (HEV) (380-530 nm) light blocked by the composition is at least 30%. ASPECT 118.

In aspects, the invention provides the composition of any one or more of aspects 1-118, wherein the percentage of visible light (400-700 nm) blocked by the composition is at least 20%. ASPECT 119.

In aspects, the invention provides the composition of any one or more of aspects 1-119, wherein the composition further comprises an effective amount of a non-sodium chloride electrolyte (e.g., magnesium sulfate), an effective amount of a non-glycerin electrolyte (e.g., propanediol), or both. ASPECT 120.

In aspects, the invention provides the composition of any one or more of aspects 1-120, wherein the composition exhibits water resistance such that after 40 minutes water exposure the composition loses no more than 15% of the compositions initial SPF. ASPECT 121.

In aspects, the invention provides the composition of any one or more of aspects 1-121, wherein the composition exhibits water resistance such that after 80 minutes water exposure the composition loses no more than 15% of the compositions initial SPF. ASPECT 122.

In aspects, the invention provides the composition of any one or more of aspects 1-122, wherein the initial viscosity of the composition is 2200-4200 cps (Brookfield RVT spindle T-B @ 20 rpm @ 25° C.). ASPECT 123.

In aspects, the invention provides the composition of any one or more of aspects 1-123, wherein the viscosity of the composition 24 hours after formation is 3,500 cps-5,500 cps. ASPECT 124.

In aspects, the invention provides the composition of any one or more of aspects 1-124, wherein the composition has a viscosity of 4,500 cps-15,000 cps when stored at room temperature for a period of at least one month. ASPECT 125.

In aspects, the invention provides the composition of any one or more of aspects 1-125, wherein a first layer of the composition when distributed by manual spreading to an approximately even distribution on a surface covers at least about 70% of the surface. ASPECT 126.

In aspects, the invention provides the composition of aspect 126, wherein at least some of the area not covered by the particles in the first layer is covered by particles in a second layer above or below the first layer, such that the coverage of the surface is at least about 75%. ASPECT 127.

In aspects, the invention provides the composition of any one or more of aspects 1-127, wherein at least most of the particles in a layer of the composition when manually spread on a surface to approximately distribution are associated with no gap of more than 375 nm with another particle in any given direction. ASPECT 128.

In aspects, the invention provides the composition of any one or more of aspects 1-128, wherein the composition has a specific gravity of about 1, such as 1.0045. ASPECT 129.

In aspects, the invention provides the composition of any one or more of aspects 1-129, wherein the composition has a refractive index of 0.8-1.9, such as 0.9-1.6, e.g., 1-1.55. ASPECT 130.

In aspects, the invention provides the composition of aspect 130, wherein the composition has a refractive index of 1-1.55. ASPECT 131.

In aspects, the invention provides the composition of any one or more of aspects 1-131, wherein the ratio of non-metal-oxide particles to metal oxide particles in the composition is between 1.2:1 and 2.5:1, such as 1.4:1 to 2.2:1. ASPECT 132.

In aspects, the invention provides the composition according to any one or more of aspects 1-132, wherein the composition is free of any organic sunscreen filters/organic sunscreens, such as avobenzone. ASPECT 133.

In aspects, the invention provides a composition that consists essentially of, or consists entirely of, the elements described in any one or more of aspects 1-133. ASPECT 134.

In aspects, the invention provides a dermatologically suitable composition comprising a mixture of (1) an effective amount of mesoporous zinc oxide particles having a particle size (maximum particle size or average maximum particle size in one or more dimensions) of at least about 800 nm and (2) an effective amount of calcium sodium borosilicate particles, wherein the mesoporous zinc oxide particles and calcium sodium borosilicate particles are in a ratio of about 1:6 to about 1:12, such as about 1:7 to about 1:10. ASPECT 135.

In aspects, the invention provides a dermatologically suitable composition comprising an effective mixture of particles comprising a plurality of particle types (e.g., metal, non-metal, solid, hollow, etc.), at least three particle distinct forms ("shapes") (e.g., spherical, non-spherical, aggregates, mesoporous, irregular, platelets, etc.), and comprising microscale, mesoscale, and macroscale particle sizes, the particles comprising an effective amount of UV scattering metal oxide particles, the difference in size between at least some of the microscale particles and macroscale particles being at least about 10×, the particles being subjected to multiple rounds of prolonged homogenization of the emulsion of substrate(s) to form the composition, wherein the composition when applied to skin of a typical subject forms a stable matrix wherein changes in the light scattering properties of the composition across a selected area of skin, changes in the distribution of particles in the matrix in a selected area of skin, or both, are significantly reduced as compared to a composition lacking the mixture of particle sizes and shapes, a composition not subjected to the same homogenization conditions, or both. ASPECT 136.

In aspects, the invention provides a dermatologically suitable composition comprising a combination of (1) an effective amount of platelet-shaped particles with a particle size (maximum particle size or average maximum particle size in one or more dimensions) of between about 50 nm and about 1000 nm (e.g., with an average particle size of at least about 100 nm) that are composed of a dermatologically suitable clay bulking agent (e.g., a hectorite clay), (2) an effective amount of irregularly-shaped (e.g., non-spherical) aggregated mesoporous light scattering particles of at least about 800 nm in size, and (3) an effective amount of spherical light scattering particles comprising (a) hollow spherical particles and (b) solid spherical particles, wherein the hollow spherical particles are present in a weight concentration ratio to solid spherical particles of about 0.5:1 to about 1:1.5, such as about 0.75:1 to about 1:1.25, such as about 0.8:1 to about 1:1.2, wherein (4) (a) the ratio of the weight concentration contribution of the platelet-shaped particles to spherical particles is about 1:12 to about 1:25, (b) the ratio of the spherical particles to the irregularly-shaped aggregated mesoporous particles is about 1:2 to about 1:3, such about 1:2.5, 1:2.25, or about 1:2.75, or (c) both (a) and (b) are true. ASPECT 137.

In aspects, the invention provides a dermatologically suitable composition comprising (1) an effective amount of irregularly-shaped (e.g., non-spherical) porous UV light scattering metal oxide particles having particle sizes (or average particle size) of at least about 500 nm, such as at least about 750 nm, such as at least about 800 nm with an average particle size of ≥~1,000 nm and (2) a number of regularly shaped, spherical and non-spherical particles that are at least mostly composed of material that is dermatologically suitable and that causes the regularly-shaped particles to detectably or significantly enhance the UV scattering properties of the composition, wherein (I) the minimum average particle size for any type of particles in the composition is at least about 100 nm in size, (II) the maximum average particle size for any type of particles in the composition is about 15,000 nm in size, (III) the composition exhibits an SPF of at least about 40, such as about 50, e.g., about 30-65, about 35-65, about 30-60, about 40-60, about 45-60, or about 45-55, (IV) (a) the UVA/UVB(SPF) protection measure for the composition is at least 1/3 of the in-vivo SPF with a critical wavelength (CW)>370 nm; (b) the UVA-I/UV ratio is ≥~0.7, (average absorbance in UVA-I (340-400 nm) to the total UV (290-400 nm)), or (c) both (a) and (b) are true, and (V) a statistically significant number of test subjects in an adequately powered survey/trial report that the composition is substantially non-whitening on Fitzpatrick Skin Types I-IV. ASPECT 138.

In aspects, the invention provides a dermatologically suitable composition that significantly reduces UV exposure when applied to the skin in effective amounts, detectably or significantly reduces blue light exposure when applied to the skin in effective amounts, and detectably or significantly reduces infrared radiation exposure when applied to the skin in effective amounts, comprising (1) an effective amount of mesoporous metal oxide microparticles, (2) a natural biologic extract component that exhibits detectable or significant blue light scattering effects and detectable or significant infrared radiation, and (3) an effective amount of a dermatologically suitable glass composition (e.g., calcium sodium borosilicate) that detectably or significantly scatters blue light, wherein the weight concentration ratio of the mesoporous metal oxides to the glass composition is about 8:1 to about 12:1 (e.g., about 10:1) and the weight concentration ratio of the mesoporous metal oxides to the biological extract component is about 20:1 to about 30:1, such as about 21:1-about 27:1, e.g., about 22:1 to about 25:1 wherein the composition (I) exhibits an SPF of at least 40, such as about 50, e.g., 30-65, 35-65, 30-60, 40-60, 45-60, or 45-55, (II) the UVA/UVB(SPF) protection measure for the composition is at least 1/3 of the in-vivo SPF with a critical wavelength (CW)>370 nm; (iii) the UVA-I/UV ratio is ≥~0.7, (average absorbance in UVA-I (340-400 nm) to the total UV (290-400 nm)), or (iv) the composition exhibits a combination of some or all of (i)-(iii). ASPECT 139.

In aspects, the invention provides a dermatologically suitable composition(s) that is/are substantially free, essentially free, or entirely free of any polyethylene glycol compound(s) (PEG(s)), polypropylene glycol(s) (PPG(s)), or both, the composition(s) comprising, consisting of, or consisting essentially of a stable water-in-oil emulsion, the emulsion comprising an emulsifier component, wherein at least most of the emulsifier component on a weight basis is composed of polyglyceryl-2 sesquioleate and wherein polyglyceryl-2 sesquioleate accounts for at least about 8% (e.g., at least about 10%, such as at least about 11%) of the composition (on a weight percent basis), and (b) an effective amount of a co-emulsifier (e.g., a glyceryl dibehanate, tribehenin, and glyceryl behenate co-emulsifier, such as Compritol 888 CG Pellets), which is present in an amount accounting for at least about 0.5 wt. % of the composition, wherein the ratio of the polyglyceryl-2 sesquioleate to the co-emulsifier is about 15:1 to about 25:1, such as about 16:1, about 17:1, about 18:1, about 19:1, or about 20:1, wherein the composition comprises a mixture of mesoporous uncoated zinc dioxide aggregated microparticulate particles in a concentration of at least about 20 weight percent in combination with other regular spherical and regular non-spherical particles, wherein the other regular spherical and non-spherical particles detectably or significantly promote the UV scattering/light scattering properties of the composition, and wherein the composition exhibits an SPF of at least about 40, e.g., about 50 (e.g., about 45-65). ASPECT 140.

In aspects, the invention provides a dermatologically suitable composition comprising a mixture of (1) mesoporous light reflecting metal oxide microscale particles that have a maximum single dimension of about 100 nm-about 1,000 nm in size (or have an average size of about 100 nm-about 1,000 nm) and are at least about 50% (e.g., at least about 60%) composed of a light reflecting metal oxide in which most of the pores in the particles have a maximum dimension of about 2 nm-about 100 nm and at least about 80% (e.g., at least about 90%, about 95%, about 99%, or about 100%) of the mesoporous particles comprise zinc oxide, (2) mesoscale light scattering spherical silica particles having a maximum single dimension of about 1,000 nm to about 10,000 nm (or average particle sizes of about 1,000 nm-about 10,000 nm), and (3) light scattering spherical glass macroscale particles having a maximum single dimension of about 10,000 to about 15,000 nm (or have an average size of about 10,000 to about 15,000 nm), wherein (I) the ratio of the weight concentration of microscale particles to macroscale particles in the composition is about 15:1 to about 60:1, such as about 20:1-about 55:1 or about 30:1-about 55:1 or about 40:1 to about 50:1 and (II) the weight concentration of microscale particles to mesoscale particles in the composition is about 15:1 to about 60:1, such as about 20:1-about 55:1 or about 30:1-about 55:1 or about 40:1 to about 50:1. ASPECT 141.

In aspects, the invention provides a dermatologically suitable composition comprising a combination of (1) a microscale particle component comprising an effective amount of dermatologically suitable microscale particles having particle sizes (i.e., maximal single-dimension particle sizes; maximum length in any one direction) of about 100-about 1,000 nm (or average particle sizes of about 100-about 1000 nm), wherein at least about 50% (or at least about 60% or at least about 65%) of the microscale particle component is composed of ultraviolet (UV) light scattering particles; (2) a mesoscale particle component that comprises an effective amount of dermatologically suitable mesoscale particles having particle sizes (i.e., maximal one-dimension particle sizes; maximum length in any one direction) of about 1000-about 10,000 nm (or average particles sizes of about 1,000-about 10,000 nm), wherein at least about 50% (or at least about 60%, about 70%, about 80%, or about 90%) of the mesoscale particle component is composed of particles made of a material that causes the mesoscale particle component to significantly enhance (i.e., statistically significantly improve) the light scattering capability of the composition; and (3) a macroscale particle component comprising an effective amount of dermatologically suitable macroscale particles having particle sizes (i.e., maximal one-dimensional particle sizes) of about 10,000-about 15,000 nm (or average particle sizes of about 10,000-about 15,000 nm), wherein at least about 50% of the macroscale particle component is composed of particles that are made of a material that (a) causes the macroscale particle component to significantly enhance the light scattering capability of the composition, (b) significantly reflects, absorbs, or reflects and absorbs blue light (light with wavelengths in the range of 380-495 nm, such as 380-450 nm, e.g., 400-450 nm, 450-495 nm, or 425-475 nm), or (c) performs both (a) and (b), wherein (I) the ratio of mesoscale particles to microscale particles in the composition is about 1:5 to 1:65 (e.g., about 1:10 to about 1:40), (II) the ratio of macroscale particles to microscale particles in the composition is about 1:5 to 1:65 (e.g., about 1:10 to about 1:40), or (III) the ratio of mesoscale particles to microscale particles in the composition is about 1:5 to 1:65 (e.g., about 1:10 to about 1:40) and the ratio of macroscale particles to microscale particles in the composition is about 1:5 to 1:65 (e.g., about 1:10 to about 1:40). ASPECT 142.

In aspects, the invention provides a dermatologically suitable composition comprising a combination of (1) a microscale particle component comprising an effective amount of dermatologically suitable microscale particles having particle sizes (i.e., maximal one-dimension particle sizes; maximum length in any one direction) of about 100-about 1,000 nm (or average particle sizes of about 100-about 1000 nm), wherein at least about 50% (or at least about 60% or at least about 65%) of the microscale particle component is composed of UV scattering particles and the microscale particle component constitutes about 10-about 35% of the composition by weight (e.g., about 12-about 33%, in aspects about 25-about 33%, about 26-about 32%, or about 26.5%-about 31.5% of the composition); (2) a mesoscale particle component that comprises an effective amount of dermatologically suitable mesoscale particles having particle sizes (i.e., maximal one-dimension particle sizes; maximum length in any one direction) of about 1000-about 10000 nm (or average particles sizes of about 1,000-about 10,000 nm), wherein the mesoscale particle component constitutes about 0.5-about 2.5% of the composition and at least about 50% of the mesoscale particle component (or at least about 60%, about 70%, about 80%, or at least about 90%) is composed of particles made of a material that causes the mesoscale particle component to significantly enhance (i.e., statistically significantly improve) the light scattering capability of the composition; and (3) a macroscale particle component comprising an effective amount of dermatologically suitable macroscale particles having particle sizes (i.e., maximal one-dimensional particle sizes) of about 10,000-about 15,000 nm (or average particle sizes of about 10,000-about 15,000 nm), wherein the macroscale particle component constitutes about 0.5-about 2.5% of the composition and at least about 50% of the macroscale particle component is composed of particles that are made of a material that (a) causes the macroscale particle component to significantly enhance (e.g., statistically significantly enhance) the light scattering capability of the composition, (b) significantly reflects, absorbs, or reflects and absorbs blue light (e.g., statistically significantly increases the reflection, absorption, or reflection and absorption of blue light) (light with wavelengths in the range of about 380-about 495 nm, such as about 380-about 450 nm, e.g., about 400-about 450 nm, about 450-about 495 nm, or about 425-about 475 nm), or (c) causes the macroscale particle component to significantly enhance (e.g., statistically significantly increase) the light scattering capability of the composition and significantly reflects, absorbs, or reflects and absorbs blue light (e.g., statistically significantly increases the reflection, absorption, or reflection and absorption of blue light) (light with wavelengths in the range of about 380-about 495 nm, such as about 380-about 450 nm, e.g., about 400-about 450 nm, about 450-about 495 nm, or about 425-about 475 nm). ASPECT 143.

In aspects, the invention provides a dermatologically suitable composition comprising a mixture of (1) a microscale particle component comprising an effective amount of dermatologically suitable microscale particles having a maximum one-dimension particle size of about 100-about 1,000 nm (or average maximum particle sizes of about 100-about 1000 nm), wherein at least about 65% of the microscale particle component is composed of particles having a non-spherical/irregular shaped particles and at least about 5% (e.g., at least about 7.5%, at least about 10%, or at least about 12.5%, such as about 10%-about 20%, about 12.5%-about 25%, about 12.5%-about 20%, about 15%-about 25%, about 15%-about 20%, about 10%-about 15%, about 10%-about 12.5%, about 12.5%-about 15%, about 12.5%-about 17.5%, or about 10%-about 25%) of the microscale particle component is composed of particles having a spherical shape ("spherical particles" including substantially spherical particles, wherein a spherical particle has no single particle dimension which varies by more than about 20% from any other single dimension of the particle); (2) a mesoscale particle component that comprises an effective amount of dermatologically suitable mesoscale particles having a maximum one-dimension particle size of about 1000-about 10,000 nm (or average particles sizes of about 1,000-about 10,000 nm), wherein at least about 50% (or at least about 60%, about 70%, about 80%, about 90%, about 95%, or at least about 99%) of the mesoscale particle component is composed of particles having a spherical shape; and (3) a macroscale particle component comprising an effective amount of dermatologically suitable macroscale particles having a maximum one-dimension particle size of about 10,000-about 15,000 nm (or average particle sizes of about 10,000-about 15,000 nm), wherein at least about 50% (or at least about 60%, about 70%, about 80%, about 90%, about 95%, or at least about 99%) of the macroscale particle component is composed of particles having a spherical shape. ASPECT 144.

In aspects, the invention provides a dermatologically suitable composition comprising a mixture of (1) a microscale particle component comprising an effective amount of dermatologically suitable microscale particles having a particle size (i.e., a maximum one-dimension particle size; maximum dimension in any one direction) of about 100 nm-about 1,000 nm (or average maximum particle size of about 100 nm-about 1000 nm) and comprising (a) a collection of mesoporous, mineral oxide, stably-aggregated light scattering particulates, (b) a collection of hollow, spherical, light scattering particles; (c) a collection of platelet-shaped particles composed of a dermatologically suitable clay bulking agent; and (d) an optional collection of solid (including substantially solid) mineral oxide particles, wherein the ratios of the weight concentration of the mesoporous mineral oxide particles to the platelet-shaped particles and hollow spherical particles are each at least about 3.5:1 (e.g., at least about 4:1, about 4.5:1, or at least about 5:1, such as about 3.75:1-about 7.5:1, about 4:1-about 6.5:1, or about 4.25:1-about 6.25:1); (2) a mesoscale particle component that comprises an effective amount of dermatologically suitable mesoscale particles having a particle size (i.e., a maximum one-dimension particle size; maximum dimension in any one direction) of about 1000 nm-about 10,000 nm (or average particles size of about 1,000 nm-about 10,000 nm), wherein at least about 50% (or at least about 60%, about 70%, about 80%, about 90%, about 95%, or at least about 99%) of the mesoscale particle component is composed of solid light scattering particles; and (3) a macroscale particle component comprising an effective amount of dermatologically suitable macroscale particles having a particle size (i.e., a maximum one-dimension particle size; maximum dimension in any one direction) of about 10,000 nm-about 15,000 nm (or average particle size of about 10,000 nm-about 15,000 nm), wherein at least about 50% (or at least about 60%, about 70%, about 80%, about 90%, about 95%, or at least about 99%) of the mesoscale particle component is composed of solid light scattering particles, wherein at least most of the mesoscale particles and macroscale particles comprise different compounds comprising detectably different light scattering properties. ASPECT 145.

In aspects, the invention provides the composition of any one or more of aspects 135-145, wherein the ratio of the weight concentration of mesoscale particles to the weight concentration of macroscale particles in the composition is about 1:1 to about 1:3. ASPECT 146.

In aspects, the invention provides the composition of any one or more of aspects 135-147, wherein at least most, generally all, substantially all, or all of the mesoporous particles are composed of porous silica particles. ASPECT 147.

In aspects, the invention provides the composition of any one or more of aspects 135-147, wherein the composition further comprises microscale spherical particles composed of styrene acrylate copolymer in a weight concentration of at least about 3% of the composition. ASPECT 148.

In aspects, the invention provides the composition of any one or more of aspects 135-148, wherein the spherical particles of the composition comprise an effective number of nonporous spherical particles having a particle size (maximum particle size or average maximum particle size in one or more dimensions) of about 1,000 nm-about 15,000 nm which are at least mostly, generally, substantially, or only composed of a dermatologically suitable glass composition (e.g., calcium sodium borosilicate composition), which optionally make up about 0.4-2% of the composition by weight. ASPECT 149.

In aspects, the invention provides the composition of any one or more of aspects 135-149 or any one or more of aspects 1-134, wherein the composition comprises at least 0.2% of a particle suspending agent, which optionally mostly, generally, or entirely is composed of a hectorite clay suspending agent. ASPECT 150.

In aspects, the invention provides the composition of any one or more of aspects 135-149, wherein the composition comprises an effective amount of (e.g., at least about 0.1%, 0.15%, or 0.2% of), but less than about 0.6%, e.g., less than about 0.5%, e.g., less than about 0.4%, such as about 0.25-0.4%, e.g., about 0.3-0.4%, e.g., about 0.35% or about 0.375% of any dermatological suitable clay, such as a hectorite clay, such as disteardimonium hectorite. ASPECT 151.

In aspects, the invention provides the composition of any one or more of aspects 135-150, wherein the composition is free of any microalgae components (e.g., microalgae particle components having an average particle size of more than 1,000 nm, more than 2,500 nm, more than 5,000 nm, or more than 10,000 nm) (e.g., mostly, generally, or entirely intact diatomaceous algae cell material)), macroalgae material, or both. ASPECT 152.

In aspects, the invention provides the composition of any one or more of aspects 135-152, wherein the composition comprises less than about 2%, such as less than about 1.5% solid spherical silica ingredients or less than about 10% total silica spherical particle ingredients. ASPECT 153.

In aspects, the invention provides the composition of any one or more of aspects 135-153, wherein the composition comprises an effective amount of a salicylate free long chain branched ester dispersant/booster. ASPECT 154.

In aspects, the invention provides the composition of aspect 154, wherein the ester is mostly, generally, or entirely composed of octyldodecyl neopenthanoate, optionally where the booster is present in 10-25% of the composition, such as 12-22% of the composition, or 15-21% of the composition or 17-21% of the composition. ASPECT 155.

In aspects, the invention provides the composition of any one or more of aspects 135-155 or any one or more of aspects 1-134, wherein the composition is free of or comprises no more than about 2%, any more than about 1%, or any more than about 0.5% of any proteins or peptides, optionally with the exclusion of carnosine from the excluded peptides, or optionally wherein the peptide exclusion is limited to peptides of more than 4, 5, 10, 15, or 20 amino acids. ASPECT 156.

In aspects, the invention provides the composition of any one or more of aspects 135-156 or any one or more of aspects 1-134, wherein the composition is free of any organic sunscreen filters/organic sunscreens (e.g., any US FDA GRASE-recognized or monograph recognized sunscreen APIs other than ZnO and TiO2, such as avobenzone). ASPECT 157.

In aspects, the invention provides the composition of any one or more of aspects 135-157 or any one or more of aspects 1-134, wherein the composition is free of any polyethylene glycol compounds (PEGs). ASPECT 158.

In aspects, the invention provides the composition of any one or more of aspects 135-158 as a cosmetic agent, protectant against indoor radiation exposure, sunscreen, or any combination thereof. ASPECT 159.

Figure 8A:
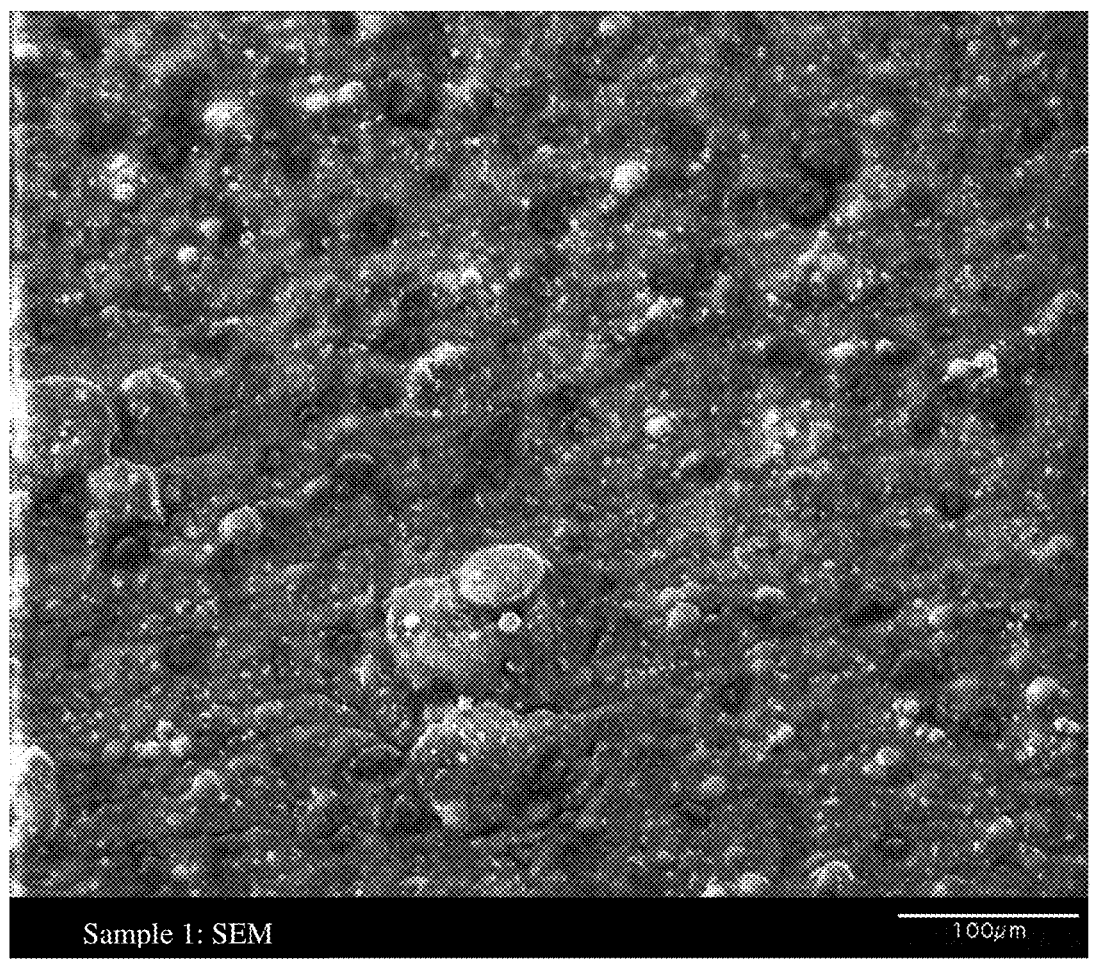
FIG. 8A provides the black and white SEM microscopy photograph of the area of an exemplary formulation of FIG. 6, also present in FIG. 6, in larger form.
Figure 8B:
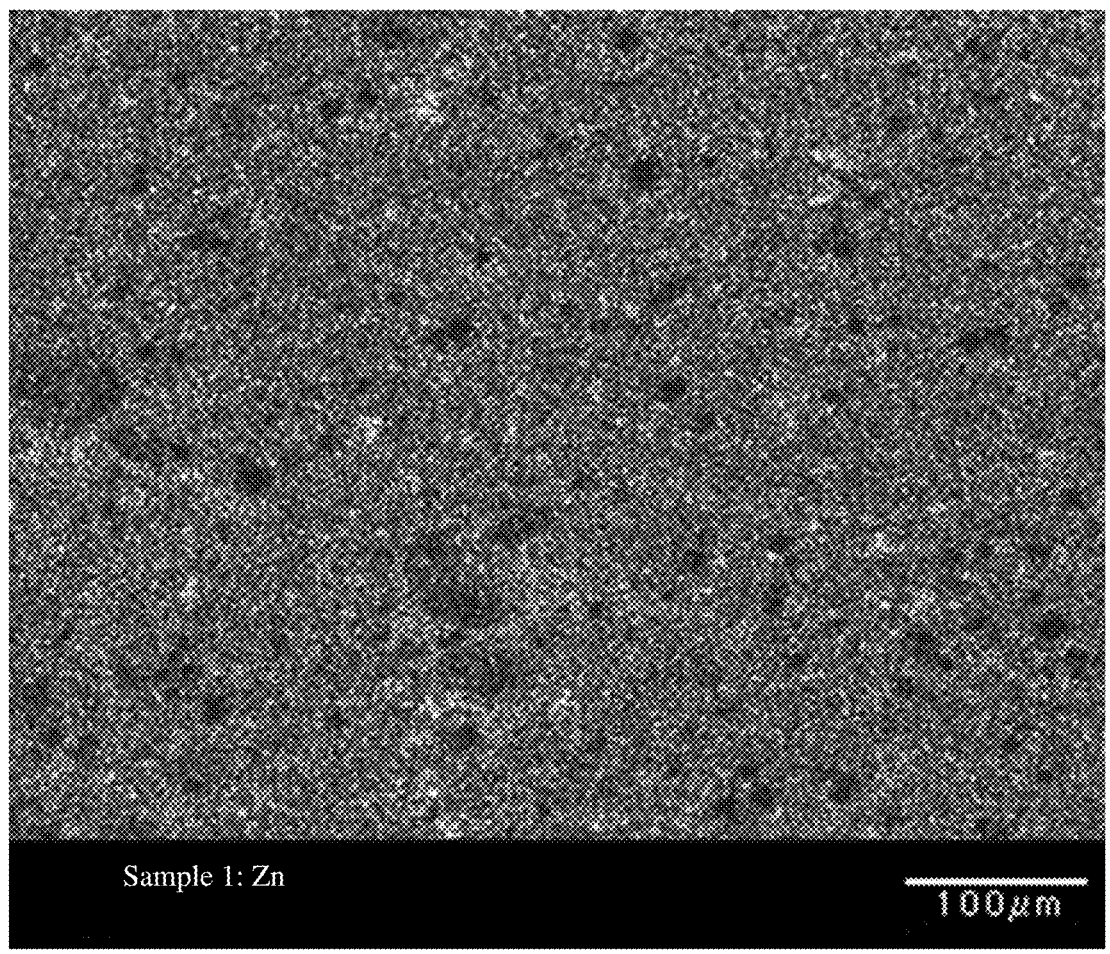
FIG. 8B provides a black and white microscopy photograph showing the elemental distribution of zinc of the area of an exemplary formulation of FIG. 6, also present in FIG. 6, in larger form.

In aspects, the invention provides a composition that is suitable for topical application comprising a matrix composition comprising a mixture of structurally diverse matrix particles, wherein upon application of the composition to a surface (such as, e.g., a plate similar that described in Example 7 or, e.g., human skin), the application result in a distribution of zinc oxide particles at least substantially similar to that shown in FIG. 8B. ASPECT 160.

Figure 8C:
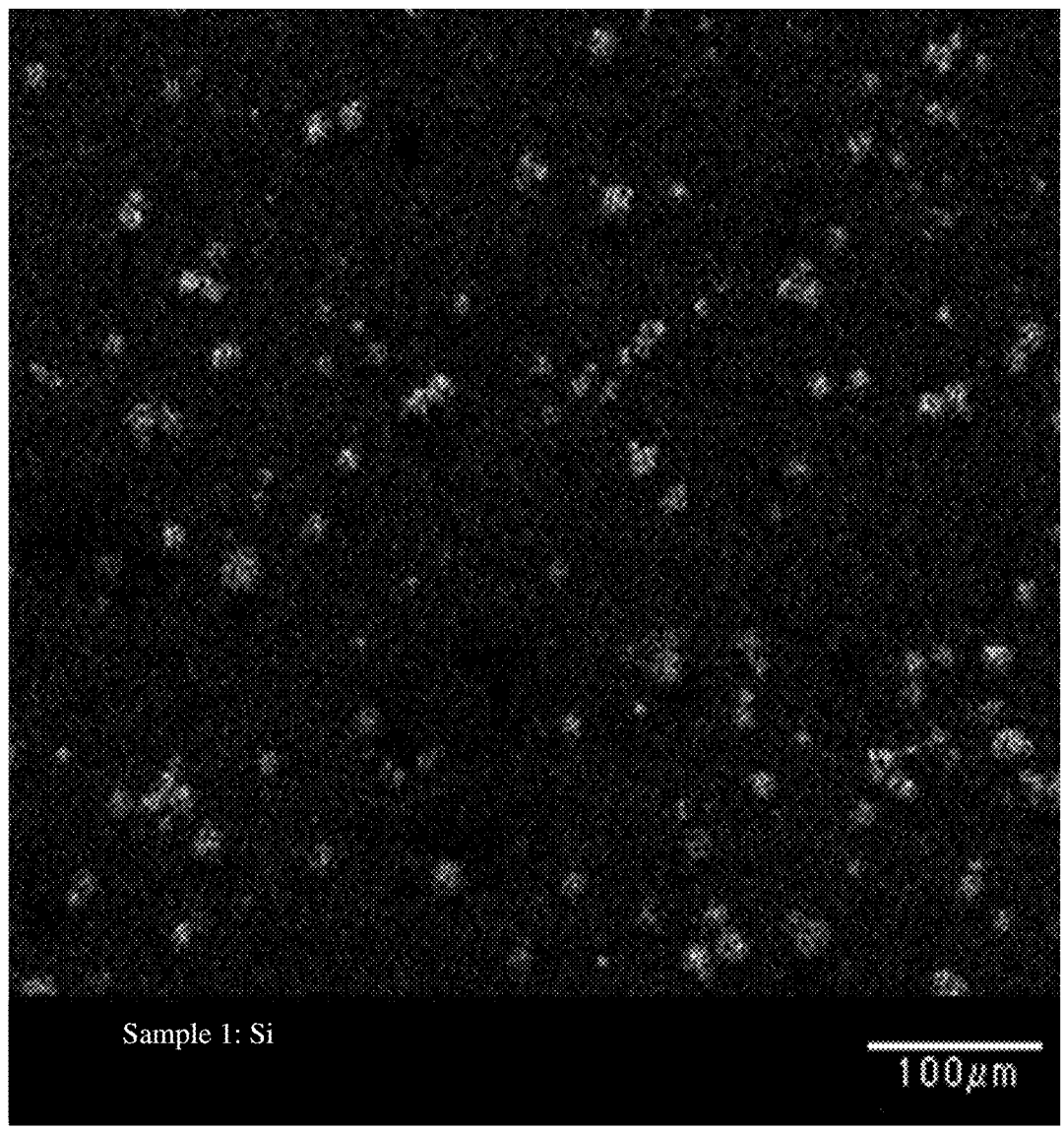
FIG. 8C provides a black and white microscopy photograph showing the elemental distribution of silicon of the area of an exemplary formulation of FIG. 6, also present in FIG. 6, in larger form.

In aspects, the invention provides a composition that is suitable for topical application comprising a matrix composition comprising a mixture of structurally diverse matrix particles, wherein upon application of the composition to a surface (such as, e.g., a plate similar that described in Example 7 or, e.g., human skin), the application result in a distribution of silicon particles at least substantially similar to that shown in FIG. 8C. ASPECT 161.

Figure 8D:
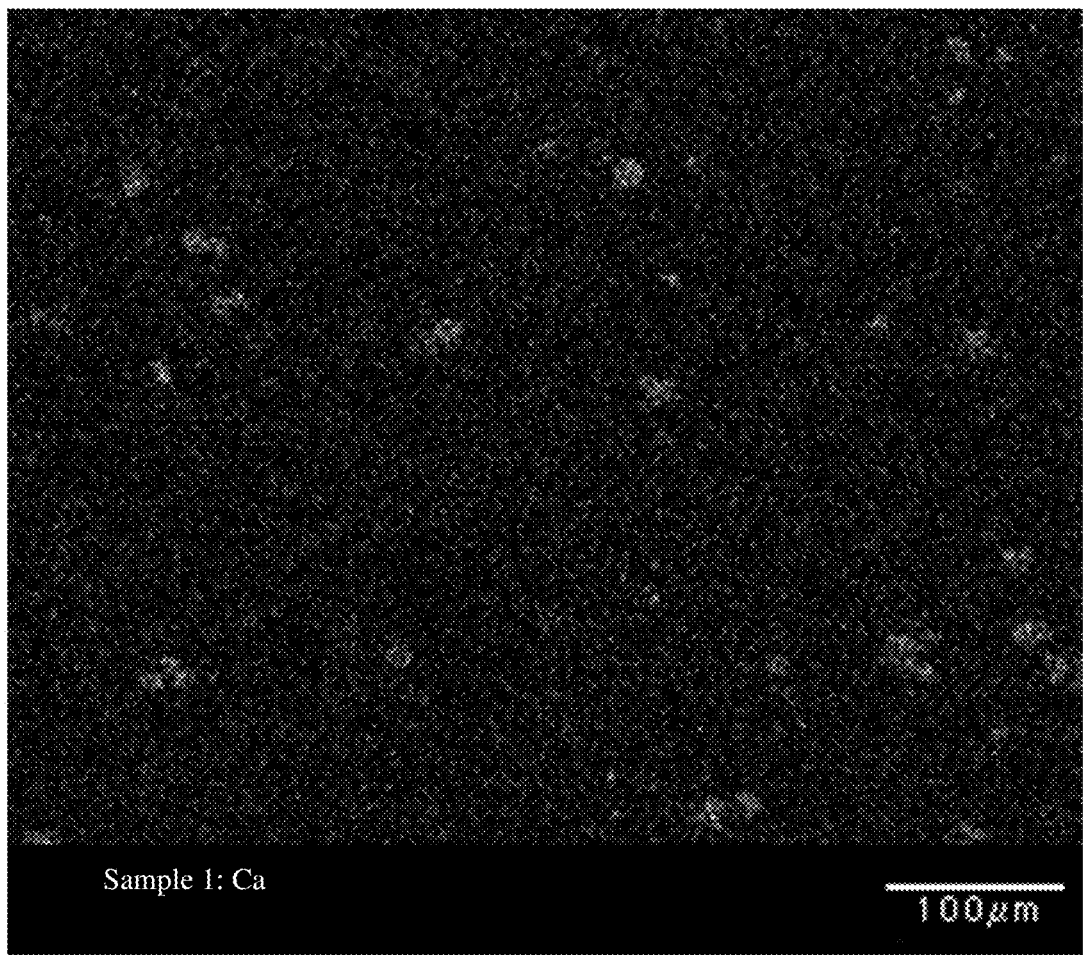
FIG. 8D provides a black and white microscopy photograph showing the elemental distribution of calcium of the area of an exemplary formulation of FIG. 6, also present in FIG. 6, in larger form.

In aspects, the invention provides a composition that is suitable for topical application comprising a matrix composition comprising a mixture of structurally diverse matrix particles, wherein upon application of the composition to a surface (such as, e.g., a plate similar that described in Example 7 or, e.g., human skin), the application result in a distribution of calcium particles at least substantially similar to that shown in FIG. 8D. ASPECT 162.

In aspects, the invention provides the composition of any one or more of aspects 160-162, wherein, uncontradicted, the composition comprises any one or more of the characteristics of compositions described in any one or more of aspects 1-159. ASPECT 163.

In aspects any aspect in this section can be combined.

DETAILED DESCRIPTION OF THE INVENTION

In this section of this disclosure combinations of elements (e.g., in compositions or methods) are discussed as are various types of elements that can form part of compositions or methods of the invention. Readers will understand that despite the inclusion of passages focused on specific elements/steps, any aspect, facet, embodiment, or other description of particular step(s) or element(s) can be applied to any general description of the composition(s)/method(s) of the invention, or any other recited element(s)/step(s) thereof, which are provided in any part of this disclosure.

The invention provides multi-dimensional, multi-particulate mineral-based composition(s) providing detectable or significant photoprotection.

In aspects, composition(s) described herein are characterizable as sunscreen(s).

In aspects, composition(s) are provided in the form of an emulsion (or comprise an emulsion), such as, e.g., a water-in-oil (W/O) emulsion. In aspects, such a composition can comprise, e.g., about 10-30%, e.g., 12.5-27.5%, 15-25%, 12.5-25%, 12.5-22.5%, 15-22.5%, 15-27.5%, 17.5-22.5%, 17.5-25%, 18-22%, or about 20% water (or similar and suitable aqueous composition). In aspects, such a composition can comprise an emulsifier component/means and in aspects a co-emulsifier (which can be considered part of such means or can be characterized as a separate means). In aspects, such compositions can further comprise, e.g., one or more types of emollients, e.g., having an emollient composition making up about 10-35%, e.g., 12-28%, 15-27.5%, 15-30%, 17-25%, 17-27.5%, 17-30%, etc. of the composition. In aspects, the emollient component is made up of a silicone composition component and a monohydric composition component (e.g., in a ratio of about 1:1.5-2.5, or about 1:2 or about in an amount in any of the formulations exemplified herein).

In aspects, composition(s) are provided in the form of anhydrous formulation(s) that lack or substantially lack or essentially lack water or aqueous components (e.g., comprise less than 1%, less than 0.5%, less than 0.2%, less than 0.1%, less than 0.05%, less than 0.01%, less than 0.001%, less than 0.0001%, or less than 0.00001% water content).

In aspects, composition(s) described herein provide significant, e.g., enhanced reflection, refraction, scatter, or other diffusion of sunlight/visible radiation compared to presently available composition(s).

In an exemplary aspect, the invention provides a matrix composition comprising a mixture of structurally diverse matrix particles (1) that are formed from at least 3, 4, or 5 different types of primary particles that are distinguishable from one another due to different characteristics, shape characteristics, or both, (2) that constitute 15-50% of the matrix composition by weight, (3) that comprise or more types of particle agglomerates, (4) where at least 33% of the weight concentration of the matrix particle mixture being composed of UV-protectant metal oxide particles having a minimum particle size of over 100 nm, (5) where scanning electron microscope analysis of the composition fails to identify any significant number of discrete matrix particles of having a size of 100 nm or less (or any discrete particles having a size of 100 nm or less, or less than 5%, 2%, or 1%, e.g., 0.5% or 0.1% or less of matrix particles having a size of 100 nm or less), and (6) where the particle mixture comprises particles that can be classified according to at least four of the following (a) a first primary particle population having a maximum particle size of 250 nm and making up less than 2% of the composition by weight, (b) a second primary particle population having an average particle size of greater than 250 nm and less than 500 nm and making up 5-15% of the composition by weight, at least 25% of the second particle population being composed of UV-protective particles that are at least mostly composed of styrene acrylate copolymer, (c) a third primary particle population having an average particle size of greater than 500 nm and less than 750 nm and making up 5-15% of the composition by weight, at least 75% of the third particle population being composed of UV protective metal oxide particles, (d) a fourth primary particle population having an average particle size of greater than 750 nm and less than 1000 nm and making up 1.75-7% of the composition by weight, at least 75% of the fourth particle population being composed of UV protective metal oxide particles, (e) a fifth primary particle population having an average particle size of greater than 1000 nm and less than 8500 nm and making up 4-9% of the composition by weight, 20-70% of the fifth particle population comprising a glass composition, and (f) a sixth primary particle population having an average particle size of 8500 nm or more and comprising less than 3.5% of the composition by weight, at least 50% of the sixth particle composition being composed of silica particles, wherein (7) the composition exhibits at least one if not all of a sun protection factor (SPF) of at least 30, a critical wavelength of at least 370 nm, UVA/UVB ratio of at least 0.333, and a UVA1 to UV ratio of at least 0.7.

Readers will recognize that matrix particles are distinguishable from primary particles in that, i.a., matrix particles may comprise, e.g., somewhat or mostly comprise, agglomerates formed by primary particles. In aspects, primary particles comprise particles of under 100 nm in size, but such "nano" sized particles form non-nano agglomerate particles in the matrix composition, such that a significant number, or, in aspects, a detectable number, of non-nano particles are not under 100 nm in size, as may be determined by scanning electron microscopy (SEM).

In an aspect, the invention provides a matrix composition that also or alternatively comprise structurally diverse matrix particles of the matrix composition are (1) distributed among five shape-defined particle populations comprising (a) spherical solid porous particles (SSPPs), (b) spherical solid nonporous particles (SSNPs), (c) irregular porous aggregate particles (IPAPs), (d) spherical hollow particles (SHPs), and (e) platelet particles (PPs) and (2) optionally the weight concentration distribution of the particles among the five shape-defined particle populations comprise at least 3, 4, or all 5 of (a) 0.5-2.5 of the composition being made up of SSPPs; (b) 0.75-10%, of the composition being made up of SSNPs; (c) 12-24% of the composition being made up of IPAPs; (d) about 3-7% SHPs; and (e) 0.5-3.5% of the composition being made up of PPs.

In another aspect, the invention provides a matrix composition that also or alternative is characterized by the matrix composition, when spread across a surface using manual distribution comprises multiple layers of the matrix particles, wherein (1) the particles in a first layer cover at least about 65% of the surface and (2) the particles in at least one other layer comprise particles in gaps in the first layer such that the first layer and second layer cover at least about 75% of the surface.

The characteristics of these and other compositions provided by the invention will be further illustrated by examining various components of the matrix compositions of the invention.

Matrix/Formulation/Composition Characteristics

In aspects, the invention is directed to a multidimensional, photo-protective particle compositions. mineral-based sunscreen composition(s) suitable for formulation as, e.g., compact(s), stick(s), lotion(s), cream(s), or other applicable form(s) of administration. In aspects, inventive composition(s) provided herein, upon application, leave minimal or no visible residue. In aspects, a mesh or multidimensional, photoprotective particle 3D matrix, or composition(s) comprising the same, comprises particles having detectably or significantly different size(s).

In aspects, compositions of the invention can be characterizable as a "3D matrix" or, e.g., "ultraviolet (UV) particulate screen," or can be described as forming a "UV mesh." In general, wherever the term composition is used herein readers will understand that it provides implicit support for such a "matrix." Such a substrate mesh or multidimensional, photoprotective particle 3D matrix provides a foundation upon which other compositional elements can be added to form a final composition. In aspects, the invention provided herein comprises a continuous/substantially continuous, flexible, substrate mesh or multidimensional, photoprotective particle 3D matrix.

A "matrix" typically is characterized by the inclusion of ≥2, typically ≥3, ≥4, or ≥5, types of different particles that are distributed throughout a media (formulation, base) in a stable manner. In aspects, particles of a matrix differ from each other by size properties, composition properties, shape properties, or a combination thereof (e.g., at least two thereof or all three thereof). As demonstrated in the Examples herein, a matrix typically comprises multiple layers of particles, e.g., ≥2, ≥3, ≥4, ≥5, or more layers of particles in at least some, most, or generally all of the composition (viewed up/down or along a vertical orientation/axis with respect to the depth of the composition). The particles in layers of a matrix may come in contact or may occupy spaces that are gaps in another layer (again, as exemplified in the Examples and figures provided herewith). In facets, the inclusion of the different size, shape, or compositional particles in the composition DOS promotes layer formation. In aspects, the distribution of particles in different, overlapping layers DOS increases the coverage of a surface (e.g., increasing coverage by ≥2.5%, ≥5%, ≥7.5%, ≥10%, ≥12.5%, or ≥15%). In aspects, the matrix composition is characterized by significant surface coverage with particles due to reduced interstitial spacing between particles arising from the inclusion of different particles, providing opportunities for better particle packing arrangements. In aspects, most particles in the matrix are not associated with any gap of more than about 500, more than about 400, more than about 350, or more than about 300 nm (e.g., 250-500, 300-450, or 300-400 nm).

In aspects, one or more or commonly two or more or three or more particles/particulates (particle/particulate populations), such as, e.g., spherical or quasi-spherical (e.g., $TiO_2$, iron oxides, silica, aluminum oxide, cerium oxide (protect in IR), etc.; hollow spherical (e.g., SunSpheres); 3D aggregated (e.g., ZnO); and, e.g., 3D photonic algal crystal (e.g., Plankton Flower Extr.); e.g., platelets (mica, synthetical mica, clay); are interlocking between each other due to different forms and sizes, forming a matrix, without leaving a detectable or significant amount of interstitial space between them for light (UV/Visible(Blue)/IR) to penetrate and reach the skin, e.g., platelets (mica, synthetical mica, clay); or, e.g., agglomerate(s) of each particle population or agglomerates of particles from multiple populations cited here, are interfacing, interlocking, or other otherwise positioning in close proximity to or between each other/one another due to different forms and sizes, forming a matrix. In aspects, the formed matrix does not leave a detectable or significant amount of interstitial space for light (UV/Visible (Blue)/IR) to penetrate and reach the skin, e.g., in aspects, to penetrate and reach the skin in sufficient amount(s) to cause detectable or significant damage, e.g., burning, such as skin damage recognized in the art (burning, etc.)

In aspects, the amount of space between particles in a composition, e.g., particles of at least 2, at least 3, at least 4, or at least 5 (e.g., 3-5, 2-4, 2-5) different size types, at least 2, at least 3, at least 4, or at least 5 different shape types (e.g., 3-5, 2-4, 2-5 different shape types) or both, is detectably or significantly reduced (i.e., statistically significantly reduced—as determined by one, two, or more appropriate, well-controlled, and adequately powered experiments) as compared to a substantially similar/identical composition lacking the number of such different particle groups.

Therefore, in aspects compositions are capable achieving the 1/3 ratio UVA/UV, protecting as well in UVA, UVA being 1/3 of the UVB which is the SPF number on the label (EU requirement). In aspects, compositions meet proposed FDA requirements of UVA 1/UV ratio.

Particles of the Matrix/Composition

In aspects, compositions comprise multiple particle population(s), each having one or more distinct characteristic(s) from any other one or more particle population(s) in the composition. Examples of characteristics that can define a distinct set of particles include, e.g., size, shape (other than size), solidity, porosity, or composition. Readers will understand that a particular type of particle can be classified in 2 or more populations. E.g., a ZnO particles of a composition can be present in 2, 3, 4, or more particle groupings defined by size based on the distribution of such particles, and can be classified in 1, 2, or 3 shape groupings (e.g., aggregates alone or in combination with rods, spheres, or platelets).

In aspects, as described in detail elsewhere herein, multiple populations of particles participate in the formation of a stable 3D mesh/matrix providing detectable or significant, e.g., effective, e.g., highly effective, protection of surface(s) to which they are applied from sunlight, environmental pollutant(s), or both.

In certain aspects, populations of particles are present within, e.g., participate in the establishment of, a photoprotective particle matrix comprising, e.g., a synergistic combination of one or more metal oxides with one or more non-metal oxide(s).

In aspects, composition(s) provided herein comprise a suspension of particles, e.g., particle population(s) provided herein, wherein the particles of the particle population(s) are evenly dispersed, and the particles have a spatial arrangement such that there is little to no, e.g., there is no detectable or significant, interstitial space present between them. In aspects composition(s) comprise a compact matrix composed of different type(s), form(s), and size(s) of particulates, suspended in a substrate, e.g., provided as an emulsion, that detectably or significantly increases the surface area of protection against UV/Visible (Blue)/IR provided by the composition.

Particle Population(s)

In aspects, an advantage of the composition(s) herein is the ability to sustain an effective distribution of multiple particle populations contained therein.

A "population" of particles typically is understood to mean a collection of particles that are defined by at least one characteristic that separates/distinguishes such particles from one or more other types of particles contained in the composition.

Populations of particles having detectably or significantly can have different compositional nature (e.g., comprise different compound(s), having detectably or significantly different forms (e.g., having detectably or significantly different shapes), having detectably or significantly different sizes, or any combination of any or all thereof.

According to certain aspects, compositions provided by the invention comprise a plurality of particle populations which work cooperatively (e.g., additively or synergistically) to provide the one or more characteristics of composition(s) as described herein (such as, e.g., photoprotection, skin aesthetic(s), etc.) (e.g., with regard to oily texture or appearance, tacky texture, etc., such as one or more characteristic(s) recognized in the art as advantageous for topical skin care product(s) often referred to as related to "cosmetic elegance," a recognized term of art.

In aspects, compositions comprise at least one population of particles comprising metal oxide(s).

In aspects, compositions comprise a population of particles comprising non-metal constituent(s), e.g., non-metal oxide constituent(s). In aspects, compositions comprise a population of silica compound particles, such as, e.g., silica (siliceous compound(s)) of one, two, or three or more different types.

According to aspects, particle(s) can belong to multiple particle population(s), e.g., zinc oxide particles can belong to a population of active ingredient particles, a population of metal oxide particles, a population of irregularly shaped particles, and the like based upon the plurality of characteristics of the zinc oxide particle(s).

Primary Particles, Aggregates, and Agglomerates

Particles can be characterized as primary particles or higher order particles (referred to in the art as particle assemblages).

Readers will understand that the term "primary particle" typically refers to a particle in the state that it was in when added to the composition, its state when the particle is highly dispersed/separated from (disassociated from) other particles, or both. In aspects, the "primary particle" in the context of what is added to form a composition of the invention is an aggregate made of other particles (which in this case may be referred to as sub-particles, so as to not confuse such aggregate constituent particles with other types of primary particles). An aggregate in this context means a composition comprising sufficiently strong chemical association that the aggregate particle generally, substantially entirely, or entirely remains in a stable structure even when the composition in which it is contained is subjected to mechanical or other forces that disrupt some, most, generally all, or substantially all agglomerates in the composition, such as, in aspects, any of the production methods of formulation modification methods described herein (e.g., exposing the composition to a dispersant). As recognized in the art, agglomerates are generally looser assemblages, formed by electrostatic forces, and as indicated, herein mean those associations where some, most, generally all, substantially all, or all of the particles will disassociate when subjected to dispersion or a process that imposes a force strong enough to break such electrostatic interactions.

Primary particles in compositions/matrices of the invention can form higher order particle structures. In aspects, most, generally all, substantially all, or all of such higher order structures are agglomerates formed between one or more types of particles. In aspects, the composition comprises one or more aggregate particle types. In aspects, compositions comprise a zinc oxide aggregate particle, e.g., irregular shape zinc oxide aggregates. In aspects, compositions comprise mesoporous zinc aggregate particles. What characterizes a particle as mesoporous will be known in the art. In aspects, zinc mesoporous particles in compositions comprise average pore diameters in the range of 2-100, 2-80, 2-50, or 2-40 (e.g., 5-50 or 5-40) nanometers.

In aspects, some, most, generally all, substantially all, or all of the particles in a composition will form agglomerates having a particle size of 1 micron or more. In aspects, generally all, substantially all, or all of the particles in a composition will form agglomerates with a size of about 1 micron or more (e.g., as confirmed by electron microscopy). Given the better characterization of primary particles in most cases, however, primary particle sizes are often used to characterize the compositions of the invention.

Size of Primary Particles

In aspects, compositions can comprise one or more population(s) of particles having an average particle size of at least 100 nm (e.g., 100 nm-20000 nm or 100 nm-10000 nm). Such particles are described as "non-nano" particles. In aspects, most, generally all, substantially all, or all of the particles of a composition are non-nano in size.

Uncontradicted, particle sizes herein are determined by the method most used in the relevant art with respect to the type of particle in question or refer to the maximum dimension of the particle in any direction/orientation (e.g., a particle having a length of 250 nm but a width of 50 nm, and a height of 1 nm would be, in one aspect, characterized as having a particle size of 250 nm). Both aspects are provided implicitly by any disclosure of particle size, to the extent that such methods are different. Uncontradicted any reference to particle size herein means the average particle size, mean particle size, or both. Any disclosure of particle size values implicitly also supports embodiments in which all, substantially all, or generally all particles in the composition are with a range defined by the particle size (e.g., disclosure of particles having a particle size of 250 nm or average particle size of 250 nm provides implicit support for a corresponding composition wherein 90% or less or 75% or less of the particles are less than 250 nm in size.

Readers will recognize that sizing of particles can be performed a variety of ways and the numbers provided herein implicitly disclose different aspects in which the particle size is measured using intensity weighted distribution, volume weighted distribution, etc. Uncontradicted, particle size measures herein were generated based on number weighted distribution. Particle size measurement methods are known in the art. In general, any suitable method can be used to analyze particle size, including, e.g., laser diffraction, light scattering methods (e.g., dynamic light scattering), or electron microscopy and related imagine analyses methods, e.g., as exemplified herein. The implicit disclosure of other measurements means that readers will recognize that such terms can be adjusted to accommodate any variations based on change of measurement. For example, calcium borosilicate particles have a mean diameter of about 11 microns according to volume-based particle size analysis vs. 3.3 microns for number-based analysis. Accordingly, volume-based analysis of particles will be adjusted upward for such particles from the ranges provided herein (such particles grouping on a volume basis to around 11 microns, rather than around 3.3 microns)

In aspects, most of the particles in a composition are in a size population of 100-1000 nm. E.g., in aspects, ≥60%, ≥65%, ≥70%, or ≥75%, e.g., about 80%, e.g., 55-85%, 60-80%, 65-85%, 65-80%, or 70-82% of the particles have an average particle size of 100-1000 nm.

In aspects, most or generally all of the particles in a composition have a particle size ~100 nm-~850 nm, ~e.g., ~100 nm-~750 nm, or ~100 nm-~500 nm. In facets, most or generally all of the particles in a composition by weight, by type, or both, have an average particle size of at least 200 nm, e.g., 200-1000 nm or 200-850 nm. In aspects, at least 2.5% of the particles in a composition, e.g., ≥3%, ≥3.5%, ≥4%, or ≥5% of the composition is composed of particles having a size distribution of ~200 nm-~1000 nm, ~250 nm-~1000 nm, ~300 nm-~1000 nm, ~350 nm-~1000 nm, ~400 nm-~1000 nm, ~450 nm-~1000 nm, ~400-~850 nm, ~450-~850 nm, ~500-~850 nm, ~500 nm-~1000 nm, ~550 nm-~1000 nm, ~600 nm-~1000 nm, ~650 nm-~1000 nm, ~700 nm-~1000 nm, ~750 nm-~1000 nm.

In aspects, compositions can comprise one or more population(s) of particles having an average particle size, e.g., having an average maximum dimension in any single direction, of between about 150 nm and about 950 nm, such as, e.g., between ~200 nm-~900 nm, ~250 nm-~850 nm, ~300 nm-~800 nm, ~350 nm-~750 nm, ~400 nm-~700 nm, ~450 nm-~650 nm, or, e.g., ~500 nm-~600 nm. In aspects, a percentage of particles as described herein has a size of between 400-7000 nm, e.g., 400-3000 nm, 400-2000 nm, or 500-1500 nm.

In aspects, compositions can comprise one or more population(s) of particles (in aspects making up 1%-15%, 1-12%, 1-10%, 1-8%, 1-7%, or 1-5%, e.g., 2-12%, 2-15%, 2-10% of the composition), the population of particles having an average particle size, e.g., having an average maximum dimension in any single direction, of between about 1000 nm and about 10000 nm, such as, e.g., between ~1000 nm-~9500 nm, ~1000 nm-~9000 nm, ~1000 nm-~8500 nm, ~1000 nm-~8000 nm, ~1000 nm-~7500 nm, ~1000 nm-~7000 nm, ~1000 nm-~6500 nm, ~1000 nm-~6000 nm, ~1000 nm-~5500 nm, ~1000 nm-~5000 nm, ~1000 nm-~4500 nm, ~1000 nm-~4000 nm, ~1000 nm-~3500 nm, ~1000 nm-~3000 nm, ~1000 nm-~2500 nm, or, e.g., ~1000 nm-~2000 nm.

In aspects, compositions can comprise one or more population(s) of particles having an average particle size, e.g., having an average maximum dimension in any single direction, of between about 1500 nm and about 10000 nm, such as, e.g., between ~2000 nm-~10000 nm, ~2500 nm-~10000 nm, ~3000 nm-~10000 nm, ~3500 nm-~10000 nm, ~4000 nm-~10000 nm, ~4500 nm-~10000 nm, ~5000 nm-~10000 nm, ~5500 nm-~10000 nm, ~6000 nm-~10000 nm, ~6500 nm-~10000 nm, ~7000 nm-~10000 nm, ~7500 nm-~10000 nm, ~8000 nm-~10000 nm, ~8500 nm-~10000 nm, or, e.g., ~9000 nm-~10000 nm.

In aspects, compositions can comprise one or more population(s) of particles having an average particle size, e.g., having an average maximum dimension in any single direction, of about 1000-8500 nm, e.g., between about 1500 nm and about 9500 nm, such as, e.g., between ~2000 nm-~9000 nm, ~2500 nm-~8500 nm, ~3000 nm-~8000 nm, ~3500 nm-~7500 nm, ~4000 nm-~7000 nm, ~4500 nm-~6500 nm, or, e.g., ~5000 nm-~6000 nm. In aspects, such a population of particles makes up about 2-12%, about 2.5-12.5%, about 2.5-15%, about 2-10%, about 3-12%, about 3-9%, 3.5-8.5%, 3.75-7.75%, or 4-7.5% of the composition.

In aspects, compositions can comprise one or more population(s) of particles having an average particle size, e.g., having an average maximum dimension in any single direction, of greater than 5000 nm, e.g., greater than 7500 nm, or greater than 8500 nm, such as, in aspects, 10000 nm and about 20000 nm, such as, e.g., between ~10000 nm-~19500 nm, ~10000 nm-~19000 nm, ~10000 nm-~18500 nm, ~10000 nm-~18000 nm, ~10000 nm-~17500 nm, ~10000 nm-~17000 nm, ~10000 nm-~16500 nm, ~10000 nm-~16000 nm, ~10000 nm-~15500 nm, ~10000 nm-~15000 nm, ~10000 nm-~14500 nm, ~10000 nm-~14000 nm, ~10000 nm-~13500 nm, ~10000 nm-~13000 nm, ~10000 nm-~12500 nm, or, e.g., ~10000 nm-~12000 nm. In aspects, such particles can make up about 0.5-5%, e.g., 0.75-3% or 1-2.5% of the composition. In general, all references to percent of the composition herein mean at least weight percent of the composition.

In aspects, compositions can comprise one or more population(s) of particles having an average particle size, e.g., having an average maximum dimension in any single direction, of between about 10500 nm and about 20000 nm, such as, e.g., between ~11000 nm-~20000 nm, ~11500 nm-~20000 nm, ~12000 nm-~20000 nm, ~12500 nm-~20000 nm, ~13000 nm-~20000 nm, ~13500 nm-~20000 nm, ~14000 nm-~20000 nm, ~14500 nm-~20000 nm, ~15000 nm-~20000 nm, ~15500 nm-~20000 nm, ~16000 nm-~20000 nm, ~16500 nm-~20000 nm, ~17000 nm-~20000 nm, ~17500 nm-~20000 nm, ~18000 nm-~20000 nm, ~18500 nm-~20000 nm, or, e.g., ~19000 nm-~20000 nm.

In aspects, compositions can comprise one or more population(s) of particles having an average particle size, e.g., having an average maximum dimension in any single direction, of between about 10500 nm and about 19500 nm, such as, e.g., between ~11000 nm-~19000 nm, ~11500 nm-~18500 nm, ~12000 nm-~18000 nm, ~12500 nm-~17500 nm, ~13000 nm-~17000 nm, ~13500 nm-~16500 nm, or, e.g., ~14000 nm-~16000 nm.

Exemplary 5 or 6 Particle Size Group Aspects

As indicated above, a composition can comprise 2, 3, 4, or more of the various types of particle populations described herein, on the same basis (e.g., size basis) or mix of bases (e.g., size and shape, size and solidity, or size and composition).

In aspects, the invention provides a dermatologically suitable composition comprising at least 4, at least 5, at least 6, at least 7, at least 8, at least 9, or more, size-defined particle populations.

Under 100 nm Group

In one aspect, the invention provides a particle size-defined population of particles having a particle size of under 100 nm. In aspects, this "under 100 nm" group comprises no detectable amount of "active" microparticles.

In aspects, there is no under 100 nm group. In aspects, all discrete particles that do not go into the solution of the matrix formulation/base are above 100 nm in size.

In other aspects, primary particles of under 100 nm in size tend to sufficiently agglomerate as matrix particles such that no significant number, or no observable number, e.g., no more than 2.5%, no more than 1%, no more than 0.5%, no more than 0.1%, or no more than 0.01% of the primary particles are observable as having a matrix particle size of 100 nm or less.

An "active" microparticle refers to a microparticle that US FDA has recognized as an active ingredient component for sunscreen products. The present FDA-recognized GRASE active particles are zinc oxide particles and titanium dioxide particles. Readers will understand that compositions can contain other metal oxide particles and that such particles may exert DOS effects in terms of light/radiation modulation (absorption, refraction, absorption, deflection, blocking, scattering, etc.).

In aspects, some, most, generally all, or all of the under 100 nm group, if present, is composed of iron oxide particles. In aspects, most, generally all, or substantially all iron oxide particles can be characterized as having an average particle size of less than 50 nm. In aspects, most, generally all, or all iron particle oxide particles in this or any other aspect/context are solid and spherical/quasi-spherical in shape. In aspects, the composition lacks any such particles or is substantially free of such particles.

In aspects, the under 100 nm group comprises some amount of clay particles, e.g., hectorite clay particles (which may have a size distribution of e.g., 4-1000 nm) (in aspects, such particles are platelet-like/flake-like in shape). Terms such as "plate," "platelet," "flake," etc., with respect to compositional particles are known in the art to refer to shapes similar to rectangular or oval shapes (having a long length than width and small height). In aspects, some, most, or generally all clay particles in a composition can be characterized as irregular (most, generally all, or substantially all particles varying detectably or significantly in size, shape, or both). In aspects, the composition lacks any such particles or is substantially free of such particles.

In aspects, some amount of natural mica particles, synthetic mica particles, or both, are found in the under 100 nm particle group. In aspects, such particles can have a distribution of 10-12,500 nm and 12-16,000 nm, respectively. Accordingly, some amount of particles of these materials may be found in this group. In aspects, the amount of either or both is less than 1.5%, less than 1.25%, less than 1%, less than 0.75%, less than 0.5%, less than 0.2%, less than 0.1%, or less than 0.05% of the composition. In aspects, the composition is free or substantially free of particles of either group in this size range. In aspects, either or both of such particles have a platelet-like shape. In aspects, the platelet-like shape can be characterized as irregular.

In aspects, the under 100 nm group further comprises cerium oxide particles. In aspects, most, generally all, substantially all, or all of the $CeO_2$ particles have an average particle size of less than 50 nm. In aspects, most, generally all, or all of such particles are solid particles. In aspects, the composition lacks any such particles or is substantially free of such particles.

In aspects, this group makes up 0-5%, e.g., 0.1-5%, 0.1-2.5%, 0.3-3%, 0.2-2%, 0.1-1.5%, 0.1-1%, 0.2-1%, 0.25-1%, 0.25-0.75%, or 0.3-0.9% of the composition.

Under 250 nm Group or 100-250 nm Group

A second size grouping of particles that can be present can be characterized by a particle size range of either under 250 nm (where there is no under 100 nm group—i.e., the composition is free of or substantially free of particles under 100 nm in size) or a range of 100-250 nm. In aspects, some of the particles in either or both of these groups are clay particles, synthetic mica particles, natural mica particles, or the other particles described in the under 100 nm group (e.g., iron oxide particles). In aspects, this group makes up 0-5%, e.g., 0.1-5%, 0.1-2.5%, 0.3-3%, 0.2-2%, 0.1-1.5%, 0.1-1%, 0.2-1%, 0.25-1%, 0.25-0.75%, or 0.3-0.9% of the composition.

Under 250 nm-500 nm Group, 250-400 nm Group, or 400-500 nm Group(s)

In aspects, compositions comprise a group defined by a particle range of 250-500 nm, or two sub-groups thereof, e.g., a group of 250-400 nm particles and a group of 400-500 nm particles.

In aspects, the 250-500 nm group or 250-400 nm group comprises styrene acylate copolymer particles. In aspects, most, generally all, substantially all, or all of the styrene acrylate copolymer particles of the composition are within the 250-500 or 250-400 nm group. In aspects, such particles make up at least 25%, at least 33%, or most of the particles in one or more of such groups. In aspects, most, generally all, or all of such particles are hollow particles. In aspects, most, generally all, or all of such particles are spherical particles.

In aspects, this/these group(s) are the smallest size groups to comprise an appreciable amount (≥~1%) of metal oxide polymers. In aspects, zinc oxide particles in these group(s) make up about 1-6%, e.g., 1.25-5% or 1.5-5%, e.g., 2-5%, 2.5-4.5% of the weight of the composition. In aspects, these groups, e.g., the 400-500 nm group, comprise(s) titanium dioxide particles, in aspects making up 0.05-1% of the composition by weight. In aspects, some amount of clay or mica particles also may be present in such/these group(s).

In aspects, a 250-500 nm group is one of the largest groups, if not the largest group, in terms of contribution to the weight of the overall composition. In aspects, such a group is the largest or second largest group in the size-defined particle population groups in the composition.

500-750 NM Group

In aspects, compositions comprise a group defined by a particle range of 500-750 nm. In aspects such a group accounts for 5-15% of the composition, such as 6.5-12.5% of the composition, e.g., 6.5-12% of the composition. In aspects, most, generally all, or all of the particles in this group are metal oxide particles. In aspects, most, generally all, or substantially all, if not all, particles in this group are zinc oxide particles. In aspects, this group contains 0.05-1.5% or 0.05-2% titanium dioxide particles (based on weight of the composition). In aspects, the ratio of titanium dioxide particles to zinc particles is 1:3 to 1:250, e.g., 1:4 to 1:200. In aspects, a 500-750 nm group is one of the largest groups, if not the largest group, in terms of contribution to the weight of the overall composition. In aspects, such a group is the largest or second largest group in the size-defined particle population groups in the composition.

750-1000 NM Group

In aspects, compositions comprise a group defined by a particle range of 750-1000 NM. In aspects, such a group makes up 1-7%, 1.5-6%, 1.75-5.75%, or 2-5% (e.g., 2-4.5%) of the composition. In aspects, the particles of this group are mostly, generally, or entirely metal oxide particles, with most, generally all, substantially all, or all of such particles being zinc oxide particles (e.g., comprising 2-4% of the weight of the composition is in zinc oxide particles of this group). In aspects, the metal oxide particles also contain titanium dioxide particles. In aspects, the relationship of titanium dioxide to zinc oxide particles in this group is defined by a ratio of 1:5 to 1:500. In aspects, this group lacks titanium dioxide particles. In aspects, this is the largest group to comprise an appreciable amount of metal oxide particles. In aspects, the amount of metal oxide particles is greater than the amount of glass/calcium borosilicate particles. In aspects, the glass/calcium borosilicate and metal oxide particles of this group are present in a ratio of about 1:4 to about 1:20, such as, e.g., about 1:5 to about 1:15.

1000-8500 nm Group

In aspects, compositions comprise a group defined by a particle range of 1000-8500 nm. In aspects, this group comprises glass bead particles. In aspects, the glass bead particles mostly, generally, or entirely are calcium borosilicate particles. In aspects, such particles are mostly, generally, or only solid particles. In aspects, such particles are mostly, generally, or only spherical or quasi-spherical particles. In aspects, such glass particles are present in a ratio of 1:1.5 to 1:4 or 1:1.5 to 1:3 to the amount of metal oxide particles in the group. In aspects, this group contributes 2-10%, 3-9%, e.g., 3.5-8.5%, 4-8% or 4-7.5% of the composition by weight. In aspects, this group contains generally all, substantially all, or all of the calcium borosilicate particles in the composition.

Over 8500 nm Group (or Over 10000 nm Group)

In aspects, compositions comprise a group defined by a particle range of ≥8500 nm or ≥10000 nm. In aspects, this group is composed mostly, generally, substantially only, or entirely of silica particles. In aspects, the silica particles are solid particles. In aspects, the silica particles are porous particles. In aspects, the silica particles exhibit oil absorption of 200-300 ml/100 g of material, e.g., 220-280- or 230-270- ml oil absorption per 100 gm of material. In aspects, this group is generally free, substantially free, or entirely free of metal oxide particles. In aspects, this group makes up about 0.5-3%, 0.5-2.5%, 0.75-2.25%, 1-2%, 1.25-1.75, or about 1.5% of the composition. As with any of such size-defined or otherwise characterized particle groups, in aspects, compositions can lack this group.

Exemplary Combination of Groups (6)

In aspects, compositions comprise 3, 4, 5, 6, or 7, etc., of any of the above-described or other groups of particles. For example, in an aspect, the invention provides a dermatologically suitable sunscreen composition comprising a particle mixture that makes up 20-50% of the composition by weight, at least 40% of the weight concentration of the overall particle mixture being composed of metal oxide particles, the particle mixture comprising particles from (1) a first primary particle population having a maximum particle size of 250 nm or less and comprising less than 3.5% of the composition by weight (0-3.5%, 0-2.5%, 0-1.5%, 0-1%, 0-0.75%, or about 0.5% of the composition by weight), wherein optionally less than 5% of the first particular population being composed of metal oxide particles, (2) a second primary particle population having an average particle size of greater than 250 nm and less than 500 nm and optionally making up 5-15% (e.g., 6-14%, 6.5-13.5%) of the composition by weight, and further optionally where at least 20%, 25%, or 35% (e.g., 15-40%, 20-35%, or 22.5-32.5%) of the second particle population are composed of UV-protective particles that are at least mostly composed of styrene acrylate copolymer, (3) a third primary particle population having an average particle size of greater than 500 nm and less than 750 nm and making up 5-15% (e.g., 6-14%, 6.5-13.5%) of the composition by weight, wherein further optionally at least 75% of the third particle population being composed of UV-protective metal oxide particles, (4) a fourth primary particle population having an average particle size of greater than 750 nm and less than 1000 nm and making up 1.75-7% of the composition by weight (e.g., 2-6%, 2-5.5%, or 2-5%), optionally where at least 75% of the fourth particle population is composed of UV-protective metal oxide particles, (5) a fifth primary particle population having an average particle size of greater than 1000 nm and less than 8500 nm and making up 3-9% of the composition by weight (e.g., 3.5-8.5% or 4-7.5%), optionally where 20-70% of the fifth particle population particles comprising a glass composition (e.g., that is optionally mostly, generally, or entirely calcium borosilicate), and (6) a sixth primary particle population having an average particle size of 8500 nm or more and comprising less than 3.5% of the composition by weight (e.g., 0-3.3%, 0.5-2%, 0.75-1.75%, or about 1.5%), optionally where at least 50% of the sixth particle composition are composed of silica particles, and wherein at least most (if not at least generally all or substantially all) of the particles in the (overall) particle mixture form agglomerates in the water-in-oil emulsion that have an average size of 1 micron or greater and the composition exhibits a sun protection factor (SPF) of at least 20 and a UVA I to UV ratio of at least 0.7.

Micro/Meso/Macro Particle Size Group Aspects

In another facet, the invention provides compositions in which some, most, generally all, substantially all, or all of the particles fall within three size groups, which can be referred to as a microparticle, mesoparticle, and macroparticle group, respectively (microparticles of the smallest group having a size of 100>x<1000, meso particles having a size of 1000>x<10000, and macroparticles having an average size of ≥10000 NM). In aspects, no nano particle (particles of less than 100 nm in size) is present in formulation, or the composition comprises less than 5%, less than 3%, less than 2%, less than 1%, less than 0.5%, less than 0.1%, less than 0.01%, or less than 0.001% nanoparticles. In aspects, the composition lacks any "active" metal oxide particles that are nano sized or is at least substantially free of such particles. In aspects, zinc particle aggregate in the composition can be, e.g., 99.9% over 100 nm (500-800 nm avg particle size). An example of various particles, some, most, generally all, or all of which that may be present in certain compositions is included in the following table—

100-about 1000 nm), wherein at least about 50% (or at least about 60% or at least about 65%) of the microscale particle component is composed of UV scattering particles and the microscale particle component constitutes about 10-about 35% of the composition by weight (e.g., about 12-about 33%, in aspects about 25-about 33%, about 26-about 32%, or about 26.5%-about 31.5% of the composition); (2) a mesoscale particle component that comprises an effective amount of dermatologically suitable mesoscale particles having particle sizes i.e., maximal singe-direction particle sizes; maximum particle size in any one direction) of about 1000-about 10000 nm (or, e.g., average particles sizes of about 1,000-about 10,000 nm), wherein the mesoscale particle component constitutes about 0.5-about 2.5% of the composition and at least about 50% of the mesoscale particle component (or at least about 60%, about 70%, about 80%, or at least about 90%) is composed of particles made of a material that causes the mesoscale particle component to significantly enhance (i.e., statistically significantly improve) the light scattering capability of the composition; and (3) a macroscale particle component comprising an effective amount of dermatologically suitable macroscale particles having particle sizes (i.e., maximal singe-direction particle sizes; maximum particle size in any one direction) of about 10,000-about 15,000 nm (or, e.g., average particle sizes of about 10,000-about 15,000 nm), wherein the macroscale particle component constitutes about 0.5-about 3% of the composition and at least about 50% of the macroscale particle component is composed of particles that are made of a material that (a) causes the macroscale (or mesoscale) particle component to significantly enhance (e.g., statistically significantly enhance) the light scattering capability of the composition, (b) significantly reflects or absorbs blue light (e.g., statistically significantly increases the reflection, absorption, or reflection and absorption of blue light) (light

|  | 100 ≥ X ≤ 1,000 | 1,000 > X < 10,000 | 10K > X < 20K (under 15,000-LS) | Particle Shape |
|---|---|---|---|---|
| ZnO | ≥800 | | | Aggregate-Irregular |
| TiO$_2$ | ≥100 | | | Spherical |
| FeO | 3-36.8 | | | Spherical |
| CeO2 | 25 | | | Spherical |
| Al2O3 | 100-500 | | | Spherical/Grain like |
| Styrene Acrylate Copolymer | ≥300 | | | Hollow Spherical |
| Mica | | | 10-12,500 | Platelets Irregular |
| Synthetic Mica | | | | Platelets |
| Fluorphlogopite | | | 12-16,000 | Platelets Irregular |
| Disteardimonium Hectorite | 43-1,000 | | | Platelets Irregular |
| Silica | | 9,930 | | Spherical, porous |
| Calcium, Sodium Borosilicate | | | 9-13,000 | Spherical, non-porous |
| Photonic Algal Crystals (80% silica) | | | 19,800 | Structured/irregular |

Various detailed examples of such compositions will now be described to further exemplify how such aspects of the invention can be combined.

In aspects, the invention provides a dermatologically suitable composition comprising a combination of (1) a microscale particle component comprising an effective amount of dermatologically suitable microscale particles having particle sizes (i.e., maximal singe-direction particle sizes; maximum particle size in any one direction) of about 100-about 1,000 nm (or, e.g., average particle sizes of about with wavelengths in the range of about 380-about 495 nm, such as about 380-about 450 nm, e.g., about 400-about 450 nm, about 450-about 495 nm, or about 425-about 475 nm), or (c) causes the macroscale/mesoscale particle component to significantly enhance (e.g., statistically significantly increase) the light scattering capability of the composition and significantly reflects, absorbs, or reflects and absorbs blue light (e.g., statistically significantly increases the reflection, absorption, or reflection and absorption of blue light) (light with wavelengths in the range of about 380-about 495 nm, such as about 380-about 450 nm, e.g., about 400-about 450 nm, about 450-about 495 nm, or about 425-about 475 nm).

In aspects, the invention provides a dermatologically suitable composition comprising a combination of (1) a microscale particle component comprising an effective amount of dermatologically suitable microscale particles having a maximum one-dimension particle size of about 100-about 1,000 nm (or, e.g., average maximum particle sizes of about 100-about 1000 nm), wherein at least about 65% of the microscale particle component is composed of particles having a non-spherical/irregular shape and at least about 5% (e.g., at least about 7.5%, at least about 10%, or at least about 12.5%, such as about 10-about 20%, about 12.5-about 25%, about 12.5-about 20%, about 15-about 25%, about 15-about 20%, about 10-about 15%, about 10-about 12.5%, about 12.5-about 15%, about 12.5-about 17.5%, or about 10-about 25%) of the microscale particle component is composed of particles having a spherical shape ("spherical particles" including substantially spherical particles, wherein a spherical particle has no single particle dimension which varies by more than about 20% from any other single dimension of the particle); (2) a mesoscale particle component that comprises an effective amount of dermatologically suitable mesoscale particles having a maximum one-dimension particle size of about 1000-about 10,000 nm (or, e.g., average particles sizes of about 1,000-about 10,000 nm), wherein at least about 50% (or at least about 60%, about 70%, about 80%, about 90%, about 95%, or at least about 99%) of the mesoscale particle component is composed of particles having a porous, spherical shape; and (3) a macroscale particle component comprising an effective amount of dermatologically suitable macroscale particles having a maximum one-dimension particle size of about 10,000-about 15,000 nm (or, e.g., average particle sizes of about 10,000-about 15,000 nm), wherein at least about 50% (or at least about 60%, about 70%, about 80%, about 90%, about 95%, or at least about 99%) of the mesoscale or macroscale particle component is composed of particles having a non-porous, spherical shape.

In aspects, the invention provides a dermatologically suitable composition comprising a combination of (1) mesoporous light reflecting metal oxide microscale particles, wherein in aspects such particles are mostly, generally, substantially only, or only provided in aggregate form, that have a maximum single dimension of about 100-about 1,000 nm in size (or, e.g., have an average size of about 100-about 1,000 nm) and are at least about 50% (e.g., at least about 60%) composed of a light reflecting metal oxide in which most of the pores in the particles have a maximum dimension of about 2-about 100 nm and at least about 80% (e.g., at least about 90%, about 95%, about 99%, or about 100%) of the mesoporous particles comprise zinc oxide, (2) mesoscale light scattering spherical silica particles having a maximum single dimension of about 1,000 to about 10,000 nm (or, e.g., average particle sizes of about 1,000-about 10,000 nm), and (3) light scattering spherical glass macroscale particles having a maximum single dimension of about 10,000 to about 15,000 nm (or, e.g., have an average size of about 10,000 to about 15,000 nm), wherein (I) the ratio of the weight concentration of microscale particles to macroscale particles in the composition is about 15:1 to about 60:1, such as about 20:1-about 55:1 or about 30:1-about 55:1 or about 40:1 to about 50:1 and (II) the weight concentration of microscale particles to mesoscale particles in the composition is about 15:1 to about 60:1, such as about 20:1-about 55:1 or about 30:1-about 55:1 or about 40:1 to about 50:1.

In aspects, the invention provides a dermatologically suitable composition comprising a combination of (1) a microscale particle component comprising an effective amount of dermatologically suitable microscale particles having a particle size (i.e., a maximum one-dimension particle size) of about 100-about 1,000 nm (or average maximum particle size of about 100-about 1000 nm) and comprising (a) a collection of mesoporous, mineral oxide, stably-aggregated light scattering particulates, (b) a collection of hollow, spherical, light scattering particles; (c) a collection of platelet-shaped particles composed of a dermatologically suitable clay bulking agent; and (d) an optional collection of solid (including substantially solid) non-zinc mineral oxide particles, wherein the ratios of the weight concentration of the mesoporous mineral oxide particles to the platelet-shaped particles and hollow spherical particles are each at least about 3.5:1 (e.g., at least about 4:1, about 4.5:1, or at least about 5:1, such as about 3.75:1-about 7.5:1, about 4:1-about 6.5:1, or about 4.25:1-about 6.25:1); (2) a mesoscale particle component that comprises an effective amount of dermatologically suitable mesoscale particles having a particle size (i.e., a maximum one-dimension particle size) of about 1000-about 10,000 nm (or, e.g., average particles size of about 1,000-about 10,000 nm), wherein at least about 50% (or at least about 60%, about 70%, about 80%, about 90%, about 95%, or at least about 99%) of the mesoscale particle component is composed of solid light scattering particles; and (3) a macroscale particle component comprising an effective amount of dermatologically suitable macroscale particles having a particle size (i.e., a maximum one-dimension particle size) of about 10,000-about 15,000 nm (or average particle size of about 10,000-about 15,000 nm), wherein at least about 50% (or at least about 60%, about 70%, about 80%, about 90%, about 95%, or at least about 99%) of the macroscale/mesoscale particle component is composed of solid light scattering particles, and wherein at least most of the mesoscale particles and macroscale particles comprise different compounds (compounds differing by one or more detectable characteristic(s)) comprising detectably or significantly different light scattering properties.

In aspects, the invention provides a dermatologically/cosmetically suitable composition comprising a combination of (1) an effective amount of mesoporous zinc oxide particles having a particle size (maximum particle size or average particle size or average maximum particle size in one or more dimensions) of at least about 800 nm and (2) an effective amount of calcium sodium borosilicate particles, wherein the calcium sodium borosilicate particles and mesoporous zinc particles are in a ratio of about 1:6 to about 1:12, such as about 1:7 to about 1:10.

In aspects, the invention provides a dermatologically suitable composition comprising a combination of (1) an effective amount of platelet-shaped particles with a particle size (maximum particle size or average maximum particle size in one or more dimensions) of between about 50 and about 1000 nm (e.g., with an average particle size of at least about 100 nm) that are composed of a dermatologically suitable clay bulking agent (e.g., a hectorite clay), (2) an effective amount of irregularly-shaped (e.g., non-spherical) aggregated mesoporous light scattering particles of at least about 800 nm in size, and (3) an effective amount of spherical light scattering particles comprising (a) hollow spherical particles and (b) solid spherical particles, wherein the solid spherical particles and present in a ratio with the hollow spherical particles of about 0.5:1 to about 1:1.5, such as about 0.75:1 to about 1:1.25, such as about 0.8:1 to about 1:1.2, wherein (4) (a) the ratio of the weight concentration contribution of the platelet-shaped particles to spherical particles is about 1:12 to about 1:25, (b) the ratio of the spherical particles to the irregularly-shaped aggregated mesoporous particles is about 1:2 to about 1:3, such about 1:2.5, 1:2.25, or about 1:2.75, or (c) both (a) and (b) are true.

In aspects, the invention provides a dermatologically suitable composition comprising (1) an effective amount of irregularly-shaped (e.g., non-spherical) porous UV light scattering metal oxide particles having particle sizes (or average particle size) of at least about 500 nm, such as at least about 750 nm, such as at least about 800 nm with an average particle size of $\geq\sim 1,000$ nm and (2) a number of regularly shaped, spherical and non-spherical particles that are at least mostly composed of material that is dermatologically suitable, which detectably or significantly enhance the UV scattering properties of the composition, wherein (I) the minimum average particle size for any type of particles in the composition is at least about 100 nm in size, (II) the maximum average particle size for any type of particles in the composition is about 15,000 nm in size, (III) the composition exhibits an SPF of at least about 40, such as about 50, e.g., about 30-65, about 35-65, about 30-60, about 40-60, about 45-60, or about 45-55, (IV) (a) the UVA/UVB (SPF) protection measure for the composition is at least 1/3 of the in-vivo SPF with a critical wavelength (CW)>370 nm; (b) the UVA-I/UV ratio is $\geq\sim 0.7$, (average absorbance in UVA-I (340-400 nm) to the total UV (290-400 nm)), or (c) both (a) and (b) are true, and (V) a statistically significant number of test subjects in an adequately powered survey/trial report that the composition is substantially non-whitening on Fitzpatrick Skin Types I-IV.

In aspects, the invention provides a dermatologically suitable composition that is substantially free, essentially free, or entirely free of any polyethylene glycol compounds (PEGs) the composition comprising, consisting of, or consisting essentially of a stable water-in-oil emulsion, the emulsion comprising an emulsifier component, wherein at least most of the emulsifier component on a weight basis is composed of polyglyceryl-2 sesquioleate and wherein polyglyceryl-2 sesquioleate accounts for at least about 8% (e.g., at least about 10%, such as at least about 11%) of the composition (on a weight percent basis), and (b) an effective amount of a co-emulsifier (e.g., a glyceryl dibehanate, tribehenin, and glyceryl behenate co-emulsifier, such as Compritol 888 CG Pellets), which is present in an amount accounting for at least about 0.5 wt. % of the composition, wherein the ratio of the polyglyceryl-2 sesquioleate to the co-emulsifier is about 15:1 to about 25:1, such as about 16:1, about 17:1, about 18:1, about 19:1, or about 20:1, wherein the composition comprises a mixture of mesoporous zinc dioxide aggregated microparticulate particles (coated or uncoated) in a concentration of at least about 20 weight percent in combination with other regular spherical and regular non-spherical particles, wherein the other regular spherical and non-spherical particles detectably or significantly promote the UV scattering/light scattering properties of the composition, and wherein the composition exhibits an SPF of at least about 40, e.g., about 50 (e.g., about 45-65).

In aspects, the invention provides a dermatologically suitable composition that significantly reduces UV exposure when applied to the skin in effective amounts, detectably or significantly reduces blue light exposure when applied to the skin in effective amounts, and detectably or significantly reduces infrared radiation exposure when applied to the skin in effective amounts, comprising (1) an effective amount of mesoporous metal oxide microparticles, (2) a natural biologic extract component that exhibits detectable or significant blue light scattering effects and detectable or significant infrared radiation, and (3) an effective amount of a dermatologically suitable glass composition (e.g., calcium sodium borosilicate) that detectably or significantly scatters blue light, wherein the weight concentration ratio of the mesoporous metal oxides to the glass composition is about 8:1 to about 12:1 (e.g., about 10:1) and the weight concentration ratio of the mesoporous metal oxides to the biological extract component is about 20:1 to about 30:1, such as about 21:1-about 27:1, e.g., about 22:1 to about 25:1 wherein the composition (I) exhibits an SPF of at least 40, such as about 50, e.g., 30-65, 35-65, 30-60, 40-60, 45-60, or 45-55, (II) the UVA/UVB (SPF) protection measure for the composition is at least 1/3 of the in-vivo SPF with a critical wavelength (CW)>370 nm; (iii) the UVA-I/UV ratio is $\geq\sim 0.7$, (average absorbance in UVA-I (340-400 nm) to the total UV (290-400 nm)), or (iv) the composition exhibits a combination of some or all of (i)-(iii).

Other examples of similar and alternative compositions are provided elsewhere.

Particle Shapes

In aspects, a mesh or multidimensional, photoprotective particle 3D matrix, or composition(s) comprising the same, comprises particles having detectably or significantly different shape(s) (in a manner other than just different size).

In aspects, particles can of a type, population, or both, can mostly, generally only, or at least substantially only have a regular shape (albeit with permissible minor deviations). Particles can have a wide-variety of shapes including cubic/ square or square-like (cuboid), round/circular and spherical/ spheroid shapes, rod-like shapes, platelet/flake-like shapes, and the like (e.g., squircular shape(s)), which are known in the art or as may be suitably developed with routine experimentation. In aspects, particles of a type, population, or composition can at least mostly, at least generally, at least substantially or can be described as spherical, spheroid, or quasi-spherical.

In one aspect, the invention provides a composition characterized by, i.a., comprising a mixture of spherical solid porous particles (SSPPs), spherical solid nonporous particles (SSNPs), irregular porous aggregate particles (IPAPs), spherical hollow particles (SHPs), and platelet particles (PPs), which, may some, mostly, generally, substantially, or entirely be characterized as irregular shaped platelet particles (ISPPs).

In aspects the composition comprises some, most, generally all, or all of the following (3, 4, or 5 of the following)—(1) about 0.5-2.5%, e.g., 1-2%, SSPPs; (2) about 0.75-10%, e.g., about 1-8% (e.g., 1-3%, 3-6%, 4-7%) of SSNPs; (3) 12-24% of IPAPs (e.g., 12-23 or 12.5-22.5% or 14-23 or 14-22.5% IPAPs); (4) 3-7%, 4-6%, or 4.5-5.5% SHPs; and (5) 0.5-3.5%, 0.5-3%, 0.75-3% (e.g., 0.5-1.3% or 2-3%) of PPs. In another aspect, the invention provides compositions characterized by the presence of 3, 4, or 5 of SSPPs, SSNPs, IPAPs, SHPs, and PPs, wherein the ratio of the present shape particle populations is approximately according to the weight concentration ratio (1) 1 part (SSPP); (2) 0.3-6 such as 0.3-5.4 or 0.3-5.7 parts SSNPs; (3) 5-20, e.g., 8-16 parts IPAPs; (4) 2-5, 2.5-4.5, or 3-4 parts SHPs; and (5) 0.2-4, e.g., 0.3-2 parts PPs. Readers using knowledge can calculate corresponding particle number ratios from such weight concentration ratios and use such particle number ratios to alternatively characterize aspects of the invention. Alternatively, in aspects, the invention is characterized by compositions comprising two shape type populations of metal oxide particles (e.g., one solid spherical/quasi spherical and one irregular porous aggregate) (optionally where such particles are also compositionally different, e.g., $TiO_2$ and ZnO) and two types of silica particles (spherical sold non-porous and spherical solid porous) (again, optionally where such silica particles have different compositions).

Uncontradicted, readers will interpret any of these terms as implicitly disclosing a corresponding element/aspect with the related term in its place. Moreover, readers will understand that "spherical" in the context of particles does not always mean perfect spherical. Accordingly, spherical particles can, uncontradicted, include particles having a shape having no single dimension that is more than about 20% greater than any one or more other dimension, such as, e.g., having no single dimension that is more than about, e.g., 18%, ~16%, ~14%, ~12%, ~10%, ~8%, ~6%, ~4%, ~2%, or, e.g., no more than about 1% greater than any other dimension. In aspects, such spherical particle(s) can be, e.g., solid or can, e.g., be porous or hollow.

In aspects, particles, e.g., spherical particles, may be porous, maybe hollow, or may be both.

"Porous" particles are known in the art. In aspects, porous particles include particles comprising at least about 1% empty space, e.g., ≥~2%, ≥~3%, ≥~4%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, or, e.g., ≥~90% empty space. In other aspects a porous particle is characterized by its ability to DOS uptake surrounding materials, e.g., to absorb oils from a base of a matrix composition.

"Hollow" particles also are known. In aspects, "hollow" particles are particles comprising at least greater than about 91% empty space wherein the empty space is contiguous and does not contain solid material within its boundary(ies.)

In aspects, solid, spherical particles can be (comprise, mostly comprise, generally consist of, or consist of), e.g., particles of $TiO_2$, FeO, CeO, $Al_2O_3$, synthetic mica (fluorflogophite), or Covabead Crystals/Glass-like particles, etc.

In aspects, porous, spherical particles can be, e.g., silica (Silispheres) and hollow spheres (styrene acrylate copolymer, e.g., SunSphere Powder.)

In aspects, porous, spherical particles, hollow spheres, or both are able to detectably or significantly reflect, redirect, or refract light.

In aspects, particles can be at least mostly, at least generally, at least substantially or can be described as non-spherical.

In aspects, a non-spherical particle is any particle that would not be recognized in the art as being spherical (spheroid, quasi-spherical, or truly spherical). In aspects, some, most, generally all, or all non-spherical particles of a composition, population, or type, have a shape having at least one dimension that is more than about 20% greater than any one or more other dimension(s), such as, e.g., having a single dimension that is more than about, e.g., 22%, ~25%, ~30%, ~35%, ~40%, ~45%, ~50%, ~55%, ~60%, ~65%, ~70%, ~75%, ~80%, ~85%, ~90%, or, e.g., ~95% greater than any one or more other dimension(s).

Like spherical particles, non-spherical, or irregularly shaped particles can be solid or non-solid, e.g., porous or hollow as described above. In aspects, exemplary non-spherical, solid particles can be (comprise, mostly comprise, generally consist of, consist of, etc.), e.g., ZnO platelets, clays, e.g., clay platelets, etc.

In aspects, exemplary non-spherical porous particles can be (comprise, mostly comprise, generally consist of, consist of, etc.), e.g., 3D Photonic Algal Crystal, mesoporous (sometimes alternatively presented as "mesoporous") ZnO aggregates, etc.

In aspects, particles can be at least mostly, at least generally, at least substantially or can be described as "platelets." Platelet particles are described elsewhere and are known in the art. In aspects, most of the particles classified as a "platelet" type particle comprise or mostly comprise a shape having one dimension that is more than about 20% greater than any one or more other dimension, such as, e.g., having no single dimension that is more than about, e.g., 18%, ~16%, ~14%, ~12%, ~10%, ~8%, ~6%, ~4%, ~2%, or, e.g., no more than about 1% greater than any other dimension.

In aspects, such platelet particle(s) can be, e.g., solid or can, e.g., be porous or hollow. In aspects, a porous particle comprises 1% empty space, e.g., ≥~2%, ≥~3%, ≥~4%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, or, e.g., ≥~90% empty space. Herein, the term "hollow" should be interpreted as comprising at least greater than about 91% empty space wherein the empty space is contiguous and does not contain solid material within its boundary(ies.). In aspects, platelet particles can be, e.g., particles of ZnO or particles of a suitable clay such as disteardimonium hectorite, etc.

In aspects, particles can be at least mostly, at least generally, at least substantially or can be described as irregular in shape. Irregular particles are known in the art, and, in aspects, irregular particles are particles that are not deemed regular in the art, are classified as such herein, or are similar to particles that are herein classified as irregular, or that do not meet the standards of "regular" characterization of particles provided herein. In aspects, particles that are "irregular" comprise a shape having at least one dimension that is more than about 20% greater than any one or more other dimension, such as, e.g., having no single dimension that is more than about, e.g., 18%, ~16%, ~14%, ~12%, ~10%, ~8%, ~6%, ~4%, ~2%, or, e.g., no more than about 1% greater than any other dimension. In aspects, such irregular particle(s) can be, e.g., solid or can, e.g., be porous or hollow.

In aspects, a "porous" particle comprises at least about 1% empty space, e.g., ≥~2%, ≥~3%, ≥~4%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, or, e.g., ≥~90% empty space. In aspects, a "hollow" particle comprises at least greater than about 91% empty space wherein the empty space is contiguous and does not contain solid material within its boundary(ies.)

In aspects, irregular particles can be, e.g., particles of ZnO, particles of clay such as disteardimonium hectorite, 3D Photonic Algal Crystal, mesoporous (sometimes alternatively presented as "mesoporous") ZnO aggregates, etc.

In aspects, mostly all, generally all, or substantially all of the metal oxides particles that are in aggregate forms in the compositions are non-spherical, mesoporous, non-nano Zinc oxides (ZnO) particles have the size of at least about 200-1000 nm, e.g., 200-850 nm, 500 nm-about 800 nm/1000 nm. In aspects, compositions further comprise regular particles of titanium dioxide ($TiO_2$), such particles optionally being solid, optionally being spherical, and optionally having a size of at least about 100 nm-about 2000 nm, e.g., at least about 350 nm-about 1000 nm, e.g., 4000 nm or 900S nm.

In aspects, compositions comprise ≥2, ≥3, ≥4, ≥5, or ≥6 types of spherical particles (e.g., comprising at least 0.1%, 0.2%, 0.3%, or 0.4% of each such type) (again where units are not specified for a percent the percentage typically refers to weight percent of the overall composition), at least one type of hollow particle, and at least 2, 3, 4, 5, or more irregular particles, some of which forming at least a class of shape (e.g., rod or platelet), and one or some of which e.g., mesoporous ZnO aggregate comprising aggregate particulates.

In aspects, compositions further comprise at least 2 or at least 3 different silica types having different compositions or properties, as exemplified below. Most, generally all, substantially all, or all of the particles of a composition can be, in aspects, classified as "non-nano" (having an average particle size of greater than 100 nm).

ZnO particles used in the emulsions of the present invention (i) can be porous (e.g., mesoporous), (ii) have a mean particle size greater than about 500 nm, optionally from about 500 nm to about 800 nm, (iii) have an SPF/UVA ratio of less than 3, and, (iv) in certain embodiments, are surface treated with triethoxycaprylsilane, but, optionally, in aspects comprise no other performance-modifying coating (i.e., in aspects most, generally all, or all of the zinc oxide particles of the composition are "uncoated" particles). A possible feature of the ZnO particles used in the mineral sunscreen emulsions of the present invention is inclusion of mostly, generally only, or substantially only particles having a non-spherical geometry. In contrast to spherical ZnO APIs, porous aggregates like ZinClear XP and ARGA-SUN-CLR-P and platelets, like Solaveil™ MicNo® have less scattering and reflection of light back on to the skin surface, producing improved aesthetics (e.g., more visible transparency and less whitening.). However, in aspects, only mesoporous ZnO aggregate particles are present in a composition of the invention.

When present, non-nano, spherical $TiO_2$ particles used in compositions can be, e.g., mostly, generally entirely, or entirely surface treated, optionally with (i) Alumina or (ii) Aluminum Hydroxide and Stearic Acid. In aspects, $TiO_2$ particles are provided in an anhydrous dispersion medium, either in (i) Caprylic/Capric Triglycerides or (ii) Coco Caprylate/Caprate and PHSA (Polyhydroxystearic Acid).

A first set of embodiments contains two, non-nano metal oxide APIs as described immediately above—irregular (i.e., non-spherical) ZnO particles—namely, MZOAs (mesoporous zinc oxide aggregates) and/or platelets—and non-nano, spherical $TiO_2$ particles.

Another set of embodiments contain only non-nano, irregular ZnO particles as the "active" (or as some, most, or generally most of the active of a composition). Optionally, the first or second embodiments can include non-nano, non-active metal oxides selected from the group of (i) $CeO_2$ (in combination $Al_2O_3$) and Poly (methyl methacrylate) and/or (ii) iron oxide(s).

In aspects, a mineral sunscreen emulsions of the present invention can contain at least two non-metal oxide particles: a first non-metal oxide particle having an average particle size of from 250 nm to 500 nm, e.g., 300-400 nm (where the "first" non-metal particle can have an average particle size of about 325-375 nm); and a second non-metal oxide particle having an average particle size of from 1,000 nm-8,500 nm (e.g., a spherical calcium borosilicate particle) or from e.g., 5,000 nm to 20,000 nm (e.g., a plankton silica particle, such a diatom-derived particle, e.g., a Plankton Flower brand particle as presently marketed as described elsewhere.

A first non-metal oxide particle can have an average particle size of from 250 nm to 500 nm can, in aspects, be (comprise, mostly comprise, etc.) a hollow spherical powder. Optionally, a 250-500 nm hollow spherical powder in the composition is Styrene/Acrylates Copolymer (Sunspheres®), optionally at a concentration of from about 3 to about 5.5%.

The second non-metal oxide can have particle having an average particle size of from 5,000 nm to 20,000 nm is a porous particulate selected from the group consisting of spherical silica powders and "Glass Crystals"—which include Calcium Sodium Borosilicate (Covabead®; average particle size 1,000-8,500 nm) or a combination *Fragilaria zeilleri, Gomphomena angustatum, Navicula radiosa, Cyclotella andancensis* (Plankton Glass Flower®; average particle size about 19,800 nm).

Compositions can comprise particles having the feature of the material sold under the trade name Silsphere™ LS-8H (Argan Co.) and Solesphere® (ASC) are two possible spherical porous silica powders having an average particle size 5,000 nm to 10,000 nm. In aspects, such particles have a size of more than 8500 nm. In aspects, such particles are porous particles and optionally exhibit media uptake properties, such as oil absorbing properties.

Compositions can comprise an effective amount of the material sold under the trade name Covabead® (Sensient), Plankton Glass Flower® (Odycea), or both. Such compositions exemplify, first non-porous the second high-porous glass crystals, having an average particle size from 1,000-15,000, typically 1,000-8,500 nm. In aspects, such particles have sizes under 15,000 nm (on average or in total or in at least substantially all cases). In possible embodiments, a porous spherical particulate and the "glass crystal" are present in a combined concentration of from 1-5%, e.g., 1.25-4.25%, 1.5-4%, or, e.g., 2.0 to 2.5%.

In possible embodiments, the mineral sunscreen emulsion of the present invention contains one or both of a mica and/or a clay (although micas and clays are related materials they typically are recognized as separate materials here and in the relevant art based on composition, cleavage characteristics, and the like). When present, a mica typically is a platelet having an average particle size of from, e.g., 10-1,000/10,000 nm up to e.g., 10,000 nm to 17,500 nm. The mica is optionally a synthetic mica, at a concentration of 0.1 to 0.5%. One possible mica is Synthetic Fluorphlogopite (Argan Co.). In certain possible embodiments, the synthetic mica is present in a blend of $TiO_2$ (CL-Gold-A from Argan Co.)

When present, the clay is a hectorite or bentonite, optionally mostly, generally only, or only disteardimonium hectorite, optionally in a concentration of, e.g., about 0.25 to 1.0%. In certain possible embodiments, the disteardimonium hectorite is dispersed in Phenyl Trimethicone and Triethyl Citrate when added to a mixture to form a matrix/composition.

In aspects, most, generally all, or all of the zinc oxide particles of a composition are mesoporous non-spherical platelets which can be in aggregate form either in anhydrous or emulsion system.

ZnO and $ZnO/TiO_2$ formulations (embodiments) in aspects do not consist of, mostly comprise, or even comprise the classical ZnO with spherical particles (e.g., Z-cote type Zn particles) that are reflecting back on the sunscreen and skin giving the unpleasant whitening effect on the skin, but rather, mostly, generally, or only comprise ZnO particles have a form that is irregular/aggregated, platelet, or rod-shaped particles).

In aspects, most of the ZnO particles are ZnO aggregates/mesoporous particles or other sponge like/highly porous particulates. In aspects, when the pores of most, generally all, or all of the ZnO particles of the composition are infiltrated with base/excipient (the matrix's substrate) the refractive index of the particles is DOS reduced, e.g., to a value close to that of the excipient, in aspects causing a DOS increase in transparency.

Particle Composition

Metallic/Metallic Oxide Particles

In one aspect, composition(s), e.g., sunscreen composition(s), provided by the invention comprise a metallic component, such as, e.g., a metallic oxide component. In aspects, compositions also comprise a non-metallic particle population. In aspects, the metallic particle population has a concentration of about 10-25%, e.g., about 12-24%, or about 13-23%, such as about 12.5-24.5% or 12.5-22.5% of the composition. In aspects, the metal oxide particles are composed of two or more types of metal oxide particles (at an element level, shape level, or both). E.g., a composition can comprise rod, aggregate, or platelet ZnO particles or a mixture of ZnO and $TiO_2$ particles, such as irregular porous aggregate ZnO particles and solid spherical/quasi-spheroid $TiO_2$ particles. In aspects, the non-metal particle population makes up about 3-~18%, e.g., about 4-17% or 4-16% (e.g., 4-12.5%, 7-16%, 5-20%, or 5-15%) of the composition. In aspects, the non-metal particles and metallic oxide particles of the composition are present in a weight concentration ratio of about 1:0.75-6 or 1:0.75-5.5 (e.g., 1:0.75-5.25). Readers can derive, if desired, particle number ratios from the information provided herein to characterize the invention based on such ratios (as this is an implicitly disclosed aspect of the invention).

According to certain aspects, compositions provided by the invention can comprise metal oxide(s) such as, natural minerals, e.g., characterizable as mineral photoprotective agent(s). In aspects, such agents are effective physical light blockers, e.g., reflectors/scatterers. In aspects metal oxide(s) can include, e.g., ZnO, titanium oxide(s) (e.g., $TiO_2$, including, e.g., coated $TiO_2$), iron oxide(s) (e.g., FeO), aluminum oxide(s) (e.g., $Al_2O_3$), cerium oxide(s) (e.g., $CeO_2$), etc. or mixtures thereof.

Sunscreen compositions are often characterizable as organic or mineral inorganic sunscreens. Organic sunscreens work by absorption of UV light. Mineral inorganic sunscreens, by contrast, attenuate UV by two mechanisms: absorption and scattering. Conventional ZnO sunscreens, e.g., ZnO sunscreens presently available, scatter and reflect visible light back to the surface of the sunscreen film, which can lead to a white appearance on skin. This light scattering by back-reflection can be minimized by reducing the size of particulates to the nanometer scale; however, this is not desired in the industry. Advantageously, composition(s) herein represent the development of a particle technology that enables provision of an at least generally, at least substantially, at least essentially, or a transparent formulation using much larger, and more particular particle size(s), e.g., particle sizes of greater than about 100 nm. Such exemplary particles/particle population(s) are provided here. In aspects, composition(s) provided by the invention comprise an active ingredient component comprising one or mineral inorganic compound(s). In certain aspects, ZnO, $TiO_2$ or both, are present in composition(s) and represent the active ingredient (or active pharmaceutical ingredient—API) component of the composition. In aspects, composition(s) provided herein comprise one or more zinc compound(s), one or more titanium compound(s), or comprising both zinc and titanium compound(s). In aspects, composition(s) comprise a population of zinc oxide ZnO particles as the active ingredient alone. In certain aspects, an API component comprises only ZnO. In aspects, composition(s) comprise a population of ZnO particles present in combination with a population of titanium dioxide ($TiO_2$) particles. In aspects, ZnO particles or both ZnO particles and $TiO_2$ particles represent a population of particles characterizable as an active ingredient particle population.

In certain aspects, ZnO particles or both ZnO particles and $TiO_2$ particles represent population(s) of particles which are constituent(s) of other particle population(s), such as metal oxide particle population(s) (e.g., metal oxide particle population(s) comprising non-zinc and non-titanium metal oxide(s)), or particle population(s) characterizable by particle type, size, shape, or other physical characteristics such as surface porosity, solid/hollow/porous structure, etc. as described herein.

In aspects, a metallic oxide component comprises zinc oxide (ZnO). In aspects, the ZnO can be particulate ZnO, e.g., the ZnO present in composition(s) is present in particle form. In aspects, the particulate ZnO, e.g., population of ZnO particles in the composition(s), has one or more of the characteristic(s) described elsewhere herein, as, as has been described, particle(s) of composition(s) can be characterized as belonging to multiple particle population(s).

In one aspect, sunscreen composition(s) provided by the invention, e.g., a metallic component of such composition(s), e.g., a metallic oxide component of such composition(s), comprise titanium dioxide ($TiO_2$). In aspects, the $TiO_2$ can be particulate $TiO_2$, e.g., the $TiO_2$ present in composition(s) is present in particle form. In aspects, the particulate $TiO_2$, e.g., population of $TiO_2$ particles in the composition(s), has one or more of the characteristic(s) described elsewhere herein, as, as has been described, particle(s) of composition(s) can be characterized as belonging to multiple particle population(s).

In aspects, $TiO_2$, is available in, e.g., provided in composition(s) as, a mixture with a second ingredient e.g., dimethicone, lecithin, methicone, or, e.g., with a second and third ingredient, e.g., $TiO_2$ and alumina with glycerin, jojoba esters, methicone silica, or stearic acid, etc. In aspects, such additional constituent(s) may be present as element(s) of a coating of the $TiO_2$ particle(s).

According to certain aspects, composition(s), e.g., sunscreen composition(s), described herein can comprise both non-nano ZnO and non-nano $TiO_2$. In aspects, such compositions can comprise an aqueous phase and a non-aqueous phase. In aspects, the phase which one or more of the active particle(s), e.g., metal particle(s), e.g., metal oxide particle(s), e.g., ZnO, $TiO_2$, or both reside(s) detectably or significantly impacts one or more performance characteristic(s) of composition(s). In aspects, one or more step(s) of production method(s), e.g., one or more homogenization step(s) of production method(s), such as one or more characteristic(s) of one or more homogenization step(s) of production method(s) (such as, e.g., time, temperature, speed, etc.) detectably or significantly impacts one or more performance characteristic(s) of composition(s) such that if any such step or characteristic thereof is detectably or significantly changed, a detectable or significant performance characteristic of the composition changes. In aspects, such change(s) can be a decrease in efficacy, a decrease in stability, or both. In aspects, a non-aqueous phase comprises about or above 15-35%, 20-35%, 20-30%, 25-35%, or about 30% of the composition. In aspects, a non-aqueous phase of composition(s) comprises one or more component(s) or compound(s), e.g., metal oxide(s), non-metal oxide(s), or both, present as dispersed particulates. In aspects, metal oxide(s), non-metal oxide(s), or both, are present in aggregate form. In aspects, only one or two types of particles are present as aggregates, but some, most, generally all, or all of the other particles form agglomerates in the matrix composition, optionally where most, generally all, or all of such agglomerates are 1 micron in size or larger.

In aspects, the synergy of one or two API and other metal oxides, with non-metal oxides such as combination one or more different silica compounds, with or without styrene acrylate copolymer, synthetic mica etc. are able to reflect/refract/scatter sun light (UV, Visible, HEV/Blue Light) in conjunction w/peptide and plant extract offer detectable or significant, e.g., high protection from UVA/UVB, IR, blue light, etc. detectable or significant anti-pollution protection, detectable or significant anti-aging effect(s), or combination(s) of any or all thereof.

According to aspects, composition(s) provided herein comprise an effective amount of non-nano metal oxide(s) to detectably or significantly block, scatter, reflect, refract, or otherwise attenuate an amount of UV radiation, blue light, infra-red light, visible light, or any combination thereof which could or would otherwise cause detectable or significant damage or change to the subject to which composition(s) are applied.

In aspects, any one or more metallic compound(s), e.g., metallic oxide compound(s) of a metallic particle population, e.g., metal oxide particle population, can be provided in aggregate form, such as, e.g., ZnO provided in aggregate form. In aspects, any one or more such compounds can be provided in mesoporous form, such as ZnO provided in mesoporous form. In aspects, any one or more such compounds can comprise an irregular, e.g., non-spherical shape, such as ZnO provided as irregularly shaped, mesoporous, aggregate particles. In certain aspects, such compounds can comprise a spherical shape, such as $TiO_2$ provided in spherical form. In aspects, compounds described here, particles of a metallic particle population, e.g., metallic oxide particle population (metallic oxide component), e.g., ZnO, $TiO_2$, or both, can be coated e.g., by silica, alumina, aluminum hydroxide, aluminum stearate, etc.

In particular aspects, compositions comprise ZnO in mesoporous, aggregate form, wherein the mesoporous aggregates have an irregular, non-spherical shape. In certain aspects, composition(s) comprise at least two metal oxide compounds, e.g., zinc oxide (e.g., uncoated ZnO) and titanium dioxide (optionally coated $TiO_2$).

Optionally, but in certain possible embodiments, one or more additional photoprotective metal oxides not characterizable as zinc or titanium compounds selected from the group of iron oxide(s), aluminum oxide(s), zirconium oxide(s), bismuth oxychloride(s), and cerium oxide(s) are incorporated in composition(s) herein, e.g., broad-spectrum sunscreen composition(s) of the present invention.

In aspects, composition(s), e.g., a multidimensional photoprotective particle matrix of composition(s) can comprise cerium oxide (CeO) compound(s), such as, e.g., cerium dioxide ($CeO_2$). In aspects, CeO compound particles, e.g., $CeO_2$ compound particles, are a constituent of a metallic oxide component. Depending on the characteristic(s) of such particles, cerium oxide particles can be characterized as constituent(s) of other component(s)/particle population(s) as well, such as, e.g., spherical particle population(s).

As with any other element (step, composition, compound, structure, etc.), uncontradicted, elements recited herein can be excluded or a composition can be generally free or substantially free of such element. For example, in aspects, the invention provides compositions that generally are free of, substantially are free of, or lack $CeO_2$.

In certain embodiments, cerium oxide, $CeO_2$ is present in composition(s), e.g., broad-spectrum photoprotective composition(s), of the present invention at a concentration of from 0.1 to 2.0%, optionally about 0.25%.

One possible exemplary form of cerium oxide suitable for use in composition(s) herein is ARG-SPHERE NIR-1/15BA000, a combination of poly(methyl methacrylate), also known in the art as PMMA, cerium oxide ($CeO_2$), and aluminum oxide from Argan Co. In aspects, compositions lack any PMMA or derivative thereof.

in aspects, the invention provides composition(s), e.g., multidimensional photoprotective particle matrix(ces) of composition(s), wherein the multidimensional photoprotective particle matrix in the composition comprises a metallic oxide particle population comprising a population of iron oxide (FeO) particle(s). Iron oxides have been used not only to reduce the white cast of ZnO and/or $TiO_2$, but also to broaden the protection offered by mineral sunscreens into the UVA and visible light spectrums, and such metal oxide particles can be, in aspects, incorporated into composition(s) provided herein. In aspects, composition(s) comprise iron oxide particles (populations thereof) that provide a detectable or significant coloration or tint to the composition, detectable prior to application of composition(s) comprising such iron oxide particle populations, upon application of composition(s), or both. In aspects, composition(s) comprise two or more types of iron oxide particles. In aspects, some, most, generally all, or all of the FeO particles are spherical, solid, or both. In aspects, two or more (e.g., 3 or more) FeO particle types having different tint properties are included in a formulation. In aspects, two or more FeO particle population(s) can be present which are distinguishable from one another, such as by their characteristic color (such as, e.g., brown, yellow, or, e.g., black). Iron oxide particles that are suitable for cosmetic compositions/sunscreens are known in the art. See, e.g., H. Dumuya et al "Impact of Iron-Oxide Containing Formulations Against Visible Light-Induced Skin Pigmentation in Skin of Color Individuals" J Drugs Dermatol. 2020 Jul. 1; 19(7):712-717. Doi: 10.36849/JDD.2020.5032; see, e.g., Y. Shao. https://nyscc.org/blog/formulating-mineral-sunscreens-for-people-of-color/(Jan. 28, 2021) (discussing use of red iron oxides at 0.2-1.0% to "neutralize the whiteness and bluing of ZnO sunscreen); and see also, e.g., N. Lowe, "An overview of ultraviolet radiation, sunscreens, and photo-induced dermatoses" Dermatol Clin. 2006 January; 24(1):9-17. Doi: 10.1016/j.det.2005.08.001 (discussing that the addition of iron oxide to mineral sunscreens can reduce the amount of UVA and visible light transmitted to the skin to 20% and iron oxide in combination with zinc oxide, can reduce the amount of UVA radiation transmitted to the skin to 1.5%).

In aspects, iron oxides may be present in broad-spectrum photoprotective compositions of the present invention at a concentration of from about 1.0 to about 7.0%, optionally from about 1.0 to about 3.0%, and still more optionally from about 1.5% to 2.0%.

In tinted formulations (containing three or more iron oxides selected from the group of black iron oxide, red iron oxide, and yellow iron oxide), amorphous spherical silica is optionally present at a concentration of at least 2.0%. In formulations, e.g., non-tinted formulations (not containing iron oxides), amorphous spherical silica is optionally present at a concentration of at least about 2.5%.

In aspects, the invention provides composition(s), e.g., multidimensional photoprotective particle matrix(ces) of composition(s), wherein the multidimensional photoprotective particle matrix in the composition comprises a metallic oxide particle population comprising a population of aluminum compound particle(s), e.g., aluminum oxide ($Al_2O_3$) compound particle(s). In aspects, $Al_2O_3$ are a constituent of a metallic oxide component (e.g., a metallic oxide particle population). Depending on the characteristic(s) of such particles, aluminum oxide particle can be characterized as constituent(s) of other component(s)/particle population(s) as well, such as, e.g., spherical particle population(s), grain-like particle population(s), or both.

According to certain aspects, one or more metal oxide compounds of a metallic oxide component (metallic oxide particle population) can comprise spherically shaped particles. In aspects, any one or more of the metal oxides $CeO_2$, FeO, or $Al_2O_3$ can be present as particle populations wherein the particles therein are present in spherical form. In aspects such particle population(s) can be present in the multidimensional photoprotective particle matrix composition alone or in any combination thereof.

According to certain embodiments, micron-sized polygonic ZnO prismatic platelets developed by Entekno Industrial, Technological and Nano Materials Corp. (Tepebasi, Eskisehir/Turkey) under the MicNo® brand (available from Croda Inc. (Plainsboro, NJ) as Solaveil™ MicNo®) are used in mineral sunscreens such as composition(s) provided herein in effective amount(s) to detectably or significantly reduce whitening and offer detectably or significantly improved SPF efficacy (greater protection per percent (%) solid). See, e.g., US pre-grant Patent Application number 2020/0247684. MicNo® platelets can be uncoated (having a >500 nm mean particle size as measured by X-Ray Disc Centrifuge) or also or alternatively as surface-treated (coated with Triethoxycaprylsilane) in powder form at a manufacturer's recommended use level of from 1-25%, or as a dispersion [C12-15 alkyl benzoate or caprylic capric triglyceride, each with polyhydroxystearic acid (PHSA), at a manufacturer's recommended use level of 2-38%. When used in powder form in a W/O emulsion, technical literature from Croda recommends combining MicNo® with PHSA in the oil phase at a ratio of 0.05 to 0.15% PHSA for every 1% powder. See Croda Europe Ltd, Solaveil™ MicNo® Product Overview (Apr. 21, 2021; Document ID 0321PCEPO2526v1EN). Sample formulation JP0305 in the above-cited brochure contains Solaveil MZP7 (Zinc Oxide (and) Triethoxycaprylylsilane), Solaveil HTP1 (Titanium Dioxide (and) Alumina (and) Stearic Acid), Sunsphere H121 (Silica from AGC) and Quaternium-18 Bentonite.

According to certain aspects, one or more particle of an active ingredient component, e.g., particles of one or more particle population(s) of a metal oxide component, e.g., particles of particle populations comprising ZnO and/or ("or") $TiO_2$ can be, and in certain possible embodiments, are coated. According to certain embodiments, at least one particle population, e.g., at least one metal particle population, e.g., at least one population of particles comprising a metal oxide, e.g., a ZnO particle population, is incorporated in uncoated form in composition(s) provided herein.

Coating can, in aspects, be accomplished by method(s) known in the art. By way of non-limiting example, starting with an aqueous pigment particle suspension, metal salts can be added in dissolved form as so-called precursor compounds. Alkaline or acid substances can then be used to set the pH value of the suspension in such a way that the precursor compounds are precipitated in the form of oxides, hydroxides, etc. Methods for modifying and hydrophobizing the surface of $TiO_2$ and ZnO are further disclosed, for example, in U.S. Pat. Nos. 5,565,591 and 5,486,631, both now expired.

Possible, but non-limiting examples of materials that can be used to coat ZnO and $TiO_2$ are silica, alumina, aluminum hydroxide, aluminum stearate, triethoxycaprylylsilane, stearic acid, caprylic/capric triglyceride, lecithin, and methicone.

Photoprotective metal oxides or particle(s) thereof can in aspects also comprise a mixture or compound of $C_{12}$ to $C_{30}$ fatty alcohols and $C_6$ to $C_{12}$ aliphatic acids, as described in U.S. Pat. No. 9,517,190.

According to certain aspects, $TiO_2$ useful in W/O emulsion composition(s) of the present invention may be commercially available in a mixture that is a "binary combination"—namely, $TiO_2$ and a second ingredient selected from the group of: dimethicone; isopropyl titanium triisostearate; methicone; polymethyl methacrylate; polyphosphorylcholine glycol acrylate; silica; simethicone; stearic acid; and triethoxycaprylylsilane.

$TiO_2$ useful in broad-spectrum sunscreen composition(s) of the present invention may also be part of a tripartite combination (i.e., $TiO_2$ and a second ingredient, and a third ingredient).

In certain embodiments, $TiO_2$ and alumina (as a second ingredient) are combined with a third ingredient selected from the group of: glycerin; jojoba esters; methicone; silica; and stearic acid.

In other embodiments, $TiO_2$ and aluminum hydroxide (as a second ingredient) are combined with a third ingredient selected from the group of: hydrogen dimethicone; isostearic acid; and stearic acid.

In further embodiments, $TiO_2$ and silica (as a second ingredient) are combined with a third ingredient selected from the group of: *Helianthus annuus* (sunflower) seed oil; dimethicone; stearic acid; jojoba esters; lauroyl lysine; sodium polyacrylate; and triethoxycaprylylsilane.

In still further embodiments, $TiO_2$ and polyhydroxystearic acid (as a second ingredient) are combined with a third ingredient selected from the group of: bisabolol; squalane; and jojoba esters.

In one embodiment, $TiO_2$ and caprylic/capric triglyceride may be combined with alumina, and polyhydroxystearic acid and one of: aluminum stearate; methicone; stearic acid; or silica.

In other embodiment, $TiO_2$ and caprylic/capric triglyceride may be combined with aluminum hydroxide, polyhydroxystearic acid and/or stearic acid.

$TiO_2$ may be combined with $C_{12-15}$ alkyl benzoate, polyhydroxystearic acid, and, optionally, alumina, in further combination with one of: methicone; cyclomethicone; aluminum stearate; stearic acid, and silica.

$ZnO/TiO_2$ may also be combined with $C_{12-15}$ alkyl benzoate in further combination with *Argania spinosa* kernel oil (and) alumina (and) methicone (and) tocopheryl acetate, dimethicone (and) polyhydroxystearic acid (and) silica, polyglyceryl-3 polyricinoleate (and) silica (and) stearic acid (and) aminopropyl-triethoxysilane, or stearic acid (and) aluminum hydroxide (and) polyhydroxystearic acid.

$ZnO/TiO_2$ may also or alternatively be combined with aluminum hydroxide in further combination with, e.g., acrylates copolymer (and) hydrated silica (and) algin, butyloctyl salicylate (and) isostearic acid (and) $C_{12-15}$ alkyl benzoate (and) stearic acid, $C_{12-15}$ alkyl benzoate (and) stearic acid (and) polyhydroxystearic acid, caprylic/capric triglyceride (and) stearic acid in further combination with (a) sorbitan olivate or (b) polyhydroxystearic acid, hydrogen dimethicone, alone or in combination with hydrogen dimethicone, hydrated silica (and) polyphosphorylcholine glycol acrylate, stearic acid or isostearic acid, polydimethylsiloxyethyl hexyl dimethicone (and) PEG-9 polydimethylsiloxyethyl dimethicone, polyglyceryl-4 isostearate (and) cetyl PEG/PPG-10/1 dimethicone (and) hexyl laurate (and) isostearic acid, *Simmondsia chinensis* (jojoba) seed oil (and) isostearic acid (and) polyhydroxystearic acid, and *Simmondsia chinensis* (jojoba) seed oil (and) polyhydroxystearic acid (and) jojoba esters. Non-limiting examples of "coated" $TiO_2$ suitable for use in composition(s) herein, e.g., broad-spectrum sunscreen composition(s) of the present invention, include the following: Sunsil® Tin50 from Sunjin Chemical Co. Ltd.: $TiO_2$ coated with silica, with a ratio of silica to $TiO_2$ of about 55:45; titanium dioxide (at least 78%; typically about 83%) coated with aluminum hydroxide (about 9%) (and) stearic acid (about 8%), available from Tayca Corp. (Osaka, Japan) under the tradename MT-100TV; titanium dioxide (74%) coated with silica (11%), aluminum hydroxide (9%), and alginic acid (5%), available from Tayca Corp. as MT100-AQ; titanium dioxide (75-82%) coated with silica (13-20%) available from Merck KgaA/EMD Chemicals (Darmstadt, Germany) under the tradename Eusolex® T-AVO; and SiClone® TD-150 (from Presperse Corp., Somerset, New Jersey) about 40% titanium dioxide with an inner coating of aluminum hydroxide and an outer coating of isostearic acid.

According to aspects, $TiO_2$ may be used in composition(s) herein, e.g., broad-spectrum sunscreen composition(s) of the present invention, in or with one of the following elements or any suitable combination thereof— a. boron nitride (and) dimethicone (and) isododecane (and) ethylene/VA copolymer;
b. butylene glycol (and) caprylyl glycol (and) oleth-10 (and) phenoxyethanol (and) polysorbate 60 (and) silica;
c. butyloctyl salicylate (and) polyhydroxystearic acid (and) dimethicone (and) hydrogen dimethicone;
d. caprylic/capric triglyceride (and) stearic acid (and) isostearic acid (and) polyhydroxystearic acid (and) polyglyceryl-3 polyricinoleate (and) lecithin;
e. cyclomethicone (and) Bis-PEG/PPG-14/14 dimethicone (and) aluminum stearate;
f. cyclopentasiloxane (and) dimethicone (and) PEG-10 dimethicone (and) silica;
g. cyclopentasiloxane (and) PEG-10 dimethicone (and) methicone;
h. ethylene/acrylic acid copolymer (and) aluminum stearate;
i. ethylhexyl palmitate (and) polyhydroxystearic acid (and) silica;
j. glycerin (and) sodium polyacrylate (and) tetrasodium EDTA (and) silica (and) sodium polyphosphate;
k. hydrogenated polydecene (and) polyhydroxystearic acid (and) one of: dimethicone; stearic acid; or triethoxycaprylylsilane;
l. isododecane (and) polyhydroxystearic acid (and) methicone;
m. isohexadecane (and) trimethylhexanoic (and) aluminum stearate (and) polyhydroxystearic acid;
n. isononyl isononanoate (and) methicone (and) polyhydroxystearic acid;
o. isopropyl myristate (and) polyhydroxystearic acid (and) silica;
p. isopropyl titanium triisostearate (and) triethoxysilylethyl polydimethylsiloxyethyl dimethicone;
q. methyl trimethicone (and) hydrogen dimethicone (and) lauryl PEG-9 polydimethylsiloxyethyl dimethicone;
r. methyl trimethicone (and) PEG-10 dimethicone (and) methicone;
s. mica (and) dimethicone (and) isododecane (and) ethylene/VA copolymer (and) stearic acid;
t. octyldodecyl myristate (and) alumina (and) polyhydroxystearic acid (and) methicone;
u. phenyl trimethicone (and) hexyl laurate (and) stearic acid (and) polyhydroxystearic acid;
v. polyglyceryl-2 caprate (and) sucrose stearate (and) *Simmondsia chinensis* (jojoba) seed oil (and) stearic acid (and) glyceryl caprylate (and) squalane;
w. *Simmondsia chinensis* (jojoba) seed oil (and) aluminum hydroxide (and) polyhydroxystearic acid (and) one of isostearic acid or jojoba esters;
x. acrylates copolymer (and) hydrated silica (and) (a) algin (and) aluminum hydroxide or (b) polyphosphorylcholine glycol acrylate;
y. butyloctyl salicylate (and) aluminum hydroxide (and) isostearic acid (and) $C_{12-15}$ alkyl benzoate (and) stearic acid;
z. $C_{12-15}$ alkyl benzoate (and) polyglyceryl-2 dipolyhydroxystearate (and) silica (and) dimethicone;
aa. caprylic/capric triglyceride (and) sorbitan olivate (and) stearic acid (and) aluminum hydroxide;
bb. caprylyl methicone (and) cyclopentasiloxane (and) $C_{12-15}$ alkyl benzoate (and) alumina (and) polyhydroxystearic acid (and) triethoxysilylethyl polydimethylsiloxyethyl hexyl dimethicone (and) PEG-9 polydimethylsiloxyethyl dimethicone;
cc. hydrated silica (and) hydrogen dimethicone and (a) aluminum hydroxide (or) hydrogen dimethicone;
dd. isododecane (and) alumina (and) methicone (and) polyhydroxystearic acid;
ee. isododecane (and) polyglyceryl-4 isostearate (and) cetyl PEG/PPG-10/1 dimethicone (and) hexyl laurate (and) aluminum hydroxide (and) isostearic acid; and
ff. isononyl isononanoate (and) polyhydroxystearic acid (and) hydrogen dimethicone (and) dimethicone.

One possible form of titanium dioxide suitable for use in broad-spectrum sunscreen compositions of the present invention is Tinoply E50C (manufactured by Chemland, Co., Ltd., Seoul, Korea) a mixture of caprylic/capric triglyceride, titanium dioxide, alumina, stearic acid, and polyhydroxystearic acid. More particularly, in Tinoply E50C (a) caprylic/capric triglyceride is present at a concentration of 47.0±2.5%, (b) titanium dioxide is present at a concentration of 39.0±2.5%, (c) alumina is present at a concentration of 6.0±2.5%, (d) stearic acid is present at a concentration 5.0±2.5%, and (e) polyhydroxystearic acid is present at a concentration of 3.0±0.5%.

Another possible form of titanium dioxide suitable for use in broad-spectrum sunscreen compositions of the present invention is Tinoply E30C—a mixture of caprylic/capric triglyceride, titanium dioxide, silica, polyhydroxystearic acid, and methicone (also manufactured by Chemland, Co., Ltd.) in which (a) caprylic/capric triglyceride is present at a concentration of about 68.2±2.5%, (b) titanium dioxide is present at a concentration of at least about 24%, (c) silica is present at a concentration of 4.5±2.5%, (d) polyhydroxystearic acid is present at a concentration 1.8±0.5%, and (e)

methicone at a concentration of 1.5±0.5%. In certain especially possible embodiment(s), the sunscreen does not include alumina.

Uncoated zinc oxide particles that can be used in composition(s) of the present invention are commercially available from numerous suppliers, including under the tradename Z-Cote® (BASF Care Creations, Florham Park, NJ). Examples of other suitable ZnO are disclosed, for example, in U.S. Pat. No. 8,545,891. As noted elsewhere, in aspects, compositions lack such ZnO particles. In aspects, the ZnO particles of compositions are generally, substantially, or entirely limited to "new geometry" zinc particles (particles with aggregate, rod, or platelet structures/shapes).

In possible embodiment(s) of the present invention, prior to mixing ZnO with $TiO_2$, ZnO is dispersed with polyhydroxystearic acid (PHSA), a polymer of hydroxystearic acid, which is commercially available under the tradename Dispersun DSP OL 300 from Innospec Performance Chemicals (Salisbury, NC). According to technical literature from Innospec, polyhydroxystearic acid increases UV absorption of sunscreens containing pigments by allowing higher concentrations of pigment to be used. Additionally, inclusion of polyhydroxystearic acid is described by Innospec as improving optical transparency and reducing whitening (when a finished formulation is applied to human skin).

In possible embodiments, polyhydroxystearic acid is present at a concentration of from about 0.25 to 1.5%, optionally at least about 0.5%. Different molecular weights of polyhydroxystearic acid may be used in broad-spectrum composition(s) of the present invention.

In certain possible embodiments, a mica, or a mica-like compound that imparts a detectable or significant shimmer, glow, or reduces the appearance of skin imperfections, is added to the formulation in effective amount(s). In aspects, a mica compound or mica-like compound imparting detectable shimmer, glow (e.g., improving light reflection characteristics, modulating skin tone, etc.), or reduction in the appearance of skin imperfection(s) or scatters or reflects radiation/light, etc. is provided to composition(s) via an iron oxides blend. One possible, but non-limiting example, of a mica-like compound suitable for use in composition(s) provided herein is synthetic Fluorphlogopite, a synthetic mineral that conforms generally to the formula: $Mg_3K[AlF_2O(SiO_3)_3]$.

Zinc Oxide Particles

In aspects, compositions comprise zinc compound(s), e.g., zinc oxide (ZnO) compound(s), in particulate form, such as in the form of zinc particle aggregate(s). In aspects, ZnO make up most or generally all of the metal oxide particles of a composition. In aspects, ZnO particles are the only metal oxide particle "active" in the composition. In aspects, ZnO particles are the only metal oxide particles in the composition. In aspects, compositions comprise multiple populations of ZnO particles in terms of shape. In aspects, compositions comprise generally or only one type of ZnO particle shape, but the composition can still include a range of different sizes of ZnO particles, which can be separated into populations based on size as exemplified elsewhere.

In aspects, the population of zinc particles, e.g., zinc particle aggregates, has an average particle size (e.g., maximum particle diameter in any one direction) of greater than 100 nm, such as, e.g., greater than about 200 nm, ≥~300 nm, ≥~400 nm, ≥~500 nm, ≥~600 nm, ≥~700 nm, ≥~800 nm, ≥~900 nm, or, e.g., ≥~1000 nm. In aspects, at least about 80%, e.g., ≥~85%, ≥~90%, ≥~95%, ≥~97%, ≥~98%, ≥~99%, or, e.g., ≥~99.9% of ZnO particles provided in aggregate form comprise a maximum diameter in any one direction of greater than 100 nm. According to certain aspects, ZnO particle population(s) present in composition(s) provided herein are characterizable as "non-nano." Registration, Evaluation, Authorisation and Restriction of Chemicals (REACh) (see, e.g., ec.europa.eu/environment/chemicals/nanotech/reach-clp/index_en.htm on the Web) and Cosmetics Europe (see, e.g., docplayer.net/54947113-Cosmetics-europe-nano-guidance-package.html on the Web) define nanoparticles and thus by default describe non-nano particles. For REACh 50% or more of the particles in the number size distribution of the particle population should have one or more external dimensions in the size range 1 nm-100 nm to be considered "nano". For Cosmetics Europe, a threshold of 10% of the mass fraction (volume) of a material should be used in order to determine whether a given material should be considered as a nanomaterial or not. In aspects, based on both the REACh definition of "nano" and the Cosmetics Europe interpretation of "nano", the ZnO particle population of composition(s) provided herein is non-nano.

In aspects, composition(s) comprise a population of ZnO particles having an average maximum diameter of between about 200 nm and about 1000 nm, such as, e.g., ~300 nm-900 nm, ~400 nm-850 nm, or, e.g., about 500 nm-about 800 nm.

In aspects, composition(s) comprising ZnO or, e.g., a combination of ZnO and $TiO_2$, do not use the classical/traditionally used ZnO provided as spherical particles which reflect back on the sunscreen and skin yielding a well-recognized, unpleasant and undesirable, whitening effect on the skin. In aspects, alternatively, composition(s) provided herein comprise ZnO particles having a non-spherical geometry, e.g., aggregates, platelets, rods, or, e.g., combination(s) thereof. In aspects, ZnO aggregates are used. In aspects, aggregates are mesoporous (sponge like), which, when pore(s) are infiltrated with the excipient, the refractive index of the particles is detectably or significantly reduced to a value close to that of the excipient, causing a significant increase in transparency. In aspects, these types of non-nano, large particles (e.g., having an average size of 500-800 nm), offer detectably or significantly less back-reflection of the light from the particles to the skin, providing UVA/UVB protection along with unexpected transparency with detectably or significantly reduced whitening to the skin. This is discussed further herein.

In aspects, ZnO can be present as mesoporous particles, e.g., in mesoporous aggregates. In aspects, such aggregates are spherical. In aspects, such aggregates are non-spherical. In aspects, such aggregates are non-spherical, three-dimensional shapes similar to a sponge. In aspects, such dispersed particulates, e.g., metal oxide(s), non-metal oxide(s), or both, are present in an amount representing about 20-40% of the composition, e.g., about 30%, about 25%, etc. of composition(s). According to certain alternative aspects, sunscreen composition(s) described herein can comprise only non-nano ZnO (e.g., compositions do not further comprise non-nano $TiO_2$.

In aspects, ZnO particles of composition(s) provided herein are aggregate ZnO particles composed of multiple smaller particles bound together to form larger, mesoporous particles. Such binding of multiple smaller particles forms a sponge-like structure. This sponge-like structure comprises a detectably or significantly different reflective index of the ZnO when present in composition(s) provided herein compared to ZnO provided in a form having structure(s) which are detectably or significantly different from that provided by the ZnO in aggregate, sponge-like structure form. In aspects, the aggregate ZnO is able maintain within pore(s) of its spongelike structure a detectable or significant amount of a different material, e.g., a non-ZnO material, e.g., a portion of a non-particulate component of a composition, for example, constituent(s) related to provision of the composition as an emulsion. In aspects, the pores of the mesoporous particles can be infiltrated with one or more excipients, e.g., an emulsion substrate.

In possible embodiments, ZnO is non-whitening when applied to the skin and has an average particle size greater than about 100 nm (i.e., "non-nano"). Such materials are sometimes described in trade literature as "transparent".

In aspects, presence of ZnO in aggregate form, compared to ZnO present in an alternative form, results in detectably or significantly less scattering of light, and reflection of light, or both, to the surface, resulting in beneficial transparency of the composition when applied to the skin. In aspects, the detectable or significant reduction in light scatter, reflection, or both, to the surface provides a detectably or significantly higher transparency of the composition when applied to the skin compared to composition(s) comprising ZnO in an alternative form (e.g., non-aggregate form). In aspects, the detectable or significant reduction in light scatter, reflection, or both, to the surface provides a detectably or significantly higher transparency of the composition when applied to the skin compared to composition(s) comprising ZnO in the same aggregated form, however, wherein one or more other constituent of such composition(s) differ(s); e.g., one or more material(s) capable of being present in the pores of the aggregated ZnO is different than that described in composition(s) provided herein.

In aspects, the refractive index of the mesoporous, aggregate ZnO particles is reduced to a value close to that of the excipient, causing a significant, e.g., statistically significant increase in transparency compared to the use of non-aggregate, non-mesoporous ZnO particles. In aspects, the refractive index of the mesoporous, aggregate ZnO particles is reduced to a value close to that of the environment within which it resides, such as, e.g., the emulsion or constituent(s) thereof. In aspects, such mesoporous, aggregate ZnO particles provide benefits over that of platelet shaped ZnO particles, as, in aspects, such aggregate, mesoporous ZnO particles provide detectably or significantly less visible whitening of the skin compared to similar products using ZnO in platelet form.

In aspects, composition(s) provided herein can comprise any suitable ZnO particle(s) capable of providing the characteristic(s) of composition(s) described. In aspects, composition(s) comprise ZnO particles (a particle population) functionally equivalent to ArgaSun CLR-P/Argan Co. and ZinClear XP (Antaria) or such particles themselves. In aspects, composition(s) can comprise ZnO particles such as ZinClear XP. Historically, non-whitening, non-nano ZnO materials were marketed under the tradename ZinClear™ formerly sold by Antaria Limited (Welshpool, Australia). See US Pre-Grant Patent Application Publications 2010/0310871 and 2010/0316582, both abandoned.

In one particular embodiment, composition(s) of the present invention contain ZnO particles (population(s) thereof) having an average particle size of greater than 100 nanometers ("non-nano ZnO"). In possible embodiments, the non-nano ZnO particles have a porous structure. One such ZnO is ARGA-SUN ZnO CLR-P from Argan Co. (Northridge, California). ARGA-SUN ZnO is a porous, highly transparent form of ZnO, which also or alternatively can be incorporated in compositions as most, generally all, or all of the ZnO particles of the composition. According to Technical Data Sheets, ARGA-SUN ZnO CLR-P has a highly porous structure that is "infiltrated" (e.g., filled) with excipient, and an average particle size distribution of less than about 800 nanometers (measured using static laser scattering). Because the particles have a refractive index close to the excipient, a "significant increase in transparency" is achieved. A technical brochure for ARGA-SUN ZnO dated Feb. 19, 2019, explains that when the pores absorb excipient (oil, silicone), the refractive index of the particles is reduced to a value close to that of the excipient, causing a significant increase in transparency. The brochure notes that an SPF of 50+ can be achieved with a mixture of ZnO and $TiO_2$. A sample formulation for a water-in-oil cream SPF 30 in the ARGA-SUN ZnO brochure contains $TiO_2$ (10%; dispersed in several ingredients including Polyhydroxystearic Acid), ZnO (ARGA-SUN-CLR-P-TE @ 12%), EWOCREAM (3.3%; a water-in-oil emulsifier from Sinerga identified as "Polyglyceryl-3 Sorbitan Linum usitatissimum (linseed oil)" and a clay, "Bentone Gel" (1.4%). Such knowledge can be combined with other elements of the present disclosure to arrive at suitable compositions for use.

In aspects, ZnO particles can be coated. In aspects, composition(s) provided herein comprise particles functionally equivalent to Solaveil MicNo or such particles themselves. Such particles are composed of platelet shaped ZnO which forms an ordered structure within the composition. In aspects, such a structure results in detectably or significantly less scattering and reflection to the surface, resulting in an improved transparency on skin compared to one or more other forms of ZnO. In aspects, compositions comprise ZnO in the form of rods.

In aspects, compositions can comprise ZnO dispersed with polyhydroxystearic acid in esters or silicones which detectably or significantly increases, blocks, reflects, refracts, etc., radiation/UV absorption of composition(s) while also imparting (alone or with other elements of this disclosure) pigmentation that detectably or significantly reduces whitening otherwise arising from the application of the composition.

In certain aspects, ZnO is present in aggregate form wherein aggregates have a maximum diameter in any single direction of, e.g., between about 6-about 800 nm (e.g., typically greater than 100 nm). In aspects, ZnO is provided as platelets having a maximum diameter in any single direction greater than about 100 nm. In aspects, zinc particles of composition(s) provided herein comprise a larger surface than traditional ZnO particles. In aspects, ZnO particles herein have a 0.59 SPF unit for 1% ZnO; SPF/UVA is 1.2<3 (EU); and CW376 nm US. In aspects, ZnO particles suitable for use in composition(s) herein include mesoporous zinc oxide aggregates (MZOAs) having an average particle size of 0.8 microns (800 nm) that produce detectably or significantly more visibly transparent mineral composition(s) than traditionally utilized zinc compound(s) or particle(s) thereof. Examples of such compositions and related principles are described in, e.g., US Pre-Grant Patent Application 2010/0310871 and 2013/00316582, both abandoned; see also, US Pre-Grant Patent Application Publication 2015/0376025. Possible also or alternatively suitable mesoporous zinc oxide aggregates (MZOAs) from Antaria have been commercialized under the tradename ZinClear XP, including in Clinique SPF 50 Broad Spectrum Mineral Sunscreen Fluid For Face commercially available since Jun. 1, 2016;

$TiO_2$— 6.3%; ZnO—4%; also contains Butyloctyl Salicylate, Silica, Iron Oxides (red and yellow). See, https://ndclist.com/ndc/49527-752.

Titanium Dioxide Particles

In aspects, compositions comprise titanium compound(s), e.g., titanium oxide compound(s), e.g., titanium dioxide ($TiO_2$), in particulate form. In aspects, composition(s) comprise a population of titanium compound(s) dioxide ($TiO_2$) particles. In aspects, compositions comprise no titanium dioxide, or less than 1%, or less than 0.5%, or less than 0.1%. In certain aspects, composition(s) herein do not comprise $TiO_2$.

In aspects, titanium oxide (TiO) compound(s), e.g., $TiO_2$, can be present in amorphous form, crystalline form, or both. In aspects, $TiO_2$ can be preset in the rutile form, anatase form, or both. Optionally 95% or more of the $TiO_2$ is in the rutile form. In aspects, about 90%, ~91%, ~92%, ~93%, ~94%, ~95%, ~96%, ~97%, ~98%, or ~99%, such as about 95% or more of the $TiO_2$ is in the rutile polymorph form. In aspects, less than about 10%, <~9%, <~8%, <~7%, <~6%, <~5%, <~4%, <~3%, <~2%, or, e.g., <~1% of any $TiO_2$ present in the composition, such as less than about 5% of the $TiO_2$, is present in anatase polymorph form.

In aspects, the population of $TiO_2$ particles, has an average particle size (e.g., maximum particle diameter in any one direction) of greater than 100 nm, such as, e.g., greater than about 200 nm, ≥~300 nm, ≥~400 nm, ≥~500 nm, ≥~600 nm, ≥~700 nm, ≥~800 nm, ≥~900 nm, or, e.g., ≥~1000 nm. In aspects, at least about 80%, e.g., ≥~85%, ≥~90%, ≥~95%, ≥~97%, ≥~98%, ≥~99%, or, e.g., ≥~99.9% of $TiO_2$ particles comprise a maximum diameter in any one direction of greater than 100 nm. In aspects, $TiO_2$ particles of composition(s) herein have an average size larger than about 100 nm in at least one, such as, e.g., in aspects, any direction, such that particles are considered non-nano $TiO_2$. In certain aspects, compositions comprise both non-nano ZnO and non-nano $TiO_2$.

In aspects, composition comprise titanium dioxide ($TiO_2$) particles having a size of at least about 100 nm-about 2000 nm, e.g., at least about 1000 nm-about 2000 nm.

In aspects, population(s) of $TiO_2$ particle(s) comprise particle(s) which are at least generally, at least substantially, at least essentially, or are regularly shaped. In aspects, $TiO_2$ particles are spherical in shape.

In aspects, $TiO_2$ is provided in uncoated form. In aspects, $TiO_2$ is provided in coated form. In aspects, $TiO_2$ can be coated with any suitable coating providing for compositional characteristic(s) provided herein. In aspects, coated $TiO_2$ particles comprise caprylic capric triglyceride, aluminum hydroxide, stearic acid, polyhydroxystearic acid, or combination(s) thereof. In aspects, $TiO_2$ is provided in a form at least substantially similar to that of AccessSUN E50C (Access Ingredients) or is the product itself.

In certain aspects, $TiO_2$ particles of composition(s) provided herein can be coated. Coated $TiO_2$ is discussed in further detail in the context of metallic oxide particle component of composition(s) and characteristic(s) thereof elsewhere herein.

Non-Metal/Non-Metal Oxide Component

As noted above, compositions can comprise a non-metal/non-metal oxide particle population/component. In aspects, such a component is present with a metallic oxide particle population/component.

In aspects, non-metal oxide(s) can comprise (1) hollow, spherical, styrene acrylate copolymer commercially obtained from 'Sun Spheres Powder', (2) irregular, non-spherical platelets of synthetic mica fluorophlogopite, (3) irregular non-spherical platelets of mica, (4) irregular, non-spherical platelets of clay, e.g., disteardimonium hectorite, (e.g., which can provide detectable or significant composition bulking effect), or (5), a combination of any or all thereof. In aspects, composition(s) can comprise a plurality of particle populations such as two or more particle populations discussed in additional detail herein.

As noted elsewhere, any element(s) provided herein are implicitly disclosed as compositions consisting of particle populations consisting of such elements, etc. The disclosure provides several functional and structural characteristics that reflect the basic and novel properties of compositions consisting of focused elements of this disclosure.

Silica Particles

In certain aspects, composition(s) provided herein further comprise, in addition to an active ingredient particle population component, a metal oxide particle population component, or both, one or more additional populations of particles, such as, e.g., one or more, e.g., two siliceous compound particle components. In aspects, compositions can comprise, in addition to any component mentioned here, an amorphous silica (optionally amorphous spherical) component. In aspects, composition(s) can further comprise a mixture of diatomaceous algae. In aspects, compositions comprise at least 0.25%, e.g., at least 0.5%, e.g., 0.75-3% calcium borosilicate particles.

According to aspects, composition(s) provided herein comprise an effective amount of non-nano, non-metal oxide(s). In aspects, non-nano non-metal oxide(s) detectably or significantly block, scatter, reflect, refract, or otherwise attenuate an amount of UV radiation, blue light, infra-red light, visible light, or any combination thereof which could or would otherwise cause detectable or significant damage or change to the subject to which composition(s) are applied. According to aspects, non-nano non-metal oxide(s) or population(s) of particles thereof, provide detectable or significant absorbent activity which serve(s) to detectably or significantly, balance composition oiliness, aesthetics, and spread ability.

In aspects, one particle population comprises one or more siliceous compounds. In aspects, the siliceous compounds detectably or significantly reflect, refract, and scatter sunlight. In aspects, siliceous compound particles can comprise (1) spherical amorphous silica particles, (2) non-porous salt of borosilicate optionally calcium borosilicate or borosilicate or both commercially obtained as 'Covabead Glass Crystals' (3) porous 3-dimensional photonic algal crystal specifically plankton glass flower (highly porous), or any combination of any or all thereof.

According to aspects, composition(s) provided herein comprise an effective amount of both non-nano metal oxide(s) and non-nano non-metal oxide(s) to block, scatter, reflect, refract, or otherwise attenuate an amount of UV radiation, blue light, infra-red light, visible light, or any combination thereof which could or would otherwise cause detectable or significant damage or change to the subject to which composition(s) are applied.

In aspects, composition(s) provided herein comprise a non-metal particulate compound component. In aspects, compositions comprise an effective amount of a non-metal particulate compound(s). In aspects, a non-metal particulate compound component can comprise, e.g., one or more siliceous compound(s). In aspects, compositions comprise an effective amount of one or more siliceous compound(s).

In aspects, a non-metal particulate compound component can comprise one or more compound(s). In aspects, a non-metal particulate compound component can comprise one or more silicas. In aspects, one or more silicas can be provided in powder form. In aspects, compositions can comprise two or more different forms of silica, e.g., two or more different silica powders (e.g., silica powder types). In aspects, use of a plurality of silicas in composition(s), or, similarly, a plurality of any type of compound provided herein, detectably or significantly increases the reflection, refraction, or scatter of sunlight (e.g., UV, visible, HEV/blue light) provided by composition(s). In aspects, such an increase in reflection, refraction or scatter of sunlight detectable or significantly increases the photoprotective quality(ies) of composition(s). In certain aspects, silica can be present in spherical, porous form.

Silica components of compositions can be solid or porous/hollow (or comprise both types) and can be spherical, other regular shape, or irregular in shape. In aspects, compositions comprise Calcium Sodium Borosilicate (Covabeads Glass Crystals), which are non-porous, spherical, glass particles.

Particles of compositions can scatter light through direct transmittance, diffused transmittance, etc. Particles can, in cases, DoS improve diffusion efficiency in a matrix/composition.

In aspects, a non-metal particulate compound component of a composition can comprise, e.g., green algae (IR), plankton glass, e.g., plankton glass in spherical or porous form ("Silipheres") or irregular plankton glass, such as, e.g., Plankton Photonic Algal—3D (non-spherical), glass-like calcium sodium borosilicate (e.g., Covabead Crystals), SunSphere (hollow spherical particles), bacterium such as, e.g., *Deinococcus radiodurans*, one or more peptides such as, e.g., Carnosine Bioidentical peptide, Elixir IR, or combinations thereof, *Echinacea Purpurea*/Symfinity, or other non-metal particulate compound(s) described herein or known in the art.

In aspects, one or more compound(s) of compositions can contribute to an anti-pollution effect of a composition as much as or, in aspects, detectably or significantly more than, or, e.g., as opposed to, a sunlight protection effect. In aspects, compounds such as, e.g., Carnosine (IR) and Symfinity provide such activity. In aspects, one or more such compounds further provides a detectable or significant anti-aging effect.

According to certain aspects, compositions herein reflect an at least additive effect of a provided combination of API metal oxide particles and non-metal particles, such as one, two, or three types of silica particles, such as, in aspects, a synergy of one or two API/metal oxides or of the various types of particles described herein, with non-metal oxides such as combination one or more different silica compounds, with styrene acrylate copolymer, synthetical mica etc. in terms of the composition's ability to reflect/refract/scatter sun light (UV, Visible, HEV/Blue Light). In aspects, such effects are in addition or an alternative to effects of the composition associated with the combination of any such particles with the optional peptide (e.g., L-carnosine) and plant/microorganism extract elements described herein (e.g., *echinacea* or *deinococcus* extract components), in terms of, e.g., DOS higher protection from UVA/UVB, IR, blue light, etc.

In aspects, compositions comprise an effective amount of Calcium Sodium Borosilicate is a "spherical glass bead" (1-13, e.g., 1-7 micron round particle) sold under the tradename Covabead® that serves as an SPF booster and provides protection to skin from damage caused by blue light (high energy blue light). At a concentration of 5%, Sensient reports an increase in SPF efficacy of 46%. Sensient Cosmetic Technologies, Covabead® Crystal 360 Skin Protection (Sep. 14, 2018). See also, Covabead Crystal Technical Data Sheet (Mar. 3, 2014; revised 3/8/2017; recommended use level from 0.1-30%).

In aspects, a siliceous compound of the broad-spectrum photoprotective compositions of the present invention is amorphous silica, also known in the art as amorphous silicon oxide hydrate. Optionally, the amorphous silica is a spherical, porous powder, still more optionally having a mean particle size ranging from about 6 microns to about 10 microns. One especially possible amorphous spherical silica is Silisphere LS-8H available from Argan Co.

A second siliceous compound that is a possible ingredient of the broad-spectrum photoprotective compositions of the present invention is a mixture of diatomaceous algae—unicellular, photosynthetic microorganisms having a nano-patterned cell encasement made of amorphous biosilica, also known in the art as a "frustule", that creates a highly efficient light trapping mechanism. See J. Romann et al. "Wavelength and orientation dependent capture of light by diatom frustule nanostructures" (2015), published online at nature.com/articles/srep17403; X. Chen et al., "Numerical and experimental investigation of light trapping effect of nanostructured diatom frustules" (2015), published online at nature.com/articles/srep11977. See also J. Mishler et al, "Biomimetic Photonic Crystals based on Diatom Algae Frustules" presented at the March 2015 meeting of the American Phytopathological Society, Abstract #A4.004.

Amorphous silica, optionally amorphous spherical silica, is present in broad-spectrum photoprotective compositions of the present invention at a concentration of from about 0.5 to about 5.0%.

Plankton Glass Flower® (INCI Name: "Plankton Extract"), a combination of diatomaceous algal species, is commercially available from Odycea SAS (Lannion, France) and distributed in the United States by Argan Co. (Northridge, California) and can be optional included or excluded. Technical data sheets and brochures describe Plankton Glass Flower as "algal photonic and porous silica crystals" or, alternatively, "planktonic material" sourced from the lakes in the volcanic region of Auvergne, France—namely, "siliceous fragments of freshwater algae species[,] mainly *Fragilaria zeilleri, Gomphomena angustatum, Navicula radiosa*, and *Cyclotella andancensis*"—that contains greater than about 75% silica. Plankton Glass Flower not only provides "UV-visible [light] attenuation due to both reflection and scattering" but also serves as an "oil absorber" and "pollutant scavenger which entraps . . . impurities [at the surface of the skin]." One, or optionally a mixture of two or more, diatomaceous algal species having photonic and porous silica crystals and a silica content of at least about 75% is/are present in broad-spectrum photoprotective compositions of the present invention at a concentration of from about 0.1 to about 2.0%, optionally from about 0.25 to about 1.0%, and even more optionally at a concentration of at least about 0.5%.

Optionally the one or more diatomaceous algal species having photonic and porous silica crystals and a silica content of at least about 75% are selected from the group consisting of *Fragilaria zeilleri, Gomphomena angustatum, Navicula radiosa*, and *Cyclotella andancensis*. In possible embodiments of the present invention the ratio of (i) one or more diatomaceous algal species having photonic and porous silica crystals and a silica content of at least about 75% to (ii) amorphous silica, optionally spherical, porous silica, is from about 1:9 to about 1:3. Total silica content in compositions of the present invention—silica found in (i) one or more diatomaceous algal species having photonic and porous silica crystals and a silica content of at least about 75% and (ii) amorphous silica, optionally amorphous, spherical silica—is optionally from about 1.0 to about 5.0%, more optionally from about 2.0 to about 4.0%.

In certain possible embodiments that contain $CeO_2$, the ratio of (1) $CeO_2$ to (2) Plankton Glass Flower (as described above) to (3) Amorphous Silica is 1:2:8.

In some especially possible embodiments of the present invention that are tinted with at least two iron oxides, the ratio of (i) one or more diatomaceous algal species having photonic and porous silica crystals and a silica content of at least about 75% to (ii) amorphous silica, optionally spherical, porous silica, is about 1:4.

In other especially possible embodiments of the present invention that are not tinted (i.e., do not contain iron oxides), the ratio of (i) one or more diatomaceous algal species having photonic and porous silica crystals and a silica content of at least about 75% to (ii) amorphous silica, optionally spherical, porous silica, is about 1:5.

The ability of photonic crystals in algae to provide protection from UV radiation is described in American Physical Society, "Photonic Crystal Sunscreen For Sea Scum." (Sep. 19, 2006) http://www.sciencedaily.com/releases/2006/09/060918202844.htm French Patent Application 3072292 filed Oct. 16, 2017, entitled "Utilisation D'Algues Microscopiques Pour la Préparation de Compositions Cosmétiques et/ou Dematocosmétiques Destinées à Protégér Des Effects Délétères de la Lumière Bleue" teaches the use of microscopic algae having a glass (siliceous) exoskeleton—un exosquelette de verre (siliceux) from the class Bacillariophyta to protect the skin from deleterious effects of blue light. More particularly, this publication teaches the uses of *Fragilaria zeilleri, Gomphomena angustatum, Navicula radiosa, Cyclotella andancensis* at concentrations from 0.01% to 10% (page 8, lines 22-23). This combination of microalgal extracts is sold under the tradename Plankton Glass Flower® by Odycea SAS (Lannion France).

Surprisingly and unexpectedly, in aspects, a synergistic combination of an amorphous spherical silica and a mixture of diatomaceous algae comprising at least two, optionally three, and still more optionally all four of *Fragilaria zeilleri, Gomphomena angustatum, Navicula radiosa*, and *Cyclotella andancensis* in further combination with Zinc Oxide and Titanium Dioxide (or, e.g., only zinc oxide) provides a sun protection factor of at least 50, with a critical wavelength of greater than about 375, without visible skin whitening on Fitzpatrick Skin Types I-IV. However, in aspects, other compositions described herein perform as well or better in terms of two or three (or more) of the performance characteristics of compositions (e.g., SPF, HEV blocking/scattering, UVA1/UV ratio, etc.).

Clays/Suspending Agents

In aspects, a composition comprises an effective amount of particle suspending agent(s). In aspects, some, most, or generally all or all of the suspending agent is composed of a clay material, e.g., a bentonite or hectorite clay. In aspects, some, most, generally all, or all of the clay component is a hectorite clay. Suitable hectorite clays include those products sold under the Bentone Gel brand that are commercially available from Elementis, PLC (East Windsor, NJ) including, e.g., Bentone Gel PTM V (Disteardimonium Hectorite dispersed in Phenyltrimethicone and Triethyl Citrate; recommended use level 2.5-25%) or Bentone V 38CG. In aspects, the clay added to an anhydrous formulation is mostly, generally only, or only a clay that is the same as or substantially similar to the clay composition of Bentone V 38CG. In aspects, an emulsion formulation comprises a clay component that is mostly, generally, or only composed of Bentone Gel PTM V or a hectorite clay composition that is substantially similar in terms of particle suspension and enhancing or at least not interfering with the function(s) of other element(s) of the composition.

In aspects, the clay is present in a ratio with metal particle actives, e.g., as exemplified elsewhere. In aspects, one or both of the ZnO and $TiO_2$ that may be present are coated with a suitable coating agent, such as, e.g., triethoxycaprylylsilane.

In aspects, compositions can comprise EWOCREAM or a substantially similar product. In aspects, the recommended use level for EWOCREAM (polyglyceryl-3 sorbityl linseedate) is 2-5%. sinerga.it/en/raw-materials/products/emulsifiers/ewocream. However, in aspects, the emulsifier of any emulsion composition is mostly, generally, or entirely, a polyglyceryl-2 emulsifier, such as polyglyceryl-2 sesquioleate (commercially available as SGS-PGO 152 from Argan).

Composition Form and Base (Emulsions and Anhydrous Formulations)

In aspects, composition(s) provided herein can be provided in any form suitable for effective application to a particular target, such as, e.g., mammalian skin, e.g., human skin. In aspects, composition(s) are provided as at least substantially anhydrous or anhydrous composition(s). In aspects, composition(s) are not provided as emulsion(s).

In some aspects, composition(s) can be provided as emulsion(s). In aspects, composition(s) provided as an emulsion can be in the form of, e.g., an oil-in-water (O/W) emulsion, a water-in-oil (W/O) emulsion, or any effective form of emulsion capable of providing the inventive composition(s) having one or more of the characteristic(s) described herein. In aspects, composition(s) are not provided in anhydrous or substantially anhydrous form.

In aspects, composition(s) are not provided as gel(s). In aspects, composition(s) are not provided in aerosolized or aerosolizable form. In aspects, composition(s) are not provided in any form not characterizable as an emulsion. In aspects, composition(s) are not provided in any form not characterizable as anhydrous or substantially anhydrous.

According to aspects, composition(s) provided herein, e.g., composition(s) provided as emulsion formulation(s), composition(s) provided as anhydrous or at least substantially anhydrous formulation(s), or both, provided by the invention comprise a metal component, e.g., a metallic oxide component, e.g., a component comprising one or both of zinc oxide (ZnO) compound(s) and titanium dioxide ($TiO_2$) compound(s). In aspects, such ZnO compound(s), $TiO_2$ compound(s), or both can be present in distinct shape(s) as is discussed elsewhere herein. In aspects, one or more metallic oxide compound(s) present in composition(s)/formulation(s) (e.g., emulsion(s)/anhydrous/substantially anhydrous formulation(s)) provide(s) detectable or significant protection from UVA radiation, UVB radiation or both. In aspects, one or more metallic oxide compound(s) provide(s) detectable or significant protection from UVA radiation compared to prior art composition(s) and disclosure(s), such as any of those incorporated by reference herein.

Emulsions

In aspects, the invention provides multi-dimensional, multi-particulate mineral sunscreen composition(s). In aspects, the sunscreen composition(s) described herein is/are provided as emulsion(s). In aspects, composition(s) are provided as water-in-oil (W/O) emulsion(s).

In aspects, composition(s) formulated as emulsion(s) are suitable for daily use. In aspects, composition(s) formulated as emulsion(s) provide one or more skin health benefit(s) (such as, e.g., detectable or significant skin hydrating effect(s). In aspects, composition(s) formulated as emulsion(s) provide one or more skin aesthetic modifying effect(s) such as, e.g., DOS skin smoothing or blurring, detectable or significant wrinkle reduction, and the like. In aspects, composition(s) formulated as emulsion(s) comprise detectable or significant skin hydrating (skin moisturizing) effect(s) such that composition(s) can be used as a daily moisturizer. Such skin health benefit(s) and skin aesthetic(s) modification effect(s) are described elsewhere herein.

In aspects, composition(s) provided herein are provided as W/O emulsion(s) wherein the W/O emulsion(s) comprise all-natural emulsification ingredient(s). In aspects, composition(s) herein comprise 100% natural emulsifier(s). In aspects, emulsifier(s) include one or more polyglycerol compound(s). In aspects, composition(s) herein are free of polyethylene glycol(s) (PEG(s)), e.g., such that composition(s) are characterizable as being PEG-free. In aspects, emulsion(s) comprise polyglyceryl-2 sesquioleate or, e.g., one or more other emulsifier(s) having at least generally the same, at least substantially effectively the same, at least substantially the same, or the same (equivalent) emulsification property(ies) or result(s) as polyglyceryl-2 sesquioleate when used in composition(s) herein. Other potentially suitable emulsifier(s) and co-emulsifier(s) for use in composition(s) provided by the invention are described elsewhere herein.

In aspects, emulsion(s) provided by the invention comprise a non-metal component, e.g., a non-metallic oxide component. In aspects, emulsion(s) provided herein comprise at least one silica compound, e.g., silica or, e.g., a silica derivative such as, e.g., Covabead® Crystals. In aspects, one or more silica compound(s) provide(s) detectable or significant protection from ultraviolet light, visible light, blue light, or any combination thereof. In aspects, emulsion(s) comprise Desertica (green algae). In aspects, emulsion(s) further comprise SunSphere Powder. In aspects, Desertica, SunSphere Powder, or both provide infrared light protection as well as a detectably or significantly increased protection from UVA and UVB light (e.g., detectably or significantly reduced amount of UVA and UVB light reaching the skin) when composition(s) comprising such constituent(s) are present on the skin compared to composition(s) lacking such compound(s). In aspects, composition(s), e.g., in the form of emulsion(s), comprise one or more acrylate(s). In aspects, one or more acrylate(s) form a detectable film upon application to a target, e.g., skin, such that composition(s) comprising emulsion(s) provides detectable or significant water resistance.

In certain aspects, composition(s), e.g., in the form of emulsion(s), comprise one or more silicone(s), e.g., linear silicone(s), or ester(s) capable of providing a detectable or significant modification of one or more visible skin aesthetic(s) (e.g., detectably or significantly mitigating the skin whitening effect of mineral(s) present in composition(s)).

In aspects, composition(s), e.g., in the form of emulsion(s), comprise one or more biological active(s), e.g., Fullerene/First. In aspects, one or more biological active(s) present in composition(s) provide(s) detectable or significant anti-aging effect, or, e.g., detectable or significant protection from one or more environmental pollutant(s). In aspects, emulsion(s) comprise no (e.g., no detectable or significant amount of) artificial preservative(s), whereby, e.g., such emulsion(s) operate as preservative-free system(s). In aspects, such composition(s) can comprise an aqueous phase and a non-aqueous phase. In aspects, the non-aqueous phase comprises at least about 60%, 65%, 70%, 75%, or 80% of the composition(s). In aspects, the non-aqueous phase of composition(s) comprises one or more component(s) or compound(s), e.g., metal oxide(s), non-metal oxide(s), or both, present as dispersed particulates. In aspects, such dispersed particulates, e.g., metal oxide(s), non-metal oxide(s), or both, make up at least about 20%, e.g., at least about 25%, at least 30%, at least about 35% (e.g., 22.5%-35%, 25%-40%, 25%-35%, etc.) of composition(s).

In aspects, composition(s) provided herein are provided as water-in-oil (W/O) emulsion(s) wherein the W/O emulsion consists of an aqueous phase dispersed in the form of small droplets, into a continuous oil phase. In aspects, the water-in-oil emulsion is a two-phase mixture of immiscible liquids, wherein an inner phase containing water soluble ingredients is dispersed in a continuous outer phase of hydrophobic ingredients such as oil, ester, and silicones, e.g., mostly, generally, or only linear silicones. In aspects, composition(s) is/are formulated as W/O emulsion(s) comprising a 100% natural emulsifier belonging to the polyglycerol compound family and which demonstrate(s) detectable or significant stability as determined by one or stability test(s) typically performed in, and recognizable by those in, the art. In aspects, composition(s) comprising a W/O emulsion does/do not contain any detectable or significant amount of one or more of cyclic silicone(s), paraben(s), polyethylene glycol(s) (PEG(s)), and polypropylene glycol(s) (PPG(s)).

In aspects, emulsion compositions comprise a silicone emollient component as described in the listing of aspects herein as exemplified in example formulations herein. In aspects, such a silicone composition based emollient component comprises 2, 3, or more distinct types of silicone compounds/compositions.

According to certain aspects, composition(s) provided herein in the form of emulsion(s) comprise a particulate component and a non-particulate component, wherein a particulate component comprises one or more composition constituent(s) which remains in particulate form while a non-particulate component comprises one or more composition constituent(s) which is present in non-particulate (e.g., liquid or dissolved form). In certain typical aspects, a particulate component comprises, as is described in detail elsewhere herein, a plurality of particle population(s) which differ from one another by the type(s) of particles comprised therein, or, e.g., the size, shape, or other physical characteristic(s) of particles comprised therein. In aspects, one or more, e.g., typically two or more, three or more, four or more, or even more constituents of composition(s) are non-particulate in nature and represent constituents of the non-particulate component of the emulsion composition(s). In aspects, a non-particulate component of an emulsion composition forms a coating of particles of at least one particle population of the particulate component during the manufacturing process of the composition(s). In aspects, a non-particulate component of an emulsion composition forms a coating of particles of at least one particle population of the particulate component during the manufacturing process of the composition(s) which is not initially provided in coated form. That is, in aspects, a particle population is provided uncoated, then, during the process of manufacture of an emulsion composition, e.g., during one or more homogenization step(s) of such method(s), constituent(s) or agent(s) of a non-particulate component of the emulsion composition(s) detectably or significantly coat some, most, generally all, substantially all, essentially all, or all particle(s) of such the population of particle(s). In aspects, some, most, generally all, substantially all, essentially all, or all particles provided in uncoated form, but coated by a non-particulate component of an emulsion composition during manufacture, remains at least mostly, at least generally, at least substantially, at least essentially, or remains entirely coated upon application of the composition (e.g., upon application to human skin).

In certain aspects, composition(s) provided as emulsion(s) comprise a particulate component and a non-particulate component, wherein the particulate component comprises at least one constituent which has a detectably or significantly porous surface. In aspects, for example, composition(s) can comprise a mesoporous metal oxide such as a mesoporous zinc oxide. In aspects, portion(s) of a non-particulate component of an emulsion can detectably or significantly fill, or, e.g., at least partially fill some, most, generally all, essentially all, or all of the pores of some, most, generally all, essentially all, or all such porous particles of a particle population. In aspects, porous particle(s) of a particle population have a refractive index which is detectably or significantly different from that of skin. In aspects, the at least partial fill of at least some pores of at least some of the porous particles of the porous particle population detectably or significantly modifies the refractive index of the particles such that the refractive index of the particles becomes detectably or significantly closer to that of skin. In aspects, the at least partial fill of at least some pores of at least some of the porous particles of the porous particle population provides for a refractive index detectably or significantly closer to that of skin than the particle population having a reduced filling of pore(s) with non-particulate emulsion constituent(s) would otherwise provide, such that the emulsion composition is detectably or significantly less whitening upon application to the skin (e.g., as compared to composition(s) where such porous particulate population(s) remain less filled or unfilled with non-particulate emulsion component).

Anhydrous Formulations

In aspects, at least about 50%, such as, e.g., ≥~55%, ≥~60%, ≥~65%, ≥~70%, ≥~75%, ≥~80%, ≥~85%, ≥~90%, or, e.g., ≥~95%, of composition(s) is present in an oil phase.

In aspects, composition(s) provided herein are provided as anhydrous formulation(s). In aspects, anhydrous composition(s) are suitable for daily use. In aspects, anhydrous formulation(s) provide one or more skin health benefit(s) (such as, e.g., detectable or significant skin hydrating effect(s). In aspects, anhydrous formulation(s) provide one or more skin aesthetic modifying effect(s) such as, e.g., skin smoothing or blurring, detectable or significant wrinkle reduction, and the like. In aspects, anhydrous composition(s) comprise detectable or significant skin hydrating (skin moisturizing) effect(s) such that composition(s) can be used as a daily moisturizer. Such skin health benefit(s) and skin aesthetic(s) modification effect(s) are described elsewhere herein.

In aspects, anhydrous composition(s) can comprise one or more coloring agent(s), e.g., pigment(s), providing a coloration, e.g. tint to the composition(s). In aspects, composition(s) can be untinted. In aspects, composition(s) are suitable for use as a daily tinted or untinted moisturizer for the face or lips (or, e.g., both) which provides detectable or significant photoprotection, such as, e.g., having a sun protection factor of at least about 30, ≥35, ≥40, ≥45, or, e.g., ≥50. In aspects, anhydrous composition(s) can be provided as, e.g., in the form of a stick, e.g., sheer stick or, e.g., tinted stick. In aspects, compositions can be provided in the form of a compact.

Base/Formulation Ingredients

Film-Forming Agents/Components

In aspects, compositions of the invention comprise an effective amount of film forming agent(s). As is known, "film forming" ingredients are chemicals that produce a continuous film on skin when applied in sufficient/suitable amount.

In aspects, the amount of film forming compounds/compositions in the composition is limited to 3% or less, e.g., 2.5% or less, 2.25% or less, 2% or less, 1.75% or less, 1.5% or less, or 1.25% or less of the composition (e.g., 0.25-2%, 0.25-1.5%, 0.5-1.75%, 0.5-1.25%, 0.75-1.25%, etc.). In general, compositions can comprise any suitable film former(s). In aspects, compositions comprise only 1-3 types, 1-2 types, or only 1 type of film forming compound/agent.

Compositions of the invention can comprise siloxane(s). Siloxanes, also known in the art as organo-substituted polysiloxanes, are linear or cyclic polymers of monomeric silicon/oxygen monomers, in which a polymeric backbone is made up of alternating silicon and oxygen atoms. The silicon atoms may carry a wide variety of substituents, which can be the same or different.

Compositions of the present invention optionally have a water resistance of 80 minutes and are comprised of at least one, optionally at least two, film-forming polysiloxane polymers that impart water repellency and wash-off resistance. In aspects a water resistance of 80 minutes means that the composition loses less than about 20%, less than about 15%, less than about 12.5%, or less than about 10% (e.g., 7.5-15%, 5-12.5%, 6-11%, etc.) of its initial SPF when subject to standard water resistance testing conditions for 80 minutes. In aspects, compositions similarly or alternatively qualify as 40-minute water resistant. In aspects, 80-minute WR means that the loss of SPF described above (any of such amounts of loss) is measured with respect to the SPF tested at 40 minutes of water exposure testing. E.g., in aspects a composition has 100% of an SPF (e.g., of 60), loses less than 10% of that at 40 minutes of water exposure (thus maintaining an SPF of at least 54), and exhibits WR at 80 minutes (e.g., exhibiting an SPF of at least 48, 49, or 50 after 80 minutes water exposure).

In aspects, most, generally all, or all of the film former component of a composition is composed of Acrylates/Dimethicone Copolymer—a copolymer of dimethicone and one or more monomers of acrylic acid, methacrylic acid, or one of their simple esters. In possible embodiments, the two film-forming polymers are (i) Bis-Vinyl Dimethicone/Dimethicone Copolymer, commercially available in combination with Dimethicone or Cetyl Dimethicone and (ii) Dimethicone (and) Acrylates/Dimethicone Copolymer. Bis-Vinyl Dimethicone/Dimethicone Copolymer is a copolymer of Dimethicone end-blocked with Vinyl Dimethicone. Dimethicone is a mixture of fully methylated linear siloxane polymers. Vinyl Dimethicone is a derivative of Dimethicone in which some of the methyl groups are replaced with vinyl groups. The vinyl groups can occur at the ends of the siloxane chain may be pendant to the siloxane chain. Bis-Vinyl Dimethicone is a derivative of Dimethicone in which one methyl group at each end of the siloxane chain is replaced with a vinyl group. Cetyl Dimethicone is a dimethyl siloxane polymer. Acrylates/Dimethicone Copolymer is a copolymer of Dimethicone and one or more monomers of Acrylic Acid, Methacrylic Acid or one of their simple esters. Each of these components may or may not be present in compositions. The structural formulas for these compositions are provided in the art, including in patent documents cited herein.

In addition to the two Dimethicone Copolymer film formers (discussed immediately above), the broad-spectrum photoprotective compositions of the invention are comprised of at least two, optionally three Silicone Compounds selected from Methicone, Dimethicone, Simethicone, Cetyl Dimethicone and Phenyl Trimethicone.

As noted elsewhere, uncontradicted, any capitalization of chemical names sometimes herein (e.g., Cetyl Dimethicone) merely reflects common industry practice, and is not meant to impart any indication that the capitalized term refers to any different composition, compound, etc., from the non-capitalized form (cetyl dimethicone). Readers will understand such practice and meaning.

In aspects, a first Silicone Compound is a Silicone Wax (optionally Cetyl Dimethicone), and a second Silicone Compound is a Silicone Fluid (optionally selected from the group of Methicone, Dimethicone, Simethicone, and Phenyl Trimethicone). Other elements of compositions can include effective amounts of methicone, simethicone, dimethicone, phenyl trimethicone and the like.

In certain possible embodiments, at least two dimethicones are included in a broad-spectrum photoprotective compositions of the invention: e.g., a first Dimethicone having a lower kinematic viscosity in the range of 0.65 to 400 centistokes (cst), optionally about 50 cst; and a second Dimethicone having a higher kinematic viscosity in the range of 1,000 to 5,000 cst. Dimethicone or phenyltrimethicone and Cetyl Dimethicone are optionally present in broad-spectrum photoprotective compositions of the invention at a concentration of from 1 about 5%; optionally less than about 4.5, still more optionally about 4.0.

SPF Boosters

Improved sunscreen efficacy—including by formulating for SPF 50+ with broad-spectrum coverage, UVA:UVB ratio of 1:3, and protection from damage caused by visible light, blue light, and infrared radiation—has been achieved through incorporation of so-called "SPF Boosters" (chemical and physical), pigment dispersants (including polyhydroxy stearic acid (PHSA), sold under the tradename Dispersun®), iron oxides, and algae/plankton.

Chemical SPF Boosters known in the art include: Butyloctyl Salicylate (HallBrite® BHB from The HallStar Co., Bedford Park, IL)(2-10%), hallstarbeauty.com/product/hallbrite-bhb/; see also U.S. Pat. Nos. 5,783,173, 5,788,954, 5,849,273, 6,350,894); Diethylhexyl 2,6-Naphthalate (Corapan®TQ from Symrise Inc., Teterboro, NJ)(1-5%); Triethyl Citrate and Tributyl Citrate (CITROFOL® AI and CITROFOL®BI, both from Jungbunzlauer; see sofw.com/en/news/latest-news/personal-care/2419-citrofol-citrate-esters-in-sunscreen-formulation (describing use of CITROFOL citrate esters to achieve stable dispersions of UV inorganic filters); octyldodecyl citrate crosspolymer (and) ethyl methicone (and) cetyl dimethicone/bis vinyl dimethicone crosspolymer (COSMOSURF®LS-1/Siltech) and Octyldodecyl Neopentanoate (Elefac® I-205 from Alzo International, Inc., Sayereville, NJ)(5-20%; see U.S. Pat. No. 5,116,604). Any or all thereof can be incorporated into compositions in suitable amounts.

E.g., broad-spectrum photoprotective compositions of the present invention contain at least one, optionally at least two, and still more optionally three SPF Boosters selected from the group of styrene/acrylates copolymer, butyloctyl salicylate, and triethyl citrate (each as described below), and polyhydroxystearic acid (described above).

Physical SPF boosters include spherical powders, each discussed below: silicas, silicates, and styrene/acrylates copolymer.

Non-nano, microspherical silica, including Solespheres® from AGC Chemicals America, Inc., (Exton, Pennsylvania) have been used to reduce whitening and increase SPF in mineral sunscreens. The Solespheres® range includes both porous silicas (3-12 microns) and non-porous silicas (4-20 microns). At 2%, Solespheres® H53 (porous, 5 microns) is reported to double the SPF of sunscreen formulations using inorganic filtering agents (ZnO and TiO2). See, AGC Chemicals America, Inc., Frequently Asked Questions About Solesphere® H-53 Silica for Sunscreen Formulations. See also, AGC Chemicals America, Inc., Solespheres® Silica for Sunscreens (reporting "significant SPF boosting" at 1-2% of H-53).

Sample mineral sunscreen formulation ACTS 22337 from AGC includes a high loading (25%) of a MZOA, Zinclear® XP65COCO (Zinc Oxide dispersed in Coco Caprylate/Caprate, Polyricinoleate and Isostearic Acid), two silicas—Solesphere® H-53 and Solesphere® NP-100 (non-porous 10 microns), and a PEG-Free water-in-oil (W/O) and water-in-silicone (W/Si) emulsifier (TMP Lauryl Dimethicone). ACTS Formula 22514 from AGC contains a high loading (30%) of surface-treated (i.e., coated) TiO2 (Caprylic/Capric Triglyceride, Titanium Dioxide, Alumina, Stearic Acid, and Polyhydroxystearic Acid), three iron oxides (red, yellow and black) and two W/O emulsifiers (TMP Lauryl Dimethicone and Sorbitan Oleate). See, Solesphere™ Silica for Sunscreen Formulations.

SunSpheres®, a Styrene/Acrylates Copolymer having an average particle size of from 300-350 nm, is sold as an SPF Booster by The Dow Chemical Company ("DCC"). See Rohm & Haas, "SUNSPHERES™ Hollow Sphere Technology: An SPF Booster for More Aesthetically Pleasing Formulations" (Feb. 22, 2007) (recommended for 1-5%). At 5% SunSpheres solids, DCC reports an increase in SPF of 60 to 70%. See, Dow Personal Care, "SunSpheres™ SPF Boosters Hollow Sphere Technology for More Aesthetically—Pleasing Formulations at Higher SPF" p. 4 (Mar. 2, 2016). This publication provides samples formulations including an SPF 32.8 water-in-oil sunscreen containing ZnO (6%), TiO2 (6%) and Sunspheres (5%). See also, "SunSpheres™ SPF Booster in Daily Wear Applications p. 2 (Mar. 2, 2016; revised Jun. 10, 2019) reporting addition of 5.5% SunSpheres solids to a ZnO Cream increased SPF by 68% (from SPF 37 to SPF 62); and addition of 3% SunSpheres solids to a TiO2 Cream increased SPF by 53% (from SPF 11.3 to SPF 17.3)

Styrene/Acrylates Copolymer is a polymer of styrene and a monomer consisting of acrylic acid, methacrylic acid or one of their simple esters. These hollow spheres are manufactured via emulsion polymerization, and are commercially available from Dow (Midland, Michigan) under the name SUNSPHERES® Powder. A February 2006 Technical Data Sheet (TDS) describes SUNSPHERES® as "rais[ing] UV protection over the whole UVA/UVB spectrum."

Butyloctyl Salicylate (CAS No. 190085-41-7), commercially available as HallBrite® BHB from the Hallstar Company (Chicago, Illinois) and SunSolv® from Innospec Performance Chemicals (Salisbury, North Carolina) is a synthetically produced ester of Salicylic Acid and a branched $C_{12}$ alcohol, 2-butyloctanol. Butyloctyl salicylate, and its uses in topical formulations, are described in the following U.S. Pat. Nos. 5,783,173; 5,788,954; 5,849,273; and 6,350,894. Triethyl Citrate is the triester of ethyl alcohol and citric acid and can be present in aspects. In aspects, such a compound is included in a composition in suitable amount to exhibit DOS effects, but in other aspects it is excluded from compositions.

Surprisingly and unexpectedly, in aspects, a broad-spectrum photoprotective compositions of the present invention containing at least one, optionally at least two, and more optionally three of the above SPF Boosters provide an SPF of at least 30, and, in possible embodiments, an SPF of at least 50, without visible whitening on Skin Types I-IV under the Fitzpatrick Skin Type system of skin classification.

In aspects, compositions comprise at least 1, optionally 2, or optionally 3 long-chain branched compounds that may boost SPF-butyloctyl salicylate, octyldodecyl neopentanoate, and polyhydroxystearic acid.

In aspects, a non-conventional broad spectrum preservative booster that can be a composition that comprises of any one of (1) 1,2, hexanediol, (2) capryl glycol, (3) tropolone or in combination thereof in the composition. In aspects, compositions comprise a preservative booster that is mostly, generally, substantially, or entirely composed of 1,2 Hexanediol, Caprylyl Glycol or a related composition (e.g., a tropolone additive variant) (e.g., the products currently sold or recently sold under the tradenames Symdiol 68 T/Symrise and Symdiol 68/Symrise. In aspects, the preservative booster is present in at least 0.7% weight of the composition, e.g., 0.75-1.25% of the composition, e.g., 0.8-1%, or about 0.9 wt. % of the compositions.

Compositions also or alternatively can comprise effective amount(s) of any one or more of *Deinococcus radiodurans* material/extracts, Himanthalia elongate Extract, Carnosine (e.g., L-carnosine), *Capparis spinosa* (Cappers), Oppuntia *Ficus indica* (Cladodes), *Olea euopaea* (Olives), Bisabolol, *Zingiber officinale* (Ginger) Root Extract, Hexyldecanol, Cetylhydroxyprol Palmitamide, Stearic Acid, *Brassica camprestris* Sterols, *Polygonum aviculare* Extr.(Knotgrass), *Camelia officiales* Extract (Green Tea), vitamins, Ubiquinone (Co Q10 Disperse), allantoin, natural waxes and squalene (oil) alone or in combination thereof.

In aspects, compositions comprise Octyldodecyl Neopentanoate, e.g., 5-25%, 7.5-22.5%, 10-25%, 10-20%, 15-22.5%, 15-20%, or 18-22%. In aspects, compositions also or alternatively comprise an effective amount of isodecyl neopentanoate (e.g., the product sold currently as Sunboost® 1033B). In aspects, this element is present in an amount corresponding to 50-150%, or 25-200% of the amounts provided herein for octyldodecyl neopentanoate. In aspects, both agents are used/incorporated in compositions in approximately similar combined amounts.

Suspending Agent/Bulking Agent (E.g., Clay)

To evenly distribute and prevent settling of metal oxide particles, mineral sunscreen often requires addition a suspending agent, often a clay or clay-like substance based on silicates. Non-limiting examples of suspending agents that can be included in compositions include hectorites (stearalkonium hectorite and disteardimonium hectorite, delaminated to different degrees) and bentonite. Bulking agents are chemically inert, solid ingredients employed as diluents for other solids. Bulking agents can also serve as "extenders" of pigments. Compositions of the present invention may, and optionally do, include a bulking agent, optionally a hectorite (or a derivative of, or reaction product with, hectorite).

Emulsifier/Emulsifiers and Co-Emulsifiers

In aspects, the invention provides a sunscreen composition formulation comprising a water-in-oil emulsion. In aspects, a stable emulsion is developed using only one naturally obtained PEG free emulsifier containing at least 2-6 glycerin units. In aspects, the emulsifier is a polyglyceryl-2 emulsifier (e.g., polyglyceryl-2 triisostearate, polyglyceryl-2 tetraisostearate, polyglyceryl-2 dipolyhydroxystearate, etc.). In aspects, some, most, generally or all of the emulsifier is composed of polygyceryl-2 sesquioleate.

The inventive broad-spectrum sunscreen W/O emulsions of the present invention optionally contain a single emulsifier that (a) has a hydrophilic-lipophilic balance in the range of 3.0 to 8.0, more optionally 3.0 to 5.0 (b) does not contain polyethylene glycol and (c) is an ester formed with polyglycerin, optionally containing 3-6 glycerin units, but in other aspects comprising only 2 glycerin units.

It is surprising and unexpected to achieve a stable emulsion (i.e., one that does not separate into oil and water phases after storage at an elevated temperature of 50° C. for one month or 40° C. for three months) with only a single emulsifier.

The mineral sunscreen emulsions of the present invention optionally contain two W/O emulsifier(s), each a polyglycerin ester having 2-6 glycerin units, an HLB of 3.5-5.0, and not containing polyethylene glycol (PEG-free).

In certain possible embodiments, the two polyglycerin ester emulsifiers have 2-4 glycerin units. More optionally, these polyglycerin ester emulsifiers are selected from the group consisting of polyglyceryl-2 sesquioleate, polyglyceryl-3 ricinoleate, polyglyceryl-3 sorbityl linseedate, and polyglyceryl-4 oleate.

In possible embodiments of the present invention, the inventive broad-spectrum photoprotective composition contains a single emulsifier having a low HLB, by which is meant from about 3.0 to about 8.0, more optionally from about 3.0 to about 5.0, and still more optionally from about 3.5 to about 4.0.

Optionally, the low HLB W/O emulsifier is present at a concentration of from about 2.25% to about 6%, optionally at least about 2.5%, more optionally at least 5%.

One possible, but non-limiting example, of a low HLB W/O emulsifier is an ester formed with Polyglycerin, optionally containing 3-6 glycerin units, but optionally containing 2 or less, or only 2 glycerin units. These low HLB W/O emulsifiers are free of polyethylene glycol (i.e., are "PEG-Free"). Non-limiting examples of possible low HLB W/O ester emulsifiers are polyglyceryl-3 oleate, polyglyceryl-3 ricinoleate, polyglyceryl-3 sesquiisostearate, polyglyceryl-3 polyricinolate, and polyglyceryl-4 oleate.

In certain aspects, the selection of the emulsifier component of composition(s) herein provides detectably or significantly different performance characteristics apart and above from specific emulsification activity. In certain aspects, detectable or significant changes in product feel are attached by modification of an emulsification component.

According to certain aspects, composition(s) comprise a single emulsifying agent (which may or may not be accompanied by co-emulsifying agent(s)). In aspects, composition(s) comprise two or more emulsifiers. In aspects, compositions comprise a single polyglycerol compound. In particular embodiments, composition(s) comprise less than three, less than 2, or, e.g., a single polyglycerol compound wherein the polyglycerol comprises ≤~4, ≤~3, or ≤~2 glycerin units. In aspects, composition(s) comprise a polyglycerol compound wherein the polyglycerol compound comprises no more than two glycerin units.

According to certain embodiments, the emulsifier component of compositions, e.g., an emulsifying ingredient, is a mixture of mono- and di-esters of a fatty acid. In aspects, the emulsifying ingredient is a mixture of mono- and di-esters of oleic acid. According to certain aspects, composition(s) comprise an emulsifying agent comprising no more than two glycerin units, wherein the emulsifier is present as a mixture of mono- and di-esters of a fatty acid such as oleic acid. In aspects, compositions comprise a polyglycerol compound or mix of polyglycerol compound(s) wherein each polyglyceryl compound has no more than a single glycerol unit to which a fatty acid, e.g., oleic acid, is not attached. In aspects, each polyglycerol compound of an emulsification component of composition(s) provided herein comprise oleic acid bound to at least 50% of its glycerin units. According to certain aspects, the ratio of fatty acid, e.g., oleic acid, to glycerin units in any polyglycerol compound of the composition is 1:1 or 1:2. In aspects, the ratio of fatty acid to polyglycerin chains is about 3:2. In aspects, the ratio of fatty acid to individual glycerin units within the emulsifying agent is about 3:4. According to certain aspects, about 60% to about 80%, e.g., about 60% of the weight of the emulsifier is represented by a fatty acid, e.g., oleic acid. In aspects, at least about 50%, at least about 60%, at least about 70%, or higher of the weight of the emulsifier is represented by a fatty acid, e.g., oleic acid.

According to aspects, compositions provided herein can comprise a continuous, flexible, water-resistant substrate. In aspects, compositions have a low viscosity, as is described elsewhere herein. In aspects, compositions are provided as a water-in-oil emulsion. In aspects, composition(s) are PEG-free. In aspects, compositions herein can comprise, e.g., one or more ester(s), one or more liner silicones, one or more film formers, one or more clay compounds, one or more antioxidants, one or more anti-irritants, one or more preservatives or preservation enhancers (e.g., "preservative booster(s)"), or any combination of any or all thereof.

"Organic Sunscreens" includes chemicals (also known in the art as 'active ingredients") that absorb UVR, and include sunscreen active ingredients that are generally recognized as safe and effective and are approved for over-the-counter use by the U.S. Food and Drug Administration ("FDA")—namely, Avobenzone; Cinoxate; Dioxybenzone; Ecamsule; Homosalate; Menthyl anthranilate; Octocrylene; Octyl methoxycinnamate; Octyl salicylate; Oxybenzone; p-Aminobenzoic acid; Padimate O; Phenylbenzimidazole sulfonic acid; Sulisobenzone; and Trolamine salicylate. Organic sunscreens also include active ingredients approved by regulatory agencies outside the United States, but not currently approved by the FDA, including, 4-Methylbenzylidene camphor, Amiloxate, Benzophenone-9, Mexoryl® XL, Neo Heliopan® AP, Parsol® SLX, Tinosorb® A2B, Tinosorb® M, Tinosorb® S, Uvasorb® HEB, Uvinul® A Plus, and Uvinul® T 150. Other organic sunscreens are known in the art and reported in the documents cited herein. Compositions of the invention are, in aspects, generally free, substantially free, or entirely free of any such agents.

Broad-spectrum photoprotective compositions of the present invention optionally include one or several ingredients that (a) reduce visible redness (i.e., erythema) or inflammation (known in the art as anti-inflammatory) or act as an antioxidant (i.e., reduce oxidative damage; also known in the art as free radical quenchers), (b) reduce the appearance of the signs of skin aging, which can include fine lines, wrinkles, uneven pigmentation (dyschromia), loss of elasticity or firmness, increased dryness, reduced skin moisture, loss of softness/suppleness (collectively "anti-aging ingredients"), or (c) oil-absorbent powders. Non-limiting examples of antioxidants and anti-aging ingredients include: vitamins and derivatives thereof, optionally, ascorbic acid (vitamin C) and its salts; ascorbyl esters of fatty acids, ascorbic acid derivatives (e.g., magnesium ascorbyl phosphate, sodium ascorbyl phosphate, ascorbyl sorbate); tocopherol (vitamin E), tocopherol sorbate, tocopherol acetate, other esters of tocopherol; coenzyme Q10 (ubiquinone, ubiquinol) and its analogues, including without limitation, idebenone; bioflavonoids; amino acids; peptides, optionally comprised of two to ten amino acids, still more optionally lipidated peptides; superoxide dismutase; dipotassium glycyrrhizinate; tea extract or coffee extract; stem cells, including stem cell lysates; ceramides; as well as ingredients known in the art as humectants, moisturizers, skin-conditioning agents, skin soothing and/or healing agents Non-limiting examples of antioxidants/radical scavengers/moisturizing agents which may be topically delivered in the broad-spectrum photoprotective compositions of the present invention include: Bisabolol; *Camellia Sinensis* Leaf Extract; *Capparis Spinosa* Fruit Extract; Hydroxyacetophenone; *Olea Europaea* (Olive) Fruit Extract, optionally containing hydroxytyrosol (10% HPLC); Opuntia *Ficus-indica* Extract; *Polygonum aviculare* Extract; *Zingiber Officinale* Root Extract. In aspects, compositions comprise one or more of *Deinococcus* Extract, carnosine, or *echinacea* compound/composition, e.g., in an amount that is about 0.25-2×, 0.33-1.5×, 0.5-1.5×, 0.5-3×, 0.5-2×, or 0.75-1.25× the amount in the exemplary compositions provided herein.

Possible, but non-limiting examples of oil-absorbent powders that may or may not be included in compositions include Nylon-12 and Polymethylsilsesquioxane. In certain embodiments, Nylon-12 is combined with Polymethyl Methacrylate or Polymethylsilsesquioxane. However, in aspects, all or most of these compounds are excluded.

Certain embodiments of the present invention include ingredients that act as pollutant scavengers (i.e., entrap or reduce the negative effects of environmental particulate matter on the skin). By "negative effects on the skin" is meant collagen degradation, overproduction of melanin, and inflammation. Non-limiting examples of possible pollutant scavengers include Plankton Glass® (described above) and Benzylidene Dimethoxydimethylindanone (available under the tradename SymUrban® from Symrise, Teterboro, NJ).

Compositions of the present invention optionally contain one or several ingredient(s) that absorb, attenuate or reduce negative effects on the skin caused by blue light and/or infrared radiation.

One non-limiting, possible example of an ingredient that counters the effects of infrared radiation on the skin is a combination of PMMA, Cerium Oxide, Aluminum Oxide, available from Argan under the tradename ARG-NIR, or, e.g., a similar ingredient which does not comprise a significant amount of, or which lacks PMMA.

One non-limiting, possible example of an ingredient that counters the effects of blue radiation on the skin is lutein, available as FloraGLO™ Lutein 5% Topical [Carthamus Tinctorius (Safflower) Seed Oil (and) *Tagetes Erecta* Flower Extract] and FloraGLO™ Lutein 10% Topical [Water-dispersible granules of Sucrose (and) Tapioca Starch (and) Xanthophyll].

Sunless tanning agents, including but not limited to the alpha-MSH biomimetic peptide Acethyl Hexapeptide-1, may be added to the broad-spectrum photoprotective compositions of the present invention.

In certain possible embodiments, broad-spectrum sunscreen compositions of the present invention contain an ingredient that reduces pigmentation induced by both infrared light and visible light (from 400-700 nm), optionally Carnosine.

Carnosine (L-carnosine is available from Symrise under the tradename Dragosine®) is heterocyclic amine. In certain possible embodiments, Carnosine is present at a concentration of from 0.01-0.2%.

Any of the elements described herein (and in any part of this disclosure) also can be excluded from compositions of the invention.

Compositions of the present invention optionally do not contain any of the following: Paraben, Formaldehyde, Chlorphenesin, and Phenoxyethanol. Instead, as a possible preservative system, compositions of the present invention have a synergistic combination of: Hydroxyacetophenone (optionally at 0.5%); a mixture of 1,2 Hexanediol (and) Caprylyl Glycol (optionally at a combined concentration of 0.5%); a mixture of Bisabolol (and) *Zingiber Officinale* (Ginger) Extract (optionally at a combined concentration of 0.1%). This synergistic combination passes the microbial enumeration test found in Chapter 61 of the US Pharmacopeia.

| Phase | Ingredient(s) | SPF 30 | SPF 55 |
|---|---|---|---|
| A | Water | Q.S. | Q.S. |
| A | Glycerin 99.7%, USP | 0.25-1.00 | 0.25-1.00 |
| A | Panthenol | 0.10-0.50 | 0.10-0.50 |
| A | Allantoin | 0.05-0.25 | 0.05-0.25 |
| A | 1,2 Hexanediol and Caprylyl Glycol | 0.10-1.00 | 0.10-1.00 |
| A | Hydroxyacetophenone | 0.10-1.00 | 0.10-1.00 |
| A | Sodium Chloride | 0.25-1.50 | 0.25-1.50 |
| A | Niacinamide | 0.10-3.00 | 0.10-3.00 |
| B | Butyl Octyl Salycilate | 15.0 | 12.5 |
| B | Squalane | 0.50-2.00 | 0.50-2.00 |
| B | Cetyl Dimethicone (and) Bis-Vinyl Dimethicone/Dimethicone Copolymer | 4.0 | 4.0 |
| B | Dimethicone (and) Bis-Vinyl Dimethicone/Dimethicone Copolymer | 4.0 | 4.0 |
| B | Styrene/Acrylates Copolymer (2.00-5.50) | 2.5 | 5.5 |
| B | Polyhydroxystearic Acid | 0.25-1.00 | 0.25-1.00 |
| B | Zinc Oxide | 5.0 | 10.00 |
| B | Iron Oxides** | 1.5-2.0 | 0.0 |
| C | Phenyl Trimethicone, Disteardimonium Hectorite, (and) Triethyl Citrate | 1.50-3.00 | 1.50-3.00 |
| C | Caprylic/Capric Triglyceride, Titanium Dioxide, Aluminum Hydroxide, Stearic Acid (and) Polyhydroxystearic Acid | 3.5 | 3.5 |
| C | Dimethicone (and) Acrylates/Dimethicone Copolymer | 1.00-3.00 | 1.00-3.00 |
| D | NIR-PMMA-Cerium Oxide, etc. | | |
| D | Plankton flower extract | | |
| D | Silica | | |

Optionally, Iron Oxides of a composition are coated with a suitable coating material. Possible, but non-limiting, examples of coated Iron Oxides are Iron Oxide, CI 7749; Iron Oxide, CI 77499 and Iron Oxide, CI 77492, each surface treated/coated with Hydrogenated Lecithin.

The following ingredients may be added to the above formulations to the indicated Phase in the indicated concentration range:

| Phase | Ingredient(s) | % wt/wt |
|---|---|---|
| A | Capparis Spinosa Fruit Extract, Opuntia Ficus-Indica Extract, Olea Europea (Olive) Leaf Extract and Starch | 0.10-3.0 |
| A | Olea Europea (Olive) Fruit Extract and Starch | 0.10-3.0 |
| A | Carosine | 0.01-0.2 |
| C | Bisabolol and Zingiber Officinale (Ginger) Root Extract | 0.01-0.1 |
| C | Tocopheryl Acetate | 0.01-3.0 |
| E | PMMA, Cerium Oxide, Aluminum Oxide | 0.10-2.0 |
| E | Ubiquinone, Tocopheryl Acetate, C12-15 Alkyl Benzoate | 0.25-2.0 |
| E | Water, Glycerin, Polygonum Aviculare Extract | 0.50-2.0 |
| E | Water, Glycerin, Camellia Oleifera Leaf Extract | 0.25-3.0 |

Such and other compositions of this invention can provide broad spectrum protection from UVR (a SPF of at least 30, optionally at least 50) and a critical wavelength of at least 370 nm, optionally 375, more optionally 377, water resistant (e.g., 40 min.), optionally 80 min, and lack undesirable ingredients in aspects, such as having no organic sunscreen filter, no salicylate(s), or no PEG compounds. Such and other compositions provided here can be, e.g., non-whitening, non-oily, non-sticky and suitable for all Fitzpatrick Skin Types without undue whitening.

Matrix Characteristics

In aspects, compositions form a continuous, and flexible substrate mesh or multidimensional, photoprotective particle 3D matrix providing detectable or significant photoprotection. In aspects, such a substrate mesh or multidimensional, photoprotective particle 3D matrix provides a foundation upon which other compositional elements can be added to form a final composition. In aspects, the invention provided herein is the continuous, flexible, substrate mesh or multidimensional, photoprotective particle 3D matrix. In aspects, the invention provided herein is the continuous, flexible, substrate mesh or multidimensional, photoprotective particle 3D matrix suitable for use as a component of a formulation. In aspects, the invention provided herein is the continuous, flexible, substrate mesh or multidimensional, photoprotective particle 3D matrix suitable for use in formulating composition(s) differing from described in greater detail herein, such as, e.g., in protective coating(s) for material(s) other than human skin. Characteristic(s) of such a 3D matrix is/are described here and elsewhere herein.

Matrix Stability

According to aspects, the invention provides a three-dimensional (3D) matrix, as previously stated also characterizable as a UV particulate screen, comprising two or more populations of particles (e.g., establishing a particle matrix), wherein the 3D matrix sustains the two or more populations of particles without detectable or significant sedimentation under conditions and over periods of time described herein. In aspects, composition(s) provided as emulsion formulations, anhydrous formulations, or both, are capable of maintaining the populations of particles within or as a 3D matrix without detectable or significant sedimentation under typical household storage conditions, e.g., under about room temperature storage conditions, for periods of time described herein.

In a specific embodiment, a population of agglomerate(s)/aggregate(s) of one or more metal oxide(s) are in stable combination with a population of non-metal oxide(s) compound(s) and a population of siliceous compound(s) in sufficient amount to form a multidimensional photoprotective 3-D particle matrix.

In aspects, the base for the particulate content of composition(s), e.g., matrix, is a water-in-oil (w/o) emulsion. According to aspects, composition(s) provided herein are particularly advantageous for their adherence, e.g., stable adherence, to skin upon application thereto, such as, e.g., providing a detectable or significant adherence to mammalian skin upon application which renders the composition capable of demonstrating a photoprotective benefit for an extended period of time and under sub-optimal conditions such as, e.g., a period of time while subjected to water exposure.

In aspects, the W/O emulsion is a lightweight emulsion that forms a film upon the surface, e.g., skin, to which it is applied upon application. In aspects, such a film stably, e.g., at least generally fixedly, at least substantially fixedly, at least essentially fixedly, or fixedly maintains a detectable or significant amount of the matrix in a stable position on the surface to which it is applied for a period of at least about 30 minutes (min.), such as, e.g., ≥~35 min, ≥~40 min, ≥~45 min, ≥~50 min, ≥~55 min, ≥~60 min, ≥~65 min, ≥~70 min, ≥~75 min, ≥~80 min, or, e.g., ≥~85 min, or, e.g., ≥~90 min. In aspects, the formation of a film by a lightweight emulsion further provides water resistance to the composition(s). In aspects, composition(s) comprising the particulate content described herein (e.g., the protective particulate content, e.g., the protective matrix) described herein is/are composition(s) provide detectable or significant water resistance for a period of at least about 30 minutes (min.), such as, e.g., ≥~35 min, ≥~40 min, ≥~45 min, ≥~50 min, ≥~55 min, ≥~60 min, ≥~65 min, ≥~70 min, ≥~75 min, ≥~80 min, or, e.g., ≥~85 min, or, e.g., ≥~90 min. Water resistance is further described elsewhere herein. In aspects, composition(s) providing detectable or significant water resistance for a period of at least about 30 minutes (min.), such as, e.g., ≥~35 min, ≥~40 min, ≥~45 min, ≥~50 min, ≥~55 min, ≥~60 min, ≥~65 min, ≥~70 min, ≥~75 min, ≥~80 min, or, e.g., ≥~85 min, or, e.g., ≥~90 min. further provide detectable or significant sun protection, provided at least in part by the 3D matrix providing protective layer(s) of light blocking particle populations on the surface to which composition(s) are applied. In aspects, the sun protection is detectably or significantly greater than a sunscreen composition lacking such a matrix. In aspects, composition(s) provided in this paragraph provide 1:3 ratio of UVA to UVB, 0.7 UVA/UVB, blue light protection, anti-pollutant protection, or other benefit(s) described further elsewhere herein.

Dispersibility

In aspects, composition(s) herein spread evenly on the skin, e.g., provide an at least mostly even, at least generally even, at least essentially even, at least substantially even, or even distribution of composition component(s) on the skin upon application. In aspects, such characteristics can be determined through any suitable spread-ability test available in the art, the result of the test showing a DOS level of spread-ability of compositions of the invention as compared to compositions not having all of the features of the composition.

In aspects, composition(s) provided by the invention, a 3D matrix provided by the invention, or, e.g., composition(s) comprising a 3D matrix described herein/provide by the invention provide an at least mostly even, at least generally even, at least essentially even, at least substantially even, or even distribution of composition component(s), e.g., at least one or more of, each, or all particle population(s) comprised therein, on the surface to which it is applied (e.g., skin) upon application. In aspects, particles of particle population(s) are provided in a dispersion. In aspects, particles of particle population(s) are provided in a dispersion. wherein the particles are at least mostly evenly, at least generally evenly, at least essentially evenly, at least substantially evenly, or evenly distributed upon the target when composition(s) comprising such dispersion of particles is applied to the target.

Matrix Structure and Photoprotection

In aspects, the 3D matrix comprises an even distribution of the at least two populations of particles, each population of particles comprising particles having a different type, different average size, different general shape, or combination of different type, different average size, and different general shape, from that of at least one other population of particles present in the matrix. In aspects, the population(s) of particles comprise population(s) of metal oxide(s) particles, population(s) of non-metal oxide(s)s particles or both; population(s) of spherical particles, non-spherical particle(s), or both; population(s) of regularly shaped particles, irregularly shaped particles, or both; platelet shaped particles, non-platelet shaped particles, or both; population(s) of porous particles, non-porous particles, or both; population(s) of solid particles, non-solid particles, or both; populations of hollow particles, non-hollow particles, or both; populations of siliceous particles, non-siliceous particles, or both; population(s) of microscale-sized particles, mesoscale-sized particles, macroscale-sized particles, or combination(s) thereof; or population(s) of particles having one or more such characteristic(s) or other characteristic(s) described herein which differ from other population(s) of particles in the matrix.

In aspects, upon administration to the skin using typical, standard, application technique(s) (e.g., application techniques typically used to apply lotions, creams, stick-based products, etc., such as self-administration of such composition(s) to human skin) not requiring special instruction, the 3D matrix is at least substantially evenly distributed over the administration area, e.g., is at least substantially evenly distributed over the surface area of skin to which the composition is applied, creating or otherwise establishing a complex, 3D "mesh" or "matrix" (e.g., sometimes referred to herein as a mesh, matrix, ultraviolet (UV) mesh, or, e.g., multidimensional, photo-protective particle 3D matrix) on the applied surface, e.g., on the skin. In aspects, the 3D mesh offers a high protection, highly effective sunscreen against ultraviolet light, visible light, HEV light, blue light, infrared light, etc.

In aspects, composition(s) provided by the invention comprise a stable matrix comprising populations of particles of detectably different type and having detectably different sizes, shapes, or one or more other physical characteristic(s), wherein changes in the light scattering properties of the composition across a selected area of skin to which composition(s) is/are applied, changes in the distribution of particles in the matrix in a selected area of skin to which composition(s) is/are applied, or both, are significantly reduced as compared to a composition lacking the mixture of particle sizes and shapes, a composition not subjected to the same homogenization conditions during manufacture, or both. Stated alternatively, in aspects, composition(s), when applied to the skin of a typical subject form a stable matrix wherein one or more light scattering property(ies), distribution of particles, or both is at least generally, at least substantially, at least essentially, is essentially, or is uniform across two or more selected areas of skin to which composition is applied, In aspects, a selected area of skin is an area of skin of at least about 5 cm$^2$, such as ≥~4 cm$^2$, ≥~3 cm$^2$, ≥~2 cm$^2$, ≥~1 cm$^2$, ≥~10 mm$^2$, ≥~9 mm$^2$, ≥~8 mm$^2$, ≥~7 mm$^2$, ≥~6 mm$^2$, ≥~5 mm$^2$, ≥~4 mm$^2$, ≥~3 mm$^2$, ≥~2 mm$^2$, or, in aspects, an area of skin ≥~1 mm$^2$. In aspects, such uniformity is detectably or significantly more uniform than that provided by a similar composition comprising at least generally the same, at least substantially the same, at least essentially the same, essentially the same, or the same particulate(s) or particulate populations. In aspects, such uniformity is detectably or significantly more uniform than that provided by a similar composition comprising at least generally the same, at least substantially the same, at least essentially the same, essentially the same, or the same particulate(s) or particulate populations but which does not utilize at least generally the same, at least substantially the same, at least essentially the same, essentially the same, or the same method of manufacture or, e.g., the same one or more homogenization step(s) or characteristic(s) thereof (such as time, temperature, mixing speed, etc.) as is described elsewhere herein.

In aspects, composition(s) described herein provide a light-deflecting protective mechanism comprised of populations of particles (e.g., compounds) comprising two or more, such as, e.g., at least about 3, ≥~4, ≥~5, ≥~6, ≥~7, ≥~8, ≥~9, ≥~10, ≥~12, ≥~14, ≥~16, ≥~18, or, e.g., ≥~20, different shapes/forms and sizes. In aspects, such particles are metal oxide particulates (e.g., ZnO, TiO$_2$, or both), non-metal oxide particulates, such as, e.g., silicas, silicates, "glass crystals" (e.g., calcium borosilicate particles), micas, synthetic micas, pigments, clays, etc., or both metal oxide and non-metal oxide particulates. In aspects, the plurality of types, shapes, forms, sizes, or otherwise different dimensions of at least two or more particles of the composition create a three-dimensional (3D) nature to the light-deflecting protective layer formed upon the spreading of composition(s), such as, e.g., upon the application to skin. In aspects, this protective mechanism is referred to as a "mesh", or a "multidimensional photo-protective particle 3D matrix". In aspects, this protective, light-deflecting mesh, or multidimensional, photo-protective particle 3D matrix, is an inventive property of composition(s) provided herein.

In aspects, the interaction of particulate content of composition(s), such particulate content comprising populations of particles being of detectably or significantly different type, having detectably or significantly different sizes, shapes, dimensions, or any combination thereof from one another (or, e.g., from at least one other population of particles in the composition(s)), allows for such populations of particles to be positioned advantageously close to one another, e.g., to advantageously interface with one another in a detectably or significantly greater compact (detectably or significantly higher density) manner than particulate content having an at least generally, an at least mostly, an at least substantially, or having the same average size, shape, dimension, or any combination thereof. In aspects, as a result, at least one layer of particles is formed, e.g., at least about 2 or at least about 3 layers of particles as formed by an application of composition having a given thickness) having (a) a detectably or significantly varied depth/thickness, due to the detectably or significantly varied size, shape, or dimension of the particle populations, and (b) an increased ability to prevent light or, e.g., UV radiation or other environmental pollutant(s) from passing through the layer of particles, due to the limited space between particles—as such space is limited due to the compact, dense nature of the particulate content of composition(s) due the varied size, shape, and dimension of particle populations making up the particulate content of composition(s).

In aspects, in addition to there being a limited ability of visible light, UV radiation, or other environmental pollutants to pass through the "mesh" or "screen" created by the particles of the composition, but light scatter, e.g., light deflection, is increased, due to the multi-dimensional nature of the particles, such that the layer of particles is characterizable as a light-deflecting mesh, or, e.g., as described above, a multidimensional, photoprotective (i.e., anti-radiation or radiation protective) particle 3D matrix. In aspects, particulate content of composition(s) detectably or significantly increases the area of light protection, UV radiation protection, environmental pollution protection, or any combination thereof, provided by any given amount (e.g., volume) of composition compared to the same amount (e.g., volume) of composition not comprising such particulate content. In aspects, particulate content of composition(s) detectably or significantly decreases a total amount of interstitial space between any two, three, four, or five or more particles (e.g., particles of any type) present in the composition comparted to the total amount of interstitial space between any same number of particles present in composition(s) not comprising the particulate content of composition(s) provided herein.

In another specific embodiment, the continuous, and flexible substrate mesh or multidimensional, photoprotective particle 3D matrix provides an at least generally, at least substantially, at least essentially, or even distribution of the populations of particles varying in their type, average particle size, shape, or dimension, e.g., population of metal oxide particles (e.g., ZnO, $TiO_2$ as API, FeO, CeO, Ca/Na Borosilicate, etc.), population of non-metallic particles, e.g., non-metallic oxides (e.g., SunSpheres, plankton, silicas, e.g., silica powders etc.) when applied to a target, such as, e.g., human skin, so as to evenly cover the target (skin) surface.

In aspects, an advantage provided by the invention described herein is the synergy of the at least one, e.g., one or two, API(s), e.g., particulate metal oxide compound(s), and optionally other one or more metal oxide compound(s) (such as, e.g., FeO, $Al_2O_3$, CeO), with one or more non-metal oxides, such as, e.g., one to three (e.g., one, two, or three, or even more) different silicas, e.g., different silica powders types, and, further, with one or more additional component(s)/compound(s) such as, e.g., styrene acrylate copolymer powder, synthetic mica, etc. to act cooperatively to detectably or significantly increase the reflection, refraction, scattering, or otherwise detectable or significant disbursement of sunlight (e.g., UV, Visible, HEV/blue light) compared to composition(s) lacking such multi-dimensionality, such diverse compositional constituents, such a continuous and flexible substrate mesh or multidimensional, photoprotective particle 3D matrix-forming capability, or any combination of any or all thereof. In aspects, an advantage provided by the invention described herein is the synergy of these elements further in conjunction with one or more additional component(s)/compound(s) such as, e.g., one or more peptides (IR) or plant extract(s) (e.g., *echinacea* extract(s)) capable of providing, e.g., a detectable or significant anti-pollution effect. In aspects, an advantage provided by the invention described herein is the synergy of these elements further in conjunction one or more additional component(s)/compound(s) such as, e.g., one or more peptides (IR) or plant extract(s) capable of providing, e.g., a detectable or significant anti-aging effect, e.g., a detectable or significant skin smoothing effect, skin hydration effect, etc.

In aspects, compositions exhibit spreading, particle size (interstitial) spacing, packing density and other characteristics as exemplified and discussed in connection with the exemplary microscopy data provided below and related aspects provided herein. In aspects, compositions are associated with multiple detectable layers of particles, the formation of which being contributed to by the mixture of particles in the composition, wherein the different layers provide overlapping coverage, thereby detectably or significantly increasing the total surface coverage of a spread of a composition of the invention (e.g., each layer having at least about 60% particle coverage, and with overlapping layers achieving ≥65, ≥70, ≥75, or ≥80% particle coverage). In aspects, the overlap coverage is more than 85% or more than 90% coverage. In aspects, the size of most, generally all, or substantially all gaps between particles in the matrix composition is less than 500 nm, less than 400 nm, or less than 300 nm. In aspects, some, most, generally all, or all particles in the matrix composition form agglomerates, such that the average visible particle in the matrix composition under SEM is at least 100 nm, e.g., at least 200 nm, at least 500 nm, at least 750 nm, or at least 1 micron.

Viscosity and Specific Gravity Characteristics

Viscosity

According to certain aspects, composition(s) are provided, e.g., as water-in-oil (W/O) emulsions, e.g., characterizable as lotion(s). In aspects, composition(s) are provided, e.g., as W/O emulsion(s) comprising relatively low viscosity(ies) (for example a detectably or significantly lower viscosity than at least substantially similar composition(s) sharing one or more ingredient(s)). In aspects, composition(s) are provided having viscosity(ies) such as a viscosity(ies) described here.

In aspects, compositions described herein comprise a low viscosity carrier. In aspects, the low viscosity carrier is the continuous, flexible, substrate mesh or multidimensional, photoprotective particle 3D matrix. In aspects, the continuous, flexible, substrate mesh or multidimensional, photoprotective particle 3D matrix, or, e.g., the composition(s) themselves, have a viscosity of less than about 5500 cps, such as, e.g., ≤~5400 cps, ≤~5300 cps, ≤~5200 cps, ≤~5100 cps, ≤~5000 cps, ≤~4900 cps, ≤~4800 cps, ≤~4700 cps, ≤~4600 cps, ≤~4500 cps, ≤~4400 cps, ≤~4300 cps, ≤~4200 cps, ≤~4100 cps, or, e.g., ≤~4800 cps.

In aspects, the continuous, flexible, substrate mesh or multidimensional, photoprotective particle 3D matrix, or, e.g., the composition(s) themselves, comprise a viscosity of less than about 4500 cps, such as, e.g., ≤~4450 cps, ≤~4400 cps, ≤~4350 cps, ≤~4300 cps, ≤~4250 cps, ≤~4200 cps, ≤~4150 cps, ≤~4100 cps, ≤~4050 cps, or, e.g., ≤~4000 cps. In aspects, the continuous, flexible, substrate mesh or multidimensional, photoprotective particle 3D matrix, or, e.g., the composition(s) themselves, comprise a viscosity of less than about 4000 cps, such as, e.g., ≤~3900 cps, ≤~3800 cps, ≤~3700 cps, ≤~3600 cps, ≤~3500 cps, ≤~3400 cps, ≤~3300 cps, ≤~3200 cps, ≤~3100 cps, or, e.g., ≤~3000 cps.

In aspects, the continuous, flexible, substrate mesh or multidimensional, photoprotective particle 3D matrix, or, e.g., the composition(s) themselves have a viscosity of between about 3000 cps and about 5500 cps, such as, e.g., ~3000 cps-~5400 cps, ~3000 cps-~5300 cps, ~3000 cps-~5200 cps, ~3000 cps-~5100 cps, ~3000 cps-~5000 cps, ~3000 cps-~4900 cps, ~3000 cps-~4800 cps, ~3000 cps-~4700 cps, ~3000 cps-~4600 cps, ~3000 cps-~4500 cps, ~3000 cps-~4400 cps, ~3000 cps-~4300 cps, ~3000 cps-~4200 cps, ~3000 cps-~4100 cps, or, e.g., ~3000 eps-~4000 eps.

In aspects, the continuous, flexible, substrate mesh or multidimensional, photoprotective particle 3D matrix, or, e.g., the composition(s) themselves have a viscosity of between about 3100 cps and about 5500 cps, such as, e.g., ~3200 cps-~5500 cps, ~3300 cps-~5500 cps, ~3400 cps-~5500 cps, ~3500 cps-~5500 cps, ~3600 cps-~5500 cps, ~3700 cps-~5500 cps, ~3800 cps-~5500 cps, ~3900 cps-~5500 cps, or, e.g., ~4000 cps-~5500 cps, ~4100 cps-~5500 cps, ~4200 cps-~5500 cps, ~4300 cps-~5500 cps, ~4400 cps-~5500 cps, or, e.g., ~4500 cps-~5500 cps.

In aspects, the continuous, flexible, substrate mesh or multidimensional, photoprotective particle 3D matrix, or, e.g., the composition(s) themselves have a viscosity of between about 3100 cps and about 5400 cps, ~3200 cps-~5300 cps, ~3300 cps-~5100 cps, ~3400 cps-~5000 cps, ~3500 cps-~4900 cps, ~3600 cps-~4800 cps, ~3700 cps-~4700 cps, ~3800 cps-~4600 cps, ~3900 cps-~4500 cps, or, e.g., ~4000 cps-~4400 cps.

In aspects, viscosity is determined using a Brookfield RVT spindle T-B® 20 rpm® 25° C. In aspects, the initial viscosity of a formulation is 2000-4500 cps, e.g., 2100-4250 cps, e.g., 2200-4200 cps. In aspects, the viscosity of the composition at about 24 hours from production is between 3000-6000 cps, e.g., 3250-5750 cps, or about 3500-5500 cps. In aspects, the viscosity after storage (e.g., for 1 week, 1 month, 3 months, etc.) e.g., at room temperature, at a range of normal storage/environmental conditions, under industry travel testing conditions, etc., is about 4000-18000, e.g., about 4200-16000, e.g., about 4500-15000 cps.

In aspects, the composition has a specific gravity of about 1, e.g., 1.0045.

In aspects, compositions have a sufficiently low viscosity so as to avoid a thick, pasty, heavy, or otherwise unpleasant feel when applied to human skin (e.g., as determined via evaluation of compositions by a statistically significant population of product users and reported as user interview(s), part of a controlled product evaluation study, or any similar relevant product evaluation test recognized in the art for establishing such aesthetic qualities.) Similarly, in aspects, compositions have a sufficiently high viscosity so as to avoid a drippy, runny, thin, or otherwise unpleasant feel when applied to human skin (e.g., as determined via evaluation of compositions by a statistically significant population of product users and reported as user interview(s), part of a controlled product evaluation study, or any similar relevant product evaluation test recognized in the art for establishing such aesthetic qualities.)

Sedimentation/Suspension

In aspects, compositions provided herein comprise a viscosity or, e.g., suspension capability(ies) to be capable of maintaining at least some, at least most, at least generally all, at least substantially all, or all particulate matter present in the composition suspended, without detectable or significant sedimentation under normal storage conditions for a commercially relevant period of time. In aspects, for example, compositions are capable of maintaining at least some, at least most, at least generally all, at least substantially all, or all particulate matter present in the composition suspended, without detectable or significant sedimentation, when stored at about 50° C. (e.g., (50° C.+/− about 5° C., ~4° C., ~3° C., ~2° C., or, e.g., ~1° C.) for a period of at least about 1 week, ~2 weeks, ~3 weeks, ~4 weeks, ~6 weeks, ~2 months, ~3 months, ~4 months, ~5 months, ~6 months, ~7 months, ~8 months, ~9 months, or, e.g., ~12 months, or even longer. In further aspects, for example, compositions are capable of maintaining at least some, at least most, at least generally all, at least substantially all, or all particulate matter present in the composition suspended, without detectable or significant sedimentation, when stored at about 40° C. (e.g., (40° C.+/− about 5° C., ~4° C., ~3° C., ~2° C., or, e.g., ~1° C.) for a period of at least about 1 week, ~2 weeks, ~3 weeks, ~4 weeks, ~6 weeks, ~2 months, ~3 months, ~4 months, ~5 months, ~6 months, ~7 months, ~8 months, ~9 months, or, e.g., ~12 months, or even longer. In still further aspects, for example, compositions are capable of maintaining at least some, at least most, at least generally all, at least substantially all, or all particulate matter present in the composition suspended, without detectable or significant sedimentation, after at least about 1, e.g., at least about 2, at least about 3, at least ~4, or, e.g., at least ~5 freeze/thaw (F/T) cycles.

In aspects one or more component(s) or compound(s) of composition(s) is present to provide detectable or significant suspension-enhancing activity. In aspects, compositions can comprise one or more clay compound(s) to detectably or significantly increase the stability of a suspension, e.g., to detectably or significantly increase the amount of time one or more particle(s) or population(s) of particle(s) are maintained in suspension.

Specific Gravity

In aspects, composition(s) provided herein have a specific gravity of between about 0.5 and about 2, such as, e.g., ~0.6-~2, ~0.7-~2, ~0.8-~2, ~0.9-~2, ~1-~2, ~1.1-~2, or, e.g., ~1.2-~2, such as, for example, ~0.5-~1.9, ~0.5-~1.8, ~0.5-~1.7, ~0.5-~1.6, ~0.5-~1.5, ~0.5-~1.4, ~0.5-~1.3, ~0.5-~1.2, or, e.g., ~0.5-~1.1. In aspects, specific gravity of the composition is about 0.9-1.1, e.g., 0.95-1.05, e.g., 0.97-1.02.

In aspects, composition(s) provided herein have a specific gravity of between about 0.6 and about 1.9, such as, e.g., ~0.7-~1.8, ~0.75-~1.7, ~0.8-~1.6, ~0.85-~1.5, ~0.9-~1.4, ~0.95-~1.3, or, e.g., ~1-~1.2 or ~1.1-~1.2, as in, for example, ~1.11, ~1.12, ~1.13, ~1.14, ~1.15, ~1.16, ~1.17, ~1.18, ~1.19, or, e.g., ~1.2.

In aspects, compositions also or alternatively include photoprotective particle matrix in the present invention is a continuous flexible water-in-oil emulsion comprising a substrate of a low viscosity of at least about 3000 cps-about 5500/6000 cps, such as about 4,000-5,000 cps, such as about 4100-4900 cps or 4100-4900 cps, e.g., 4500-5000 cps. In aspects, such a composition is a continuous flexible water-in-oil emulsion with a specific gravity of at least about 1-about 1.20, e.g., about 1-1.2 or 1-1.1. In aspects, the initial and 24-hour viscosities are as noted above (e.g., 2200-4400 cps initial, 3500-5500 24-hour), and the viscosity on storage is as noted above (4500-15000 cps).

SPF, UVA Protection, and Water Resistance

In aspects, the presence of, and the at least mostly homogenous, at least generally homogenous, at least substantially homogenous, or homogenous distribution of, a plurality of populations of particles provides a detectable or significant increase in the photoprotection of skin when applied thereto compared to compositions lacking such a plurality of particle populations and, in particular, the even distribution and maintenance of the even distribution of, such particles.

In aspects, the plurality of particle populations of composition(s) provided herein (e.g., of 3D matrices of such composition(s) described herein) detectably or significantly increases the protected surface area of skin within a treated area of skin compared to a similar composition lacking such distributive uniformity and diversity of particulate size. In aspects, the plurality of particle populations, in particular the plurality of particle populations having detectably different sizes, shapes, or both, detectably or significantly increases the reflection, refraction, scattering, or diffusion of the UV light, visible light, blue light, high energy blue light or any combination thereof. In aspects, the detectable or significant increase in reflection, refraction, scattering, or diffusion of light results in a detectably or significantly superior photoprotective composition compared to similar compositions lacking such a diversity of particle populations (e.g., populations of such diverse size and shape).

In aspects, the ZnO particles exhibit DOS less back-reflection of the light from the particles to the skin than classic Z-cote particles, providing UVA/UVB protection along with unexpected transparency with less whitening to the skin.

SPF

In aspects, sunscreen(s) described herein provide a sun protection factor (SPF) of at least about 30, such as, e.g., at least about 35, at least about 40, at least about 45 or, e.g., at least about 50. In common aspects, sunscreen composition(s) provided by the invention provide an SPF of at least about 50.

In aspects, sunscreen composition(s) provided herein provide an SPF/UVA protection factor of less than about 3, such as, e.g., ≤~2.8, ≤~2.6, ≤~2.4, ≤~2.2, or, e.g., ≤~2, In aspects composition(s) can provide an SPF/UVA protection factor of less than about 2, such as, e.g., ≤~1.8, ≤~1.6, ≤~1.4, ≤~1.2, or, e.g., ≤~1.

In aspects, sunscreen composition(s) provided herein provide an SPF/UVA protection factor of greater than about 3, such as, e.g., ≥~3.2, ≥~3.4, ≥~3.6, ≥~3.8, ≥~4, ≥~4.2, ≥~4.4, ≥~4.6, ≥~4.8, or, e.g., ≥~5. In aspects, sunscreen composition(s) provided by the invention provide an SPF/UVA protection factor of greater than about 5, such as, e.g., ≥~5.2, ≥~5.4, ≥~5.6, ≥~5.8, ≥~6, ≥~6.2, ≥~6.4, ≥~6.6, ≥~6.8, or, e.g., ≥~7.

According to aspects, the invention provides sunscreen composition(s) providing a UVA1/UV protection factor of at least about 0.7, such as, e.g., ≥~0.8, ≥~0.9, ≥~1, ≥~1.1, ≥~1.2, ≥~1.3, ≥~1.4, ≥~1.5, ≥~1.6, ≥~1.7, ≥~1.8, ≥~1.9, or, e.g., ≥~2.

In aspects, compositions herein provide such detectable or significantly improved photoprotection not only against UVB radiation but also against UVA radiation. In aspects, compositions herein comprise, e.g., attain, the 1:3 ratio of UVA:UVB protection, a requirement of the European Union, Australia, New Zealand, regulatory bodies and the Environmental Working Group (EWG).

Critical Wavelength

In aspects, sunscreen composition(s) provided herein have a critical wavelength of greater than about 370 nm, 372 nm, or 375 nm (e.g., 90% AUC), such as, e.g., ≥ than about 380 nm, ≥~385 nm, ≥~390 nm, ≥~395 nm, ≥~400 nm, ≥~405 nm, ≥~410 nm, ≥~415 nm, or, e.g., ≥~420 nm.

In aspects, compositions comprise an effective amount of a *deinococcus* extract (e.g., the product sold under the tradename "The First"). The presence of such an extract in the ZnO formula helps with scattering/protection against UV/IR and blue light radiation.

In possible embodiments, mineral sunscreen emulsions of the present invention are water resistant for 40 or 80 minutes as defined in Section 352.76 of Title 21 of the U.S. Code of Federal Regulations and contain at least one, optionally at least two, film-forming polymers. Two possible but non-limiting examples of film-forming polymers that help provide 40 or 80 minutes of water resistance are (i) Dimethicone (and) Acrylates/Dimethicone Copolymer or (ii) Bis-Vinyl Dimethicone/Dimethicone Copolymer. The film-forming polymers are optionally dispersed in one or more of Dimethicone, Cetyl Dimethicone and/or Phenyl Trimethicone.

Typically, the mineral sunscreen emulsions of the present invention have an SPF of at least 50. Typically, compositions of the invention can be characterized as broad-spectrum sunscreens. The term "broad-spectrum" refers to a level of protection from UVR provided by wearing a sunscreen that has a minimum critical wavelength of 370 nm and a sun protection factor (SPF) value of 15 or higher. "Critical wavelength" is the wavelength for which the section under the integrated optical density curve starting at 290 nm is equal to 90 percent of the integrated section between 290 nm to 400 nm. Standards and test methods for determining "broad-spectrum" protection from UVR are set out in the final Sunscreen Monograph promulgated by the FDA on Jun. 17, 2011. See "Labeling and Effectiveness Testing; Sunscreen Drug Products for Over-the-Counter Human Use" published at Volume 76 of the Federal Register starting at page 35620, the disclosure of which is incorporated herein by reference. In aspects, compositions herein are characterized by critical wavelength (CW) characteristics, as described elsewhere.

Superior Aesthetics

According to certain aspects, the invention provides sunscreen composition(s) providing effective levels of environmental protection (e.g., provides efficacious protection from ultraviolet radiation, visible light (HEV), one or more other environmental other pollutants, or any combination of any or all thereof.

In aspects, inventive compositions provide detectably or significantly superior aesthetics upon application to a user/subject of any of the four (IV) Fitzpatrick skin types, such as, e.g., not providing a visibly "white" appearance (characterizable as non-whitening). In aspects, compositions also achieve this result for Fitzpatrick Skin Types V and VI (thus, in aspects, matrix compositions are also non-whitening on Fitzpatrick Skin Types T-VI). The evaluation of skin whitening effects of compositions can be performed using any suitable method (e.g., any "step for" evaluating skin whitening on the Fitzpatrick Skin Type skin tested), including methods exemplified herein or using any other art-recognized suitable method for evaluating whether there is a DOS change in skin color brought about by application of a product which can include, e.g., computer/AI-assisted photography or other spectral analysis of the skin before and after application (e.g., 1, 2, 5, 10, 15, 30, or 60, or more minutes after application).

In aspects, compositions are characterized in not causing a DOS sticky or tacky feeling on the skin (e.g., compositions are characterizable as non-tacky), not causing an unpleasant slippery, glossy, or greasy feel (characterizable as non-greasy feel), or any combination thereof. Such determinations can be made by, e.g., studies with typical users, with skin evaluation experts, or both (e.g., using a statistically significant evaluation of a population). Alternatively, known tests for such measures can be performed such as measuring tackiness, measuring greasy-feel-relevant measurements, etc. In aspects, compositions are judged as lightweight. Any of these characteristics also can be determined to be "improved" with respect to one, some, most, generally all, or all of the prior art products described in the Background hereto or otherwise on the market at the time of this disclosure (and that contain mineral oxides and act as a sunscreen product).

In aspects, such aesthetic characteristics can be as cosmetically elegant, and can be demonstrated by, e.g., standard measurements known to be associated with such characteristics and/or by the determination through well-controlled, adequate studies with a significantly significant number of adequate test subjects reporting such a characteristic.

In aspects, compositions provided herein provide both effective levels of environmental protection, as determined by, e.g., anti-oxidation effects (DOS), or other effects associated with environmentally protective ingredients that can be incorporated in effective amounts in compositions (e.g., *echinacea* extract).

In aspects, the combination of protection cosmetic suitability/elegance as one novel advantage of composition(s) provided by the invention.

In aspects, such characteristic(s) is/are achieved through the creation of a protective, light-deflecting mesh. In aspects, compositions provide cosmetic effects, independent of radiation scattering effects, which can include, e.g., a mattifying effect (e.g., a DOS skin smoothing effect determined by typical user survey/test, expert test, photographic analysis (e.g., AI/softer-aided analysis of skin texture after application) and blurring of fine lines and skin imperfection or other forms of treatment of cosmetic conditions (red skin, aging effects, skin dyspigmentation, etc.).

In aspects, compositions comprise one or more additional non-radiation-scattering APIs that provide such effects. Such effects, commonly referred to as light-diffusing effect(s), are known in the art. In aspects as exemplified, such effects include protection against blue light, IR radiation, or both.

Non-Whitening Properties/Water Resistance Properties

In aspects, the invention provides compositions having any of the various features/elements provided herein (e.g., a composition that exhibits multidimensional photo-protective 3-D particle matrix composition) which has broad spectrum protection from ultraviolet radiations comprising (i) a sun protection factor (SPF) of at least about 30, 40, 50, or 60 (or range formed of any thereof) and has minimum critical wavelength of more than 370 nm (2) a water resistance time of at least about 40 min-about 80 min in water and (3) are visibly non-whitening on Fitzpatrick Skin Types I-IV (e.g., as determined by clinical study or through any other tool validated to determine if a significant whitening effect has occurred from the application of a typical amount of the applicable composition to the skin).

In aspects, composition(s) comprise one or more component(s) or compound(s) which provide detectable or significant water resistance, e.g., detectable or significant resistance to the removal of the composition after application to a target, e.g., skin when exposed to water. In aspects, compositions herein provide water resistance for a period of at least about 10 minutes, after application $\geq$~15 minutes, $\geq$~20 minutes, $\geq$~30 minutes, $\geq$~35 minutes, $\geq$~40 minutes, $\geq$~45 minutes, $\geq$~50 minutes, $\geq$~55 minutes, or, e.g., $\geq$~60 minutes, $\geq$~65 minutes, $\geq$~70 minutes, $\geq$~75 minutes, $\geq$~80 minutes, $\geq$~85 minutes, or, e.g., $\geq$~90 minutes, such as, e.g., when the target (e.g., human skin) is exposed to water for such period(s). In aspects, such a water resistance agent can be any water resistance agent, such as, e.g., one or more acrylates. In aspects, compositions exhibit a low level of SPF functionality loss after, e.g., 40 minutes water exposure (e.g., using standard test methods, as exemplified herein) (e.g., a loss of less than 20%, 15%, 10%, or less than 7.5% or less than 5%) or, in aspects, a loss after 80 minutes (as compared to baseline or 40 minutes of water exposure) (of a similar amount of SPF loss, e.g., less than 12.5%, less than 9% loss, less than 8% loss, less than 6% loss, or less than 4% loss against one or both thereof).

In aspects, the invention provides a sunscreen composition comprising multidimensional photoprotective particle matrix in the composition with skin conditioning and SPF boosting film forming polymers wherein the sunscreen composition comprising the film forming polymer can be acrylates or dimethicone copolymer or combination thereof.

Compositions of the invention can and often do comprise a matrix composed of various ingredients (e.g., silicone polymers, emulsifiers, etc.) that form a substrate that sustain all the various particle types described in other parts of this disclosure. In aspects, such substrates have low viscosity (e.g., having characteristics provided elsewhere herein), and are generally are non-settling and stable (exhibiting detectably or significantly improved properties over prior art compositions). In exemplary aspects, such compositions comprise a mixture of two or more siliceous compounds, such as amorphous spherical silica or a mixture of siliceous algae products. In aspects, compositions also or alternatively comprise one, optionally two vinyl dimethicone cross polymers which may be combined with at least one PEG ether of lauryl alcohol. In aspects, however, such compositions are PEG-free, are salicylate compound free, or both.

Refractive Index

Skin has refractive index of about 1.35-about 1.55. Compositions provided herein comprise a refractive index close to that of the skin, e.g., generally the same as, substantially the same as, essentially the same as, or the same as skin.

Compositions provided herein can comprise a refractive index within about 20%, 15%, 10%, or 5% of the skin. Compositions provided herein can comprise a refractive index of about 1 or about 1.5 (e.g., about 1-1.5). In aspects, composition(s) described herein are non-whitening (not DOS whitening) when applied to Fitzpatrick I-IV skin types. In aspects, some, many, or most of the particles of the composition have a refractive index of less than 2, e.g., less than 1.8, or less than 1.65. In aspects, pigmenting agents, such as iron oxide pigments of the composition have a refractive index of 2 or more, such as 2.2 or more or 2.4 or more.

Skin Health & Aesthetics

In aspects, composition(s) provided herein are suitable for daily use, e.g., daily application to human skin. In aspects, composition(s) are non-comodogenic. In aspects, composition(s) provide one or more aesthetic benefit(s) to skin upon which it/they are applied. In aspects, composition(s) demonstrate detectable or significant skin hydrating (skin moisturizing) effect(s) such that composition(s) are effective for use as a daily moisturizer. In aspects, composition(s) can comprise one or more coloring agent(s), e.g., pigment(s), providing a coloration, e.g. tint to the composition(s). In aspects, composition(s) can be untinted. In aspects, composition(s) are suitable for use as a daily tinted or untinted moisturizer for the face or lips (or, e.g., both) which provide(s) detectable or significant photoprotection, such as, e.g., having a sun protection factor of at least about 30, $\geq$35, $\geq$40, $\geq$45, or, e.g., $\geq$50.

In aspects, composition(s) can further provide detectable or significant protection from one or more environmental pollutant(s). In aspects, composition(s) provide one or more anti-aging benefit(s) such as, e.g., moisturization/hydration, or, e.g., a detectable or significant reduction in one or more visible skin imperfections when applied in effective amount(s) for effective period(s) of time. According to certain aspects, composition(s) comprise a combination of detectably or significantly different types of particles, the particles having detectably or significantly different forms (shapes) and having detectably or significantly different sizes, wherein the combination of such a plurality of particulates provides a detectable or significant, e.g., visible, decrease in one or more skin imperfection(s), such as, e.g., fine line(s), wrinkle(s), or other unevenness present in skin. In aspects, such composition(s) and the plurality and diversity of particulate(s) thereof "fill" such skin imperfections and provide detectable or significant, e.g., visible, skin "smoothing" or "blurring" effect(s). In aspects, composition(s) provide a detectable or significant, e.g., visible, mattifying effect, e.g., detectably or significantly reducing skin shine for a period of at least about 2 hours, such as, e.g., $\geq$4 hours, $\geq$6 hours, $\geq$8 hours, $\geq$10 hours, $\geq$12 hours, $\geq$14 hours, $\geq$16 hours, $\geq$18 hours, $\geq$20 hours, $\geq$22 hours, or, e.g., for a period of at least about 24 hours, after initial application (e.g., application to human skin) such as, e.g., providing an "all-day" mattifying effect or providing "all-day" shine control.

Optionally Present or Excluded Elements

According to aspects, the invention provides composition(s) which are characterizable by the presence of, or alternatively, the absence of, one or more characteristics, one or more constituents, or both. Any of the compositions or components of any of the references incorporated here by reference can be excluded from the scope of compositions provided here (or alternatively incorporated in compositions of the invention). The following is a list of other exemplary compositions that may or may not be included or excluded from compositions of the invention.

In aspects, the composition(s) are not a foam. In aspects, the composition(s) are not foamable. In aspects, the compositions is not a gel. In aspects, the composition is not associated with a wipe or other mechanical delivery system.

In certain aspects, the composition(s) comprise or lack amino group-containing silicone polymers. In aspects, the composition(s) comprise or lack vinylpyrrolidone. In aspects, the composition(s) comprise or lack a hydrogel. In aspects, the composition(s) comprise or lack phenylene-1, 4-bis-(2-benzimidazyl)-3,3/,5,5/-tetrasulfonic. In aspects, the composition(s) comprise or lack acid or a salt. In aspects, the composition(s) comprise or lack calcium phosphate. In aspects, the composition(s) comprise or lack cerium oxide, aluminum oxide, or both. In aspects, the composition(s) comprise or lack polyglyceryl-3 sorbityl linseedate. In aspects, the composition(s) comprise or lack an environmental protectant selected from the group consisting of benzylidene dimethoxydimethylindanone, tocopheryl acetate, bisabolol and *Zingiber officinale* root. In aspects, the composition(s) comprise or lack gallium nitride-based nanoparticle(s). In aspects, the composition(s) comprise or lack one SPF-boosting emollient selected from the group consisting of octyldodecyl neopentanoate. In aspects, the composition(s) comprise or lack butyl octyl salycilate, and cetyl dimethicone. In aspects, the composition(s) comprise or lack vitamin D.

In certain further aspects, the composition(s) comprise or lack phosphorus acid monomers. In aspects, the composition(s) comprise or lack copolymer particle(s)/particle population(s) comprising polymerized units derived from (i) 0.1 to 20 weight % of phosphorus acid monomers, wherein the phosphorus acid monomers comprise phosphoethyl methacrylate, and (ii) 80 to 99.9 weight % of comonomers, wherein the comonomers include at least one of butyl acrylate, methyl methacrylate, methacrylic acid. In aspects, composition(s) comprise or lack one, more, or all/each of isostearic acid, sodium carboxymethyl cellulose, or a silicone containing a carboxyl group such as carboxydecyl trisiloxane. In aspects, the composition(s) comprise or lack octyltriethoxysilane and/or dimethylpolysiloxane. In aspects, the composition(s) comprise or lack dispersion of a hydrophobized zinc oxide and/or titanium dioxide homogeneously in an oil phase with carboxydecyl trisiloxane acting as a dispersant. In aspects, the composition(s) comprise or lack polyalkylene glycol comprising a polyethylene glycol, polypropylene glycol and/or polybutylene glycol.

Still further, in aspects, the composition(s) comprise or lack bis-ethylhexyloxyphenol methoxyphenyl triazine. In aspects, the composition(s) comprise or lack zinc oxide particles comprising a surface that is covered with a passivating aluminum oxide or silicon dioxide layer. In aspects, ZnO, TiO2, or both, can be coated e.g., by silica, alumina, aluminum hydroxide, aluminum stearate, etc. In certain aspects, ZnO is uncoated.

In aspects, the composition(s) comprise or lack di(phytosteryl/2-octyldodecyl)N-lauroyl-L-glutamategraph(s). In aspects, the composition(s) comprise or lack di(phytosteryl/ 2-octyldodecyl)N-lauroyl-L-glutamate, phytosteryl macadamiate, and cholesteryl macadamiate: di(phytosteryl/2-octyldodecyl)N-lauroyl-L-glutamate. In aspects, the composition(s) comprise or lack nonionic surfactant which is characterizable is a polyoxyethylene/methylpolysiloxane copolymer. In aspects, the composition(s) comprise or lack one, more, or all of xanthan gum, salicylates, ethylhexyl salicylate, trisodium EDTA, EDTA, triazine or triazone compounds.

In aspects, the composition(s) comprise or lack one, more, or all of dibutyl adipate ethylhexylglycerin, polyoxyethylene methylpolysiloxane copolymer. In aspects, the composition(s) comprise or lack a hydrotrope, such as urea—triethanol lactatelsodium lactate. In aspects, compositions comprise or lack one or more of sorbitol, glycerin, glucose, ethylene, diethylene, triethylene, polyglycol, propyleneglycol, mannitol, glucosides, hyaluronic acid, and larger molecules including mucopolysaccharides, chitin liquid-polysaccharide glucosamine, proteins, and collagen.

In aspects, the composition(s) comprise or lack shea butter, 0.4% (w/w) caprylyl glycol, cyclopentasiloxane, tocopheryl acetate. In aspects, the composition(s) comprise or lack vitamin E or derivatives thereof such as tocopherol and tocopherol acetate.

In aspects, the composition(s) comprise or lack one, more, or all of dibutyl adipate ethylhexylglycerin, polyoxyethylene methylpolysiloxane copolymer. In aspects, the composition(s) comprise or lack a hydrotrope, such as urea-triethanol lactatelsodium lactate, sorbitol, glycerin, glucose, ethylene, diethylene, triethylene, polyglycol, propyleneglycol, mannitol, glucosides, hyaluronic acid, and larger molecules including mucopolysaccharides, chitin liquid-polysaccharide glucosamine, proteins, and collagen. In aspects, the composition(s) comprise or lack a hydrotrope, such as urea-triethanol lactatelsodium lactate. In aspects, compositions comprise or lack sorbitol, glycerin, glucose, ethylene, diethylene, triethylene, polyglycol, propyleneglycol, mannitol, glucosides, hyaluronic acid, and larger molecules including mucopolysaccharides, chitin liquid-polysaccharide glucosamine, proteins, and collagen.

In aspects, the composition(s) comprise or lack a divalent polyol including alkylene glycol. In aspects, composition(s) comprise or lack one or more of ethylene glycol, propylene glycol, and 1,3-butylene glycol, dialkylene glycol such as diethylene glycol and dipropylene glycol; and polyalkylene glycol such as polyethylene glycol and polypropylene glycol. In some aspects, composition(s) comprise or lack alkylene glycol, dialkylene glycol, or both.

In aspects, the composition(s) comprise or lack titanium dioxide. In aspects, the composition(s) comprise or lack an iron oxide. In aspects, composition(s) comprise or lack an iron oxide comprising a coating.

In aspects, the composition(s) comprise or lack the aromatic silicone phenyl methicone. In aspects, composition(s) lack the alkylmethyl methicone caprylyl methicone.

In aspects, the composition(s) comprise or lack one or more of dimethiconol, dimethicone, phenyl methicone, stearoxytrimethylsilane, lauryl PEG/PPG-18 methicone, and polymethylsilsesquioxane.

In aspects, the composition(s) comprise or lack particulate titanium oxide having an average primary particle size of 0.01 to 0.2 μm. In aspects, composition(s) comprise or lack particulate zinc oxide having an average primary particle size of 0.01 to 0.033 μm. In aspects, composition(s) comprise or lack particulate zinc oxide having an average primary particle size of less than 100 μm or a size such as, e.g., about 0.01 to 0.033 μm.

In aspects, the composition(s) comprise or lack 2-ethylhexyl p-methoxycinnamate, 4-tert-butyl-4'-methoxydibenzoylmethane, methyl hydrogen-polysiloxane, trimethylsiloxy silicate, or alkyl polysiloxane. In aspects, composition(s) comprise or lack particle(s) of this paragraph in a diameter within the range of 0.38-1.5 μm. In aspects, composition(s) comprise or lack particle(s) of this paragraph in a diameter within the range of 8-150 nm.

In aspects, the composition(s) comprise or lack cerium dioxide (CeO2) or zirconium dioxide (ZrO2).

In aspects, the composition(s) comprise or lack polyester copolymers including octyldodecyl citrate crosspolymer. In aspects, the composition(s) comprise or lack siloxane star-graft copolymer coating, or comprise or lack hydrocarbon including isododecane, dodecane, tridecane, isohexadecane, pentadecane, or combinations thereof.

In aspects, the composition(s) comprise or lack octylmethoxy cinnamate, ethylhexyl methoxycinnamate, octocrylene, avobenzone, butylmnethoxydibenzoylmethane, oxybenzone, octyltriazone, menthyl anthranilate, 3,4-methylbenzylidene camphor and bis-ethylhexyloxyphenol methoxyphenyltriazine.

In aspects, the composition(s) comprise or lack styrene, alpha-methyl styrene, vinyl toluene, vinyl naphthalene, acrylonitrile, methacrylonitrile, (meth)acrylamide, C1-C20 alkyl esters of (meth)acrylic acid, (meth)acrylic acid, itaconic acid, fumaric acid, maleic acid, sulfoethyl (meth) acrylate, sulfopropyl (meth)acrylate, styrene sulfonic acid, vinyl sulfonic acid, 2-(meth)acrylamido-2-methyl propanesulfonic acid, amine-containing (meth)acrylate monomer, salts thereof, or combinations thereof.

In aspects, the composition(s) comprise or lack a phospholipid selected from phosphatidyl cholines, phosphatidyl ethanolamines, phosphatidyl serines, phosphatidyl inositols and mixtures thereof. In aspects, composition(s) comprise or lack lecithin.

In aspects, the composition(s) comprise or lack one or more fatty alcohols, fatty acids, esters of fatty alcohols or fatty acids, or a combination thereof.

In aspects, the composition(s) comprise or lack butyl methoxydibenzoylmethane, octocrylene, homosalate, 2-phenylbenzimidazol-sulphonic acid, ethylhexyl methoxycinnamate, ethyl hexyl salicylate, or mixture(s) thereof.

In aspects, the composition(s) comprise or lack one or more of simethicone, methicone, dimethicone, polysilicones-15, stearic acid, octyl trimethoxy silane, dimethicone, octyl tri(m)ethoxy silane, or dimethoxydiphenylsilanetriethoxycaprylylsilane cross-polymer.

In aspects, the composition(s) comprise or lack a significant amount of glycerine; comprise or lack completely or comprise or lack an amount greater than or equal to about 0.05 wt. % to less than or equal to about 0.15 wt. % xanthan gum; comprise or lack completely or comprise or lack an amount greater than or equal to about 0.05 wt. % to less than or equal to about 1 wt. % vanillin; comprise or lack completely or comprise or lack an amount greater than or equal to about 0.05 wt. % to less than or equal to about 1 wt. % tiare; comprise or lack completely or comprise or lack an amount greater than or equal to about 0.5 wt. % to less than or equal to about 3 wt. % a tocopherol mixture.

In aspects, the composition(s) comprise or lack a significant amount of glycerine, comprise or lack greater than or equal to about 0.05 wt. % to less than or equal to about 0.15 wt. % xanthan gum; greater than or equal to about 0.05 wt. % to less than or equal to about 1 wt. % vanillin; greater than or equal to about 0.05 wt. % to less than or equal to about 1 wt. % tiare; greater than or equal to about 0.5 wt. % to less than or equal to about 3 wt. % a tocopherol mixture.

In aspects, the composition(s) comprise or lack a humectant comprising glycerin, propylene glycol, diglycerin, sodium pyroglutamic acid (sodium PCA), hyaluronic acid, pentylene glycol, squalene, sodium hyaluronate, butylene glycol, aloe vera, coconut butter, coconut oil, grape seed oil, *Rubus idaeus* seed oil, shea butter, or a combination thereof.

In aspects, the composition(s) comprise or lack a thickener comprising xanthan gum, cellulose gum, *sclerotium* gum, pectin, carrageenan, *Acacia senegal* gum, corn starch, *ceratonia* silique gum, *caesalpinia* spinose gum, bentonite, microcrystalline cellulose, or a combination thereof.

In aspects, the composition(s) comprise or lack a dispersing agent comprising polyhydroxystearic acid, isostearic acid, silicone oil, polyglyceryl-3 diisostearate, polyglyceryl-2 dipolyhydroxystearate, or a combination thereof.

In aspects, the composition(s) comprise or lack a an emulsifier comprising sorbitan monolaurate, glyceryl stearate, polyglyceryl-3 distearate, glyceryl stearate citrate, polyglyceryl-4 oleate, glyceryl oleate, polyglyceryl-4 caprate, polyglyceryl-3 diisostearate, polyglyceryl 3-ricinoleate, polyglyceryl-5 laurate, glyceryl cocoate, glyceryl caprylate, sorbitan tristearate, polyglyceryl-3 pentaolivate, sorbitan olivate, palmitic acid, stearic acid, myristic acid, decyl glucoside, sorbitan oleate, sorbitan stearate, polyglyceryl-10 laurate, polyglyceryl-10 diisostearate, polyglyceryl-2 isostearate, polyglyceryl-6 isostearate, sucrose cocoate, sucrose laurate, sucrose myristate, sucrose palmitate, sucrose stearate, cetearyl glucoside, or a combination thereof.

In aspects, the composition(s) comprise or lack an emollient comprising cetyl alcohol, butylene glycol, propanediol, cetearyl alcohol, hexyl laurate, myristyl myristate, dicaprylyl ether, caprylic/capric triglyceride, cetyl esters, cetyl palmitate, triisostearine, undecylenic glycerides, lauryl alcohol, decyl oleate, C15-19 alkanes, C20-22 alcohols, almond oil, candelilla cera, lanolin, hydrogenated vegetable oil, apricot kernel oil, beeswax, avocado oil, babassu oil, sweet almond oil, cocoa butter, jojoba oil, olive oil, hydrogenated castor oil, flax seed oil, jojoba esters, sunflower oil, canola oil, rice germ oil, or a combination thereof.

In aspects, the composition(s) comprise or lack a preservative comprising benzoic acid, benzyl alcohol, sorbic acid, ethyl lactate, sodium benzoate, or a combination thereof.

In aspects, the composition(s) comprise or lack an antioxidant comprising tocopherol mixture, ubiquinone, ascorbyl palmitate, triethyl citrate, ferulic acid, or a combination thereof.

In aspects, the composition(s) comprise or lack an odorant comprising an essential oil, an herbal distillate, etc.

In aspects, the composition(s) comprise or lack sorbitan monolaurate, glyceryl stearate; cetyl alcohol; almond oil; or benzoic acid.

In aspects, the composition(s) comprise or lack butyloctyl salicylate, and a dermatologically acceptable vehicle. The compositions may further comprise or lack additional ingredients such as cyclopentasiloxane, neopentyl glycol diheptanoate, butylene glycol, caprylyl methicone, PEG-9 polydimethylsiloxyethyl dimethicone, glycerin, polyglyceryl-6 polyricinoleate, lauric acid, aluminum hydroxide, potassium sorbate, and citric acid.

In aspects, the composition(s) comprise or lack cyclopentasiloxane, neopentyl glycol diheptanoate, or butylene glycol. In aspects, the composition(s) comprise or lack caprylyl methicone, PEG-9 polydimethylsiloxyethyl dimethicone, or glycerin.

In aspects, the composition(s) comprise or lack polyglyceryl-6 polyricinoleate. In aspects, the composition(s) comprise or lack one or more of lauric acid, aluminum hydroxide, potassium sorbate, or citric acid.

In aspects, the composition(s) comprise or lack polylactic acid particles.

In aspects, the composition(s) comprise or lack coating materials comprising a combination of (i) silicon dioxide, (ii) magnesium fluoride, (iii) one or more fluoropolymers, (iv) aluminum oxide, (v) zinc sulfide, and (vi) titanium dioxide.

In aspects, the composition(s) comprise or lack multiple distinct fluoropolymers.

In aspects, the composition(s) comprise or lack detectable or significant aggregation of porous titanium oxide particles.

In aspects, the composition(s) comprise or lack aliphatic alcohol is a polyhydric alcohol. In aspects, the composition(s) comprise or lack carboxylic acid is acetic acid.

In aspects, the composition(s) comprise or lack alkali is sodium carbonate.

In aspects, the composition(s) comprise or lack the metal oxide of the peptide-based metal oxide sunscreen agent is selected from the group consisting of titanium dioxide, zinc oxide, cerium oxide and iron oxide and combinations thereof.

In aspects, the composition(s) comprise or lack the inorganic particles being coated with poly[C8-C20 hydroxycarboxylic acid].

In aspects, the composition(s) comprise or lack selecting one or more suspension particles to be utilized in conjunction with the multiple zinc oxide particles in a sunscreen composition, interfacially active polymer is selected from the group consisting of lignosulfonate, lignin, alkali metal salts of humic acid, alkali metal salts of tannic acid, and mixtures thereof.

In aspects, the composition(s) comprise or lack ne zinc oxide surface-treated with an ethoxylated alkyl silane.

In aspects, the composition(s) comprise or lack the surface-treated zinc oxide comprises at least one zinc oxide surface-treated with triethoxycaprylylsilane.

In aspects, the composition(s) comprise or lack SPF boosters that comprise butyloctyl salicylate or ethylhexyl methoxycrylene.

In aspects, the composition(s) comprise or lack a lipophilic acrylate-based oil thickener.

In aspects, the composition(s) comprise or lack broad range of functionalized side chain crystalline polymer.

In aspects, the composition(s) comprise or lack at least one lipophilic acrylate-based oil thickener comprises C12-22 alkyl acrylate/hydroxyethylacrylate copolymer.

In aspects, the composition(s) comprise or lack distearyldimethylammonium chloride or bisethylhexyloxyphenolmethoxyphenyltriazine. In aspects, the composition(s) comprise or lack the UVB absorber is octylmethoxy cinnamate.

In aspects, the composition(s) comprise or lack the liquid-state higher fatty acid is isostearic acid.

In aspects, the composition(s) comprise or lack the non-ionic surfactant is polyoxyethylene hydrogenated castor oil.

In aspects, the composition(s) comprise or lack the volatile oil is light liquid isoparaffin.

In aspects the compositions comprises or lacks decamethylcyclopentasiloxane, and an alkyl trimethicone having 6 to 12 carbons.

In aspects, the composition(s) comprise or lack melanin, or a combination of melanin and lignin compounds.

In aspects, the composition(s) comprise or lack steareth-2, steareth-20, or a combination thereof.

In aspects, the composition(s) comprise or lack butyl methoxydibenzoylmethane. In aspects, the composition(s) comprise or lack ethylhexyl salicylate. In aspects, the composition(s) comprise or lack octocrylene. In aspects, the composition(s) comprise or lack homosalate; boron nitride, polymethylsilsesquioxane powders, or a copolymer of allyl methacrylate, or glycerine. In aspects, the composition(s) comprise or lack Hydroxyacetophenone. In aspects, the composition(s) comprise or lack Sodium chloride. In aspects, the composition(s) comprise or lack Caramel.

In aspects, the composition(s) comprise or lack talc, barium sulfate, kaolin, lauroyllysine, starch, boron nitride, precipitated calcium carbonate, magnesium carbonate, magnesium hydrogen carbonate, hydroxyapatite, or montmorillonite. In aspects, the composition(s) comprise or lack polytetrafluoroethylene (PTFE) wax particles. In aspects, the composition(s) comprise or lack Isododecane. In aspects, the composition(s) comprise or lack Isohexadecane. In aspects, the composition(s) comprise or lack Isodecyl neopentanoate.

In aspects, the composition(s) comprise or lack Propylene glycol related compounds, n-butyl ether, or metal fluorides (e.g., magnesium fluoride and calcium fluoride). In aspects, the composition(s) comprise or lack polyurethane, polycarbonate, polystyrene, an acrylic polymer, an alkyd polymer, polyester, siloxane polymer, polysulfide, an epoxy-containing polymer or a polymer derived from an epoxy-containing polymer 2007/0085063 A1 ride).

In aspects, the composition(s) comprise or lack Ethyl 3-ethoxypropionate. In aspects, the composition(s) comprise or lack Propylene glycol methylether acetate, Octyltrimethicone, Hexyltrimethicone, Decamethylcyclopentasiloxane, cyclopentasiloxane, Octamethylcyclotetrasiloxane, cyclotetradimethylsiloxane, Dodecamethylcyclohexasiloxane, Decamethyltetrasiloxane.

In aspects, the composition(s) comprise or lack polyurethanes. In aspects, the composition(s) comprise or lack acrylic polymers, alkyd polymers, polyesters, siloxane-containing polymers, polysulfides, epoxy-containing polymers, or polymers derived from epoxy-containing polymers. In aspects, the composition(s) comprise or lack Phenylbenzimidazole. In aspects, the composition(s) comprise or lack Sulfonic Acid. In aspects, the composition(s) comprise or lack Isopropyl Palmitate. In aspects, the composition(s) comprise or lack Butylene Glycol. In aspects, the composition(s) comprise or lack Triethanolamine. In aspects, the composition(s) comprise or lack Glycerin. In aspects, the composition(s) comprise or lack Stearic Acid. In aspects, the composition(s) comprise or lack Cetyl Alcohol. In aspects, the composition(s) comprise or lack DEA Cetyl Phosphate. In aspects, the composition(s) comprise or lack PVP Eicosene Copolymer. In aspects, the composition(s) comprise or lack Stearyl Alcohol.

In aspects, the composition(s) comprise or lack any compound classified as a Carbomer, such as Carbomer 954. In aspects, the composition(s) comprise or lack Acrylates/C10-C30. In aspects, the composition(s) comprise or lack Alkyl crylate. In aspects, the composition(s) comprise or lack any form of EDTA, e.g., Disodium EDTA. In aspects, the composition(s) comprise or lack *Helianthus Annus* Seed Wax. In aspects, the composition(s) comprise or lack Ozokerite. In aspects, the composition(s) comprise or lack Polyethylene. In aspects, the composition(s) comprise or lack Tribehenin.

In aspects, the composition(s) comprise or lack olive oil, such as Hydrogenated Olive Oil (and) Hydrogenated Olive Oil. In aspects, the composition(s) comprise or lack DimethiconeNinyldimethicone Crosspolymer, Laureth-3, or Laureth-25. In aspects, the composition(s) comprise or lack 1,2 Hexanediol and Caprylyl Glycol.

In aspects, the composition(s) comprise or lack Benzylidene Dimethoxydimethylindanone. In aspects, the composition(s) comprise or lack Phenethyl Alcohol or Caprylyl Glycol. In aspects, the composition(s) comprise or lack Benzylidene Dimethoxydimethylindanone.

In aspects, the composition(s) comprise or lack Kaolin. In aspects, the composition(s) comprise or lack lecithin, or Hydrogenated Lecithin. In aspects, the composition(s) comprise or lack Hydroxyacetophenone. In aspects, the composition(s) comprise or lack Caramel.

In aspects, the composition(s) comprise or lack Caprylic/Capric Triglyceride. In aspects, the composition(s) comprise or lack Butyl Octyl Salycilate.

In aspects, the composition(s) comprise or lack Bisabolol and *Zingiber O./ficinale* (Ginger) Root Extract.

In aspects, the composition(s) comprise or lack Tocopheryl Acetate. As with any other disclosure here, in aspects, the compositions comprise only low amounts of such elements, e.g., less than 0.2% or about 0.1% or less of the element (e.g., a tocopheryl).

In aspects, the composition(s) comprise or lack 1,2 Hexanediol and Caprylyl Glycol. In aspects, the composition(s) comprise or lack Benzylidene Dimethoxydimethylindanone. In aspects, the composition(s) comprise or lack PMMA, Cerium Oxide, Aluminum Oxide. In aspects, the composition(s) comprise or lack alpha hydroxy acids, calamine, menthol, proteins and protein hydrolysates, sugar and derivatives thereof, or glycyrrhetinic.

In aspects, the composition(s) comprise or lack any aerogel or specifically hydrophobic silica aerogel. In aspects, the composition(s) comprise or lack silica silylate. In aspects, the composition(s) comprise or lack allantoin. In aspects, the composition(s) comprise or lack any organosiloxane emulsifier. In aspects, the composition(s) comprise or lack Ethylhexyl Palmitate, squalene, or squalane. In aspects, the composition(s) lack Polyglyceryl-3 or Polyceryl-4 or higher ordered polyglyceryl ingredients. In aspects, the composition(s) comprise or lack Microcrystalline Wax. In aspects, the composition(s) comprise or lack Mineral Oil.

In aspects, the composition(s) comprise or lack Hydrogenated Glycerides. In aspects, the composition(s) comprise or lack any Alkyl Benzoate. In aspects, the composition(s) comprise or lack Cyclopentasiloxane. In aspects, the composition(s) comprise or lack Polyglyceryl-4 Isostearate In aspects, the composition(s) comprise or lack any type of petrolatum. In aspects, the composition(s) comprise or lack Silsoft 034 Caprylyl Methicone. In aspects, the composition(s) comprise or lack Distearyldimonium Chloride. In aspects, the composition(s) comprise or lack Propylene, e.g., Propylene Carbonate. In aspects, the composition(s) comprise or lack Carbonate. In aspects, the composition(s) comprise or lack Carnauba wax. In aspects, the composition(s) comprise or lack Laurie acid. In aspects, compositions comprise or lack urea, sodium chloride, or both. In aspects, the composition(s) comprise or lack Methylparaben or propylparaben or other parabens. In aspects, the composition(s) comprise or lack polysorbates, such as polysorbate 20 or 80. In aspects, the composition(s) comprise or lack one vinyl pyrrolidone. In aspects, the composition(s) comprise or lack vinyl caprolactam monomer(s) or vinyl acetate monomer(s). In aspects, the composition(s) comprise or lack PVPVA. In aspects, the composition(s) comprise or lack Behenyl alcohol, Ceteareth compositions, Diisopropyl adipate or Homosalate or Octisalate or Octinoxate. In aspects, the composition(s) comprise or lack Benzophenone compounds/compositions. In aspects, the composition(s) comprise or lack Octocrylene. In aspects, the composition(s) comprise or lack Triethanolamine. In aspects, the composition(s) comprise or lack Propylene glycol. In aspects, the composition(s) comprise or lack diazolidinyl urea (and) methylparaben (and) propylparaben.

Method of Manufacture

In aspects, the invention provides methods of producing compositions having any combination of characteristics described above. In aspects, compositions are produced through the combinations of multiple phases. In aspects, the order in which compositional constituent(s) are added, or, e.g., to which phase they are added, detectably or significantly changes one or more characteristic(s) of the composition(s). In aspects, methods comprise forming a substrate/carrier, into which various particles and other ingredients are dispersed. Methods of manufacture, as exemplified below, comprise multiple homogenization steps. In aspects, the number of homogenization steps, character of homogenization (such as time, speed, temperature, etc.), stage of manufacture at which homogenization step(s) occur, or combination(s) thereof detectably or significantly alter one or more product characteristics. In aspects, methods herein are key to performance characteristic(s) of resulting composition(s). In aspects, some, most, or all of such steps comprise homogenization for at least 15, at least 20, at least 25, or at least 30 minutes (e.g., about 30 or about 35 minutes). Homogenization methods are exemplified below and known in the art. By applying these methods and using the ingredients described herein, a substrate that stably sustains the various particles of the matrix and provides low viscosity, with a non-settling and stable nature, can be obtained. Thus, in aspects, the invention provides a sunscreen composition, wherein the multidimensional photoprotective particle matrix in the composition is formulated in multiple steps wherein formulation of sunscreen composition comprises of combination of one or more phase, primarily two phases. An example method can comprise forming a first phase comprising hydrator(s), electrolytes, and other readily mixable ingredients (e.g., carnosine, antioxidant/anti-radiation biologics/extracts, such as *deinococcus* extract, *Echinacea* extract, or both, and the like) with heating and mixing to emulsify. A second phase is formed comprising, e.g., emollient(s) and dispersant(s) (e.g., polyhydroxy stearic acid), and metal oxide polymers, which is then homogenized for ≥25, e.g., about 30 or about 35 minutes, under suitable conditions (e.g., at 10,000 rpM @ 75-80 degrees C.). A third phase can be formed. A melting step can be applied (mixing for 5-15, 5-10, or about 5 minutes at e.g., 85 degrees C.), and emulsifier(s) added, with further mixing. Emulsification can be performed using high speed mixing at temperature (e.g., 70-80, such as 72-75 degrees C.), applied to the oil phase while slowly adding the water phase. Additional homogenization can be applied at e.g., 5000-10,000 RPM, such as 6,000-8,000 RPM, often comprising two or more speeds, for a suitable period (e.g., 10 minutes), while allowing cooling (e.g., to about 50 degrees C.). Powders can be added to the composition and further homogenization performed (which may, at least in part, serve to de-aerate the product) while allowing it to cool to near room temperature (e.g., about 30 degrees C.). Such methods are further exemplified below. Such methods can provide products with unique properties, as described elsewhere herein (broad-spectrum protection, high SPF, etc.).

In aspects, the invention provides compositions produced by processes described herein and by substantially similar processes. In this respect, an aspect of the invention is products produced by such processes. Such products can include novel and inventive characteristics, including, i.a., the ability to provide a more stable protective particulate matrix in the product when applied to skin, a better distribution of disperse/varied particles contained in the matrix/composition, less whitening effects (e.g., as described elsewhere herein), UV radiation protection as described elsewhere herein, and protection against other forms of radiation (e.g., blue light, IR, etc.), as well as perceived cosmetic elegance characteristics (e.g., lack of tackiness/stickiness, etc., as determined by well-powered adequate studies).

The various components described in this disclosure as associated with a function can, where appropriate, be described as "means" for carrying out such a function, indicating that known alternatives for suitably carrying out the function are within the scope of such disclosure. For example, compositions of the invention can include an effective amount of means for emulsification (including emulsifiers provided here and equivalents), preservative means, dispersion means, surfactant means, emollient means, SPF boosting means, odor masking means, absorbent means, film forming means, anti-oxidation means, thickening means, viscosity-enhancing means, light scattering means, UV radiation scattering means, hydration means, electrolyte provision means, carrier means, absorbency means, and the like.

An exemplary production scheme of a composition of the invention is as follows and in aspects the invention provides compositions provided by a method comprising most, generally all, substantially all, or all of these steps or wherein the steps are (1) substantially similar or generally similar or about the same or essentially the same or (2) do not result in a significant change in most, generally all, or all of the structural, functional, or both structural and functional elements of the composition—

Develop a Water Phase:
Water Heat to 70-75C and Mix Adding:
  Add Electrolyte (MgSO 7H2O)
  Add Hydrator—Propanediol
  Add Extracts if included (e.g., *Deinococcus* Ferment/First; *Echinacea Purpurea* etc)
  Add Peptide if present (e.g., Carnosine)
Develop an Oil Phase:
  Add generally all, substantially all, or all the oils (esters, silicones) and the dispersant agent (e.g., Polyhydroxystearic Acid)
  Add uncoated Aggregates or Platelets ZnO) HOMO (homogenize) @ 8500 rpm @ 65-75 C-30 min (to disperse and coat evenly the ZnO)
  Add (Styrene Acrylates Copolymer/) Sunsphere and continue to homogenize (HOMO) @ 8500 rpm, @ 65-77 C-40 min to disperse for untinted and HOMO up to 1 h 30 min for the tinted with the added Iron pigment.
  Add Co-emulsifier, e.g., Glyceryl Behenate/Compritol 888
  Add Film Former, Dimethicone/Dimethicone Crosspolymer
  Add Anti-Irritant, VitE, Preservative booster maintaining the temperature @ 70-75 C
Perform an Emulsification of Water in Oil Emulsion:
  Mix Oil Phase @ 70-75 C with high a speed/agitation (4000-5000 rpm) and start adding the Water Phase, very slowly, almost drop by drop, without letting the water to pool on the surface of the Oil Phase. Mix for ten min.
  HOMO the emulsion 2 min @ 8,500 rpm and 2 min @ 6,000 rpm
  Add TiO2 in the case of a ZnO/TiO2 formulation. Mix @ 3000, rpm, for 10 min to disperse.
  Start Cooling with mixing at 40-45 C.
  Add with mixing odor masking agent (e.g., Phenethyl Alcohol, Caprylyl Glycol/Feniol)
  Add aesthetic modifier silicone (Dimethicone,Trisiloxane/Xiameter MPX-1184)
  Add Premix Powders (Silica/Silisphere LS-8H and Calcium, Sodium Borosilicate/Cocabeads Crystal)
  HOMOGENIZE @ 40 C: 2 min @ 8,500 rpm and 2 min @ 2,900 rpm
  DO NOT RETURN to Mixing
  Evacuate the batch at 30-35C.

Methods of Use

The invention further provides methods of using any of the above-described compositions (formulations) or compositions comprising any suitable combination of such characteristics/features. In aspects, compositions are used as a cosmetic agent. In aspects, compositions are used as protectants against IR radiation, UV radiation, blue light radiation, or a combination thereof. In aspects, compositions are used as sunscreens. In aspects, compositions are used as environmental protectants.

In aspects, compositions are used for multiple effect(s) such as those listed here. In aspects, such sunscreens are water-resistant (e.g., for 40-80 minutes, such at least 40 minutes, about 80 minutes, or longer).

In aspects, application of effective amounts of compositions detectably or significantly reduces the risk of skin cancer.

In aspects, application of effective amounts of compositions detectably or significantly reduces the appearance of aging. In aspects, compositions provided herein include agents for reducing redness, reducing signs of aging (e.g., fine lines, wrinkles, or both), addressing uneven pigmentation, or a combination thereof.

Typically, such ingredients are oil-soluble or water-soluble and compatible with the products described herein. Examples of such products are known and described in, e.g., several of the references disclosed herein by incorporation. Thus, method aspects can result in, e.g., detectably or significantly (a) reducing the appearance of fine lines/wrinkles, (b) improving skin barrier function (i.e., by reducing the rate/extent of trans-epidermal water loss), (c) making the skin feel smoother, more supple and softer, (d) creating the appearance of more even skin tone (reducing dyschromia) or (and/or) (e) imparting "glow"/radiance (also described in the art as "brightness"), by adequately administering effective amount of compositions over a suitable course of treatment/treatment (application) regimen.

Other uses of compositions are described herein and in the incorporated references.

ACTUAL AND PROPHETIC EXEMPLARY COMPOSITIONS, CHARACTERISTICS, METHODS AND RESULTS ("EXAMPLES")

The following detailed exemplary expository descriptions or experiments involving embodiments, applications, or related principles, of or otherwise related to the invention ("Examples") are provided to assist reader(s) in further understanding aspect(s) of the invention or principle(s) related to the invention or practice of aspect(s) of the invention.

Any particular material(s), method(s), step(s), and condition(s) employed/described in the following Examples, and any results thereof, are merely intended to further illustrate aspects of the invention. These Examples reflect exemplary embodiments of the invention, and the specific methods, findings, principles of such Examples, and the general implications thereof, can be combined with any other part of this disclosure. However, readers should understand that the invention is not limited by these Examples or any part thereof.

Although not disclosed herein for sake of brevity, over 100 unique metal oxide polymer sunscreen compositions were developed and evaluated in the course of developing the invention and the compositions specifically disclosed herein exhibit beneficial properties in several areas (stability, appearance, non-whitening effect, SPF, critical wavelength, other radiation protection characteristics, such as UVA/UVB and UVA1/UV ratio characteristics, water resistance, etc.

Many exemplary compositions of the invention are described in the Examples which follow. To aid the reader in understanding, and to connect repeatedly tested exemplary compositions from one Example to another, the following table is provided for at least some exemplary compositions described herein. Primary composition identifiers are provided in column 1. If data from such sample is available in a specific Example ("Ex. #"), it is identified in subsequent columns, along with the sample identifier used in the specific testing of such compositions in each Examples.

| Primary Composition Identifier | Ex. 6 (In-vitro) | Ex. 7 (Micro.) | Ex. 8 (In-vitro) | Ex. 9 (Appl.) | Ex. 11 (Homo.) | Ex. 12 (WR) |
|---|---|---|---|---|---|---|
| 009-74 | — | — | — | — | — | 17-644 |
| 009-118 | — | — | — | — | — | 18-1219 |
| 021-042 | A-0057 | — | — | — | — | — |
| 021-046 XP(5) | A-0878 | — | — | A-1516 | — | — |
| 021-048-XP((5)-10 | — | 1 | — | — | 1 | — |
| 021-046 XP(5)-22 | — | 2 | A-1515 | A-1515 | — | — |
| 021-046 XP(5)-28 | — | — | A-1554 | — | — | — |
| 021-048-XP(7)-8 | — | 4 | — | — | — | — |
| 021-048-XP(7)-20 | — | 3 | — | — | — | — |
| 021-048-XP(7)-26 | — | — | — | — | — | — |
| 021-048-XP(7)-30 | — | — | — | — | — | — |

Example 1

Example 1 depicts a first water-in-oil (W/O) sunscreen emulsion composition (exemplary composition 1) primarily comprising non-nano zinc oxide (ZnO) as the active ingredient in the composition, the composition being presented in Table 1. Example 1 further describes a method of preparing such composition(s).

Preparation of a Water-In-Oil (W/O) Sunscreen Emulsion

A water-in-oil emulsion composition was prepared according to the following phase production method. Each phase comprises one or more steps. Phases described here may comprise one or more steps not specifically described.

Phase 1—Water Phase. A water phase was prepared by accurately weighing all ingredients numbered 1 to 6 in Table 1 below. All weighed ingredients were placed together in a first container. The ingredients were heated to a temperature of between about 72° C. and about 75° C. The ingredients were stirred continuously to ensure uniform mixing, and mixing was continued until the mixture was homogenous. This established a water phase.

Phase 2—Oil Phase. An oil phase was prepared similarly to the steps described in Phase 1. All ingredients numbered 7 to 12 in Table 1 below were weighed. All weighed ingredients were placed together in a second container. The ingredients were heated to a temperature of between about 70° C. and about 90° C., such as between about 75° C. and about 85° C. in the second container. The ingredients were mixed until a uniform dispersion was achieved. After a uniform dispersion was achieved, the mixture was homogenized for at least about 20 minutes, such as, e.g., at least about 22 minutes, at least about 24 minutes, at least about 26 minutes, at least about 28 minutes, at least about 30 minutes, at least about 32 minutes, at least about 34 minutes, at least about 36 minutes, at least about 38 minutes, or, e.g., at least about 40 minutes, such as, e.g., about 30 minutes, was complete, an SPF booster and pigments, numbered 13-16 in Table 1 below, were added. The mixture was homogenized for about at least about 1 hour, such as at least about 1.25 hours, at least about 1.5 hours, at least about 1.75 hours, at least about 2 hours, at least about 2.25 hours, at least about 2.5 hours, at least about 2.75 hours, or, e.g., at least bout 3 hours, such as, e.g., about 1 hour and 40 minutes at a speed of about between about 5000 RPM and 15000 RPM, such as a speed of between about 6000 RPM and about 14000 rpm, about 7000 RPM and about 13000 RPM, about 8000 RPM and about 12000 RPM, about 9000 RPM and about 11000 RPM, or, e.g., about 10000 RPM. A co-emulsifier, identified as number 17 in Table 1 below, was added to the mixture and was melted by constant stirring for at least about 1 minute, such as, e.g., at least about 2 minutes, at least about 3 minutes, at least about 4 minutes, at least about 5 minutes, at least about 6 minutes, at least about 7 minutes, at least about 8 minutes, at least about 9 minutes, or, e.g., at least about 10 minutes, such as about 5 minutes, at a temperature of between about 80° C. and about 90° C., e.g., about 85° C. Emulsifiers, identified as numbered items 18-23 in Table 1 below, were then added and mixed at a temperature of between about 70° C. and about 80° C., such as, e.g., about 72° C. and about 75° C. until uniformity was achieved. While mixing the oil phase at high speed, the water phase (Phase 1) was slowly added to the oil phase. This initiated the emulsification process.

Emulsification—The mixture resulting from the previously described steps was continuously mixed for at least about 1 minute, at least about 2 minutes, at least about 3 minutes, at least about 4 minutes, or at least about 5 minutes, such as, e.g., at least about 6 minutes, at least about 7 minutes, at least about 8 minutes, at least about 9 minutes, or, e.g., at least about 10 minutes, such as, e.g., at least about 11, about 12, about 13, about 14, or, e.g., at least about 15 minutes, such as about 10 minutes. The mixture was then homogenized for at least about 1 minute, at least about 2 minutes, at least about 3 minutes, at least about 4 minutes, or, e.g., at least about 5 minutes, such as, e.g., about 2 minutes, at a speed of between about 6000 RPM and about 10000 RPM, such as, e.g., about 6500 RPM and about 9500 RPM, about 7000 RPM and about 9000 RPM, about 7500 RPM and about 8500 RPM, or, e.g., about 8000 RPM, followed by another at least about 1 minute, at least about 2 minutes, at least about 3 minutes, at least about 4 minutes, or, e.g., at least about 5 minutes, such as, e.g., about 2 minutes at a speed of about 4000 RPM and about 8000 RPM, such as, e.g., about 4500 RPM and about 7500 RPM, about 5000 RPM and about 7000 RPM, about 5500 RPM and about 6500 RPM, or, e.g., about 6000 rpm. Continued mixing was followed by a cooling period wherein the mixture was allowed to cool at a temperature of between about 30° C. and about 50° C., such as, e.g., between about 35° C. and about 45° C., such as, e.g., at about 40° C. After this, items 24 and 25 were added and mixed followed by addition of premix powder of items 26-27 uniformly and temperature is maintained at 40° C. A further homogenization step was performed for a period of at least about 1 minute, at least about 2 minutes, at least about 3 minutes, at least about 4 minutes, at least about 5 minutes, at least about 6 minutes, at least about 7 minutes, at least about 8 minutes, at least about 9 minutes, or, e.g., at least about 10 minutes, such as, e.g., about 4 minutes, at a speed of between about 6000 RPM and about 10000 RPM, such as, e.g., about 6500 RPM and about 9500 RPM, about 7000 RPM and about 9000 RPM, about 7500 RPM and about 8500 RPM, or, e.g., about 8000 RPM while being maintained at a temperature of between about 30° C. and about 50° C., such as, e.g., about 40° C. The mixture was then cooled to a temperature of between about 20° C. and about 40° C., such as, e.g., about 30° C.

TABLE 1

Exemplary Composition 1.

| Ingred. Number | Ingredient/Item | Wt. % |
|---|---|---|
| 1. | Water | 18-22 |
| 2. | Propanediol | 1-5 |
| 3. | Magnesium sulfate | 0.1-1 |
| 4. | Carnosine | 0.1-0.5 |
| 5. | *Deinococcus* extract, Butylene glycol, Water | 0.5-2 |
| 6. | *Echinacea purpurea* extract | 0.05-0.5 |
| 7. | Octyldodecyl Neopenthanoate | 15-20 |
| 8. | Cetyl Dimethicone, Dimethicone, Bis-vinyl dimethicone/Dimethicone copolymer | 1-5 |
| 9. | Phenyl Trimethicone, Bis-Vinyl, Dimethicone/Dimethicone copolymer | 1-4 |
| 10. | Squalene | 0.1-1 |
| 11. | Polyhydroxystearic acid | 0.5-1.5 |
| 12. | Zinc oxide | 20-25 |
| 13. | Styrene/Acrylates copolymer | 1-6 |
| 14. | Iron oxide brown | 0.1-0.6 |
| 15. | Iron oxide yellow | 0.8-1.3 |
| 16. | Iron oxide black | 0.08-0.2 |

TABLE 1-continued

Exemplary Composition 1.

| Ingred. Number | Ingredient/Item | Wt. % |
|---|---|---|
| 17. | Glyceryl dibehanate, Tribehenin, Glyceryl behanate | 0.5-1 |
| 18. | Phenyl trimethicone, Disteardimonium hectorite, Triethyl citrate | 1-5 |
| 19. | Bisabolol and *Zingiber officinale* (Ginger) root extract. | 0.08-0.15 |
| 20. | Dimethicone, Dimethicone cross polymer | 0.5-0.1 |
| 21. | Tocopheryl acetate | 0.008-0.015 |
| 22. | 1,2 Hexanediol, Caprylyl glycol, Tropolon | 0.7-1.2 |
| 23. | Polygceryl-2 sesquioleate | 8-12 |
| 24. | Phenethyl alcohol & Caprylyl glycol | 0.04-0.08 |
| 25. | Dimethicone, Trisiloxane | 1-4 |
| 26. | Calcium, Sodium borosilicate | 1-4 |
| 27. | Silica | 0.4-0.8 |

Readers will understand that sometimes compositions, compounds, or molecules herein are presented in capitalized form, according to common practice in the industry. Such capitalized presentation does not change the scope or meaning of the relevant term.

The matrix composition prepared by the above water-in-oil (W/O) method is subjected to stability testing. The composition of Example 1 (exemplary composition 1) is demonstrated to be highly stable and has sustained dispersion of particles in the composition matrix without detectable or significant sedimentation as evaluated over a time period of about 1 to about 6 months, e.g., about 1 months, about 2 months, about 3 months, about 4 months, about 5 months, about 6 months, or more, when stored at a temperature of about 50° C. or when stored at a temperature of about 40° C. The non-settling and non-phasing out characteristic(s) of the matrix is theorized to be due to the even distribution of differently sized particles in the matrix and their cordial association with each other which directly accentuates the aesthetic applications of this sunscreen product.

Example 2

Example 2 depicts a second sunscreen formulation (exemplary composition 2), provided in Table 2, below. Exemplary composition 2 comprises the same ingredients as exemplary composition 1 (provided in Table 1) with slightly modified ingredient concentration(s) but lacks iron oxides in the composition. Iron oxides are used as a pigment. In the composition of the present example, the sunscreen composition does not provide any tint or color to the skin upon application.

TABLE 2

Exemplary Composition 2.

| Ingred. Number | Ingredient/Item | Wt. % |
|---|---|---|
| 1. | Water | 18-22 |
| 2. | Propanediol | 1-5 |
| 3. | Magnesium sulfate | 0.1-1 |
| 4. | Carnosine | 0.1-0.5 |
| 5. | *Deinococcus* extract, Butylene glycol, Water | 0.5-2 |
| 6. | *Echinacea purpurea* extract | 0.05-0.5 |
| 7. | Octyldodecyl Neopenthanoate | 15-20 |
| 8. | Cetyl Dimethicone, Dimethicone, Bis-vinyl dimethicone/Dimethicone copolymer | 1-5 |
| 9. | Phenyl Trimethicone, Bis-Vinyl, Dimethicone/Dimethicone copolymer | 1-5 |

TABLE 2-continued

Exemplary Composition 2.

| Ingred. Number | Ingredient/Item | Wt. % |
|---|---|---|
| 10. | Squalene | 0.1-1 |
| 11. | Polyhydroxystearic acid | 0.5-1.5 |
| 12. | Zinc oxide | 18-25 |
| 13. | Styrene/Acrylates copolymer | 1-6 |
| 14. | Glyceryl dibehanate, Tribehenin, Glyceryl behanate | 0.5-1 |
| 15. | Phenyl trimethicone, Disteardimonium hectorite, Triethyl citrate | 1-5 |
| 16. | Bisabolol and *Zingiber officinale* (Ginger) root extract. | 0.08-0.15 |
| 17. | Dimethicone, Dimethicone cross polymer | 0.5-1 |
| 18. | Tocopheryl acetate | 0.008-0.015 |
| 19. | 1,2 Hexanediol, Caprylyl glycol, Tropolon | 0.7-1.2 |
| 20. | Polygceryl-2 sesquioleate | 8-12 |
| 21. | Phenethyl alcohol & Caprylyl glycol | 0.04-0.08 |
| 22. | Dimethicone, Trisiloxane | 1-4 |
| 23. | Calcium, Sodium borosilicate | 1-4 |
| 24. | Silica | 0.4-0.8 |

The matrix composition of Example 2 was prepared according to the water-in-oil (W/G) emulsion method described in Example 1.

The matrix composition of Example 2 is subjected to stability testing. The composition is evaluated for stability and sustainability of dispersion of particles in the matrix. Stability, a significant measure of predicted shelf life of the composition, is evaluated by placing the composition at temperatures of between about 30° C. and about 60° C. for between about 1 and about 4 months. Results show that the composition has surprisingly high stability characteristic(s), demonstrating no detectable or significant settling or phasing out of the matrix for a period of 3-6 months at about 40° C. and 1 month at about 50° C. with 3 F/T cycles. The non-settling and non-phasing out characteristic(s) of the matrix is theorized to be due to the even distribution of differently sized particles in the matrix and their cordial association with each other which directly accentuates the aesthetic applications of this sunscreen product.

Example 3

The compositions exemplified above in Example 1 and Example 2 are evaluated for stability according to other parameters of stability, namely viscosity (a measures of a fluid's resistance to flow, e.g., how much internal friction is present) and specific gravity. Viscosity of the composition is measured using a viscometer under appropriate conditions (e.g., at 25° C.) and is evaluated at regular time intervals of 1 month, 2 months and 3 months. Results demonstrate that the composition comprises a continuously flexible substrate having a low viscosity of between about 3000 and about 5500 cps with specific gravity of between about 1.12 and about 1.20. Such measures are sustainable without any detectable or significant sedimentation for about 3 months.

Example 4

The compositions exemplified above in Example 1 and Example 2 are subjected to aesthetic property testing, e.g., testing related to the identification of the sensorial property (ies) of the compositions. The compositions perform surprisingly well in terms of enhanced sensorial properties as determined by a statistically significant number of skilled skin care professionals in an adequately powered population of skin care professionals. The results demonstrate that when compositions are applied to a region of skin on the forearm of individual (s) and allowed to dry, the composition is found to be non-greasy, non-oily, non-sticky, and smoothly glides with evenly spread-ability on all Fitzpatrick Skin Types (Type I-IV).

Example 5

The compositions exemplified above in Example 1 and Example 2 are evaluated for adverse whitening on the skin. The whitening on the skin is evaluated by immersing the arm of an individual in water for approximately 1-2 minutes, then applying compositions of the invention to the wet area of the arm and rubbing the compositions into the skin. The compositions are applied in amounts generally effective to provide a continuous film to the skin area. The compositions of Example 1 and Example 2 surprisingly exhibit negligible or no discernible whitening when applied to the skin.

Example 6

The compositions exemplified above and described specifically below in Table 3 were tested for sun protection factor (SPF) using an in-vitro ISO 24443 assay according to United States Food and Drug Administration (US FDA) regulation. The compositions were further subjected to additional testing procedures, such as in-house in-vitro high energy visible light radiation protection potential assays and in-house in-vitro visible light radiation protection potential assays to determine their ability to block harmful radiations from sunlight. Laboratory analysis results demonstrated that both compositions meet and exceed ISO 24443 SPF/UVA and UVA/SPF ratios as well as proposed FDA UVA I/UV ratio requirements. FIGS. 1-4 are provided herein to illustrate these results.

TABLE 3

Tested formulations analyzed in in-vitro testing. Ingredients in wt. %.

| Test ID No.: | A-0057 | A-0878 |
|---|---|---|
| Client ID No.: | 021-042 | 021-046-XP (5) |
| Description: | ZnO-Only (22.5%) Platelets | ZnO-Only (22.5%) Aggregates |

TABLE 3-continued

Tested formulations analyzed in in-vitro testing. Ingredients in wt. %.

| Test ID No.: | A-0057 | A-0878 |
|---|---|---|
| Composition: | | |
| Water | 20.795 | 20.08 |
| Magnesium Sulfate | 1.05 | 0.75 |
| Propanediol | 1 | 2.5 |
| Deinococcus Extract, Propanediol, 1,2-Hexanediol, Water (FIRST, Access Ingredients) | 1 | 1 |
| Scenedesmus Desertico Extr. (DESERTICA, Access Ingredients) | 0.5 | — |
| Carnosine/ Dragosine (Symrise) | — | 0.2 |
| Echinacea Purpurea (Symfinity, Symrise) | — | 0.1 |
| Octyldodecyl Neopentanoate/(Elefac I-205/Alzo) | 19 | 19 |
| Cetyl dimethicone, Dimethicone, Bis-vinyl Dimethicone/ Dimethicone Copolymer (Jeesilc CD-405, Jeen) | 2 | 3.25 |
| Phenyl trimethicone, Bis-vinyl dimethicone/ Dimethicone copolymer (Jeesilc PTMF-405, Jeen) | 5 | 3 |
| Squalane (Jeen or Neossence) | — | 0.5 |
| Polyhydroxystearic acid (Dispersun DSP-OL 300 Innospec/Chemtech) | 1.05 | 1.1 |
| Zinc oxide (MicNo, SOLA VEIL MZP7-PW- (MV) 98%, Croda) | 22.5 | — |
| Zinc oxide (ZinClear XP, Antaria, Deveraux) | — | 22.5 |
| Stearene Acrylate Copolymer (SunSphere PWD, Dow Corning) | 4.5 | 4.5 |
| Disteardimonium Hectorite, Phenyl trimethicone, Triethyl citrate (Bentone Gel, PTMV, Elementis, DD Chem) | 2.3 | 2.3 |
| Glyceryl dibehenate, Tribehenin, Glyceryl behenate (Compritol 888, Gatephosse, Omya) | — | 0.7 |
| Bisabolol, Zingiber officinales (ginger) Extract (SymRelief 100, Symrise) | 0.1 | 0.1 |
| Dimethicone, Dimethicone Copolymer (AcceSIL FF16, Access Ingredients) | 0.25 | 0.75 |
| Vit E Acetate (USP, Jeen) | 0.01 | 0.01 |
| 1,2 Hexanediol, Caprylyl glycol, Tropolone (Symdiol 68, Symrise) | 0.9 | 0.9 |
| Polyglyceryl-10 Caprylate/Caprate (Syneth C15K RSPO MB, Lonza/Deveraux) | 0.015 | — |
| Polyglyceryl-10 Decaoleate (Syneth 03 K RSPO, Lonza, Deveraux) | 12 | — |
| Polyglyceryl-2 sesquioleate (SGS-PGO 152, Argan) | — | 11 |
| Dimethicone, Trisiloxane (Xiameter PMX-1184 Silicone Fluid, Dow/Univar) | 2.5 | 2.6 |
| Fullerene, Squalane/Fullerene-C60 (C60 Co., AE Chemie) | 1 | — |
| Phenetyl Alcohol, Caprypyl Glycol, Feniol (Argan) | 0.03 | 0.06 |
| Silica (Silisphere LS 8H, Argan) | 0.5 | 0.6 |
| Calcium, Sodium Borosilicate (Covabeads crystals, Sensient) | 2 | 2.5 |

FIG. 1 provides a first set of data, illustrating ISO 24443 RATIO results.

FIG. 2 provides results from in-house in-vitro high energy visible light radiation protection potential testing, and in-house in-vitro visible light radiation protection potential.

Figure 3B:
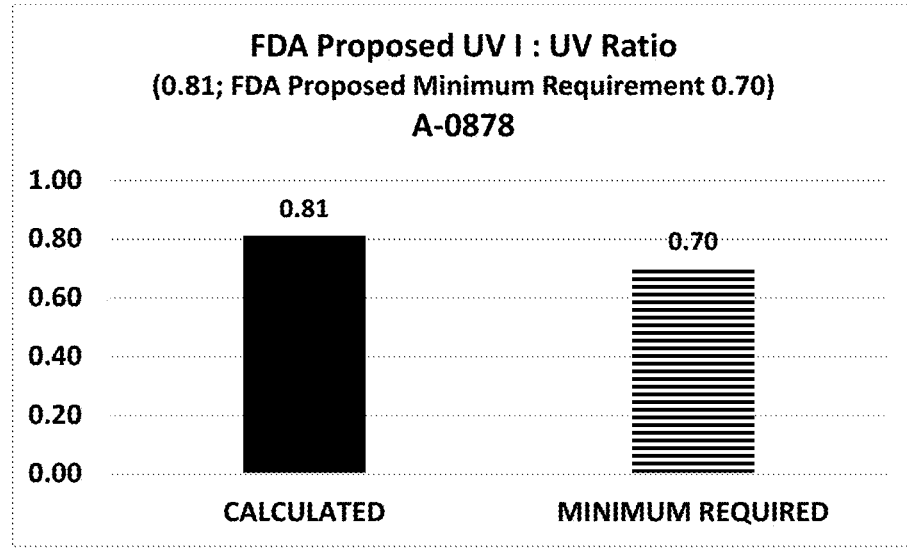
Figure 4A:
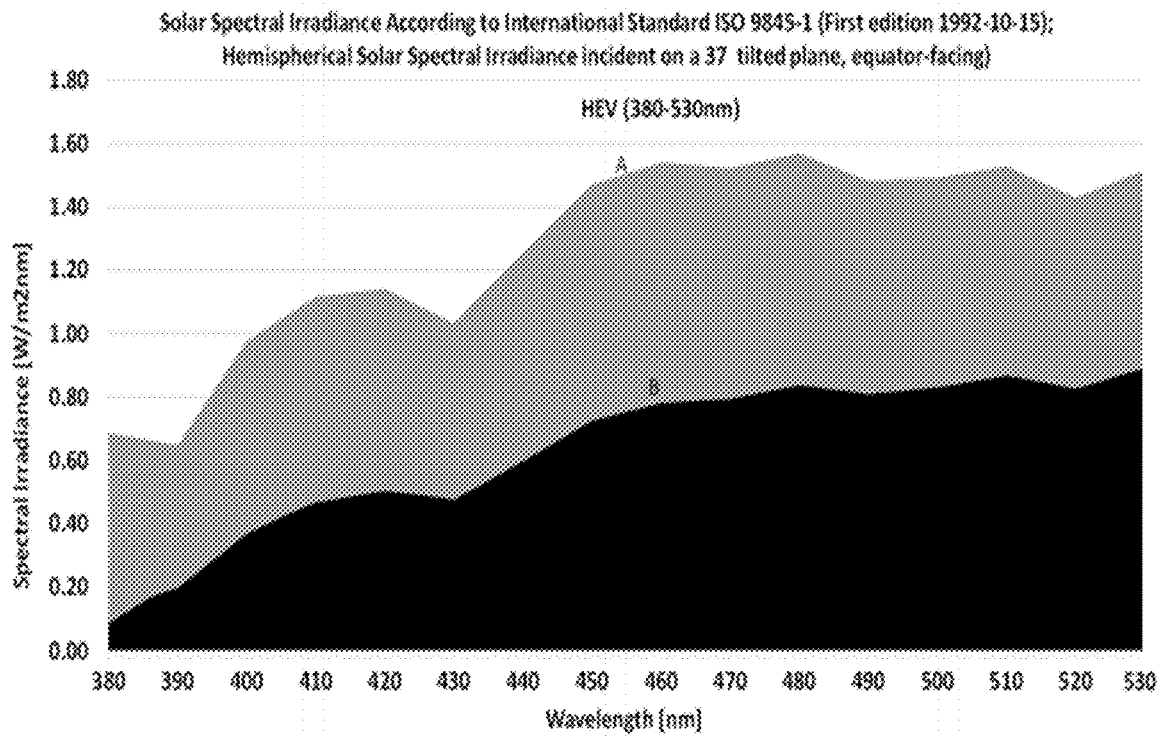
FIGS. 4A, 4B, 4C, and 4D provide(s) results of in-house in-vitro high energy visible light ("blue light") radiation protection potential (FIGS. 4A and 4B) and in-house in-vitro visible light radiation protection potential (FIGS. 4C and 4D) for two exemplary formulations.
Figure 4B:
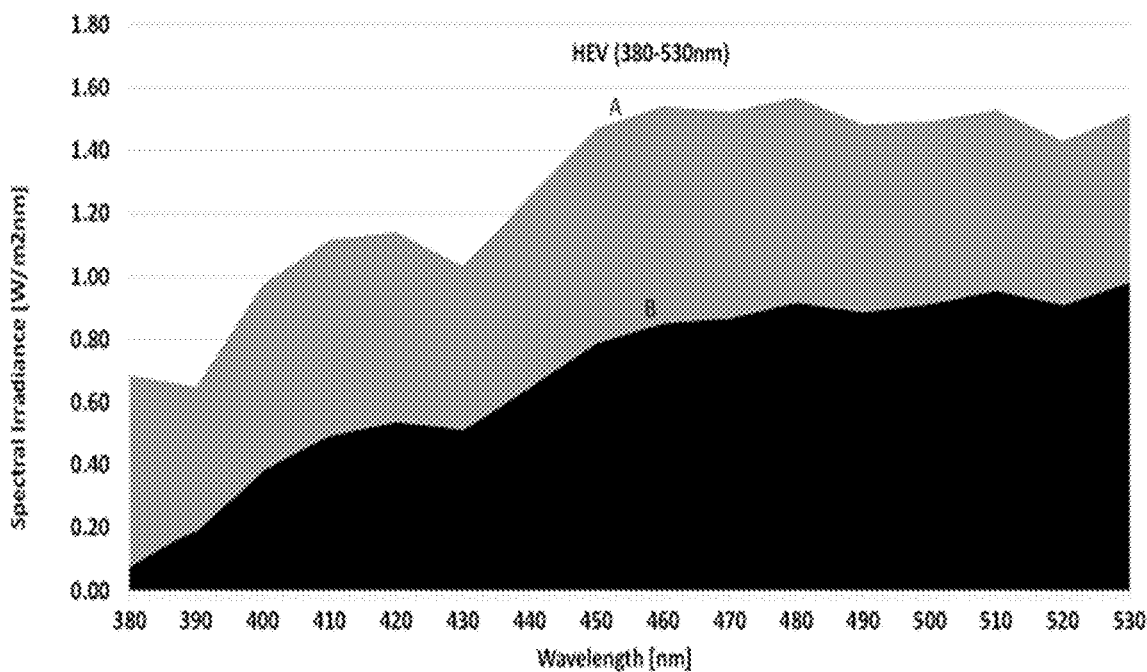
Figure 4C:
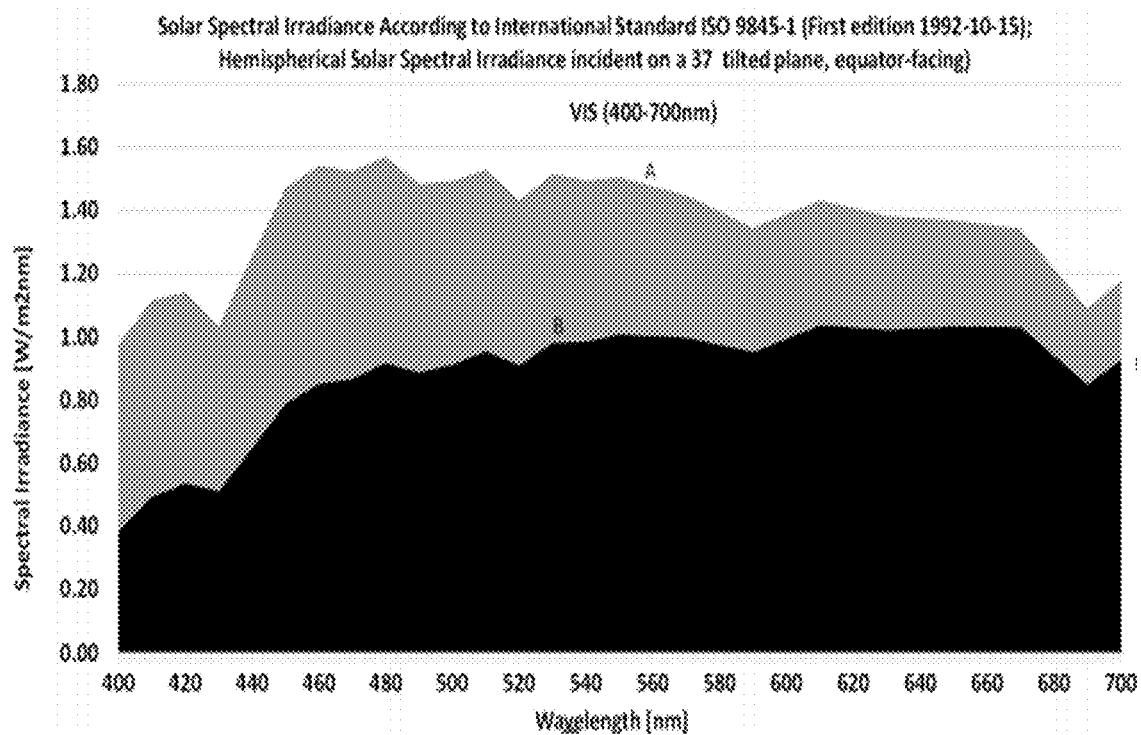
Figure 4D:
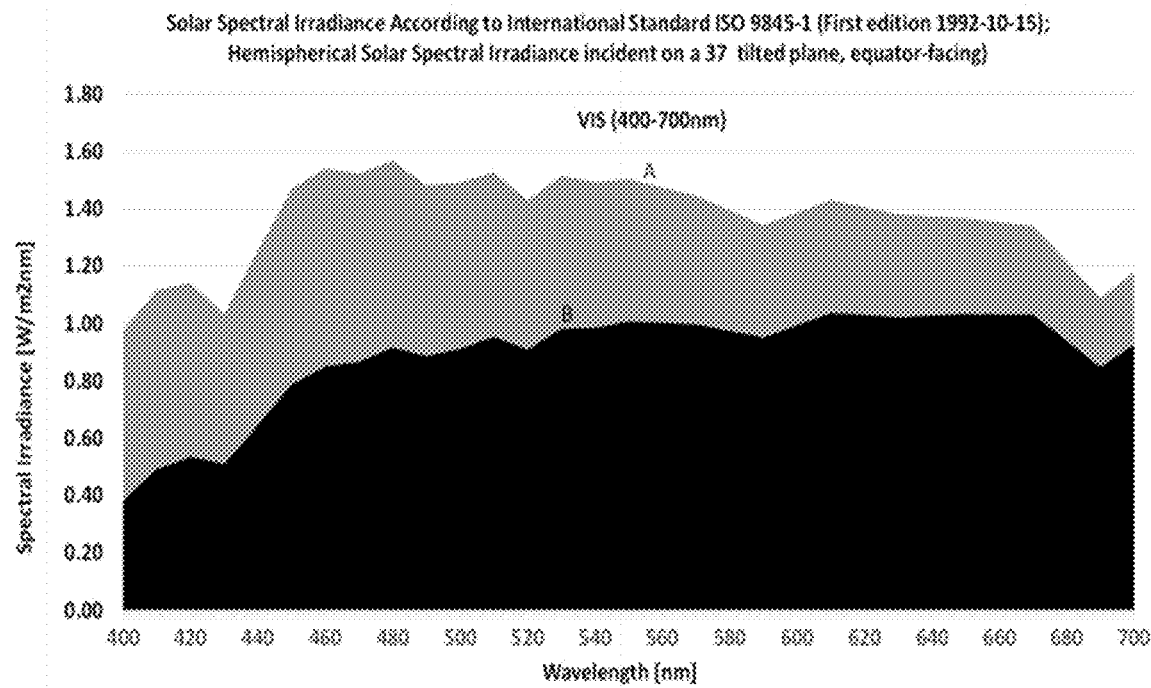

FIG. 3 provides UVA I/UV Ratio results.

FIGS. 4A, 4B, 4C, and 4D, provide(s) a third set of results, including additional in-house in-vitro high energy visible light radiation protection potential and in-house in-vitro visible light radiation protection potential. FIGS. 4A-4D each comprise indicators A and B. Indicator A in each Figure is positioned at the location indicating Solar Spectral Irradiance according to International Standard ISO 9845-1. Indicator B is positioned at the location indicating Solar Spectral Irradiance according to International Standard ISO 9845-1 transmitted through the test product.

Additionally, water resistance data was collected on Sample A-0878. The objective of the water resistance study was to evaluate the effectiveness of a test material as a sunscreen product by determining the Sun Protection Factor (SPF) on human skin (using a modification of the method to include one subject instead of the minimum of ten cited in the reference) as defined by the FDA Sunscreen Final Rule; 21 CFR Parts 201 and 310 [Docket No. FDA-1978-N-0018] (Formerly Docket No. 1978N-0038), RIN 0910-AF43, Labeling and Effectiveness Testing: Sunscreen Drug Products For Over-the Counter Human Use [FR Doc. 2011-14766 Filed Jun. 14, 2011: Publication Date: Jun. 17, 2011] using a Xenon arc solar simulator as the UV source.

The objective of the first 40-minute water resistance study was to evaluate the effectiveness of a test material as a sunscreen product by determining the Sun Protection Factor (SPF) on human skin (using a modification of the method to include one subject instead of the minimum of ten cited in the reference) as defined by the FDA Sunscreen Final Rule: 21 CFR Parts 201 and 310 [Docket No. FDA-1978-N-0018] (Formerly Docket No. 1978N-0038), RIN 0910-AF43, Labeling and Effectiveness Testing: Sunscreen Drug Products For Over-the Counter Human Use [FR Doc. 2011-14766 Filed Jun. 14, 2011 Publication Date: Jun. 17, 2011] using a Xenon arc solar simulator as the UV source. This test was conducted immediately following a 40-minute water immersion experiment which was carried out under controlled conditions as described in the above-mentioned FDA Sunscreen Final Rule. conditions as described in the above-mentioned FDA Sunscreen Final Rule. A second study was conducted following much of the same procedure described here.

One subject was enrolled in the study and completed the study. The subject was identified as a 43-y.o. Caucasian female.

Standards for inclusion in the study included the following: (a) Individuals between eighteen (18) and seventy (70) years old; (b) Individuals who completed a preliminary medical history form mandated by the testing laboratory and are in general good health; (c) Individuals who have read, understood and signed an informed consent document relating to the specific type of study they were inducted; (d) Individuals free of any dermatological or systemic disorder which, in the opinion of the Investigator, would interfere with the results; (e) Individuals free of any acute or chronic disease that might interfere with or increase the risk of study participation, at the discretion of the Investigator; (f) Individuals with untanned skin on the test area and with Fitzpatrick Skin Type I, II, Ill and/or with ITA0 value ~28° by colorimetric method; (g) Individuals with no uneven skin tones, pigmentation, scars, other irregularities or hair in test site areas that would interfere with SPF determination; (h) Individuals able to cooperate with the Investigator and research staff, willing to have test materials applied according to the protocol, and complete the full course of the study; (i) Individuals willing to refrain from using any sunscreen products 24 hours prior to study initiation and for the entire duration of study; and (j) Individuals willing to refrain from using tanning beds and having sun exposure to the back area eight weeks prior to SPF testing and for the entire duration of study; (k) Individuals with excessive hair on their back who are willing to have hair removed by laboratory technicians prior to commencement of study.

Exclusion criteria included: (a) Individuals who are under a doctor's care for a condition which would interfere with the results, at the discretion of the Investigator; (b) Children and individuals below the age of consent or older than seventy (70) years (c) Individuals who are currently taking any medication (topical or systemic) with photo-sensitizing and/or anti-inflammatory potential; (d) Subjects with a history of dermatological conditions such as any form of skin cancer, melanoma, lupus, psoriasis, connective tissue disease or any disease that would increase the risk associated with study participation; (e) Individuals diagnosed with chronic skin allergies that in the opinion of the Investigator, would interfere with SPF determination; (f) Subjects who have used tanning beds within eight weeks prior to SPF testing; (g) Subjects having had sun exposure on the back area within the immediate eight weeks prior to SPF testing; (h) Subjects having excessive hair in the test area on the day of commencement (may be shaved up to 3 days prior to the test day); (i) Individuals with a history of adverse effects upon sun exposure; (j) Female volunteers who indicate that they are pregnant or lactating; (k) Individuals with blemishes, nevi, sunburn, suntan, scars, moles, active dermal lesions or uneven pigmentation in the test sites; and (l) Individuals with known hypersensitivity to any sunscreen products.

All appropriate informed consent and medical history assessment was completed, and IRB approval received. Healthy volunteers between 18 and 70 years old were recruited for this study. The panel consisted of fair-skin individuals with Fitzpatrick Skin Types I, II or III defined as follows i-Federal Register Vol. 64, No. 98: 27690, 1999): Type I (always burns easily; never tans based on the first 30-45 minutes of sun exposure after a winter season without sun exposure); Type II (always burns easily; tans minimally under the same conditions cited previously; Type III (burns moderately, tans gradually under the same conditions cited previously).

The light source employed was a 150 watt Xenon Arc Solar Simulator (Solar Light Co., Philadelphia, Pennsylvania, Model 14S, Model 15S or Model 16S) or a 300 watt Xenon Arc Solar Simulator (Solar Light Co., Philadelphia, Pennsylvania, Model 601-300 V2.5 Multiport) each having a continuous emission spectrum from 290 to 400 nanometers: equipped with dichroic mirrors (which reflect all radiation below 400 nm), a 1 mm Schott WG-320 filter (which absorbs all radiation below 290 nm) to produce simulated solar UVA-UVB emission spectra. A xenon arc was selected on the basis of its black body radiation temperature of 6000° K which reirradiates a continuous UV spectra (all wavelengths) in proportions substantially equivalent to that of natural sunlight. A 1 mm UG 11 filter (black lens) was added to remove reflected heat (infrared, greater than 700 nm) and remaining visible radiation. The solar simulators were allowed a warmup time of at least 15 minutes before use to stabilize output intensity. Model 14S, Model 15S or Model 16S Solar Simulator UVB radiation, expressed as MED/h, was monitored continuously during exposure using a Model DCS-1 Sunburn UV Meter/Dose Controller System (Solar Light Co., Philadelphia, Pennsylvania) formerly known as the Robertson-Berger Sunburn Meter (R-8 meter).

Measurements were taken at a position within 8 mm from the surface of the skin. The size of the exposure site is 1 cm in diameter. It is critically important to ensure the emerging beam produces confluent circles of UV light. This is accomplished by placing a white paper over the exit port. Should the circles be out of confluence it is necessary to adjust the lamp and/or mirrors bringing the beams into one homogeneous light path. Model 601-300 V2.5 Multiport Solar Simulator Ports 1-6 (each 8 mm by 8 mm) are wiped clean using a Kimwipe and alcohol prior to measurement. The PMA2108 LLG (UVB detector, Solar Light Co., Philadelphia, Pennsylvania) along with DCS-2 controller were used to ensure that proper output, again expressed as MED/h is achieved. The size of the exposure site was ≥0.5 cm2.

The infrascapular area of the back to the right and left side of the midline was used. Within this area, 30 cm2 rectangular test sites were delineated with a gentian violet surgical skin marker. Sites were observed to ensure uniform pigmentation, skin tone and texture, and absence of warts, moles, nevi, scars, blemishes and active dermal lesions. Any areas that might be expected to produce erratic results were not used for UV exposures. This test was employed to determine the substantivity of a test product and its ability to resist 40 minutes of water immersion. The procedure for this study is outlined in the Federal Register/Vol. 76, No. 117, 21 CFR Parts 201 and 310 published on Friday Jun. 17, 2011. If necessary, one test site area served to determine each subject's Minimal Erythema Dose (MED). A minimum of five progressive U V light doses were administered within this site. The individual subject's MED is the shortest time of exposure that produces minimally perceptible erythema at 16 to 24 hours post irradiation. The test material and in-house water resistant standard (7% Padimate 0/3% Oxybenzone) with known SPF as control were shaken and/or swirled with a glass rod before use and were evenly applied using plastic volumetric syringes or another device such as weigh boat or a spatula or where requested, weighed powders or concentrated sprays were evenly applied to rectangular areas measuring a minimum of 30 cm2 for a final concentration of 2.0 mg/cm$^2$. Evenness of application was verified by observation with a Wood's Lamp.

The water-resistant SPF value was determined by the product's ability to resist a 40-minute period of water immersion, achieved through the following test regimen: After application of the sunscreen product followed by the waiting period, a total of 40 minutes water immersion was scheduled; 20 minutes in the water, 15-minute rest (without towel drying), 20 minutes in the water. Immersion was achieved indoors in a whirlpool tub with water circulating by a 1 h.p. pump at 3450 RPM. Each panelist spent twenty minutes in the water, immediately followed by a fifteen-minute rest period out of the water until a total of forty minutes in the water were achieved. The whirlpool bath was set at 23'C to 32° C. at moderate agitation. The water and air temperatures and relative humidity were recorded. After the last immersion, the test sites were air dried without toweling for at least fifteen minutes prior to exposure of treated areas to the solar simulation. The protected sites received a series of progressive UV light doses (minimum five) based upon previously determined MED and the intended SPF as follows (all immediate responses were recorded):

SPF 163: MED times 0.76×, 0.87×, 1.00×, 1.15× and 1.32×

SPF 50: MED times 0.76×, 0.87×, 1.00×, 1.15× and 1.32× where x equals the expected SPF of the product.

Sixteen to twenty-four hours post exposure, the subjects were instructed to return to the testing facility for evaluation of delayed erythemic responses. The technician who evaluated the MED did not know the identity of the test product application sites and UV exposures. Also, he/she was not the same person to have applied the sunscreen product to the test site or administered the doses of UV radiation.

$$SPF = \frac{\text{Protected } MED}{\text{Final unprotected } MED}$$

Visual Grading Scale:
- 0=No Erythema
- ?=Questionable Erythema
- 1=Minimal Erythema
- 2=Slight Erythema
- 3=Well-Defined Erythema
- 4=Erythema and Edema
- 5=Erythema and Edema in vesicles The determination of all MEDs was carried out in a room with matte, neutral wall colors.

According to the reference, the mean SPF value (x) is calculated using a minimum of 10 evaluable subjects per formulation. The standard deviation was determined (s). The upper 5% point was obtained from the t distribution table with n-I degrees of freedom (t). The standard error (SE) was calculated by $(s)L/\sqrt{n}$ (where n equals the number of subjects who provided valid test results). Therefore, the label SPF value for panels using a minimum of 10 evaluable subjects is the largest whole number less than the mean SPF minus (t×SE).

Label SPF=Mean SPF−(t×SE)

The above procedure and associated step(s) were repeated in an 80-minute water resistance study comprising 2 enrolled subjects, both of which completed the study. The subjects ages ranged from 45-56; one male, one female, both Caucasian.

Figures 5, 6A:
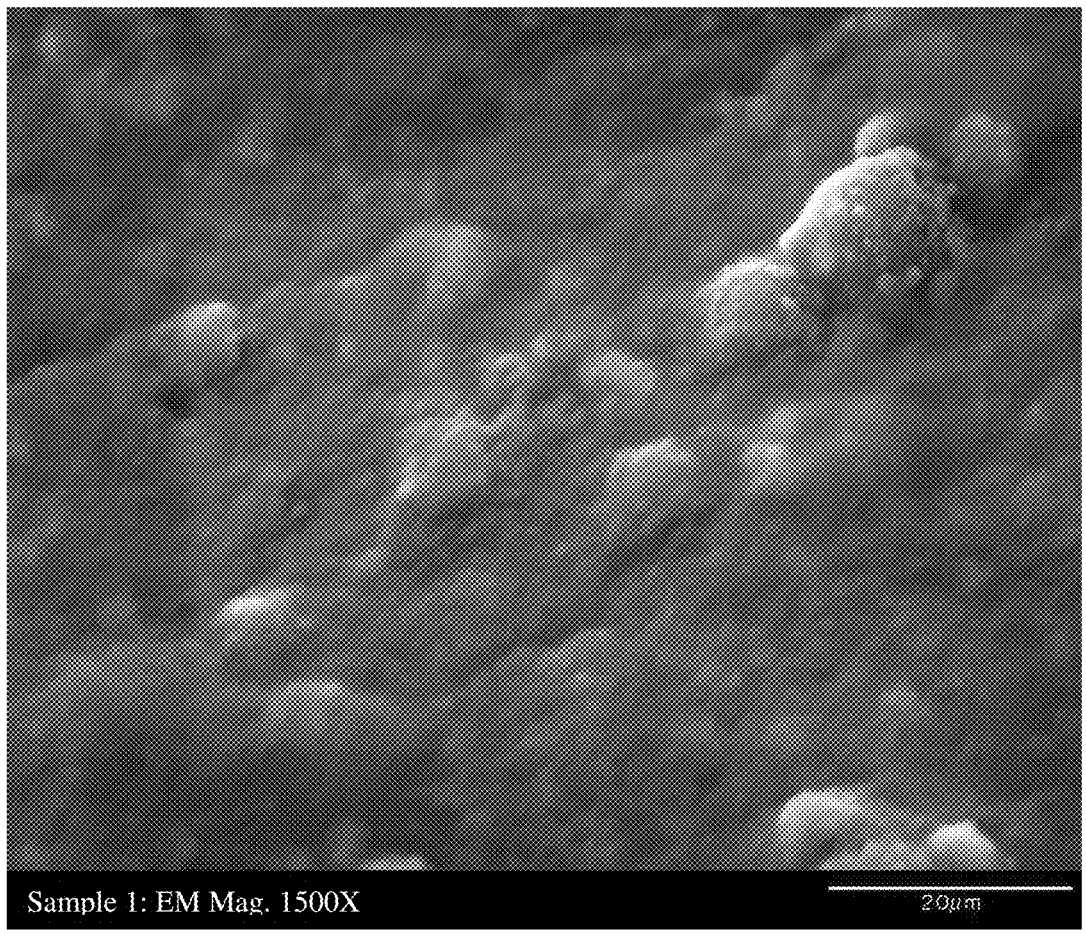
FIG. 5 provides results for water resistance testing at 40 minutes and 80 minutes of an exemplary composition.
FIGS. 6A and 6B provide black and white microscopy photograph images showing embedded particles of an exemplary emulsion formulation at 1500× and 2240×, respectively.

40- and 80-minute water resistance data is provided in FIG. 5. Data demonstrate that compositions tested maintain water resistance for tested time periods.

Example 7

This Example describes experiments performed to assess the particulate distribution properties of exemplary sunscreen compositions. The aim of these studies was to characterize the distribution of particles in an emulsion matrix upon application of the emulsion to a surface.

Four (4) sample compositions formulated as emulsions were provided for this study, comprising compositions as described in Table 4 (below). Two (2) of the four (4) samples comprised zinc oxide and titanium dioxide, with one being a color-tinted ("tone/tinted") formulation. The remaining two (2) of the four (4) samples comprised zinc oxide only, with again one being a tone/tinted formulation.

TABLE 4

Exemplary Formulations Analyzed in Particle Distribution Tests

| Test ID No.: | 1 | 2 | 3 | 4 |
|---|---|---|---|---|
| Client ID No.: | 021-046-XP (5)-10 | 021-046-XP (5)-22 | 021-048-XP (7)-20 | 021-048-XP (7)-8 |
| Description: | ZnO-Only | ZnO + TiO$_2$ | ZnO + TiO$_2$ (Tone/Tinted) | ZnO-Only (Tone/Tinted) |
| Composition: | | | | |
| Water | 19.38 | 22.86 | 22.27 | 19 |
| Magnesium Sulfate | 0.85 | 0.85 | 0.85 | 0.85 |
| Propanediol | 2.5 | 2.5 | 2.5 | 2.25 |
| Deinococcus Extract, Propanediol, 1,2-Hexanediol, Water (FIRST, Access Ingredients) | 1 | 1 | 1 | 1 |
| Carnosine/Dragosine (Symrise) | 0.2 | 0.2 | 0.2 | 0.2 |
| Echinacea Purpurea (Symfinity, Symrise) | 0.1 | 0.1 | 0.1 | 0.1 |
| Octyldodecyl Neopentanoate/ (Elefac I-205/Alzo) | 19 | 19 | 19 | 19 |
| Cetyl dimethicone, Dimethicone, Bis-vinyl Dimethicone/Dimethicone Copolymer (Jeesilc CD-405, Jeen) | 3.75 | 3.75 | 3.75 | 3.25 |
| Phenyl trimethicone, Bis-vinyl dimethicone/Dimethicone copolymer (Jeesilc PTMF-405, Jeen) | 2.5 | 2.5 | 2.5 | 2.24 |
| Polyhydroxystearic acid (Dispersun DSP-OL 300 Innospec/Chemtech) | 1.1 | 1.08 | 1.08 | 1.1 |
| Zinc oxide (ZinClear XP, Antaria, Deveraux) | 22.5 | 10 | 10 | 22.5 |
| Stearene Acrylate Copolymer (SunSphere PWD, Dow Corning) | 4.5 | 5.5 | 4.5 | 4.5 |
| Caprylic Capric Triglyceride, Titanium Dioxide, Aluminum Hydroxide, Stearic Acid, Polyhydroxystearic Acid/AccessSUN E50C (41.56%) | — | 8.54 (3.55% active) | 8.54 (3.55% active) | — |
| Synthetic Fluorphlogophite, Titanium Dioxide CL Gold A (Argan) | — | 0.25 | — | — |
| ARG-PCC-Iron Oxides (Red, Yellow, Black) | — | — | 1.74 | 1.74 |
| Disteardimonium Hectorite, Phenyl trimethicone, Triethyl citrate (Bentone Gel, PTMV, Elementis, DD Chem) | 3.5 | 3.5 | 3.6 | 3.5 |

TABLE 4-continued

Exemplary Formulations Analyzed in Particle Distribution Tests

| Test ID No.: | 1 | 2 | 3 | 4 |
|---|---|---|---|---|
| Glyceryl dibehenate, Tribehenin, Glyceryl behenate (Compritol 888, Gatephosse, Omya) | 0.75 | 0.8 | 0.8 | 0.9 |
| Bisabolol, Zingiber officinales (ginger) Extract (SymRelief 100, Symrise) | 0.1 | 0.1 | 0.1 | 0.1 |
| Dimethicone, Dimethicone Copolymer (AcceSIL FF16, Access Ingredients) | 0.75 | 1 | 1 | 0.75 |
| Vit E Acetate (USP, Jeen) | 0.01 | 0.01 | 0.01 | 0.01 |
| 1,2 Hexanediol, Caprylyl glycol, Tropolone (Symdiol 68, Symrise) | 0.9 | 0.9 | 0.9 | 0.9 |
| Polyglyceryl-2 sesquioleate (SGS-PGO 152, Argan) | 11.1 | 11.1 | 11.1 | 11.1 |
| Dimethicone, Trisiloxane (Xiameter PMX-1184 Silicone Fluid, Dow/Univar) | 1.75 | 1.5 | 1.5 | 1.75 |
| Phenetyl Alcohol, Caprypyl Glycol, Feniol (Argan) | 0.06 | 0.06 | 0.06 | 0.06 |
| Silica (Silisphere LS 8H, Argan) | 1.2 | 1.4 | 1.4 | 1 |
| Calcium, Sodium Borosilicate (Covabeads crystals, Sensient) | 2.5 | 1.5 | 1.5 | 2.2 |

Several means of examining the particle locations in the applied form of compositions were considered including light microscopy (LM), transmission electron microscopy (TEM), and scanning electron microscopy (SEM) with energy-dispersive x-ray spectroscopy (EDS).

Compositions were expected to comprise particles having an average size as small as (but likely not smaller than) 100 nm. Accordingly, many of the particles of interest were too small to be imaged in the light microscope. A sufficiently thin application of the product would have been required to facilitate both electron beam penetration by TEM, yet a sufficiently thick application would have been required to capture 3-dimensional matrix of the particles. Accordingly, SEM with EDS was selected for the experiments provided here. LM and TEM techniques are reserved for possible future studies.

Scanning electron microscopy (SEM) is a technique utilizing a highly focused electron beam (less than 10 nm diameter) which is (can be) scanned in a raster (a rectangular scanning pattern known in the art) on the sample surface. Interactions between the sample(s) and the incident electrons lead to the ejection of low energy secondary electrons about the location of the incident electron beam. The intensity of secondary electrons produced at each point is used to form a picture of the sample. Magnification factors from 10× to 300,000× can be obtained. The depth of field is inherently quite large allowing the resulting micrographs to be in focus at all points across a rough surface.

Energy dispersive x-ray spectroscopy (EDS) is a method suitable for analyzing the main component(s) as well as low-level (nominally 0.1%) contaminant(s) in relatively thick (several micron) layers of sample. In EDS methods, a focused beam of electrons is used to bombard a solid to knock out electrons from inner electron orbital shells of atoms in the near surface region of the sample. Electrons from outer shells can move into the inner shell vacancies as replacements for the ejected electrons. For each such atomic relaxation transition, the energy difference between the outer and inner shell electrons is released by the atom. This energy is emitted either as a characteristic x-ray or as an outer shell electron which has absorbed the energy released by the atomic relaxation process. EDS spectra display an intensity versus energy plot of x-rays emitted by the sample bombarded by the electron beam of a scanning electron microscope.

After initial experimentation, the following test method was established.

First a layer of each sample was applied to the surface of polished silicon wafer(s). The silicon wafer(s) supplied a smooth substrate and is consistent with the thickness attributed to in-vitro studies of this formulation type. The layers produced represented 3-dimensional dispersions of the particle-bearing emulsions with the emulsion being a coating over the particles at the surface level.

The prepared samples were then examined by SEM/EDS to characterize the elements associated with the various particles embedded in the emulsion matrix. Only those elements carbon and heavier in the periodic table were included in this study.

To sufficiently expose the particles in the near-surface region of the emulsions for examination in the electron microscope, the samples were first subjected to an oxygen plasma etch to selectively remove the emulsion by conversion to $CO_2$ and methane. However, this etching proved insufficient in the timeframe required by the study. Accordingly, the etching was then augmented by exposure to Argon ion beam etching of a 3 mm diameter area to accelerate the removal of the emulsion component from the surface of the distributed particles.

The exposed particles were then examined using SEM to provide images of the particle locations in the surface layer of particles.

In detail, the four (4) prepared samples were placed onto the goniometer stage of a scanning electron microscope marketed by Topcon (ISI), Inc. of Paramus, NJ. EDS data were collected from the samples for elemental identification using a Si(Li) crystal detector manufactured by Gresham Scientific Instruments Ltd. of Buckinghamshire, UK coupled to a multichannel analyzer interface manufactured by 4 pi Analysis, Inc. and resident in an Apple Macintosh® G4 workstation. SEM images were obtained using an imaging interface also from 4 pi Analysis, Inc.

The EDS results for the four (4) samples were collected and analyzed. Summarized exemplary results are shown below in Table 5.

TABLE 5

Estimated weight concentrations (%) within 1-2 μm EDS analyzed layer.

| SAMPLE ID. | C | O | Mg | Al | Si | S | K | Ca | Ti | Fe | Zn | SUM |
|---|---|---|---|---|---|---|---|---|---|---|---|---|
| #1 021-046-XP (5)-10 (ZnO) | 16.34 | 54.91 | 0.64 | 0.24 | 3.98 | 0.26 | 0.02 | 0.14 | — | — | 23.46 | 99.99 |
| #2 021-046-XP (5)-22 (ZnO + TiO2) | 22.01 | 65.63 | 0.32 | 0.37 | 2.68 | 0.14 | 0.05 | 0.04 | 2.41 | — | 6.36 | 100.01 |
| #3 021-048-XP (7)-20 (ZnO + TiO2 + tone) | 22.31 | 65.86 | 0.40 | 0.33 | 2.52 | 0.15 | 0.07 | 0.05 | 1.49 | 0.38 | 6.44 | 100.00 |
| #4 021-048-XP (7)-8 (ZnO + tone) | 17.94 | 57.44 | 0.78 | 0.31 | 3.14 | 0.16 | 0.12 | 0.06 | — | 0.49 | 19.56 | 100.00 |

Weight, atomic, and oxide concentrations were calculated and can be viewed in the spectral data collected (not provided). Representative data in Table 6 includes the estimated weight concentration(s) of the examined element(s). The EDS data show the anticipated elemental compositions of the applied emulsions with the Ti, Zn and Fe being indicative of the product formulation version. To clearly demonstrate this finding, the expected weight of each of Ti, Zn, and Fe for the tested samples is compared to the result for each in Table 6 below.

TABLE 6

Expected Ti, Zn, and Fe weight concentration compared to results by EDS. Expected Ti, Zn, and Fe amounts estimated based upon ingredient(s) provided in the table above.

| SAMPLE ID. | Expected Ti | Ti by EDS | Expected Fe | Fe by EDS | Expected Zn | Zn by EDS |
|---|---|---|---|---|---|---|
| #1: 021-046-XP (5)-10 (ZnO) | 0 | — | 0 | — | 22.5 | 23.46 |
| #2: 021-046-XP (5)-22 (ZnO + TiO2) | 3.55* | 2.41 | 0 | — | 10 | 6.36 |
| #3: 021-048-XP (7)-20 (ZnO + TiO2 + tone) | 3.55 | 1.49 | 1.74 | 0.38 | 10 | 6.44 |
| #4: 021-048-XP (7)-8 (ZnO + tone) | 0 | — | 1.74 | 0.49 | 22.5 | 19.56 |

(*Formulation comprises a second ingredient comprising some amount of titanium dioxide. Further - note that the TiO2 product is present at 8.54% as shown in the composition table above, however active is present at only 41.56% making the expected TiO2 amount 3.55%.)

Any minor discrepancies between expected weight and weight measured by EDS identifiable in Table 10 is expected to be an effect of the method. A very small, select area of sample is measured by EDS; any one, very small, select area of a sample may vary slightly from any other very small, select area of a sample in its elemental composition. In such circumstances, while the overall composition may be quite homogeneous, the level of detection in EDS analysis will identify such small variations. Further, assumptions are inherent in the method with regard to the state of the element(s) being measured (e.g., when in oxide form, for example, $TiO_2$, such a compound structure may not always be exact due to the nature of molecular bonding recognized in the art.) As such, the discrepancies noted here are interpreted by the analyst and expert reviewer of the data collected and provided in part here as closely representative of the expected constitution of analyzed samples.

SEM imagery was collected and analyzed; results for Sample 1 and Sample 2 were most complete at the time of this submission and thus are the focus of SEM findings presented here.

Figure 6B:
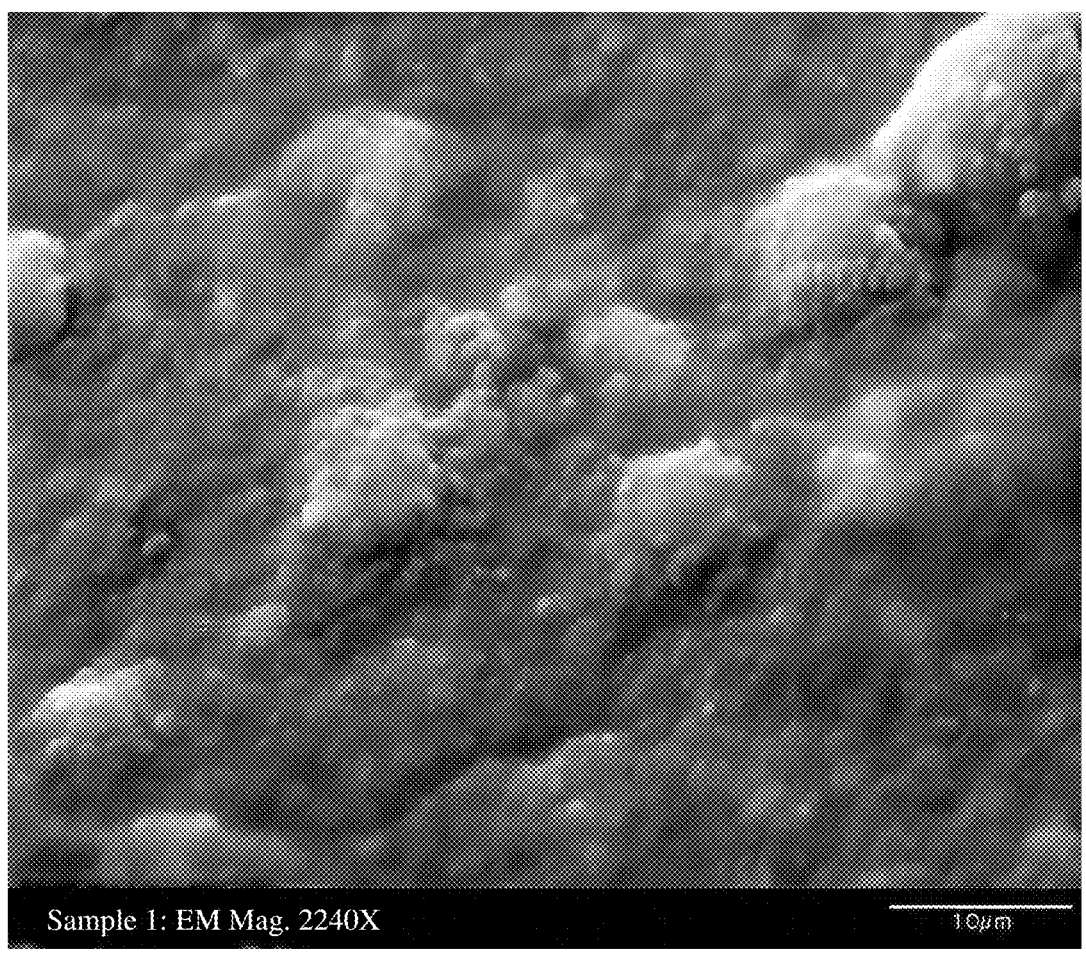

Secondary electron images and elemental distribution maps, initially, for the as applied surface for sample 1 (comprising zinc oxide only; no titanium dioxide). The images show particles present with an overcoating of emulsion observed between the largest particles though indications of smaller particles are noted. FIGS. 6A and 6B show the embedded particles of the emulsion at 1500× accompanied by a 20 μm scale (FIG. 6A) and 2240× accompanied by a 10 μm scale (FIG. 6B).

Figure 7:
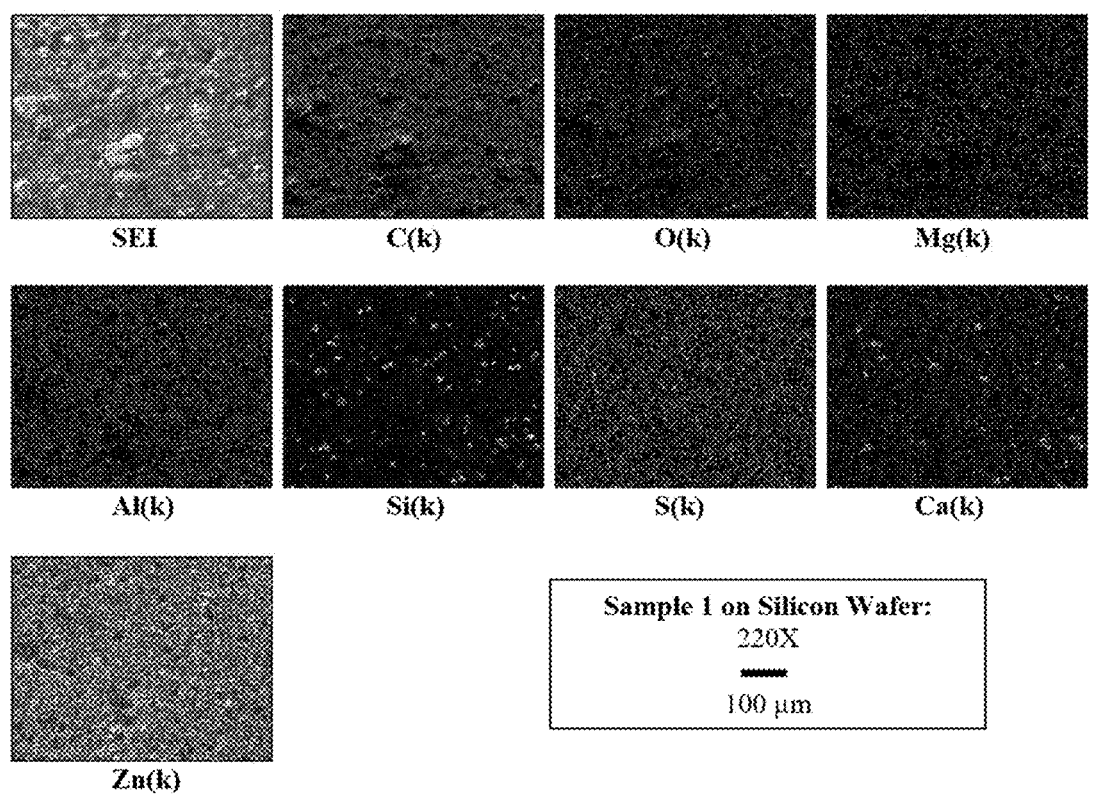
FIG. 7 provides a collection of black and white microscopy photograph images providing an elemental distribution map of a portion of an exemplary formulation.

As the EDS method of analysis looks substantially below the surface level in an organic matrix, the elemental distribution map shows the locations where the elements expected for the various particles in the formulation are present in higher and lower concentrations. FIG. 7 provides an area map at 220× magnification. The first image (SEI) (first row, far left) provides a secondary electron image (SEI) of the application field being considered (analyzed), showing particulate matter at least substantially filling or filling the entirety of the field, demonstrating that as spread upon the silicon wafer, the composition demonstrates a distribution of particles that at least substantially covers the application area. The second image (first row, second from left) provides only an analysis of carbon, showing a substantially uniform distribution of carbon-containing compound(s). The third image (first row, third from left) provides only an analysis of oxygen, showing a similarly uniform distribution of oxygen-containing compound(s). The fourth image (first row, far right) provides only an analysis of magnesium, again showing the uniform distribution of magnesium-containing compounds. The second row of images, images 5, 6, 7, and 8 of the grid (aluminum (Al), silicon (Si), sulfur (S), and calcium (Ca) continue the demonstration of relatively uniform distribution of each respective element. Finally, image 9, bottom row, shows zinc only, demonstrating, again, a uniform distribution of zinc-containing compound(s).

FIGS. 8A, 8B, 8C, and 8D provide larger version of the map images for the full SEM image (FIG. 8A), zinc (FIG. 8B), silicon (FIG. 8C), and calcium (FIG. 8D), wherein the relatively even distribution of each element across the field of view is evident.

The 220× area map and exemplary individual element images shown in FIGS. 7 and 8A-8D as applicable indicate(s) that the particles of the tested composition are distributed over most of the applied surface, in fact are quite uniformly distributed over the applied surface, with Zn being the predominant particle and particles containing Al, Si, Ca, S and Mg being more widely distributed. These results demonstrate that the tested composition provides a uniformity of distribution of its elemental constituents upon application. This is indicative of a well-homogenized, stable composition, capable of delivering a consistent coverage of the target surface (e.g., human skin) by compositional constituent(s) therein, especially, i.e., light-protective particulate matter therein.

Figure 9:
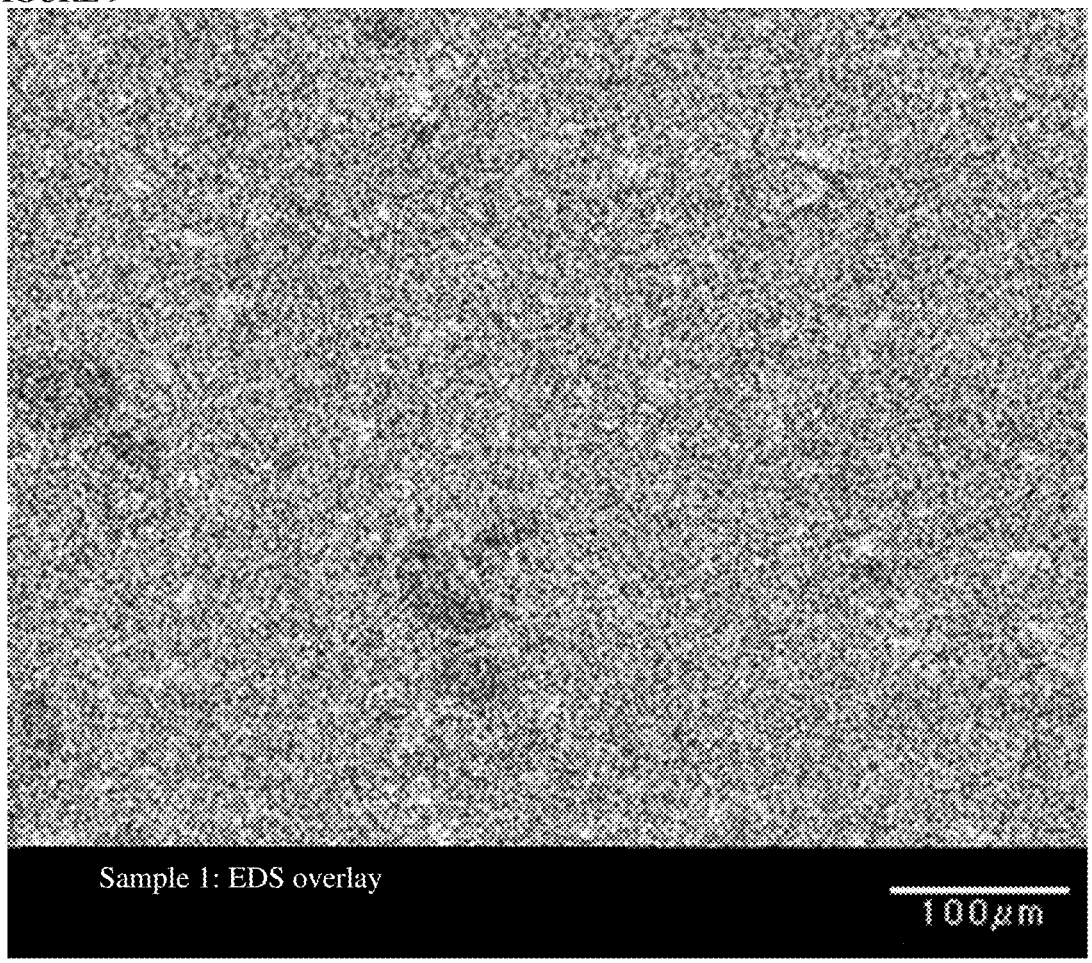
FIG. 9 provides an overlay image of the plurality of elemental distribution black and white microscopy photographs of FIG. 7.

In order to estimate the total amount of surface coverage by particulate matter in the outer layer of particles, the EDS maps described above were overlaid. FIG. 9 provides the overlay image of all analyzed elements. The amount of positive presence for a particle component was calculated using NIH Image software. In the image, area of coverage by one or more particulate element(s) measured is white in color; any space not covered by one or more particulate element(s) is colored black. Even by simple, visual analysis not using image software, one can observe very little uncovered surface area. Results of the image analysis calculate a surface coverage of approximately 82.7% by particulate material. It is relevant to note that even though FIG. 9 represents an overlay of individual element imagery, each image alone and the resulting overlay still represent only a single layer of the composition itself. Upon common application of such an emulsion (lotion) product, multiple layers, e.g., at least about 2, ≥~3, ≥~4, ≥~5, or perhaps more are likely to be formed. Each layer would be expected to comprise particulate matter in different locations. It is expected that each subsequent layer of particles would have a similar coverage and that when overlapped the multiple layers would serve to provide a near complete coverage of the substrate when viewed along a normal to the surface. While a single layer as estimated here may leave about 17.3% of surface area uncovered, a second layer of particulate matter would be expected to fill a significant amount of such empty space, thereby reducing the surface area of skin remaining unprotected by particulate matter. Similarly, each additional layer would further reduce such remaining uncovered surface area. It is believed that with very few layers, e.g., about 2 or about 3 layers of composition as would be naturally applied to/on the target surface (e.g., human skin) using typical application techniques, little to no unprotected surface area (e.g., of skin) would remain.

These results again demonstrate the uniformity of the tested composition and the uniformity of spread of constituent(s) thereof. These and other results described herein indicate that such composition(s) (those tested) and those at least generally, at least substantially, at least essentially, or the same as those tested, made according to an at least generally, at least substantially, at least essentially, or the same method(s) or method(s) comprising at least generally the same, at least substantially the same, at least essentially the same, or the same homogenization step(s) yield satisfactorily uniform and consistent surface coverage by UV-light protective compilation of particle population(s), creating or representing a matrix or mesh as described elsewhere herein.

Figure 10:
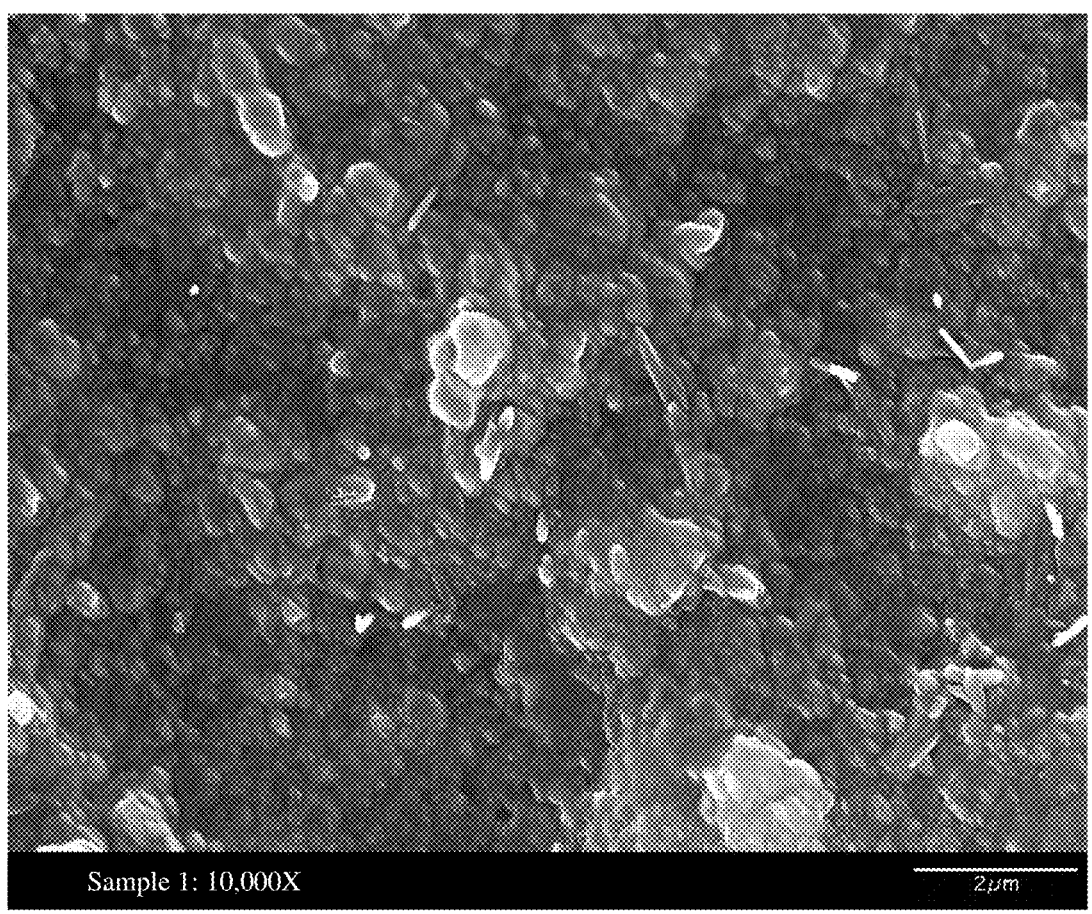
FIG. 10 provide a high magnification (10,000×) black and white microscopy photograph image of an exemplary formulation.
Figure 11:
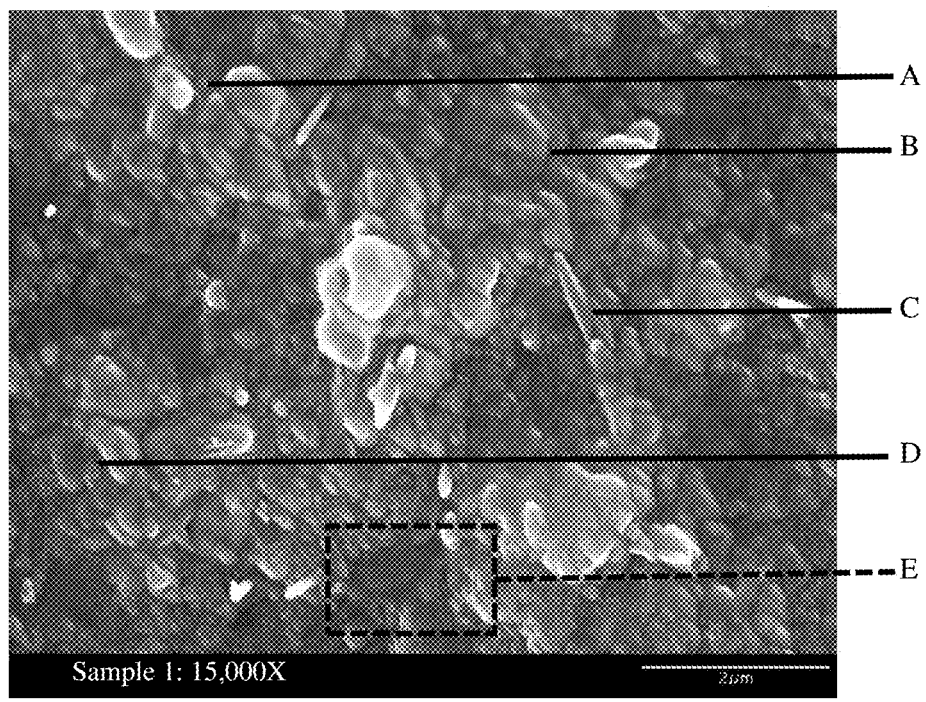
FIG. 11 provide a high magnification black and white microscopy photograph image of the same portion of the exemplary formulation in FIG. 9, but at 15,000× magnification, and highlights varying spacing between particles as well as effects of etching or lack thereof.

Additional images at higher magnification are provided in FIGS. 10 and 11. FIGS. 10 and 11 illustrate the high degree of surface coverage by the particles in the tested emulsion(s). FIG. 10 provides an SEM image of sample 1 at 10,000× magnification, provided with a 2 μm scale. FIG. 11 shows the same area of sample 1 as FIG. 10, but at 15,000× magnification, provided again with a 2 μm scale. FIG. 11 includes areas A, B, C, D, and E where space between particles is visible. Identified particle separations vary from 0 to several hundred nm depending on which particle pairs are selected for the determination. For example, gap A represents a distance of approximately 325 nm; gap B represents a distance of approximately 26 nm; gap C represents a distance of approximately 0 nm (e.g., there is no space between two particles); gap D represents a distance of approximately 130 nm. Clearly gaps of many different sizes can be identified. However, importantly, FIGS. 9 and 10 further illustrate that within most, generally all, substantially all, or all gaps, one or more particles of a second (lower) layer are visible within it. That is, even when particle separations are large, the image shows that particles in the next layer below that being viewed fill the gap, thus providing light protection even if gaps in a first layer of particles exists.

Further identified by a dashed square in FIG. 11, labeled as E, is an area of the image (a region of the sample) where emulsion material has not been removed during the etching process. It is clear in the image that there are lower layer particles being covered by this region of remaining emulsion. The amount of remaining emulsion present is an indication of the degree of coverage for this imaged layer of particles. The value for this layer is in the order of 75-80% coverage. With the particles observed in the emulsion locations from the next layer, the coverage is estimated to be over 90% when the multiple layers are included.

Figure 12A:
FIGS. 12A, 12B, and 12C provides black and white microscopy photograph images of the same portion of an exemplary formulation at 10,000×, 30,000×, and 50,000×, respectively, wherein the majority of particles shown are particles of titanium dioxide.
Figure 12B:
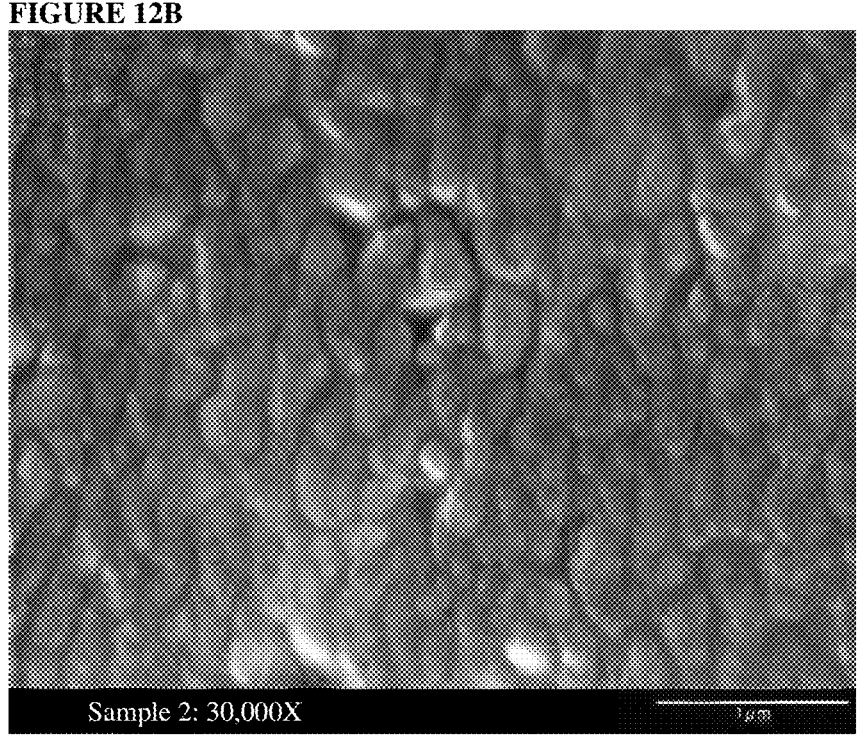
Figure 12C:
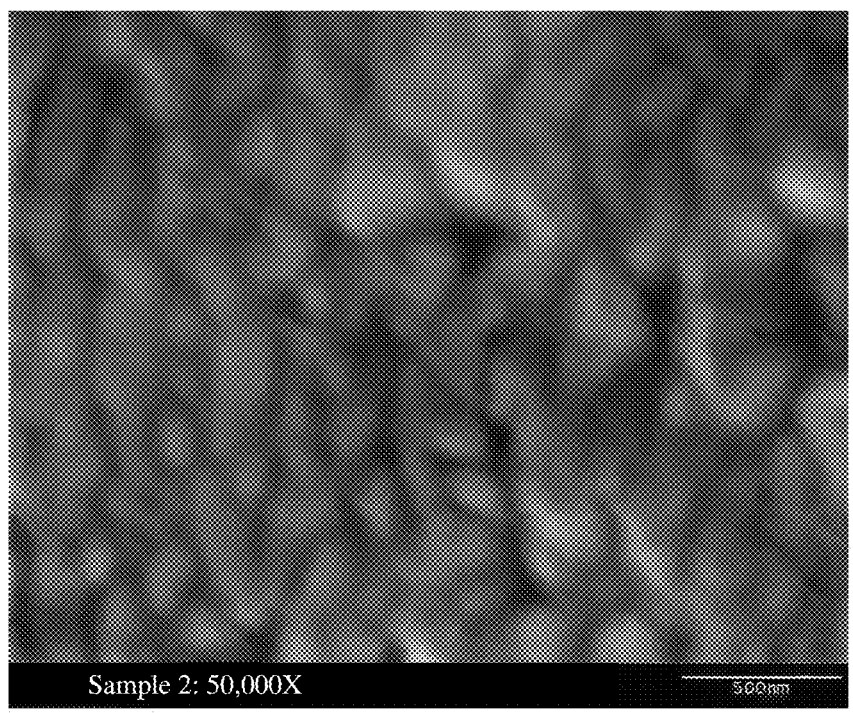

Images collected for, e.g., Sample 2 (and others) appear to show a similar coverage. Sample 2, as an example, differs from Sample 1 in that it contains $TiO_2$ particles. FIGS. 12A, 12B, and 12C are provided for an area of Sample 2 at 10000×, 30000×, and 50000×, and 2 μm, 1 μm, and 500 nm scales, respectively, comprising $TiO_2$ particles. The images first further demonstrate the relative uniformity of $TiO_2$ particles within the composition and upon application, reiterating and supporting the data provided above. Particles fill nearly the entire plane viewed. These images further demonstrate that the particle size for $TiO_2$ is greater than 100 nm. It is relevant to remind the reader that FIGS. 12A-12C, and similar images provided herein, provide visual insights according to 2 dimensions; in this particular set of images, for example, it is important to remind the reader that such visible particles have dimensions reaching toward and away from the reader; such a dimension can be, e.g., shorter than a dimension of the same particle(s) visible to the reader or, e.g., longer than a dimension of the same particle(s) visible to the reader. As $TiO_2$ particles are typically known to be being quasi-spherical (or by other terms of related or unrelated art such as "equi-axied," "equi-axial," or "spherically equivalent," one expects that dimensions of $TiO_2$ particles reaching toward and away from the reader are at least generally, at least substantially, at least essentially, or the same as those visible to the reader.

Of particular note is the "fuzziness" of FIG. 12C, Sample 2 at 50000× magnification. The fuzziness of this image is caused by the presence of the emulsion, surrounding and maintaining the particles therein.

It is also of interest to note that it is commonly observed that $TiO_2$ particles often are found on the outermost (top) layer of particles in analyzed samples. It is theorized that this may not be random. Multiple phenomena may be at play causing this result. One hypothesis is that this is a result of the method of manufacture, where $TiO_2$ particles are added as a paste late in the manufacturing process, prior to final homogenization step(s). Another hypothesis is that this is a function of the surface to which composition(s) are applied but which may be replicated on multiple surfaces, such as, e.g., more rough or uneven surfaces such as skin. Further hypotheses are directed to the wicking properties and associated activity of $TiO_2$ particles within an emulsion. The phenomenon of $TiO_2$ particles commonly forming a top layer and, in certain observed cases "masking" other particles, e.g., ZnO particles, at the surface layer may, in aspects, contribute to product efficacy.

Figure 13A:
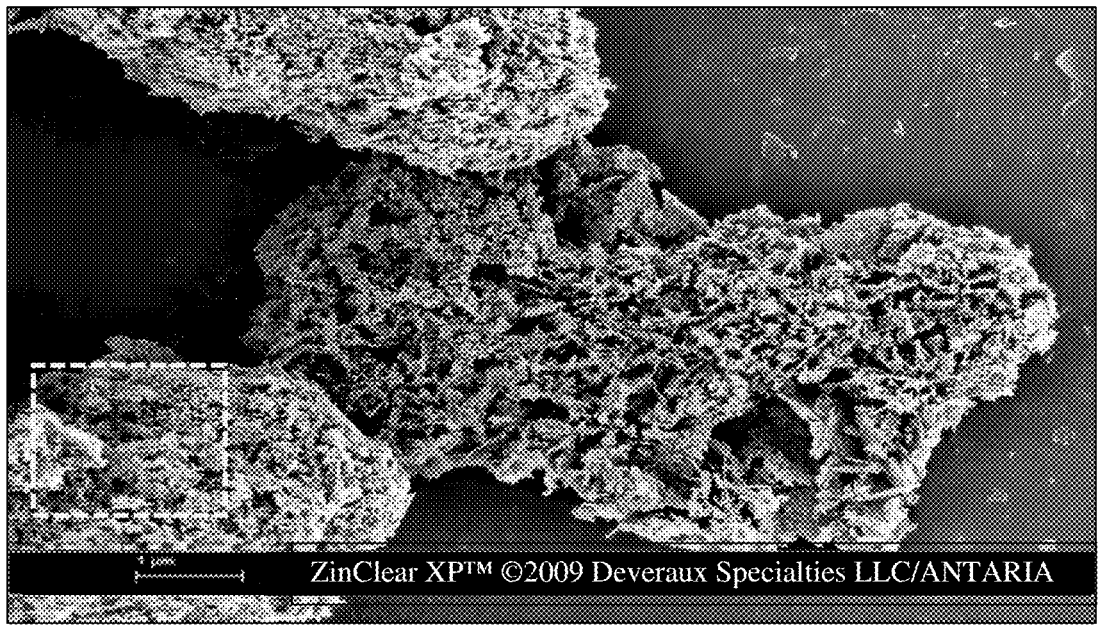
FIG. 13A provides a black and white microscopy photograph of zinc oxide particles utilized in composition(s) provided here, published and owned by the product manufacturer.
Figure 13B:
FIG. 13B provides an expanded (magnified) view of a portion of the photograph provided in FIG. 13A.

Finally, the analysis provided in this Example attempted to characterize the state of ZnO particles relative to observed high magnification images of tested compositions. High magnification image 13C, Sample 1 at 50000× magnification, appears to show small areas, indicated by small, black spots, of empty space. ZnO particles present in composition(s) tested in this Example are aggregated zinc oxide particles. FIG. 13A provides a microscopic image of ZnO particles utilized in composition(s) tested in this Example (image obtained from ZinClear XP™ product brochure, ©2009, Deveraux Specialties LLC/ANTARIA, Dated June 2014. Clearly visible in this image is the significant porosity of the zinc particles. It is believed that at least in part, the non-whitening characteristic of present formulation(s) is derived from the fact that other constituent(s) of compositions, such as emulsion excipient(s), at least partially fill the pores of the zinc oxide causing the reflective index of the at least partially filled zinc oxide particles to change such that it is closer to that of skin (the reflective index of skin being about 1.35-about 1.55), causing little to no whitening of the product when applied to Fitzpatrick I-IV skin types. FIG. 13A comprises a white dashed box indicating the portion of the image magnified and presented as FIG. 13B. FIG. 13B thus represents an expanded view of the image extracted from the literature. Expanding the section of the image (wherein empty pore space is indicated by black coloration) and comparing with, e.g., Sample 1 at 50000× magnification, as provided in FIG. 13C, it is apparent that the features in the product visible in high magnification images such as FIG. 13C are indicative of and correspond to the structure of the ZnO particles. When present, empty poor space in tested compositions is actually quite minimal compared to that present in bare zinc oxide particles. Thus, FIG. 13C and similar high-resolution images show a uniform dispersion of emulsion in the applied layer of product. The comparison of, e.g., FIGS. 13B and 13C indicates that the emulsion is at least partially filling some, most, generally all, or all pores of the porous zinc oxide particles. This phenomenon provides, at least in part, the non-whitening effect of composition(s) provided herein.

Example 8

Exemplary compositions were tested for sun protection factor (SPF) using an in-vitro ISO 24443 assay according to United States Food and Drug Administration (US FDA) regulation. The compositions were further subjected to additional testing procedures, such as in-house in-vitro high energy visible light radiation protection potential assays and in-house in-vitro visible light radiation protection potential assays to determine their ability to block harmful radiations from sunlight. Compositions tested are provided in Table 7 below.

TABLE 7

Exemplary Compositions Tested.

| Test ID No.: | A-1515 | A-1554 |
|---|---|---|
| Client ID No.: | 021-046-XP (5)-22 | 021-046 XP (5)-28 |
| Description: | ZnO (10%) + TiO₂ (3.5%) | ZnO (14%) + TiO₂ (3%) |

TABLE 7-continued

Exemplary Compositions Tested.

| Composition: | | |
|---|---|---|
| Water | 22.86 | 20.89 |
| Magnesium Sulfate | 0.85 | 0.85 |
| Propanediol | 2.5 | 2.5 |
| Deinococcus Extract, Propanediol, 1,2-Hexanediol, Water (FIRST, Access Ingredients) | 1 | 1 |
| Carnosine/Dragosine (Symrise) | 0.2 | 0.2 |
| Echinacea Purpurea (Symfinity, Symrise) | 0.1 | 0.1 |
| Octyldodecyl Neopentanoate/(Elefac I-205/Alzo) | 19 | 19 |
| Cetyl dimethicone, Dimethicone, Bis-vinyl Dimethicone/Dimethicone Copolymer (Jeesilc CD-405, Jeen) | 3.75 | 3.75 |
| Phenyl trimethicone, Bis-vinyl dimethicone/Dimethicone copolymer (Jeesilc PTMF-405, Jeen) | 2.5 | 2.5 |
| Squalane (Jeen or Neossence) | — | — |
| Polyhydroxystearic acid (Dispersun DSP-OL 300 Innospec/Chemtech) | 1.08 | 1.08 |
| Zinc oxide (ZinClear XP, Antaria, Deveraux) | 10 | 14 |
| Stearene Acrylate Copolymer (SunSphere PWD, Dow Corning) | 5.5 | 5 |
| Caprylic Capric Triglyceride, Titanium Dioxide, Aluminum Hydroxide, Stearic Acid, Polyhydroxystearic Acid/AccessSUN E50C (41.56%) | 8.54 (3.55% active) | 7.21 |
| Synthetic Fluorphlogopite, Titanium Dioxide CL Gold A (Argan) | 0.25 | 0.25 |
| ARG-PCC-Iron Oxides (Red, Yellow) | — | — |
| Disteardimonium Hectorite, Phenyl trimethicone, Triethyl citrate (Bentone Gel, PTMV, Elementis, DD Chem) | 3.5 | 3.5 |
| Glyceryl dibehenate, Tribehenin, Glyceryl behenate (Compritol 888, Gatephosse, Omya) | 0.8 | 0.8 |
| Bisabolol, Zingiber officinales (ginger) Extract (SymRelief 100, Symrise) | 0.1 | 0.1 |
| Dimethicone, Dimethicone Copolymer (AcceSIL FF16, Access Ingredients) | 1 | 1 |
| Vit E Acetate (USP, Jeen) | 0.01 | 0.01 |
| 1,2 Hexanediol, Caprylyl glycol, Tropolone (Symdiol 68, Symrise) | 0.9 | 0.9 |
| Polyglyceryl-2 sesquioleate (SGS-PGO 152, Argan) | 11.1 | 11.1 |
| Dimethicone, Trisiloxane (Xiameter PMX-1184 Silicone Fluid, Dow/Univar) | 1.5 | 1.3 |
| Phenetyl Alcohol, Caprypyl Glycol, Feniol (Argan) | 0.06 | 0.06 |
| Silica (Silisphere LS 8H, Argan) | 1.4 | 1.4 |
| Calcium, Sodium Borosilicate (Covabeads crystals, Sensient) | 1.5 | 1.5 |

FIG. 14 provides a first set of data, illustrating ISO 24443 RATIO results obtained from testing the two compositions. The In-vitro ISO 24443 and in-vitro FDA results demonstrate that tested products meet and exceed both ISO 24443 SPF/UVA and UVA/SPF (maximum label SPF 36) as well as proposed FDA UVA I/UV ratio requirements including Critical Wavelength.

FIG. 15 provides results from in-house in-vitro high energy visible light (HEV 380-530 nm; "blue light") radiation protection potential testing, and in-house in-vitro visible light (VIS 400-700 nm; "visible light") radiation protection potential, for the two tested compositions.

FIG. 16 provides results of SPF/UVA and UVA/SPF ratios as per ISO 24443 for the tested compositions, including labeled SPF in vivo/UVA-PF; UVA/PF/labeled SPF in vivo; labeled SPF in vivo/UVA-PF; UVA/PF/labeled SPF in vivo; labeled SPF in vivo/UVA-PF; and UVA/PF/labeled SPF in vivo. As shown, tested compositions meet requirements for SPF 30 and SPF 36 labeling.

Figure 17A:
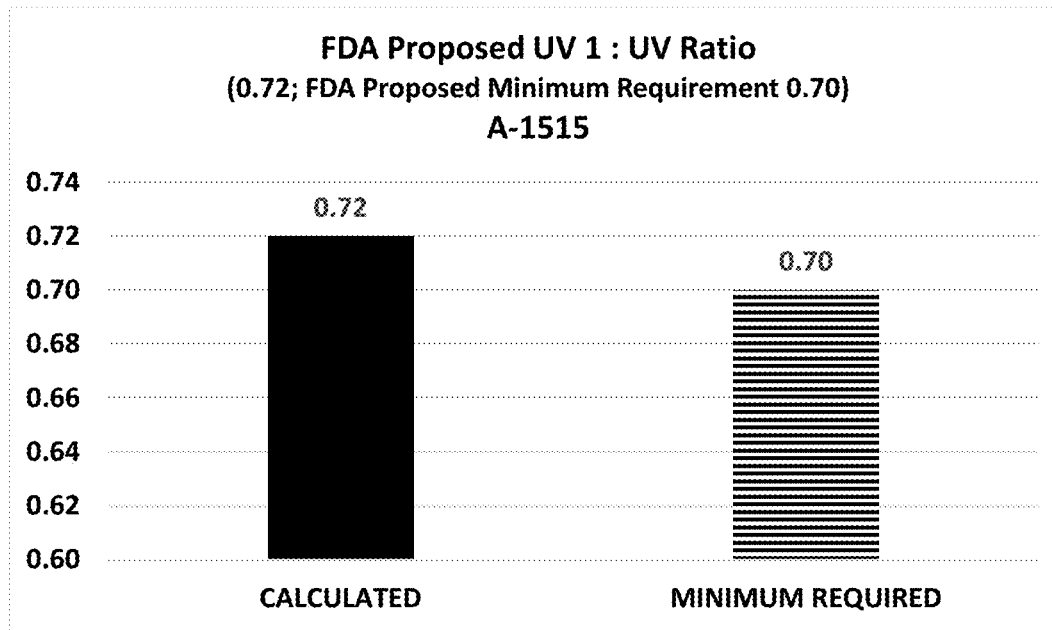
FIGS. 17A and 17B provide results of FDA proposed UVA I/UV Ratio for two exemplary compositions.
Figure 17B:
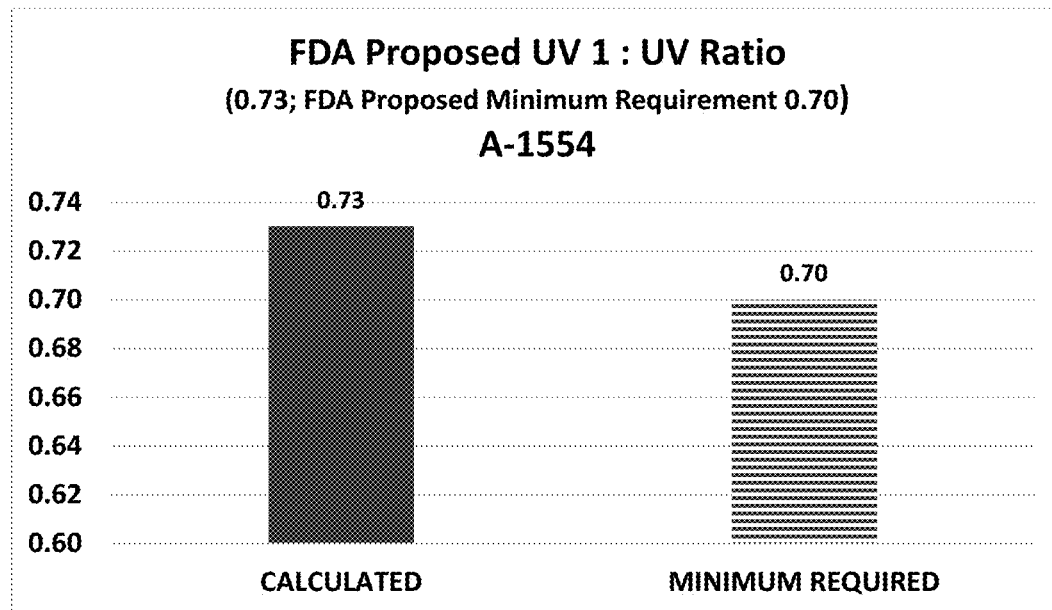

FIGS. 17A and 17B provides results of proposed UVA I/UV ratio as per the United States Food and Drug Administration (FDA) for the two tested compositions. As shown, both tested compositions meet the proposed UVA I/UV ratio as per the US FDA.

FIGS. 18A, 18B, 18C, and 18D provide(s) in-house in-vitro high energy visible light radiation protection potential and in-house in-vitro visible light radiation protection potential for the two tested compositions. FIGS. 18A-18D each comprise indicators A and B. Indicator A in each Figure is positioned at the location indicating Solar Spectral Irradiance according to International Standard ISO 9845-1. Indicator B is positioned at the location indicating Solar Spectral Irradiance according to International Standard ISO 9845-1 transmitted through the test product.

Laboratory analysis results demonstrated that both compositions meet and exceed ISO 24443 SPF/UVA and UVA/SPF ratios as well as proposed FDA UVA T/UV ratio requirements for SPF 30 and SPF 36 label requirements. Further critical wavelength requirements are met.

Additionally, water resistance testing was performed, and preliminary data was collected on Sample A-1554. Procedures for testing were similar to those described in Example 6, performed according to the procedure described in the FDA monograph addressing 80-minute immersion in water (or as discussed in Example 6). The water-resistant SPF value was determined by the product's ability to resist a, 80-minute period of water immersion, achieved through the following test regimen: After application of the sunscreen product followed by the waiting period, a total of 80 minutes water immersion was scheduled: 20 minutes in the water, 15-minute rest (without towel drying), 20 minutes in the water, 15-minute rest (without towel drying), 20 minutes in the water, 15-minute rest (without towel drying), 20 minutes in the water. Immersion was achieved indoors in a whirlpool tub with water circulating by a 1 h.p. pump at 3450 RPM. Each panelist spent twenty minutes in the water, immediately followed by a fifteen-minute rest period out of the water until a total of eighty minutes in the water were achieved. The whirlpool bath was set at 23° C. to 32° C. at moderate agitation. The water and air temperatures and relative humidity were recorded. After the last immersion, the test sites were air dried without toweling for at least fifteen minutes prior to exposure of treated areas to the solar simulation. The protected sites received a series of progressive UV light doses (minimum five) based upon previously determined MED and the intended SPF as follows (all immediate responses were recorded):

SPF 16.3: MED times 0.76×, 0.87×, 1.00×, 1.15× and 132×

SPF12: MED times 0.69×, 0.83×, 1.00×, 1.20×, and 1.44× where x equals the expected SPF of the product, SPF 50: MED times 0.76×, 0.87×, 1.00×, 1.15×. and 1.32× where x equals the expected SPF of the product.

The 80-minute water resistance data is provided in FIG. 19.

Example 9

Two exemplary compositions were tested for appearance upon skin application. The two exemplary composition(s) tested in this Example are provided in Table 8, below.

TABLE 8

Exemplary Compositions Tested.

| Test ID No.: | A-1515 | A-1516 |
|---|---|---|
| Client ID No.: | 021-046-XP (5)-22 | 021-046 XP (5) |
| Description: | ZnO (10%) + TiO$_2$ (3.5%) | ZnO (22.5%) |
| Composition: | | |
| Water | 22.86 | 20.08 |
| Magnesium Sulfate | 0.85 | 0.75 |
| Propanediol | 2.5 | 2.5 |
| Deinococcus Extract, Propanediol, 1,2-Hexanediol, Water (FIRST, Access Ingredients) | 1 | 1 |
| Carnosine/Dragosine (Symrise) | 0.2 | 0.2 |
| *Echinacea Purpurea* (Symfinity, Symrise) | 0.1 | 0.1 |
| Octyldodecyl Neopentanoate/(Elefac I-205/Alzo) | 19 | 19 |
| Cetyl dimethicone, Dimethicone, Bis-vinyl Dimethicone/Dimethicone Copolymer (Jeesilc CD-405, Jeen) | 3.75 | 3.25 |
| Phenyl trimethicone, Bis-vinyl dimethicone/Dimethicone copolymer (Jeesilc PTMF-405, Jeen) | 2.5 | 3 |
| Squalane (Jeen or Neossence) | — | 0.5 |
| Polyhydroxystearic acid (Dispersun DSP-OL 300 Innospec/Chemtech) | 1.08 | 1.1 |
| Zinc oxide (ZinClear XP, Antaria, Deveraux) | 10 | 22.5 |
| Stearene Acrylate Copolymer (SunSphere PWD, Dow Corning) | 5.5 | 4.5 |
| Caprylic Capric Triglyceride, Titanium Dioxide, Aluminum Hydroxide, Stearic Acid, Polyhydroxystearic Acid/AccessSUN E50C (41.56%) | 8.54 (3.55% active) | — |
| Synthetic Fluorphlogophite, Titanium Dioxide CL Gold A (Argan) | 0.25 | — |
| ARG-PCC-Iron Oxides (Red, Yellow) | — | — |
| Disteardimonium Hectorite, Phenyl trimethicone, Triethyl citrate (Bentone Gel, PTMV, Elementis, DD Chem) | 3.5 | 2.3 |
| Glyceryl dibehenate, Tribehenin, Glyceryl behenate (Compritol 888, Gatephosse, Omya) | 0.8 | 0.7 |
| Bisabolol, *Zingiber officinales* (ginger) Extract (SymRelief 100, Symrise) | 0.1 | 0.1 |
| Dimethicone, Dimethicone Copolymer (AcceSIL FF16, Access Ingredients) | 1 | 0.75 |
| Vit E Acetate (USP, Jeen) | 0.01 | 0.01 |
| 1,2 Hexanediol, Caprylyl glycol, Tropolone (Symdiol 68, Symrise) | 0.9 | 0.9 |
| Polyglyceryl-2 sesquioleate (SGS-PGO 152, Argan) | 11.1 | 11 |
| Dimethicone, Trisiloxane (Xiameter PMX-1184 Silicone Fluid, Dow/Univar) | 1.5 | 2.6 |
| Phenetyl Alcohol, Caprypyl Glycol, Feniol (Argan) | 0.06 | 0.06 |
| Silica (Silisphere LS 8H, Argan) | 1.4 | 0.6 |
| Calcium, Sodium Borosilicate (Covabeads crystals, Sensient) | 1.5 | 2.5 |

FIGS. 20A and 20B provide black and white photographs of portions of Fitzpatrick Type IV skin. To the left in each photograph is an area of the skin indicated as "clear", meaning that no product was applied to that area of skin. To the right in each photograph is an area of the skin indicated as "applied," indicating that product was applied to that area of skin. A double-lined indicator is present in the header of the figure to indicate the separation of the two areas. FIG. 20A shows the area of skin to which sample A-1515 was applied. FIG. 20B shows the area of skin to which sample A-1516 was applied.

Figure 18A:
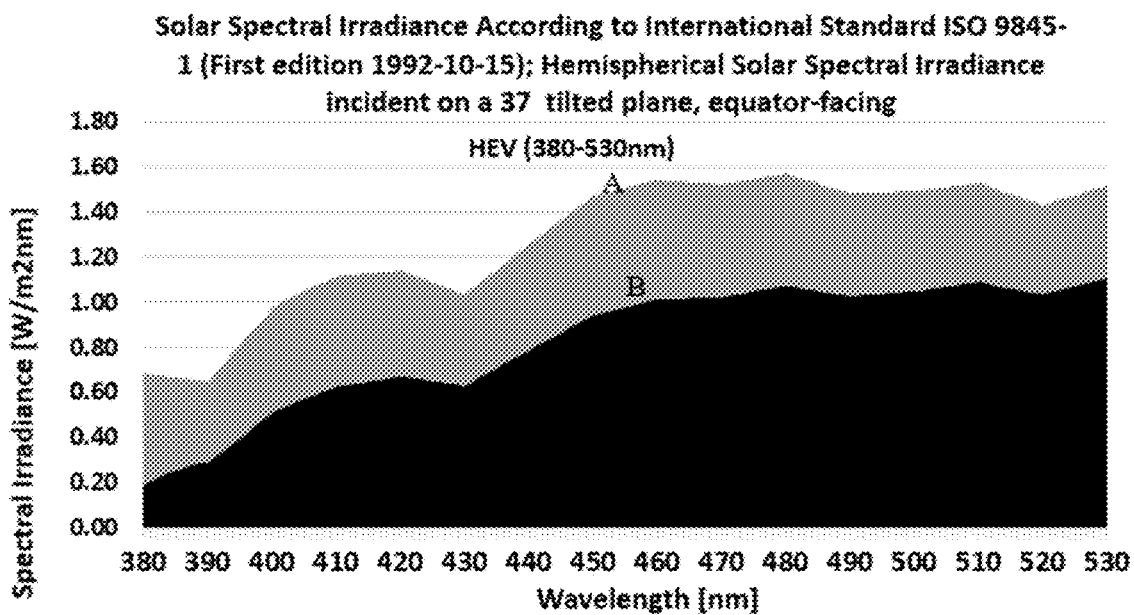
FIGS. 18A, 18B, 18C, and 18D provide results of in-house in-vitro high energy visible light ("blue light") radiation protection potential (FIGS. 18A and 18B) and in-house in-vitro visible light radiation protection potential (FIGS. 18C and 18D) for two exemplary formulations.
Figure 18B:
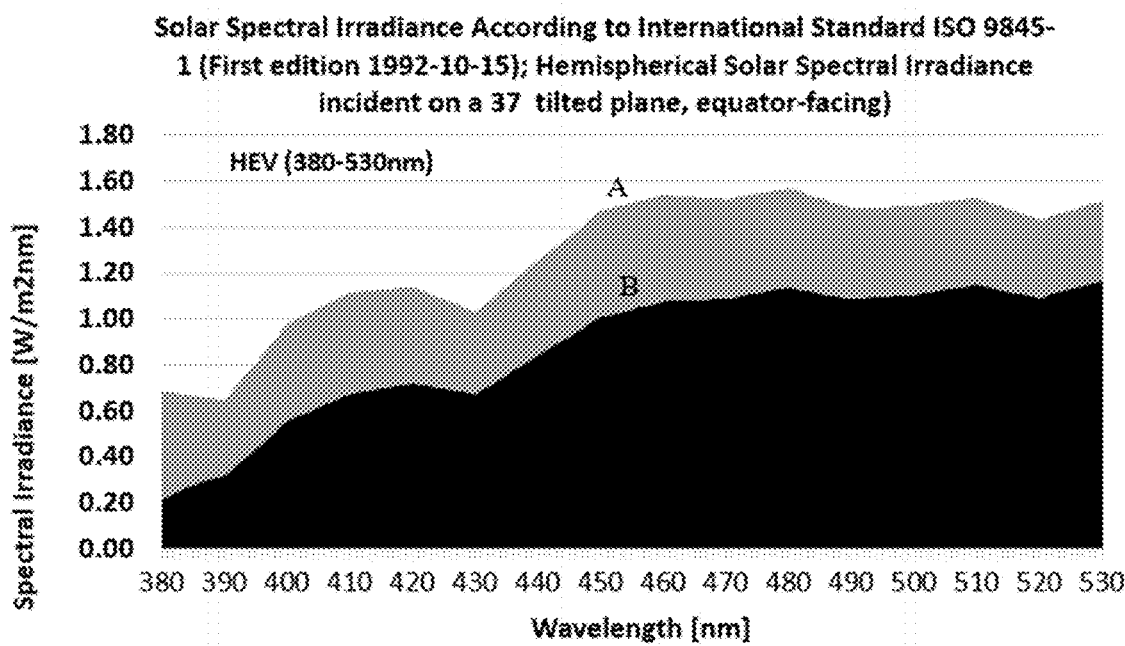
Figure 18C:
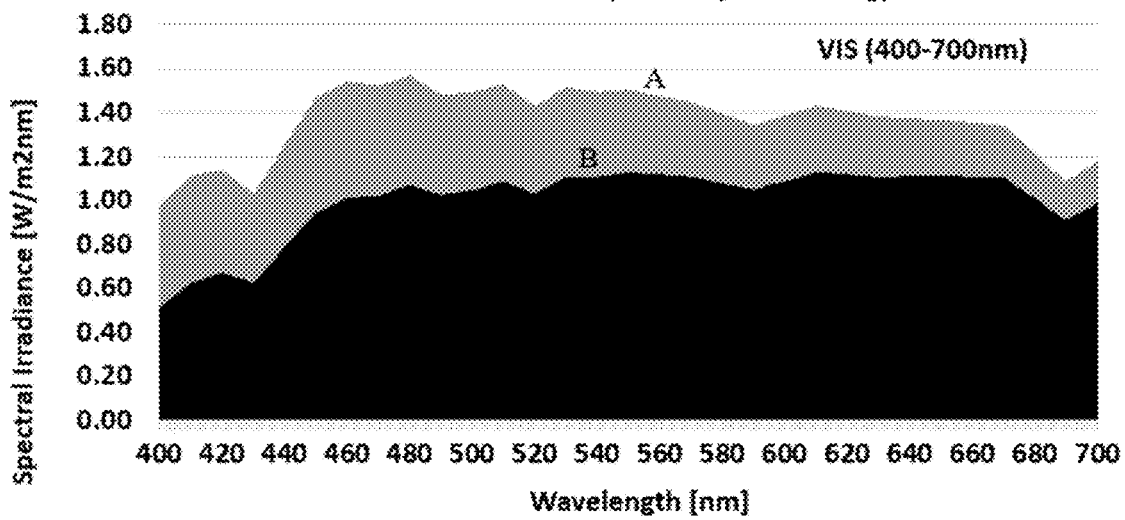
Figure 18D:
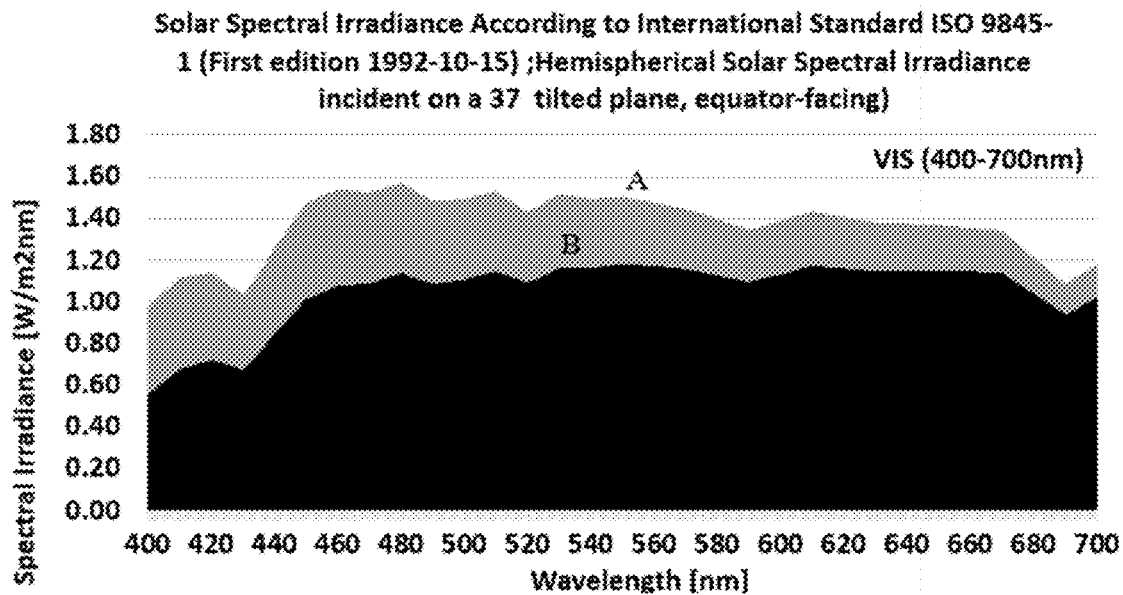

As can be seen by careful analysis of the photograph in each of FIGS. 18A and 18B, the application of product(s) is non-discernable. That is, both tested compositions demonstrate a non-whitening appearance on Fitzpatrick Type IV skin.

Example 10

A number of the various formulations of emulsion compositions described in these Examples were tested over the course of formulation development. The exemplified lightweight emulsion (e.g., lotion) sunscreen compositions demonstrating an SPF of at least 30, at least 36, or at least 50, described herein, and further demonstrating a water resistance of at least 40 minutes, such as at least 80 minutes, provided in tinted/tone or untinted form, have been demonstrate the following characteristics identified in Table 9 below.

TABLE 9

Characteristics of lightweight emulsion sunscreens provided by the invention.

| | |
|---|---|
| Color | Off-White or Neutral Beige (tinted) to Match Standard |
| Odor | Light, characteristic, to Match Standard |
| Appearance | Smooth, light textured lotion, free of any agglomerates; To Match Standard |
| pH @ 25° C. | N/A (due to emulsion type) |
| Viscosity Brookfield RVT spindle T-B @ 20 rpm @ 25° C. | Initial: 2,200 cps-4,200 cps<br>24 Hours: 3,500 cps-5,500 cps<br>SelfLife: 4,500 cps-15,000 cps |
| Specific Gravity | 1.0045-1.0455 or Report Value |

Example 11

To demonstrate the importance of homogenization step(s) of production method(s) described herein, a non-homogenized sample and a homogenized sample were imaged at 25× magnification under a stereo light microscope with transmitted light. The composition of the sample tested is shown in Table 10 below.

TABLE 10

Exemplary formulation: homogenization experimentation.

| Test ID No.: | 1 |
|---|---|
| Client ID No.: | 021-046-XP (5)-10 |
| Description: | ZnO-Only |
| Composition: | |
| Water | 19.38 |
| Magnesium Sulfate | 0.85 |
| Propanediol | 2.5 |
| Deinococcus Extract, Propanediol, 1,2-Hexanediol, Water (FIRST, Access Ingredients) | 1 |
| Carnosine/Dragosine (Symrise) | 0.2 |
| Echinacea Purpurea (Symfinity, Symrise) | 0.1 |
| Octyldodecyl Neopentanoate/(Elefac I-205/Alzo) | 19 |
| Cetyl dimethicone, Dimethicone, Bis-vinyl Dimethicone/Dimethicone Copolymer (Jeesilc CD-405, Jeen) | 3.75 |
| Phenyl trimethicone, Bis-vinyl dimethicone/Dimethicone copolymer (Jeesilc PTMF-405, Jeen) | 2.5 |
| Polyhydroxystearic acid (Dispersun DSP-OL 300 Innospec/Chemtech) | 1.1 |
| Zinc oxide (ZinClear XP, Antaria, Deveraux) | 22.5 |
| Stearene Acrylate Copolymer (SunSphere PWD, Dow Corning) | 4.5 |
| Disteardimonium Hectorite, Phenyl trimethicone, Triethyl citrate (Bentone Gel, PTMV, Elementis, DD Chem) | 3.5 |

TABLE 10-continued

Exemplary formulation: homogenization experimentation.

| Test ID No.: | 1 |
|---|---|
| Glyceryl dibehenate, Tribehenin, Glyceryl behenate (Compritol 888, Gatephosse, Omya) | 0.75 |
| Bisabolol, Zingiber officinales (ginger) Extract (SymRelief 100, Symrise) | 0.1 |
| Dimethicone, Dimethicone Copolymer (AcceSIL FF16, Access Ingredients) | 0.75 |
| Vit E Acetate (USP, Jeen) | 0.01 |
| 1,2 Hexanediol, Caprylyl glycol, Tropolone (Symdiol 68, Symrise) | 0.9 |
| Polyglyceryl-2 sesquioleate (SGS-PGO 152, Argan) | 11.1 |
| Dimethicone, Trisiloxane (Xiameter PMX-1184 Silicone Fluid, Dow/Univar) | 1.75 |
| Phenetyl Alcohol, Caprypyl Glycol, Feniol (Argan) | 0.06 |
| Silica (Silisphere LS 8H, Argan) | 1.2 |
| Calcium, Sodium Borosilicate (Covabeads crystals, Sensient) | 2.5 |

Figure 21:
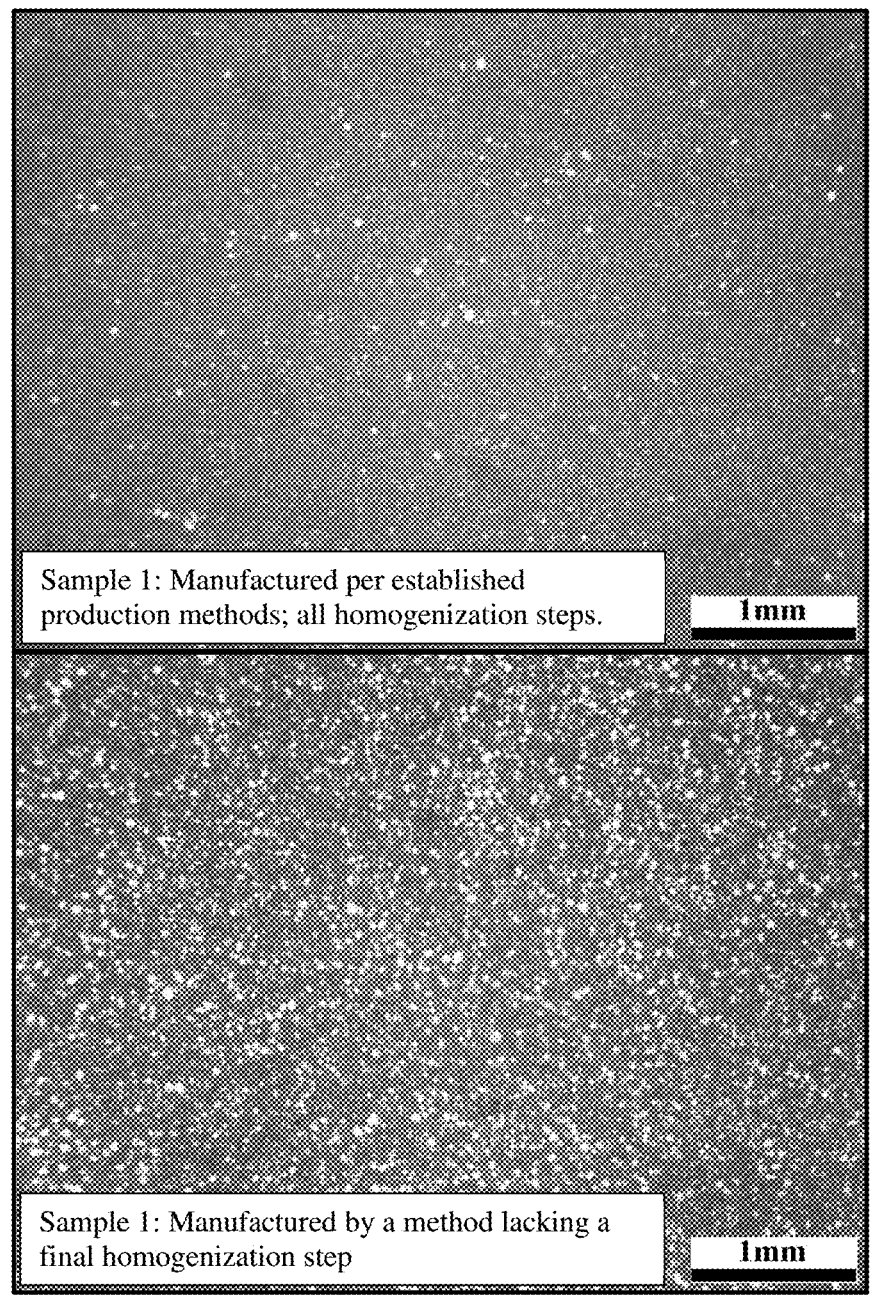
FIG. 21 provides comparison photographs of an exemplary composition made using a first method of manufacture versus a second method of manufacture lacking a final homogenization step.

FIG. 21 shows comparison images of Sample 1 when produced according to method(s) of manufacture disclosed herein (top of FIG. 21) and Sample 1 when manufactured according to methods of manufacture described herein wherein the method lacks (excludes) the final homogenization step (bottom of FIG. 21). Images were obtained using a stereo light microscope with transmitted light.

As shown in FIG. 21, method(s) of manufacture lacking the final homogenization step yield an emulsion comprising a large number of agglomerates, the agglomerates being collections of particles at least loosely associated with one another. Initial homogenization step(s) during the process of manufacture mix samples and the particulate matter thereof, creating at least an initial, at least substantially even distribution of particles throughout the emulsion, yet appear(s) to leave a large number of these particulate agglomerates which have not completely wicked to the emulsion; that is, an incomplete interaction has occurred between the emulsion liquid and the solid surface of the particle(s). FIG. 21 demonstrates that the additional homogenization step yields a reduction in the size of agglomerates or the at least general or at least substantial elimination of agglomerates, yielding composition(s) having smaller such particle population(s). In one aspect, the final homogenization allows for the emulsion to be drawn into or to move into the agglomerated particles sufficiently to separate the individual (or, e.g., smaller groups of) particles from one another thus detectably or significantly reducing agglomerate size. In another aspect, the final homogenization serves to break apart the agglomerates such that they physically break apart during the homogenization process and thus relatively smaller (in size) particulate population(s) are established. Sufficient force is required for this to occur. Accordingly, the final homogenization step allows for such individual particles or smaller groups of particles (smaller agglomerates) to be established and mixed into the emulsion matrix. It is expected that with each additional homogenization step, additional agglomerate breakdown could occur, thus further reducing the size of agglomerate(s) or at least generally, at least substantially, at least essentially, or eliminating such agglomerate population(s). It is demonstrated by other data presented here (see, e.g., Example 7 providing SEM/EDS data) that a sufficient number of potential agglomerates are removed when samples are processed according to methods of manufacture described herein comprising the final homogenization step to allow for a high percentage of particulate coverage of the underlying surface to which they are applied.

Example 12

The following Table 11 provides exemplary lotion and anhydrous compositions utilized in 80-minute water resistance testing.

TABLE 11

Exemplary compositions. Ingredients in wt. %.

| Formula # | 009-74 (Lotion) | 009-118 (Stick/compact) |
|---|---|---|
| Composition: | | |
| Water | 31.49 | — |
| Sodium Chloride | 0.75 | — |
| Glycerin | 0.50 | — |
| Hydroxyacetophenone/Symsave H/Symrise | 0.50 | — |
| Water, Hydrogenated Phosphaditylcholine, Glycerin, Ubiquinone/BP-CoQ10/Jeen/Vantage | 0.50 | — |
| Water, Glycerin, Polygonium Aviculare Extract/Elix-IR/LucasMayer | 1.00 | — |
| Water, Glycerin, *Camellia Sinensis* Leaf Extract/Green Tea Extract/Jeen/Vantage | 0.50 | — |
| Panthenol/DL-Panthenol/Jeen/Vantage | 0.25 | — |
| Allantoin/Allantoin/Jeen/Vantage | 0.05 | — |
| Niacinamide/Niacinamide PC/DSM | 1.00 | — |
| *Capparis Spinosa* Fruit Extract, Opuntia Ficus-Indica Extract, *Olea Europea* (Olive) Leaf Extract, Starch/Skin Save Starch/Botanical Plus/Jeen/Vantage | 0.15 | — |
| *Olea Europea* (Olive) Fruit Extract, Starch/Skin Olea-HT 10 Starch/Botanical Plus/Jeen/Vantage | 0.15 | — |
| Caprylic/Capric Triglycerides and *Himanthalia Elongata* Extract/Marine Bamboo TG/Odycea/Argan | 0.50 | 1.00 |
| Butyloctyl Salicylate/Hallbrite BHB/HallStar/Azelis | 13.0 | 20.00 |
| Octyldodecyl Neopentanoate/Elefac I-205/Alzo | — | 7.50 |
| Dimethicone, Bis-Vinyl Dimethicone/Dimethicone Copolymer/Jeesilc PS DMLV 50/Jeen | 4.0 | 4.30 |
| Cethyl Dimethicone, Dimethicone, Bis-Vinyl Dimethicone/Dimethicone Copolymer/Jeesilc CD-405/Jeen | 4.0 | — |
| Phenyl Trimethicone, Bis-Vinyl Dimethicone/Dimethicone Copolymer/Jeesilc PTMF-405/Jeen | — | 15.35 |
| Caprylic/Capric Triglyceride/CCTG/Argan | | 4.90 |
| Squalane/Jeen/Vantage | 2.0 | — |
| Polyhydroxystearic Acid/Dispersun DSP-OL 300 Innospec/Chemtech | 1.0 | 0.50 |
| Zinc Oxide CLR-P/Argan (Aggregates) | 10.0 | 10.00 |
| Styrene Acrylates Copolymer/SunSphere PWD/Dow/Dow Corning | 5.5 | — |
| Caprylic Capric Triglyceride, Titanium Dioxide, Aluminum Hydroxide, Stearic Acid, Polyhydroxystearic Acid/AccessSUN E50C (41.56% active)-Access Ingredients | 8.54 (3.55% active) | 12.20 |
| Disteardimonium Hectorite, Phenyl Trimethicone, Triethyl Citrate/Bentone Gel, PTMV/Elementis/DD Chem | 2.25 | — |
| Disteardimonium Hectorite/Bentone V 38CG/Elementis/DD Chem | — | 0.50 |
| Bisabolol, *Zingiber Officinales* (Ginger) Extr./SymRelief 100/Symrise | 0.10 | 0.10 |
| Hexyldecanol, Bisabolol, Cethylhydroxyproline Palmitamide, Stearic Acid, *Brasica Campestris*, Sterols/SymRepair/Symrise | — | 1.00 |
| Dimethicone, Dimethicone Copolymer/AcceSIL FF16/Access Ingredients | 2.00 | 2.00 |
| Vit E Acetate, USP/Jeen | 0.25 | 0.10 |
| 1,2 Hexanediol, Caprylyl Glycol/Symdiol 68/Symrise | 0.50 | 0.50 |
| Polyglyceryl-4 Oleateate Jeechem 100/Jeen/Ventage | 6.00 | — |
| Tribehenin | — | 2.00 |
| Ozoketite | — | 5.00 |
| Polyethelene | — | 2.60 |
| *Prunus Armeniaca* (Apricot) Kernel Oil Hydrogenated Vegetables Oil | — | 2.00 |
| Dimethicone/Vinyl Dimethicone Copolymer, Lauterh-3, Laureth-25/Emul-6081/Access Ingredients | — | 0.50 |
| Vinyl Dimethicone/Methicone Silsesquioxane Crosspolymer/KSP-101/ShinEtsu/ChemTech or AccessSIL P-1400/Access Ingredients | — | 3.25 |
| Water, Simethicone/Xiameter AFE-1510 Antifoam/Dow Corning | — | 0.20 |
| Phenetyl Alcohol, Caprypyl Glycol/Feniol/Argan | 0.02 | 0.05 |
| Plankton Glass Flower/Odycea/Argan | 0.50 | 0.10 |
| Silica/Silisphere LS 8H/Argan | 2.75 | 4.10 |
| Cerium Oxide, Aluminum Oxide, PMMA/Arg Sphere NIR-1/15BA000/Argan | 0.25 | 0.25 |

80-minute water resistance testing was performed using the above sample formulations. Results are shown in Table 12 below.

TABLE 12

Water resistance testing results.

FDA 2011 Static & 80 Minutes Water Resistance SPF Testing
Sample ID: 009-074 (SPF 55 Mineral Sunscreen Lotion)
Sample Test ID No. 17-644
Subjects: n = 5

| Subject ID No. | Sex | Age | Skin Type | Base MEDu Joules/M2 | 1902I FDA Std. Static SPF | Static SPF | 80 Min WR SPF |
|---|---|---|---|---|---|---|---|
| 2235 | M | 34 | I | 49.58/49.58 | 15.00 | 63.20 | 63.20 |
| 2234 | F | 49 | III | 59.50/79.33 | 13.50 | 54.50 | 54.50 |
| 2161 | F | 49 | II | 59.50/59.50 | 18.00 | 72.67 | 72.67 |
| 1985 | F | 67 | I | 49.58/49.58 | 18.00 | 55.00 | 63.20 |
| 2007 | M | 45 | I | 49.58/49.58 | 18.00 | 72.80 | 55.00 |
| MEAN: | | | | | 16.50 | 63.63 | 61.71 |
| STD DEV.: | | | | | 2.12 | 9.00 | 7.44 |
| A = ts/sq root n | | | | | 1.23 | 5.22 | 4.31 |
| X − A | | | | | 15.27 | 58.42 | 57.40 |
| PROJECTED LABEL SPF | | | | | 14 | 58 | 57 |

ISO 24444 Static & Colipa 80 Min WR SPF Testing
Sample ID: 009-118 (SPF 50 + Untinted Stick)
Sample Test ID No. 18-1219
Subjects: n = 10

| Subject ID No. | Sex | Age | Skin Type | Base MEDu Joules/M2 | 1902L FDA Std. Static SPF | Static SPF | 80 Min WR SPF |
|---|---|---|---|---|---|---|---|
| 2112 | F | 39 | I | 49.58/49.58 | 15.00 | 75.20 | 67.20 |
| 2566 | F | 54 | II | 59.50/59.50 | 18.00 | 60.00 | 67.17 |
| 2565 | M | 40 | II | 59.50/59.50 | 15.00 | 67.17 | 67.17 |
| 2236 | F | 64 | II | 59.50/59.50 | 15.00 | 67.17 | 67.17 |
| 2572 | F | 38 | I | 49.58/59.50 | 14.99 | 62.64 | 62.64 |
| 2008 | M | 58 | II | 59.50/59.50 | 15.00 | 60.00 | 67.17 |
| 2574 | F | 44 | I | 49.58/49.58 | 15.00 | 67.20 | 67.20 |
| 2576 | M | 56 | II | 59.50/59.50 | 15.00 | 75.33 | 67.17 |
| 1451 | F | 29 | I | 49.58/49.58 | 18.00 | 67.20 | 67.20 |
| 2027 | M | 58 | I | 49.58/49.58 | 18.00 | 67.20 | 67.20 |
| MEAN: | | | | | 15.9 | 66.9 | 66.7 |
| STD DEV.: | | | | | 1.45 | 5.31 | 1.44 |
| STD ERROR OF MEAN: | | | | | 0.46 | 1.68 | 0.83 |
| STD % ERROR OF MEAN: | | | | | 2.88 | 2.51 | 1.25 |
| C = (t value) SEM | | | | | 1.04 | 3.80 | 1.88 |
| CI % | | | | | 6.54 | 5.68 | 2.82 |
| 95% CI = SPF − C to SPF + C | | | | | 14.9-15.9 | 63.1-70.7 | 64.8-68.6 |

Example 13

Example 13 provides a compilation of exemplary formulations provided by the invention. In certain aspects, one or more composition(s) demonstrate better performance according to one or more performance characteristics described herein. Exemplary formulations are provided in Tables 13-18.

TABLE 13

Exemplary formulations. Ingredients in wt. %.

| Formula # | 009-118 | 009-120 | 021-006(12) | 021-006(20) |
|---|---|---|---|---|
| Description (Type) | Stick/Compact | Stick/Compact | Stick/Compact | Stick/Compact |
| Composition: | | | | |
| Caprylic/Capric Triglycerides and *Himanthalia Elongata* | 1.00 | 1.00 | — | — |
| Extract/Marine Bamboo TG/Odycea/Argan | | | | |
| Butyloctyl Salicylate/Hallbrite BHB/HallStar/Azelis | 20.00 | 20.00 | — | — |
| Octyldodecyl Neopentanoate/Elefac I-205/Alzo | 7.50 | 4.575 | 35.00 | 35.00 |
| Dimethicone, Bis-Vinyl Dimethicone/Dimethicone Copolymer/Jeesilc PS DMLV 50/Jeen | 4.30 | 3.0 | — | — |
| Phenyl Trimethicone, Bis-Vinyl Dimethicone/Dimethicone Copolymer/Jeesilc PTMF-405/Jeen | 15.35 | 15.25 | 10.0 | 10.0 |

TABLE 13-continued

Exemplary formulations. Ingredients in wt. %.

| Formula # | 009-118 | 009-120 | 021-006(12) | 021-006(20) |
|---|---|---|---|---|
| Caprylic/Capric Triglyceride/CCTG/Argan | 4.90 | 4.00 | 3.35 | 3.00 |
| Ethylhexyl Olivate, Squalane/Botanessential Olivate S-EHO/DDChemco | — | — | 4.00 | 3.50 |
| Polyhydroxystearic Acid/Dispersun DSP-OL 300 Innospec/Chemtech | 0.50 | 0.50 | — | — |
| Zinc Oxide/MicNo (Platelets) SOLAVEIL MZP7-PW-(MV) 98%/Croda | — | — | 22.50 | 22.50 |
| Zinc Oxide CLR-P/Argan (Aggregates) | 10.00 | 10.0 | — | — |
| Titanium Dioxide, Triethoxycoprylylsiane/Titan-TE/Argan | — | 3.50 | — | — |
| ARG-PCC-Iron Oxides (Red, Yellow, Black) | — | 3.675 | — | 3.19 |
| Disteardimonium Hectorite/Bentone V 38CG/Elementis/DD Chem | 0.50 | 0.50 | 0.50 | 0.50 |
| Bisabolol, *Zingiber Officinales* (Ginger) Extr./SymRelief 100/Symrise | 0.10 | 0.10 | 0.10 | 0.10 |
| Hexyldecanol, Bisabolol, Cethylhydroxyproline Palmitamide, Stearic Acid, *Brasica Campestris*, Sterols/SymRepair/Symrise | 1.00 | 1.00 | — | — |
| Dimethicone, Dimethicone Copolymer/AcceSIL FF16/Access Ingredients | 2.00 | 2.00 | 2.00 | 2.00 |
| Vit E Acetate, USP/Jeen | 0.10 | 0.10 | 0.25 | 0.05 |
| 1,2 Hexanediol, Caprylyl Glycol/Symdiol 68/Symrise | 0.50 | 0.50 | 0.50 | 0.50 |
| Tribehenin | 2.00 | 2.00 | 2.00 | 2.00 |
| Ozoketite | 5.00 | 5.00 | 6.00 | 5.00 |
| Polyethelene | 2.60 | 2.50 | 4.50 | 4.50 |
| *Prunus Armeniaca* (Apricot) Kernel Oil Hydrogenated Vegetables Oil | 2.00 | 2.00 | 2.00 | 2.00 |
| Karanja Butter/AEBikira Karanja Butter/AE Chemie | — | — | 1.00 | 1.00 |
| Sucrose Stearate/Sisterna/MMP | — | — | — | 0.50 |
| Dimethicone/Vinyl Dimethicone Copolymer, Lauterh-3, Laureth-25/Emul-6081/Access Ingredients | 0.50 | 0.50 | — | — |
| Vinyl Dimethicone/Methicone Silsesquioxane Crosspolymer/KSP-101/ShinEtsu/ChemTech or AccessSIL P-1400/Access Ingredients | 3.25 | 2.50 | 2.00 | 1.36 |
| Water, Simethicone/Xiameter AFE-1510 Antifoam/Dow Corning | 0.20 | 0.20 | — | — |
| Fullerene, Squalane/Fullerene-C60/C60 Co./AE Chemie | — | — | 1.00 | 1.00 |
| Phenetyl Alcohol, Caprypyl Glycol/Feniol/Argan | 0.05 | 0.05 | 0.05 | 0.05 |
| Plankton Glass Flower/Odycea/Argan | 0.10 | 0.10 | — | — |
| Silica/Silisphere LS 8H/Argan | 4.10 | 3.00 | 1.25 | 1.25 |
| Calcium, Sodium Borosilicate/Covabeads Crystals/Sensient | — | — | 2.00 | 1.00 |
| Cerium Oxide, Aluminum Oxide, PMMA/Arg Sphere NIR-1/15BA000/Argan | 0.25 | 0.25 | — | — |

TABLE 14

Exemplary Formulations. Ingredients in wt. %.

| Formula # | 009-74 | 009-302 | 009-308 |
|---|---|---|---|
| Description (Type) | Lotion | Lotion | Lotion |
| Composition: | | | |
| Water | 31.49 | 33.12 | 33.41 |
| Sodium Chloride | 0.75 | 0.75 | 0.75 |
| Glycerin | 0.50 | 0.50 | 0.50 |
| Hydroxyacetophenone/Symsave H/Symrise | 0.50 | — | — |
| Water, Hydrogenated Phosphaditylcholine, Glycerin, Ubiquinone/BP-CoQ10/Jeen/Vantage | 0.50 | 0.25 | 0.25 |
| Water, Glycerin, Polygonium Aviculare Extract/Elix-IR/LucasMayer | 1.00 | 1.00 | 1.00 |
| Water, Glycerin, *Camellia Sinensis* Leaf Extract/Green Tea Extract/Jeen/Vantage | 0.50 | 0.25 | 0.25 |
| Panthenol/DL-Panthenol/Jeen/Vantage | 0.25 | 0.05 | 0.05 |
| Allantoin/Allantoin/Jeen/Vantage | 0.05 | 0.02 | 0.02 |
| Niacinamide/Niacinamide PC/DSM | 1.00 | 0.10 | 0.10 |
| *Capparis Spinosa* Fruit Extract, *Opuntia Ficus-Indica* Extract, *Olea Europea* (Olive) Leaf Extract, Starch/Skin Save Starch/Botanical Plus/Jeen/Vantage | 0.15 | 0.01 | 0.01 |
| *Olea Europea* (Olive) Fruit Extract, Starch/Skin Olea-HT 10 Starch/Botanical Plus/Jeen/Vantage | 0.15 | 0.01 | 0.01 |
| Caprylic/Capric Triglycerides and *Himanthalia Elongata* Extract/Marine Bamboo TG/Odycea/Argan | 0.50 | 0.25 | 0.25 |
| Butyloctyl Salicylate/Hallbrite BHB/HallStar/Azelis | 13.0 | 13.00 | 16.0 |
| Dimethicone, Bis-Vinyl Dimethicone/Dimethicone Copolymer/Jeesilc PS DMLV 50/Jeen | 4.0 | 3.00 | 3.0 |
| Cethyl Dimethicone, Dimethicone, Bis-Vinyl Dimethicone/Dimethicone Copolymer/Jeesile CD-405/Jeen | 4.0 | 3.00 | 3.0 |
| Squalane/Jeen/Vantage | 2.0 | 2.00 | 2.0 |
| Polyhydroxystearic Acid/Dispersun DSP-OL 300 Innospec/Chemtech | 1.0 | 1.80 | 1.8 |
| Zinc Oxide CLR-P/Argan (Aggregates) | 10.0 | 10.00 | 10.0 |
| Styrene Acrylates Copolymer/SunSphere PWD/Dow/Dow Corning | 5.5 | 5.50 | 5.5 |
| Caprylic Capric Triglyceride, Titanium Dioxide, Aluminum Hydroxide, Stearic Acid, Polyhydroxystearic Acid/AccessSUN E50C (41.56% active)-Access Ingredients | 8.54 (3.55% active) | 8.54 (3.55% active) | 8.54 (3.55% active) |
| Synthetic Fluorphlogopite, Titanium Dioxide/CL Gold A/Argan | — | — | 0.25 |
| ARG-PCC-Iron Oxides (Red, Yellow, Black) | — | 1.70 | — |
| Disteardimonium Hectorite, Phenyl Trimethicone, Triethyl Citrate/Bentone Gel, PTMV/Elementis/DD Chem | 2.25 | 2.25 | 2.25 |

TABLE 14-continued

Exemplary Formulations. Ingredients in wt. %.

| Formula # | 009-74 | 009-302 | 009-308 |
|---|---|---|---|
| Bisabolol, *Zingiber Officinales* (Ginger) Extr./SymRelief 100/Symrise | 0.10 | 0.10 | 0.10 |
| Dimethicone, Dimethicone Copolymer/AcceSIL FF16/Access Ingredients | 2.00 | 0.70 | 0.70 |
| Vit E Acetate, USP/Jeen | 0.25 | 0.25 | 0.25 |
| 1,2 Hexanediol, Caprylyl Glycol, Tropolone/Symdiol 68 T/Symrise | — | 0.90 | 0.90 |
| 1,2 Hexanediol, Caprylyl Glycol/Symdiol 68/Symrise | 0.50 | — | — |
| Polyglyceryl-3 Sorbityl Linseedate EvoCream/Senerga/Argan | — | 5.75 | 5.30 |
| Polyglyceryl-4 Oleateate Jeechem 100/Jeen/Ventage | 6.00 | 2.00 | 2.00 |
| Phenetyl Alcohol, Caprypyl Glycol/Feniol/Argan | 0.02 | 0.06 | 0.06 |
| Plankton Glass Flower/Odycea/Argan | 0.50 | 0.10 | 0.10 |
| Silica/Silisphere LS 8H/Argan | 2.75 | 1.50 | 1.40 |
| Cerium Oxide, Aluminum Oxide, PMMA/Arg Sphere NIR-1/15BA000/Argan | 0.25 | 0.25 | 0.25 |

TABLE 15

Exemplary Formulations. Ingredients in wt. %.

| Formula # | 021-042 | 021-046 XP(5) |
|---|---|---|
| Description (Type) | Lotion | Lotion |
| Composition: | | |
| Water | 20.795 | 20.08 |
| Magnesium Sulfate | 1.050 | 0.75 |
| Propanediol | 1.000 | 2.50 |
| Deinococcus Extract, Propanediol, 1,2-Hexanediol, Water/FIRST/Access Ingredients | 1.000 | 1.00 |
| Carnosine/Dragosine/Symrise | — | 0.20 |
| *Echinacea Purpurea*/Symfinity/Symrise | — | 0.10 |
| Scenedesmus Deserticola Extr./DESERTICA/Access Ingredients | 0.500 | — |
| Octyldodecyl Neopentanoate/Elefac I-205/Alzo | 19.000 | 19.00 |
| Cethyl Dimethicone, Dimethicone, Bis-Vinyl Dimethicone/Dimethicone Copolymer/Jeesilc CD-405/Jeen | 2.000 | 3.25 |
| Phenyl Trimethicone, Bis-Vinyl Dimethicone/Dimethicone Copolymer/Jeesilc PTMF-405/Jeen | 5.000 | 3.00 |
| Squalane/Jeen/Vantage | — | 0.50 |
| Ethylhexyl Olivate, Squalane/Botanessential Olivate S-EHO/DDChemco | — | — |
| Polyhydroxystearic Acid/Dispersun DSP-OL 300 Innospec/Chemtech | 1.050 | 1.10 |
| Zinc Oxide/MicNo (Platelets) SOLAVEIL MZP7-PW-(MV) 98%/Croda | 22.500 | — |
| Zinc Oxide/ZinClear XP/Antaria/Deveraux (Aggregates) SOLAVEIL MZP7-PW-(MV) 98%/Croda | — | 22.5 |
| Styrene Acrylates Copolymer/SunSphere PWD/Dow/Dow Corning | 4.500 | 4.50 |
| Disteardimonium Hectorite, Phenyl Trimethicone, Triethyl Citrate/Bentone Gel, PTMV/Elementis/DD Chem | 2.300 | 2.30 |
| Glyceryl Dibehenate, Tribehenin, Glyceryl Behenate/Compritol 888/Gatephosse/Omya | — | 0.70 |
| Bisabolol, *Zingiber Officinales* (Ginger) Extr./SymRelief 100/Symrise | 0.100 | 0.10 |
| Dimethicone, Dimethicone Copolymer/AcceSIL FF16/Access Ingredients | 0.250 | 0.75 |
| Vit E Acetate, USP/Jeen | 0.010 | 0.01 |

TABLE 15-continued

Exemplary Formulations. Ingredients in wt. %.

| Formula # | 021-042 | 021-046 XP(5) |
|---|---|---|
| 1,2 Hexanediol, Caprylyl Glycol, Tropolone/Symdiol 68 T/Symrise | 0.900 | 0.90 |
| Polyglyceryl-10 Caprylate/Caprate Syneth C15K RSPO MB/Lonza/Deveraux | 0.015 | — |
| Polyglyceryl-10 Decaoleate Syneth 03 K RSPO/Lonza/Deveraux | 12.000 | — |
| Polyglyceryl-2 Sesquioleate SGS-PGO 152/Argan | — | 11.000 |
| Dimethicone, Trisiloxane/Xiameter PMX-1184 Silicone Fluid/Dow/Univar | 2.500 | 2.60 |
| Dimethicone/Vinyl Dimethicone Copolymer, Lauterh-3, Laureth-25/Emul-6081/Access Ingredients | — | — |
| Fullerene, Squalane/Fullerene-C60/C60 Co./AE Chemie | 1.000 | — |
| Phenetyl Alcohol, Caprypyl Glycol/Feniol/Argan | 0.030 | 0.06 |
| Silica/Silisphere LS 8H/Argan | 0.500 | 0.60 |
| Calcium, Sodium Borosilicate/Covabeads Crystals/Sensient | 2.000 | 2.50 |

TABLE 16

Exemplary Formulations. Ingredients in wt. %.

| Formula # | 021-046 XP(5)-10 | 021-046 XP(5)-28 | 021-046 XP(5)-22 | 021-046 XP(5)-32 |
|---|---|---|---|---|
| Description (Type) | Lotion | Lotion | Lotion | Lotion (higher SPF expected) |
| Composition: | | | | |
| Water | 19.38 | 20.89 | 22.86 | 22.10 |
| Magnesium Sulfate | 0.85 | 0.85 | 0.85 | 0.85 |
| Propanediol | 2.50 | 2.50 | 2.50 | 2.50 |
| Deinococcus Extract, Propanediol, 1,2-Hexanediol, Water/FIRST/Access Ingredients | 1.00 | 1.00 | 1.00 | 1.00 |
| Carnosine/Dragosine/Symrise | 0.20 | 0.20 | 0.20 | 0.20 |
| *Echinacea Purpurea*/Symfinity/Symrise | 0.10 | 0.10 | 0.10 | 0.10 |
| Octyldodecyl Neopentanoate/Elefac I-205/Alzo | 19.00 | 19.00 | 19.00 | 19.00 |
| Cethyl Dimethicone, Dimethicone, Bis-Vinyl Dimethicone/Dimethicone Copolymer/Jeesilc CD-405/Jeen | 3.75 | 3.75 | 3.75 | 3.75 |
| Phenyl Trimethicone, Bis-Vinyl Dimethicone/Dimethicone Copolymer/Jeesilc PTMF-405/Jeen | 2.50 | 2.50 | 2.50 | 2.50 |
| Polyhydroxystearic Acid/Dispersun DSP-OL 300 Innospec/Chemtech | 1.10 | 1.08 | 1.08 | 1.08 |
| Zinc Oxide/ZinClear XP/Antaria/Deveraux (Aggregates) SOLAVEIL MZP7-PW-(MV) 98%/Croda | 22.5 | 14.0 | 10.0 | 20.0 |
| Styrene Acrylates Copolymer/SunSphere PWD/Dow/Dow Corning | 4.50 | 5.00 | 5.5 | 5.00 |
| Caprylic Capric Triglyceride, Titanium Dioxide, Aluminum Hydroxide, Stearic Acid, Polyhydroxystearic Acid/AccessSUN E50C (41.56% active)-Access Ingredients | — | 7.21 | — | 2.41 (1% active) |

TABLE 16-continued

Exemplary Formulations. Ingredients in wt. %.

| Formula # | 021-046 XP(5)-10 | 021-046 XP(5)-28 | 021-046 XP(5)-22 | 021-046 XP(5)-32 |
|---|---|---|---|---|
| Synthetic Fluorphlogophite, Titanium Dioxide/CL Gold A/Argan | — | 0.25 | 0.25 | 0.25 |
| Disteardimonium Hectorite, Phenyl Trimethicone, Triethyl Citrate/Bentone Gel, PTMV/Elementis/DD Chem | 3.50 | 3.50 | 3.50 | 3.50 |
| Glyceryl Dibehenate, Tribehenin, Glyceryl Behenate/Compritol 888/Gatephosse/Omya | 0.75 | 0.80 | 0.80 | 0.80 |
| Bisabolol, *Zingiber Officinales* (Ginger) Extr./SymRelief 100/Symrise | 0.10 | 0.10 | 0.10 | 0.10 |
| Dimethicone, Dimethicone Copolymer/AcceSIL FF16/Access Ingredients | 0.75 | 1.00 | 1.00 | 1.00 |
| Vit E Acetate, USP/Jeen | 0.01 | 0.01 | 0.01 | 0.01 |
| 1,2 Hexanediol, Caprylyl Glycol/Symdiol 68/Symrise | 0.90 | 0.90 | 0.90 | 0.90 |
| Polyglyceryl-2 Sesquioleate SGS-PGO 152/Argan | 11.10 | 11.10 | 11.10 | 11.10 |
| Dimethicone, Trisiloxane/Xiameter PMX-1184 Silicone Fluid/Dow/Univar | 1.75 | 1.30 | 1.75 | 1.30 |
| Phenetyl Alcohol, Caprypyl Glycol/Feniol/Argan | 0.06 | 0.06 | 0.06 | 0.06 |
| Silica/Silisphere LS 8H/Argan | 1.20 | 1.40 | 1.20 | 1.40 |
| Calcium, Sodium Borosilicate/Covabeads Crystals/Sensient | 2.50 | 1.50 | 2.50 | 1.50 |

TABLE 17

Exemplary Formulations. Ingredients in wt. %.

| Formula # | 021-048 XP(7)-8 | 021-048 XP(7)-20 | 021-048 XP(7)-26 | 021-048 XP(7)-30 |
|---|---|---|---|---|
| Description (Type): | Lotion | Lotion | Lotion | Lotion |
| Composition: | | | | |
| Water | 19.00 | 22.27 | 22.12 | 20.00 |
| Magnesium Sulfate | 0.85 | 0.85 | 0.85 | 0.85 |
| Propanediol | 2.25 | 2.50 | 2.50 | 2.50 |
| Deinococcus Extract, Propanediol, 1,2-Hexanediol, Water/FIRST/Access Ingredients | 1.00 | 1.00 | 1.00 | 1.00 |
| Carnosine/Dragosine/Symrise | 0.20 | 0.20 | 0.20 | 0.20 |
| *Echinacea Purpurea*/Symfinity/Symrise | 0.10 | 0.10 | 0.10 | 0.10 |
| Octyldodecyl Neopentanoate/Elefac I-205/Alzo | 19.00 | 19.00 | 19.00 | 19.00 |
| Cethyl Dimethicone, Dimethicone, Bis-Vinyl Dimethicone/Dimethicone Copolymer/Jeesilc CD-405/Jeen | 3.25 | 3.75 | 3.75 | 3.75 |
| Phenyl Trimethicone, Bis-Vinyl Dimethicone/Dimethicone Copolymer/Jeesilc PTMF-405/Jeen | 2.24 | 2.50 | 2.50 | 2.21 |
| Polyhydroxystearic Acid/Dispersun DSP-OL 300 Innospec/Chemtech | 1.10 | 1.08 | 1.08 | 1.08 |
| Zinc Oxide/ZinClear XP/Antaria/Deveraux (Aggregates) SOLA VEIL MZP7-PW-(MV) 98%/Croda | 22.5 | 10.0 | 10.0 | 14.0 |

TABLE 17-continued

Exemplary Formulations. Ingredients in wt. %.

| Formula # | 021-048 XP(7)-8 | 021-048 XP(7)-20 | 021-048 XP(7)-26 | 021-048 XP(7)-30 |
|---|---|---|---|---|
| Styrene Acrylates Copolymer/SunSphere PWD/Dow/Dow Corning | 4.50 | 4.50 | 4.50 | 4.50 |
| Caprylic Capric Triglyceride, Titanium Dioxide, Aluminum Hydroxide, Stearic Acid, Polyhydroxystearic Acid/AccessSUN E50C (1.56% active)-Access Ingredients | — | 8.54 (3.55% active) | 8.54 (3.55% active) | 7.2 (3.0% active) |
| ARG-PCC-Iron Oxides (Red, Yellow, Black) | 1.74 | 1.74 | 1.74 | 1.74 |
| Disteardimonium Hectorite, Phenyl Trimethicone, Triethyl Citrate/Bentone Gel, PTMV/Elementis/DD Chem | 3.50 | 3.60 | 3.70 | 3.70 |
| Glyceryl Dibehenate, Tribehenin, Glyceryl Behenate/Compritol 888/Gatephosse/Omya | 0.9 | 0.80 | 0.85 | 0.85 |
| Bisabolol, *Zingiber Officinales* (Ginger) Extr./SymRelief 100/Symrise | 0.1 | 0.10 | 0.10 | 0.10 |
| Dimethicone, Dimethicone Copolymer/AcceSIL FF16/Access Ingredients | 0.75 | 1.00 | 1.00 | 1.00 |
| Vit E Acetate, USP/Jeen | 0.01 | 0.01 | 0.01 | 0.01 |
| 1,2 Hexanediol, Caprylyl Glycol/Symdiol 68/Symrise | 0.9 | 0.90 | 0.90 | 0.90 |
| Polyglyceryl-2 Sesquioleate SGS-PGO 152/Argan | 11.1 | 11.10 | 11.10 | 11.10 |
| Dimethicone, Trisiloxane/Xiameter PMX-1184 Silicone Fluid/Dow/Univar | 1.75 | 1.50 | 1.50 | 1.25 |
| Phenetyl Alcohol, Caprypyl Glycol/Feniol/Argan | 0.06 | 0.06 | 0.06 | 0.06 |
| Silica/Silisphere LS 8H/Argan | 1.00 | 1.40 | 1.40 | 1.40 |
| Calcium, Sodium Borosilicate/Covabeads Crystals/Sensient | 2.20 | 1.50 | 1.50 | 1.50 |

TABLE 18

Exemplary Formulations. Ingredients in wt. %.

| Formula # | 009-74 (Lotion) |
|---|---|
| Composition: | |
| Water | 31.49 |
| Sodium Chloride | 0.75 |
| Glycerin | 0.50 |
| Hydroxyacetophenone/Symsave H/Symrise | 0.50 |
| Water, Hydrogenated Phosphaditylcholine, Glycerin, Ubiquinone/BP-CoQ10/Jeen/Vantage | 0.50 |
| Water, Glycerin, Polygonium Aviculare Extract/Elix-IR/LucasMayer | 1.00 |
| Water, Glycerin, *Camellia Sinensis* Leaf Extract/Green Tea Extract/Jeen/Vantage | 0.50 |
| Panthenol/DL-Panthenol/Jeen/Vantage | 0.25 |
| Allantoin/Allantoin/Jeen/Vantage | 0.05 |
| Niacinamide/Niacinamide PC/DSM | 1.00 |
| *Capparis Spinosa* Fruit Extract, *Opuntia Ficus-Indica* Extract, *Olea Europea* (Olive) Leaf Extract, Starch/Skin Save Starch/Botanical Plus/Jeen/Vantage | 0.15 |
| *Olea Europea* (Olive) Fruit Extract, Starch/Skin Olea-HT 10 Starch/Botanical Plus/Jeen/Vantage | 0.15 |
| Caprylic/Capric Triglycerides and *Himanthalia Elongata* Extract/Marine Bamboo TG/Odycea/Argan | 0.50 |
| Butyloctyl Salicylate/Hallbrite BHB/HallStar/Azelis | 13.0 |
| Dimethicone, Bis-Vinyl Dimethicone/Dimethicone Copolymer/Jeesilc PS DMLV 50/Jeen | 4.0 |

TABLE 18-continued

Exemplary Formulations. Ingredients in wt. %.

| Formula # | 009-74 (Lotion) |
|---|---|
| Cethyl Dimethicone, Dimethicone, Bis-Vinyl Dimethicone/Dimethicone Copolymer/Jeesilc CD-405/Jeen | 4.0 |
| Squalane/Jeen/Vantage | 2.0 |
| Polyhydroxystearic Acid/Dispersun DSP-OL 300 Innospec/Chemtech | 1.0 |
| Zinc Oxide CLR-P/Argan (Aggregates) | 10.0 |
| Styrene Acrylates Copolymer/SunSphere PWD/Dow/Dow Corning | 5.5 |
| Caprylic Capric Triglyceride, Titanium Dioxide, Aluminum Hydroxide, Stearic Acid, Polyhydroxystearic Acid/AccessSUN E50C (41.56% active)-Access Ingredients | 8.54 (3.55% active) |
| Disteardimonium Hectorite, Phenyl Trimethicone, Triethyl Citrate/Bentone Gel, PTMV/Elementis/DD Chem | 2.25 |
| Bisabolol, Zingiber Officinales (Ginger) Extr./SymRelief 100/Symrise | 0.10 |
| Dimethicone, Dimethicone Copolymer/AcceSIL FF16/Access Ingredients | 2.00 |
| Vit E Acetate, USP/Jeen | 0.25 |
| 1,2 Hexanediol, Caprylyl Glycol/Symdiol 68/Symrise | 0.50 |
| Polyglyceryl-4 Oleateate/Jeechem 100/Jeen/Ventage | 6.00 |
| Phenetyl Alcohol, Caprypyl Glycol/Feniol/Argan | 0.02 |
| Plankton Glass Flower/Odycea/Argan | 0.50 |
| Silica/Silisphere LS 8H/Argan | 2.75 |
| Cerium Oxide, Aluminum Oxide, PMMA/Arg Sphere NIR-1/15BA000/Argan | 0.25 |

What is claimed is:

1. A composition suitable for topical administration comprising a matrix composition comprising a mixture of structurally diverse matrix particles (1) that are formed from at least five different types of primary particles that are distinguishable from one another due to different size characteristics, shape characteristics, or both, (2) that constitute 15-50% of the one A matrix composition by weight, (3) that comprise one more types of particle agglomerates, (4) where at least 33% of the weight concentration of the matrix particle mixture is composed of UV-protectant metal oxide particles having a minimum particle size of over 100 nm, (5) where scanning electron microscope analysis of the composition fails to identify any significant number of discrete matrix particles of having a size of 100 nm or less, and (6) where the particle mixture comprises particles that can be classified as (a) a first primary particle population having a maximum particle size of 250 nm and making up less than 2% of the composition by weight, (b) a second primary particle population having an average particle size of greater than 250 nm and less than 500 nm and making up 5-15% of the composition by weight, at least 25% of the second particle population being composed of UV-protective particles that are at least mostly composed of styrene acrylate copolymer, (c) a third primary particle population having an average particle size of greater than 500 nm and less than 750 nm and making up 5-15% of the composition by weight, at least 75% of the third particle population being composed of UV protective metal oxide particles, (d) a fourth primary particle population having an average particle size of greater than 750 nm and less than 1000 nm and making up 1.75-7% of the composition by weight, at least 75% of the fourth particle population being composed of UV protective metal oxide particles, (e) a fifth primary particle population having an average particle size of greater than 1000 nm and less than 8500 nm and making up 4-9% of the composition by weight, 20-70% of the fifth particle population comprising a glass composition, and (f) a sixth primary particle population having an average particle size of 8500 nm or more and making up less than 3.5% of the composition by weight, at least 50% of the sixth particle composition being composed of silica particles, wherein (7) the composition exhibits a sun protection factor (SPF) of at least 30, a critical wavelength of at least 370 nm, a UVA/UVB ratio of at least 0.333, and a UVA1 to UV ratio of at least 0.7.

2. The composition of claim 1, wherein the structurally diverse matrix particles of the matrix composition are (1) distributed among five shape-defined particle populations comprising (a) spherical solid porous particles (SSPPs), (b) spherical solid nonporous particles (SSNPs), (c) irregular porous aggregate particles (IPAPs), (d) spherical hollow particles (SHPs), and (e) platelet particles (PPs) and (2) the weight concentration distribution of the particles among the five shape-defined particle populations is (a) 0.5-2.5% of the composition by weight being made up of SSPPs; (b) 0.75-10% of the composition by weight being made up of SSNPs; (c) 12-24% of the composition by weight being made up of IPAPs; (d) about 3-7% of the composition by weight being made up of SHPs; and (e) 0.5-3.5% of the composition by weight being made up of PPs.

3. The composition of claim 2, wherein the matrix composition when spread across a surface using manual distribution comprises multiple layers of the matrix particles, wherein (1) thee particles in a first layer cover at least about 65% of the surface and (2) the particles in at least one other layer comprise particles positioned in gaps in the first layer such that the first layer and second layer cover at least about 75% of the surface.

4. The composition of claim 3, wherein the particles of the first primary particle population comprise hectorite clay particles.

5. The composition of claim 3 wherein the second primary particle population comprises styrene acrylate copolymer particles and zinc oxide particles in a weight concentration ratio of 1:3 to 1:1, wherein at least most of the styrene acrylate copolymer particles have a hollow spherical shape.

6. The composition of claim 3, wherein the highest concentration of metal oxide particles in any primary particle population is in the third primary particle population.

7. The composition of claim 3, wherein at least 15% of the particles in the fifth primary particle population are solid, nonporous, spherical or quasi-spherical calcium borosilicate particles.

8. The composition of claim 3, wherein at least 75% of the particles of the sixth primary particle composition are composed at least mostly of a silica material having a solid, spherical or semi-spherical shape and porous structure.

9. The composition of claim 3, wherein at least 75% of the metal oxide particles in the composition are irregularly shaped zinc oxide aggregate particles and the irregularly shaped zinc oxide aggregate particles make up 12-24% of the composition by weight.

10. The composition of claim 9, wherein the composition comprises at least 0.2% of a hectorite clay suspending agent.

11. The composition of claim 9, wherein the composition further comprises 0.1-4% by weight spherical or quasi-spherical titanium dioxide particles.

12. The composition of claim 10, wherein the composition further comprises 0.75-3% by weight iron oxide particles, wherein most of the iron oxide particles are contained in the first primary particle population, and the composition comprises at least 0.2% of a natural or synthetic mica.

13. The composition of claim 1, wherein the composition comprises a dimethicone, dimethicone copolymer film-forming component present in the composition in an amount representing 0.5-2.5% of the composition by weight.

14. The composition of claim 1, wherein the composition is an anhydrous composition comprising a structural wax component that makes up about 5-20% of the composition by weight and wherein the composition comprises less than 0.5% by weight water.

15. The composition of claim 1, wherein the composition is a water-in-oil emulsion comprising polyglyceryl-2 sesquioleate making up 8-14% of the composition by weight.

* * * * *